United States Patent
Nielsen et al.

(10) Patent No.: US 8,952,162 B2
(45) Date of Patent: Feb. 10, 2015

(54) TRIAZOLOPYRIDINES AS PHOSPHODIESTERASE INHIBITORS FOR TREATMENT OF DERMAL DISEASES

(75) Inventors: Simon Feldbæk Nielsen, Herlev (DK); Thomas Vifian, Hillerød (DK); Anne Marie Horneman, Humlebæk (DK); Jesper Færgemann Lau, Farum (DK)

(73) Assignee: Leo Pharma A/S, Ballerup (DK)

( * ) Notice: Subject to any disclaimer, the term of this patent is extended or adjusted under 35 U.S.C. 154(b) by 369 days.

(21) Appl. No.: 13/140,505

(22) PCT Filed: Dec. 18, 2009

(86) PCT No.: PCT/DK2009/000262
§ 371 (c)(1), (2), (4) Date: Sep. 16, 2011

(87) PCT Pub. No.: WO2010/069322
PCT Pub. Date: Jun. 24, 2010

(65) Prior Publication Data
US 2012/0028974 A1 Feb. 2, 2012

Related U.S. Application Data

(60) Provisional application No. 61/139,445, filed on Dec. 19, 2008.

(51) Int. Cl.
*C07D 471/04* (2006.01)
*A61K 31/437* (2006.01)

(52) U.S. Cl.
CPC .................................. *C07D 471/04* (2013.01)
USPC ........................................... 546/118; 514/303

(58) Field of Classification Search
USPC ........................................... 546/118; 514/303
See application file for complete search history.

(56) References Cited

U.S. PATENT DOCUMENTS

| | | |
|---|---|---|
| 2008/0207902 A1 | 8/2008 | Kohno et al. |
| 2010/0130738 A1 | 5/2010 | Kohno et al. |
| 2010/0160335 A1 | 6/2010 | Kohno et al. |
| 2011/0224250 A1 | 9/2011 | Kohno et al. |

FOREIGN PATENT DOCUMENTS

| | | |
|---|---|---|
| EP | 0 771 794 A1 | 5/1997 |
| EP | 0 943 613 A1 | 9/1999 |
| EP | 2348018 A1 | 7/2011 |
| JP | 2007-091597 A | 4/2007 |
| JP | 2008-024599 A | 2/2008 |
| JP | 2008024599 A * | 2/2008 |
| JP | 2008-069144 A | 3/2008 |
| JP | 2009-040711 A | 2/2009 |
| WO | WO 03/010167 A1 | 2/2003 |
| WO | WO 03/031445 A1 | 4/2003 |
| WO | WO 2008/006540 A1 | 1/2008 |
| WO | WO 2008/125111 A1 | 10/2008 |

OTHER PUBLICATIONS

Whitman "Phosphodiesterase 4 Inhibition in the Treatment of Psoriasis, Psoriatic Arthritis and Other Chronic Inflammatory Diseases" Dermatol Ther (Heidelb) (2013) 3:1-15.*
Trisha Gura "Cancer Models: Systems for Identifying New Drugs Are Often Faulty" Science Nov. 7, 1997: vol. 278. No. 5340, pp. 1041-1042.*
Simone, Oncology: Introduction, Cecil Textbook of Medicine, 20th Edition, 1996 vol. 1, pp. 1004-1010.*
Card et al., "Structural Basis for the Activity of Drugs that Inhibit Phosphodiesterases", Structure, vol. 12, 2004, pp. 2233-2247.
Holden et al., "Monocyte Localization of Elevated cAMP Phosphodiesterase Activity in Atopic Dermatitis", Journal of Investigative Dermatology, 1986, 87, 3, pp. 372-376.
Houslay et al., "Phosphodiesterase-4 as a therapeutic target", DDT, vol. 10, No. 22, 2005, pp. 1503-1519.
Huang et al., "Phosphodiesterase 4 Inhibitors for the Treatment of Asthma and COPD", Current Medicinal Chemistry, 2006, 13, pp. 3253-3262.
Kroegel et al., "Phosphodiesterase-4 Inhibitors as a Novel Approach for the Treatment of Respiratory Disease: cilomilast" Expert Opin., Investig. Drugs (2007), 16(1), pp. 109-124.
Lipworth, "Phosphodiesterase-4 Inhibitors for Asthma and Chronic Obstructive Pulmonary Disease", Lancet 2005, 365, pp. 167-175.
Nettekoven et al. "Synthetic Access to 2-Amido-5-aryl-8-methoxy-triazolopyridine and 2-Amido-5-morpholino-8-methoxy-triazolopyridine Derivatives as Potential Inhibitors of the Adenosine Receptor Subtypes", Synthesis, No. 11, 2003, pp. 1649-1652, XP-002416826.
Smith et al., "Selective phosphodiesterase 4 inhibitors in the treatment of allergy and inflammation", Current Opinion in Investigational Drugs, 2005, 6(11), pp. 1136-1141.
Yamazaki et al., "Cyclization of Isothiosemicarbazones.Part 10. A Novel Route to 2-Amino[1,2,4]triazolo[1,5-a]pyridine Derivatives", J. Chem.Soc. Perkin Trans. 1994, pp. 825-828, XP-002416827.

* cited by examiner

*Primary Examiner* — David K O Dell
(74) *Attorney, Agent, or Firm* — Birch, Stewart, Kolasch & Birch, LLP

(57) ABSTRACT

The present invention relates to a compound according to formula I, wherein $R_1$, $R_2$ and A are as defined herein, which exhibit PDE4 inhibitory activity and may be used in the treatment of inflammatory diseases or autoimmune diseases, in particular inflammatory or proliferative dermal diseases.

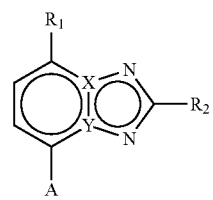

24 Claims, No Drawings

TRIAZOLOPYRIDINES AS PHOSPHODIESTERASE INHIBITORS FOR TREATMENT OF DERMAL DISEASES

FIELD OF THE INVENTION

This application is the National Phase of PCT/DK2009/000262 filed on Dec. 18, 2009, which claims priority under 35 U.S.C. 119(e) to U.S. Provisional Application No. 61/139,445 filed on Dec. 19, 2008 all of which are hereby expressly incorporated by reference into the present application.

The present invention relates to novel compounds with phosphodiesterase inhibitory activity, as well as to their use as therapeutic agents in the treatment of inflammatory diseases and conditions.

BACKGROUND OF THE INVENTION

Phosphodiesterases are enzymes that catalyse the hydrolysis of cyclic AMP and/or cyclic GMP in cells to 5-AMP and 5-GMP, respectively, and as such they are critical to cellular regulation of cAMP or cGMP levels. Of the 11 phosphodiesterases identified so far, phosphodiesterase (PDE) 4, PDE7 and PDE8 are selective for cAMP. PDE4 is the most important modulator of cAMP expressed in immune and inflammatory cells such as neutrophils, macrophages and T-lymphocytes (Z. Huang and J. A. Mancini, *Current Med. Chem.* 13, 2006, pp. 3253-3262). As cAMP is a key second messenger in the modulation of inflammatory responses, PDE4 has been found to regulate inflammatory responses of inflammatory cells by modulating proinflammatory cytokines such as TNFα, IL-2, IFN-γ, GM-CSF and LTB4. Inhibition of PDE4 has therefore become an attractive target for the therapy of inflammatory diseases such as asthma, chronic obstructive pulmonary disease (COPD), rheumatoid arthritis, atopic dermatitis, inflammatory bowel disease such as Crohn's disease etc. (M. D. Houslay et al., *Drug Discovery Today* 10 (22), 2005, pp. 1503-1519). As atopic dermatitis (AD) patients have increased PDE-activity, PDE4-inhibition would also appear to be a viable treatment of AD (Journal of Investigative Dermatology (1986), 87(3), 372-6).

The PDE4 gene family consists at least of four genes, A, B, C and D, which have a high degree of homology (V. Boswell Smith and D. Spina, *Curr. Opinion Investig. Drugs* 6(11), 2006, pp. 1136-1141). The four PDE4 isoforms are differentially expressed in different tissues and cell types. Thus, PDE4B is predominantly expressed in monocytes and neutrophils, but not in cortex and epithelial cells, while PDE4D is expressed in lung, cortex, cerebellum and T-cells (C. Kroegel and M. Foerster, *Exp. Opinion Investig. Drugs* 16(1), 2007, pp. 109-124). It has been speculated that inhibition of PDE4D in the brain is associated with the adverse effects found when administering PDE4 inhibitors clinically, primarily nausea and emesis, whereas inhibition of PDE4B is associated with anti-inflammatory effects (B. Lipworth, *Lancet* 365, 2005, pp. 167-175). However, the PDE inhibitors developed so far are not believed to be specific for any of the four PDE4 isoforms.

Numerous PDE4 inhibitors have been studied for their therapeutic effect on inflammatory diseases, primarily asthma and COPD.

The first of these, theophylline, is a weak, non-selective phosphodiesterase inhibitor used in the treatment of respiratory diseases such as asthma and COPD. Treatment with theophylline may, however, give rise to both mild and severe adverse effects, e.g. arrhythmia and convulsions, restricting the clinical utility of theophylline (Kroegel and Foerster, supra). As phosphodiesterase has remained an attractive target for anti-inflammatory therapy, several other, more selective PDE4 inhibitors have been developed and investigated in a clinical setting. The clinical development of many of the first-generation PDE4 inhibitors such as rolipram was discontinued due to dose-limiting side effects, primarily nausea and emesis. Second-generation PDE4 inhibitors with apparently less pronounced adverse effects are currently in clinical trials (Houslay, supra). PDE-4 inhibitors are for example disclosed in EP 0771794 and EP 0943613.

WO 2008/125111 discloses triazolopyridine compounds with a potent PDE4 inhibiting activity. These compounds include a linker including a carbonyl group between a bicyclic, heterocyclic ring system and a monocyclic ring system. It has been shown for a related compound, piclamilast, that the linker is extremely important for the positioning of the monocyclic ring such that it may interact with the PDE4 enzyme (Card G. L., England B. P., Suzuki Y., Fong D., Powell B., Lee B., Luu C., Tabrizizad M., Gillette S., Ibrahim P. N., Ards D. R., Bollag G., Milburn M. V., Kim S. H., Schlessinger J., Zhang K. Y., "Structural basis for the activity of drugs that inhibit phosphodiesterases", *Structure* 2004 December; 12(12); 2233-47) to give the desired inhibitory effect.

SUMMARY OF THE INVENTION

The inventors have surprisingly found that novel compounds of the present invention which are similar to those disclosed in WO 2008/125111, but which do not include a carbonyl linker between the two ring systems exhibit PDE4 inhibitory activity even though the linker is absent. Thus, the compounds may be useful as therapeutic agents for inflammatory allergic diseases such as bronchial asthma, COPD, allergic rhinitis, and nephritis; autoimmune diseases such as rheumatoid arthritis, multiple sclerosis, Crohn's disease, and systemic lupus erythematosus; diseases of the central nervous system such as depression, amnesia, and dementia; organopathy associated with ischemic reflux caused by cardiac failure, shock, and cerebrovascular diseases, and the like; insulin-resistant diabetes; wounds; AIDS, and the like.

Compounds of the present invention may also be beneficial in preventing, treating or ameliorating a variety of diseases, such as dermal diseases or conditions, such as proliferative and inflammatory skin disorders and in particular psoriasis, epidermal inflammation, alopecia, skin atrophy, steroid induced skin atrophy, skin ageing, photo skin ageing, acne, dermatitis, atopic dermatitis, seborrheic dermatitis, contact dermatitis, urticaria, pruritis, and eczema.

Accordingly, the present invention relates to a compound of general formula I,

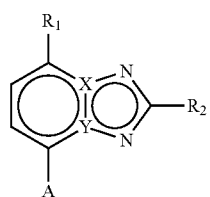

wherein $R_1$ is halogen, hydroxy, cyano or thiocyano,
or $R_1$ is alkyl, alkenyl, alkynyl, alkoxy, alkylthio, —S(O)alkyl, —S(O)$_2$alkyl, cycloalkyl, cycloalkoxy, heterocycloalkyl, heterocycloalkenyl, aryl, heteroaryl, amino, —C(O)alkyl, —C(O)Oalkyl, OC(O)alkyl, —NHC(O)alkyl, —N(alkyl)C(O)alkyl, —C(O)NH-(alkyl), —C(O)N-(alkyl)(alkyl), sulfamoyl, sulfinamoyl, —NHS(O)$_2$alkyl or —N(alkyl)S(O)$_2$alkyl, each of which is optionally substituted with one or more substituents selected from $R_3$;

$R_2$ is hydrogen, cyano or halogen, or $R_2$ is alkyl, cycloalkyl, alkenyl, alkynyl, aryl, heteroaryl, alkylcycloalkyl, alkylheterocycloalkyl, cycloalkylalkyl, cycloalkylalkenyl, cycloalkylalkynyl, cycloalkenylalkyl, cycloalkenylalkenyl, cycloalkenylalkynyl, heterocycloalkyl, heterocycloalkylalkyl, heterocycloalkenyl, heterocycloalkenylalkyl, heterocycloalkenylalkenyl, heterocycloalkenylalkynyl, arylalkyl, arylalkenyl, arylalkynyl, heteroarylalkyl, heteroarylalkenyl, heteroarylalkynyl, alkoxy, cycloalkyloxy, alkylthio, cycloalkylthio, —S(O)alkyl, —S(O)$_2$-alkyl, sulfamoyl, sulfinamoyl, —C(O)OR$_3$, —C(O)R$_3$, —NR$_5$R$_6$, -alkyl(NR$_5$R$_6$), -cycloalkyl(NR$_5$R$_6$), -cycloalkylalkyl(NR$_5$R$_6$), -alkylcycloalkyl(NR$_5$R$_6$), —C(O)NR$_7$R$_8$, -alkyl(C(O)NR$_7$R$_8$), -cycloalkyl(C(O)NR$_7$R$_8$), -cycloalkylalkyl(C(O)NR$_7$R$_8$), or -alkylcycloalkyl(C(O)NR$_7$R$_8$), each of which is optionally substituted with one or more substituents selected from $R_4$;

$R_3$ is hydrogen, halogen, aryl, heteroaryl, hydroxy, alkyl, cycloalkyl, heterocycloalkyl, alkoxy, oxo, cyano, amino, aminoalkyl, alkylamino or dialkylamino;

$R_4$ is hydrogen, halogen, hydroxy, oxo, cyano, carboxy, or trihalomethyl, or $R_4$ is NR$_5$R$_6$, —C(O)NR$_7$R$_8$, —C(O)R$_7$, —COOR$_7$, —NR$_5$C(O)NR$_7$R$_8$, —OC(O)NR$_7$R$_8$, —OC(O)R$_3$, NC(O)R$_7$, —OR$_7$, —NC(O)OR$_3$, —NSO$_2$R$_7$, —SO$_2$NR$_7$R$_8$, or —SO$_2$R$_7$R$_8$, alkyl, cycloalkyl, alkenyl, alkynyl, aryl, heteroaryl, cycloalkylalkyl, cycloalkylalkenyl, cycloalkylalkynyl, cycloalkenylalkyl, cycloalkenylalkenyl, cycloalkenylalkynyl, heterocycloalkyl, heterocycloalkylalkyl, heterocycloalkenyl, heterocycloalkenylalkyl, heterocycloalkenylalkenyl, heterocycloalkenylalkynyl, arylalkyl, arylalkenyl, arylalkynyl, heteroarylalkyl, heteroarylalkenyl, heteroarylalkynyl, alkoxy, cycloalkyloxy, alkylthio, cycloalkylthio, sulfamoyl, sulfinamoyl, alkylamino or cycloalkylamino, each of which is optionally substituted with one or more substituents selected from $R_9$;

$R_5$ and $R_6$ each independently represents hydrogen, alkyl, alkenyl, cycloalkyl, heterocycloalkyl, —C(O)alkyl, —C(O)Oalkyl, —C(O)cycloalkyl, —C(O)N-alkyl, carboxyalkyl, —C(O)alkyl-C(O)OH, —C(O)alkyl-C(O)N-alkyl, —C(O)N-aryl, —S(O)$_2$alkyl, —S(O)alkyl, —S(O)$_2$aryl, —S(O)$_2$N-alkyl, —S(O)aryl, aryl, heteroaryl alkylaryl or alkylheteroaryl, each of which is optionally substituted with hydroxy or one or more halogens, or $R_5$ and $R_6$ together with the nitrogen atom to which they are attached form a heterocycloalkyl ring, wherein said ring is optionally substituted with one or more alkyl groups;

$R_7$ and $R_8$ each independently represents hydrogen, alkyl, cycloalkyl, alkenyl, heteroaryl, heterocycloalkyl, carboxyalkyl, carbamoylalkyl, alkyloxyalkyl, alkenyloxyalkyl, aryl, arylalkyl, alkylaryl, heteroaryl, heteroarylalkyl, or alkylheteroaryl, each of which is optionally substituted with one or more substituents selected from the group consisting of hydroxy, halogen, oxo, cyano, alkyl, cycloalkyl, alkenyl, alkoxy, aryl, heteroaryl, heterocycloalkyl, —S(O)$_2$-alkyl, —S(O)$_2$—NR$_{11}$R$_{12}$, —NC(O)-alkyl, —C(O)N-alkyl, —NC(O)O-alkyl, —OC(O)N-alkyl, —NC(O)NR$_{11}$R$_{12}$, —NR$_{11}$SO$_2$-alkyl, —S(O)-alkyl, or $R_7$ and $R_8$ together with the nitrogen atom to which they are attached form a heterocycloalkyl ring, wherein said ring is optionally substituted with one or more alkyl groups;

$R_9$ is hydrogen, halogen, hydroxy, alkoxy, carboxy or trihalomethyl;

X and Y are either C and N or N and C, respectively;

A is aryl, cycloalkyl, cycloalkenyl, heteroaryl, heterocycloalkyl or heterocycloalkenyl, each being optionally substituted with one or more substituents selected from the group consisting of $R_{10}$;

$R_{10}$ is hydrogen, cyano, halogen, hydroxy, or oxo, or $R_{10}$ is alkyl, cycloalkyl, alkenyl, alkynyl, aryl, heteroaryl, cycloalkylalkyl, cycloalkylalkenyl, cycloalkylalkynyl, cycloalkenylalkyl, cycloalkenylalkenyl, cycloalkenylalkynyl, heterocycloalkyl, heterocycloalkenyl, heterocycloalkenylalkyl, heterocycloalkenylalkenyl, heterocycloalkenylalkynyl, arylalkyl, arylalkenyl, arylalkynyl, heteroarylalkyl, heteroarylalkenyl, heteroarylalkynyl, alkoxy, cycloalkyloxy, alkylthio, cycloalkylthio, —S(O)alkyl, —S(O)$_2$-alkyl, sulfamoyl, sulfinamoyl, —C(O)OR$_3$, —C(O)R$_3$, —NR$_5$R$_6$, -alkyl(NR$_5$R$_6$), -cycloalkyl(NR$_5$R$_6$), -cycloalkylalkyl(NR$_5$R$_6$), -alkylcycloalkyl(NR$_5$R$_6$), —C(O)NR$_7$R$_8$, -alkyl(C(O)NR$_7$R$_8$), -cycloalkyl(C(O)NR$_7$R$_8$), -cycloalkylalkyl(C(O)NR$_7$R$_8$) or -alkylcycloalkyl(C(O)NR$_7$R$_8$), each of which is optionally substituted with one or more substituents selected from $R_4$;

$R_{11}$ and $R_{12}$ each independently represents hydrogen or alkyl; and pharmaceutically acceptable salts, hydrates, N-oxides or solvates thereof.

In another aspect, the invention relates to a compound of general formula I as defined herein for use in therapy, such as for the use in the treatment of dermal diseases or conditions or acute or chronic cutaneous wound disorders.

In another aspect, the invention relates to a pharmaceutical composition comprising a compound of general formula I as defined above together with a pharmaceutically acceptable vehicle or excipient or pharmaceutically acceptable carrier(s), optionally together with one or more other therapeutically active compound(s).

In yet another aspect, the invention relates to the use of a compound of general formula I as defined above, and pharmaceutically acceptable and physiologically cleavable esters, pharmaceutically acceptable salts, hydrates, N-oxides or solvates thereof, in the manufacture of a medicament for the prophylaxis, treatment or amelioration of dermal diseases or conditions, or acute or chronic cutaneous wound disorders.

In yet another aspect, the invention relates to a method of preventing, treating or ameliorating dermal diseases or conditions, or acute or chronic cutaneous wound disorders, the method comprising administering to a person suffering from at least one of said diseases an effective amount of one or more compounds of formula I as defined above and pharmaceutically acceptable and physiologically cleavable esters, pharmaceutically acceptable salts, hydrates, N-oxides or solvates thereof;

optionally together with a pharmaceutically acceptable carrier or one or more excipients, optionally in combination with other therapeutically active compounds.

DETAILED DESCRIPTION OF THE INVENTION

In the present context, the term "aryl" is intended to indicate a radical of aromatic carbocyclic rings comprising 6-20 carbon atoms, such as 6-14 carbon atoms, preferably 6-10 carbon atoms, in particular 5- or 6-membered rings, optionally fused carbocyclic rings with at least one aromatic ring, such as phenyl, naphthyl, indenyl and indanyl.

The term "heteroaryl" is intended to indicate radicals of heterocyclic aromatic rings comprising 1-6 heteroatoms (selected from O, S and N) and 1-20 carbon atoms, such as 1-5 heteroatoms and 1-10 carbon atoms, such as 1-5 heteroatoms and 1-6 carbon atoms, such as 1-5 heteroatoms and 1-3 carbon atoms, in particular 5- or 6-membered rings with 1-4 heteroatoms selected from O, S and N, or optionally fused bicyclic rings with 1-4 heteroatoms, and wherein at least one ring is aromatic, e.g. pyridyl, quinolyl, isoquinolyl, indolyl, dihydroisoindolyl, tetrazolyl, thiazolyl, imidazolyl, pyrazolyl, oxazolyl, isoxazolyl, thienyl, pyrazinyl, pyridazinyl, isothiazolyl, benzimidazolyl, benzopyridyl, benzofuranyl and isobenzofuranyl.

The term "alkyl" is intended to indicate the radical obtained when one hydrogen atom is removed from a hydrocarbon. Said alkyl may be branched or straight and may comprise 1-20, preferably 1-12, such as 1-6, such as 1-4 carbon atoms. The term includes the subclasses normal alkyl (n-alkyl), secondary and tertiary alkyl, such as methyl, ethyl, n-propyl, isopropyl, n-butyl, isobutyl, sec.-butyl, tert.-butyl, pentyl, isopentyl, hexyl and isohexyl.

The term "cycloalkyl" is intended to indicate a saturated cycloalkane radical, including polycyclic radicals, such as bicyclic or tricyclic radicals, comprising 3-20 carbon atoms, preferably 3-10 carbon atoms, in particular 3-8 carbon atoms, such as 3-6 carbon atoms, such as 4-5 carbon atoms, e.g. cyclopropyl, cyclobutyl, cyclopentyl, cyclohexyl, cycloheptyl, cyclooctyl, bicyclo[2.2.1]heptyl and adamantyl.

The term "cycloalkenyl" is intended to indicate mono-, di- tri- or tetraunsaturated non-aromatic cyclic hydrocarbon radicals, including polycyclic radicals, comprising 3-20 carbon atoms, typically comprising 3-10 carbon atoms, such as 3-6 carbon atoms, such as 4-5-carbon atoms, e.g. cyclopropenyl, cyclobutenyl, cyclopentenyl, cyclohexenyl, bicyclo[2.2.1]heptenyl, or bicyclo[4.1.0]heptenyl.

The term "heterocycloalkyl" is intended to indicate a cycloalkane radical as defined above, comprising 1-6 heteroatoms, preferably 1, 2, or 3 heteroatoms, selected from O, N, or S, e.g. piperidine, [1,3]dioxolane and [1,3]dioxole.

The term "heterocycloalkenyl" is intended to indicate a cycloalkenyl radical as defined above, including polycyclic radicals, optionally fused with carbocyclic rings, comprising 1-6 heteroatoms, preferably 1-3 heteroatoms, selected from O, N, or S, e.g. 1,6-dihydropyridinyl, 2,3-dihydrobenzofuranyl, 4,5-dihydro-1H-[1,2,4]-triazolyl, 4,5-dihydro-oxazolyl, 1H-indazolyl, 1-H-pyrazolyl, or 4,5-dihydro-isoxazolyl.

The term "alkenyl" is intended to indicate a mono-, di-, tri-, tetra- or pentaunsaturated hydrocarbon radical comprising 2-10 carbon atoms, in particular 2-6 carbon atoms, such as 2-4 carbon atoms, e.g. ethenyl, propenyl, butenyl, pentenyl or hexenyl.

The term "alkynyl" is intended to indicate an hydrocarbon radical comprising 1-5 C—C triple bonds and 2-20 carbon atoms, the alkane chain typically comprising 2-10 carbon atoms, in particular 2-6 carbon atoms, such as 2-4 carbon atoms, e.g. ethynyl, propynyl, butynyl, pentynyl or hexynyl.

The term "halogen" is intended to indicate a substituent from the 7$^{th}$ main group of the periodic table, such as fluoro, chloro, bromo and iodo.

The term "alkoxy" is intended to indicate a radical of the formula —OR', wherein R' is alkyl as indicated above, e.g. methoxy, ethoxy, n-propoxy, isopropoxy, butoxy, etc. The term "cycloalkyloxy" is intended to indicate a radical of the formula —O-Cyc, wherein Cyc is cycloalkyl as defined above.

The term "amino" is intended to indicate a radical of the formula —N(R)$_2$, wherein each R independently represents hydrogen, alkyl, alkenyl, cycloalkyl, or aryl as indicated above, e.g. —NH$_2$, aminophenyl, methylamino, diethylamino, cyclohexylamino, —NH-phenyl, tert-butylamino or ethylamino.

When two or more of the above defined terms are used in combination, such as arylalkyl, heteroarylalkyl, cycloalkylalkyl and the like, it is to be understood that the first mentioned radical is a substituent on the latter mentioned radical, where the point of attachment to another part of the molecule, is on the latter radical.

Thus, the term "cycloalkylalkyl" is intended to indicate a radical of the formula —R'-cycloalkyl, wherein R' is alkyl as defined above such as;

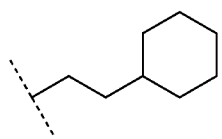

The term "cycloalkenylalkyl" is intended to indicate a radical of the formula —R'-cycloalkenyl, wherein R' is alkyl as defined above such as;

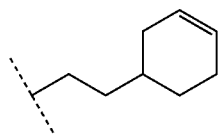

The term "heterocycloalkenylalkyl" is intended to indicate a radical of the formula —R'-cycloalkenyl, wherein R' is alkyl as defined above such as;

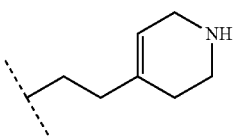

The term "arylalkyl" is intended to indicate a radical of the formula —R'—Ar, wherein R' is alkyl as defined above and Ar is aryl as defined above such as;

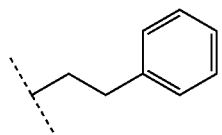

The term "arylalkenyl" is intended to indicate a radical of formula —R"—Ar, wherein Ar is aryl as defined above and R" is alkenyl as defined above such as;

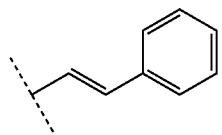

The term "arylalkynyl" is intended to indicate a radical of formula —R'''—Ar, wherein Ar is aryl as defined above and R''' is alkynyl as defined above such as;

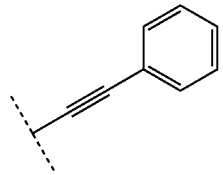

The term "heteroarylalkyl" is intended to indicate a radical of the formula —R'-Het, wherein R' is alkyl as defined above and Het is heteroaryl as defined above such as;

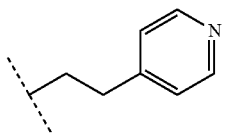

The term "heteroarylalkenyl" is intended to indicate a radical of the formula —R''-Het, wherein R'' is alkenyl as defined above and Het is heteroaryl as defined above such as;

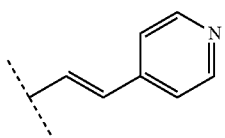

The term "heteroarylalkynyl" is intended to indicate a radical of the formula —R'''-Het, wherein R''' is alkynyl as defined above and Het is heteroaryl as defined above such as;

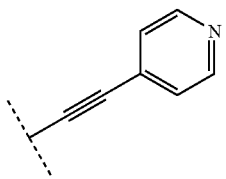

The term "alkylthio" is intended to indicate a radical of the formula —SR', wherein R' is alkyl as indicated above. The term "cycloalkylthio" is intended to indicate a radical of the formula —S-Cyc, wherein Cyc is cycloalkyl as defined above.

The term "sulfamoyl" is intended to indicate a radical of formula —S(O)$_2$NH$_2$.

The term "sulfinamoyl" is intended to indicate a radical of formula —S(O)NH$_2$.

The term "pharmaceutically acceptable salt" is intended to indicate salts prepared by reacting a compound of formula I with a suitable inorganic or organic acid, such as hydrochloric, hydrobromic, hydroiodic, sulfuric, nitric, phosphoric, formic, acetic, 2,2-dichloroaetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid. Pharmaceutically acceptable salts of compounds of formula I may also be prepared by reaction with a suitable base such as sodium hydroxide, potassium hydroxide, magnesium hydroxide, calcium hydroxide, silver hydroxide, ammonia or the like, or suitable non-toxic amines, such as lower alkylamines, for example triethylamine, hydroxy-lower alkylamines, for example 2-hydroxyethylamine, bis-(2-hydroxyethyl)-amine, cycloalkylamines, for example dicyclohexylamine, or benzylamines, for example N,N'-dibenzylethylenediamine, and dibenzylamine, or L-arginine or L-lysine. Salts obtained by reaction with a suitable base include, but are not limited to sodium salts, choline salts, 2-(dimethylamino)-ethanol salts, 4-(2-hydroxyethyl)-morpholin salts, L-lysine salts, N-(2-hydroxyethyl)-pyrrolidine salts, ethanolamine salts, potassium salts, tetrabutylammonium salts, benzyltrimethylammonium salts, cetyltrimethylammonium salts, tetramethylammonium salts, tetrapropylammonium salts, tris(hydroxymethyl)aminomethane salts, N-methyl-D-glucamine salts, silver salts, benzethonium salts, and triethanolamine salts.

The term "solvate" is intended to indicate a species formed by interaction between a compound, e.g. a compound of formula I, and a solvent, e.g. alcohol, glycerol or water, wherein said species are in a solid form. When water is the solvent, said species is referred to as a hydrate.

Embodiments of the Present Invention

In an embodiment of the present invention, R$_2$ is hydrogen, cyano, halogen, or R$_2$ is alkyl, cycloalkyl, alkenyl, alkynyl, aryl, heteroaryl, alkylcycloalkyl, alkylheterocycloalkyl, cycloalkylalkyl, cycloalkylalkenyl, cycloalkylalkynyl, cycloalkenylalkyl, cycloalkenylalkenyl, cycloalkenylalkynyl, heterocycloalkyl, heterocycloalkylalkyl, heterocycloalkenyl, heterocycloalkenylalkyl, heterocycloalkenylalkenyl, heterocycloalkenylalkynyl, arylalkyl, arylalkenyl, arylalkynyl, heteroarylalkyl, heteroarylalkenyl, heteroarylalkynyl, —C(O)OR$_3$, —C(O)R$_3$, -alkyl(NR$_5$R$_6$), -cycloalkyl(NR$_5$R$_6$), -cycloalkylalkyl(NR$_5$R$_6$), -alkylcycloalkyl(NR$_5$R$_6$), —C(O)NR$_7$R$_8$, -alkyl(C(O)NR$_7$R$_8$), -cycloalkyl(C(O)NR$_7$R$_8$), -cycloalkylalkyl(C(O)NR$_7$R$_8$), -alkylcycloalkyl(C(O)NR$_7$R$_8$) each of which is optionally substituted with one or more substituents selected from R$_4$ as defined above.

In an embodiment of the present invention, A may be optionally substituted with R$_{10}$, wherein R$_{10}$ is different from hydrogen. For example, A may be optionally substituted aryl such as optionally substituted phenyl or optionally substituted indanyl. When A is phenyl, it may suitably be substituted with cyano, halogen, aryl, alkyl, heteroaryl, sulfamoyl, —C(O)R$_3$, —C(O)OR$_3$ or —NR$_5$R$_6$, wherein R$_3$, R$_5$ and R$_6$ are as defined above.

In an alternative embodiment, A is optionally substituted heteroaryl such as optionally substituted pyridyl, optionally substituted benzofuranyl, optionally substituted 3H-isobenzofuran-1-on-yl or optionally substituted 2,3-dihydro-isoindol-1-on-yl.

When A is pyridyl, benzofuranyl, 3H-isobenzofuran-1-on-yl or 2,3-dihydro-isoindol-1-on-yl, it may suitably be substituted with one or more substituents selected from chlorine, fluorine, or bromine.

In an embodiment of the invention A is optionally substituted heterocycloalkyl or optionally substituted heterocycloalkenyl such as optionally substituted piperidinyl or optionally substituted pyridazinyl.

In an embodiment of the invention R$_{10}$ is hydrogen, cyano, halogen, oxo, alkyl, alkoxy, cycloalkyloxy, —S(O)alkyl, —S(O)$_2$-alkyl, —C(O)R$_3$, —C(O)OR$_3$, —C(O)NR$_7$R$_8$, wherein R$_3$, R$_7$ and R$_8$ are as defined above.

In an embodiment of the invention $R_{10}$ is cyano, halogen, oxo, alkyl, alkoxy, or —C(O)$R_3$, wherein $R_3$ is as defined above.

In an embodiment of the invention, $R_1$ is halogen, hydroxy or thiocyano, or $R_1$ is alkyl, alkenyl, alkynyl, alkoxy, alkylthio, —S(O)alkyl, —S(O)$_2$alkyl, cycloalkyl, cycloalkoxy, heterocycloalkyl, heterocycloalkenyl, aryl, heteroaryl, —C(O)alkyl, —C(O)Oalkyl, —NHC(O)alkyl, —N(alkyl)C(O)alkyl, —C(O)NH-(alkyl), —C(O)N-(alkyl)(alkyl), sulfamoyl, sulfinamoyl, —NHS(O)$_2$alkyl or —N(alkyl)S(O)$_2$alkyl, each of which is optionally substituted with one or more substituents selected from $R_3$, wherein $R_3$ is as defined above.

More specifically, $R_1$ may be $C_{1-6}$ alkoxy, such as methoxy, mono-, di- or trifluormethoxy, halogen, or hydroxy.

In an embodiment of the present invention the compound of general formula I is a compound of general formula Ia

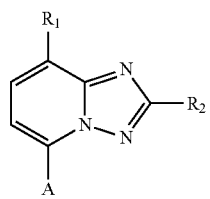

Ia wherein $R_1$, $R_2$ and A are as defined above.

In another embodiment of the invention the compound of general formula I is a compound of general formula Ib

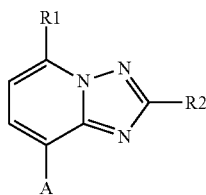

Ib wherein $R_1$, $R_2$ and A are as defined above.

In an embodiment of the invention $R_2$ is alkyl, cycloalkyl, heteroaryl, alkylcycloalkyl, alkylheterocycloalkyl, cycloalkylalkyl, heterocycloalkyl, heterocycloalkylalkyl, -cycloalkyl(C(O)NR$_7$R$_8$), or -cycloalkylalkyl(C(O)NR$_7$R$_8$), each of which is optionally substituted with one or more substituents selected from $R_4$; wherein $R_4$ is as defined above.

In an embodiment of the invention $R_2$ is alkyl, cycloalkyl, alkylcycloalkyl, or cycloalkyl(C(O)NR$_7$R$_8$), each of which is optionally substituted with one or more substituents selected from $R_4$, wherein $R_4$ is as defined above.

In an embodiment of the invention $R_2$ is optionally substituted $C_{1-6}$ alkyl or optionally substituted $C_{3-6}$ cycloalkyl, such as is optionally substituted cyclopropyl.

In an embodiment of the invention $R_3$ is halogen, alkyl, cycloalkyl, heterocycloalkyl, or oxo.

In an embodiment of the invention $R_3$ is alkyl or heterocycloalkyl.

In an embodiment of the invention $R_4$ is halogen, hydroxy, or cyano, or $R_4$ is NR$_5$R$_6$, —C(O)NR$_7$R$_8$, —COOR$_7$, —NR$_5$C(O)NR$_7$R$_8$, —OC(O)NR$_7$R$_8$, —OC(O)R$_3$, —NC(O)R$_7$, —OR$_7$, —NC(O)OR$_3$, —NSO$_2$R$_7$, —SO$_2$NR$_7$R$_8$, —SO$_2$R$_7$R$_8$, alkyl, cycloalkyl, cycloalkylalkyl, heterocycloalkyl, or heterocycloalkylalkyl, each of which is optionally substituted with one or more substituents selected from $R_9$;

wherein $R_3$, $R_5$, $R_6$, $R_7$, $R_8$, and $R_9$ are as defined above.

In an embodiment of the invention $R_4$ is hydroxy or cyano, or $R_4$ is —C(O)NR$_7$R$_8$, —COOR$_7$, —NR$_5$C(O)NR$_7$R$_8$, —OC(O)NR$_7$R$_8$, —NC(O)R$_7$, —OR$_7$, —NC(O)OR$_3$, alkyl, which is optionally substituted with one or more substituents selected from $R_9$; wherein $R_9$ is hydrogen, halogen, or hydroxyl, and wherein $R_3$, $R_7$ and $R_8$ are as defined above.

In an embodiment of the invention $R_5$ and $R_6$ each independently represents hydrogen, alkyl, alkenyl, cycloalkyl, or heterocycloalkyl, or $R_5$ and $R_6$ together with the nitrogen atom to which they are attached form a heterocycloalkyl ring, wherein said ring is optionally substituted with one or more alkyl groups.

In an embodiment of the invention $R_7$ and $R_8$ each independently represents hydrogen, alkyl, cycloalkyl, heterocycloalkyl, or alkenyloxyalkyl, each of which is optionally substituted with one or more substituents selected from the group consisting of hydroxy, halogen, oxo, cyano, alkyl, cycloalkyl, alkoxy, aryl, heteroaryl, heterocycloalkyl, —S(O)$_2$-alkyl, —S(O)$_2$—NR$_{11}$R$_{12}$, —NC(O)-alkyl, —C(O)N-alkyl, —NC(O)O-alkyl, —OC(O)N-alkyl, —NR$_{11}$SO$_2$-alkyl, —S(O)-alkyl, or $R_7$ and $R_8$ together with the nitrogen atom to which they are attached form a heterocycloalkyl ring, wherein said ring is optionally substituted with one or more alkyl groups; wherein $R_{11}$ and $R_{12}$ are hydrogen or $C_{1-4}$ alkyl.

In an embodiment of the invention $R_7$ and $R_8$ each independently represents hydrogen, alkyl, cycloalkyl, alkenyloxyalkyl, each of which is optionally substituted with one or more substituents selected from the group consisting of hydroxy, oxo, cyano, alkyl, cycloalkyl, alkoxy, aryl, heteroaryl, —S(O)$_2$-alkyl, —S(O)$_2$—NR$_{11}$R$_{12}$, —NC(O)-alkyl, —NR$_{11}$SO$_2$-alkyl, or $R_7$ and $R_8$ together with the nitrogen atom to which they are attached form a heterocycloalkyl ring, wherein said ring is optionally substituted with one or more alkyl groups; wherein $R_{11}$ and $R_{12}$ are hydrogen or $C_{1-4}$ alkyl.

Examples of compounds of formula I may be selected from the group consisting of

2-Cyclopropyl-8-methoxy-5-(3-acetyl-phenyl)-[1,2,4]triazolo[1,5-a]pyridine,

2-Cyclopropyl-8-methoxy-5-phenyl-[1,2,4]triazolo[1,5-a]pyridine,

2-Cyclopropyl-8-methoxy-5-(4-methoxy-phenyl)-[1,2,4]triazolo[1,5-a]pyridine,

2-Cyclopropyl-8-methoxy-5-(4-trifluoromethyl-phenyl)-[1,2,4]triazolo[1,5-a]pyridine, 2-Cyclopropyl-5-(3,4-dimethoxy-phenyl)-8-methoxy-[1,2,4]triazolo[1,5-a]pyridine, 2-Cyclopropyl-8-methoxy-5-thiophen-2-yl-[1,2,4]triazolo[1,5-a]pyridine, N-[3-(2-Cyclopropyl-8-methoxy-[1,2,4]triazolo[1,5-a]pyridin-5-yl)-phenyl]-acetamide, 2-Cyclopropyl-8-methoxy-5-(3-trifluoromethoxy-phenyl)-[1,2,4]triazolo[1,5-a]pyridine, 2-Cyclopropyl-8-methoxy-5-(3-methoxy-phenyl)-[1,2,4]triazolo[1,5-a]pyridine, 1-[5-(2-Cyclopropyl-8-methoxy-[1,2,4]triazolo[1,5-a]pyridin-5-yl)-thiophen-2-yl]-ethanone, 2-Cyclopropyl-8-methoxy-5-pyrimidin-5-yl-[1,2,4]triazolo[1,5-a]pyridine, 2-Cyclopropyl-5-(3-methanesulfonyl-phenyl)-8-methoxy-[1,2,4]triazolo[1,5-a]pyridine, N-[3-(2-Cyclopropyl-8-methoxy-[1,2,4]triazolo[1,5-a]pyridin-5-yl)-phenyl]-methanesulfonamide, 3-(2-Cyclopropyl-8-methoxy-[1,2,4]triazolo[1,5-a]pyridin-5-yl)-N-methyl-benzamide,
2-Cyclopropyl-8-methoxy-5-(4-acetyl-phenyl)-[1,2,4]triazolo[1,5-a]pyridine,
N-[4-(2-Cyclopropyl-8-methoxy-[1,2,4]triazolo[1,5-a]pyridin-5-yl)-phenyl]-acetamide,
3-(2-Cyclopropyl-8-methoxy-[1,2,4]triazolo[1,5-a]pyridin-5-yl)-benzoic acid methyl ester,
2-Cyclopropyl-8-methoxy-5-pyridin-3-yl-[1,2,4]triazolo[1,5-a]pyridine,
4-(2-Cyclopropyl-8-methoxy-[1,2,4]triazolo[1,5-a]pyridin-5-yl)-benzoic acid methyl ester,
2-Cyclopropyl-5-(4-methanesulfonyl-phenyl)-8-methoxy-[1,2,4]triazolo[1,5-a]pyridine,
2-Cyclopropyl-5-(2-fluoro-phenyl)-8-methoxy-[1,2,4]triazolo[1,5-a]pyridine,
2-Cyclopropyl-8-methoxy-5-[4-(2-methoxy-ethoxy)-phenyl]-[1,2,4]triazolo[1,5-a]pyridine,
4-(2-Cyclopropyl-8-methoxy-[1,2,4]triazolo[1,5-a]pyridin-5-yl)-benzamide,
5-(3-Butoxy-phenyl)-2-cyclopropyl-8-methoxy-[1,2,4]triazolo[1,5-a]pyridine,
2-Cyclopropyl-5-(3-fluoro-phenyl)-8-methoxy-[1,2,4]triazolo[1,5-a]pyridine,
2-Cyclopropyl-8-methoxy-5-pyridin-4-yl-[1,2,4]triazolo[1,5-a]pyridine,
2-Cyclopropyl-5-(2,4-dichloro-phenyl)-8-methoxy-[1,2,4]triazolo[1,5-a]pyridine,
2-Cyclopropyl-8-methoxy-5-[4-(morpholine-4-sulfonyl)-phenyl]-[1,2,4]triazolo[1,5-a]pyridine,
N-[4-(2-Cyclopropyl-8-methoxy-[1,2,4]triazolo[1,5-a]pyridin-5-yl)-benzyl]-acetamide,
N-[4-(2-Cyclopropyl-8-methoxy-[1,2,4]triazolo[1,5-a]pyridin-5-yl)-benzyl]-methanesulfonamide,
2-Cyclopropyl-5-(4-fluoro-phenyl)-8-methoxy-[1,2,4]triazolo[1,5-a]pyridine,
4-(2-Cyclopropyl-8-methoxy-[1,2,4]triazolo[1,5-a]pyridin-5-yl)-benzonitrile,
3-[4-(2-Cyclopropyl-8-methoxy-[1,2,4]triazolo[1,5-a]pyridin-5-yl)-phenyl]-propionic acid methyl ester,
4-(2-Cyclopropyl-8-methoxy-[1,2,4]triazolo[1,5-a]pyridin-5-yl)-N-(2-hydroxy-ethyl)-benzenesulfonamide,
3-(2-Cyclopropyl-8-methoxy-[1,2,4]triazolo[1,5-a]pyridin-5-yl)-benzonitrile,
3-(2-Cyclopropyl-8-methoxy-[1,2,4]triazolo[1,5-a]pyridin-5-yl)-benzoic acid,
[3-(2-Cyclopropyl-8-methoxy-[1,2,4]triazolo[1,5-a]pyridin-5-yl)-phenyl]-methanol, 3-(2-Cyclopropyl-8-methoxy-[1,2,4]triazolo[1,5-a]pyridin-5-yl)-N,N-dimethyl-benzamide,
3-(2-Cyclopropyl-8-methoxy-[1,2,4]triazolo[1,5-a]pyridin-5-yl)-benzamide,
4-(2-Cyclopropyl-8-methoxy-[1,2,4]triazolo[1,5-a]pyridin-5-yl)-benzoic acid,
4-(2-Cyclopropyl-8-methoxy-[1,2,4]triazolo[1,5-a]pyridin-5-yl)-N,N-dimethyl-benzamide,
4-(2-Cyclopropyl-8-methoxy-[1,2,4]triazolo[1,5-a]pyridin-5-yl)-N-methyl-benzamide,
2-Cyclopropyl-8-methoxy-5-piperidin-1-yl-[1,2,4]triazolo[1,5-a]pyridine,
1-[3-(2-Cyclopropyl-8-hydroxy-[1,2,4]triazolo[1,5-a]pyridin-5-yl)-phenyl]-ethanone,
2-(2-Cyclopropyl-8-methoxy-[1,2,4]triazolo[1,5-a]pyridin-5-yl)-isonicotinonitrile,
1-[5-(4-Cyano-phenyl)-8-methoxy-[1,2,4]triazolo[1,5-a]pyridin-2-yl]-cyclopropanecarboxylic acid ethyl ester,
1-[5-(4-Cyano-phenyl)-8-methoxy-[1,2,4]triazolo[1,5-a]pyridin-2-yl]-cyclopropanecarboxylic acid,
1-[5-(4-Cyano-phenyl)-8-methoxy-[1,2,4]triazolo[1,5-a]pyridin-2-yl]-cyclopropanecarboxylic acid amide,
1-[5-(5-Cyano-pyridin-3-yl)-8-methoxy-[1,2,4]triazolo[1,5-a]pyridin-2-yl]-cyclopropanecarboxylic acid isopropylamide,
3-[2-(1-Hydroxymethyl-cyclopropyl)-8-methoxy-[1,2,4]triazolo[1,5-a]pyridin-5-yl]-benzonitrile,
Pyrrolidine-1-carboxylic acid 1-[5-(3-cyano-phenyl)-8-methoxy-[1,2,4]triazolo[1,5-a]pyridin-2-yl]-cyclopropylmethyl ester,
Isopropyl-carbamic acid 1-[5-(3-cyano-phenyl)-8-methoxy-[1,2,4]triazolo[1,5-a]pyridin-2-yl]-cyclopropylmethyl ester,
3-[2-(1-Benzyloxymethyl-cyclopropyl)-8-methoxy-[1,2,4]triazolo[1,5-a]pyridin-5-yl]-benzonitrile,
N-{1-[5-(3-Cyano-phenyl)-8-methoxy-[1,2,4]triazolo[1,5-a]pyridin-2-yl]-cyclopropylmethyl}-isobutyramide,
{1-[5-(3-Cyano-phenyl)-8-methoxy-[1,2,4]triazolo[1,5-a]pyridin-2-yl]-cyclopropylmethyl}-carbamic acid cyclopentyl ester,
Pyrrolidine-1-carboxylic acid {1-[5-(3-cyano-phenyl)-8-methoxy-[1,2,4]triazolo[1,5-a]pyridin-2-yl]-cyclopropylmethyl}-amide,
6-(2-Cyclopropyl-8-methoxy-[1,2,4]triazolo[1,5-a]pyridin-5-yl)-5-methyl-4,5-dihydro-2H-pyridazin-3-one,
5-(2-Cyclopropyl-8-methoxy-[1,2,4]triazolo[1,5-a]pyridin-5-yl)-nicotinonitrile,
5-(2-Cyclopropyl-8-methoxy-[1,2,4]triazolo[1,5-a]pyridin-5-yl)-indan-1-one,
4-(2-Cyclopropyl-8-methoxy-[1,2,4]triazolo[1,5-a]pyridin-5-yl)-2-methyl-benzonitrile,
4-(2-Cyclopropyl-8-methoxy-[1,2,4]triazolo[1,5-a]pyridin-5-yl)-indan-1-one,
3-(2-Cyclopropyl-8-methoxy-[1,2,4]triazolo[1,5-a]pyridin-5-yl)-5-fluoro-benzonitrile,
4-(2-Cyclopropyl-8-methoxy-[1,2,4]triazolo[1,5-a]pyridin-5-yl)-2-fluoro-benzonitrile,
4-(2-Cyclopropyl-8-methoxy-[1,2,4]triazolo[1,5-a]pyridin-5-yl)-2-methoxy-benzonitrile,
5-(2-Cyclopropyl-8-methoxy-[1,2,4]triazolo[1,5-a]pyridin-5-yl)-3H-isobenzofuran-1-one,
3-(2-Cyclopropyl-8-methoxy-[1,2,4]triazolo[1,5-a]pyridin-5-yl)-5-hydroxymethyl-benzonitrile,
3-(2-Cyclopropyl-8-methoxy-[1,2,4]triazolo[1,5-a]pyridin-5-yl)-5-methoxy-benzonitrile,
4-(2-Cyclopropyl-8-methoxy-[1,2,4]triazolo[1,5-a]pyridin-5-yl)-3H-isobenzofuran-1-one,
5-(2-Cyclopropyl-8-methoxy-[1,2,4]triazolo[1,5-a]pyridin-5-yl)-2,3-dihydro-isoindol-1-one,
1-[8-Methoxy-5-(1-oxo-indan-4-yl)-[1,2,4]triazolo[1,5-a]pyridin-2-yl]-cyclopropanecarboxylic acid benzylamide,
1-[5-(5-Cyano-pyridin-3-yl)-8-methoxy-[1,2,4]triazolo[1,5-a]pyridin-2-yl]-cyclopropanecarboxylic acid benzylamide,
1-[5-(4-Cyano-3-methoxy-phenyl)-8-methoxy-[1,2,4]triazolo[1,5-a]pyridin-2-yl]-cyclopropanecarboxylic acid cyclohexylmethyl-amide,
1-[5-(4-Cyano-3-methoxy-phenyl)-8-methoxy-[1,2,4]triazolo[1,5-a]pyridin-2-yl]-cyclopropanecarboxylic acid isopropylamide,
1-[8-Methoxy-5-(1-oxo-indan-4-yl)-[1,2,4]triazolo[1,5-a]pyridin-2-yl]-cyclopropanecarboxylic acid cyclohexylmethyl-amide, 1-[5-(4-Cyano-3-methoxy-phenyl)-8-methoxy-[1,2,4]triazolo[1,5-a]pyridin-2-yl]-cyclopropanecarboxylic acid (2-methanesulfonyl-ethyl)-amide,
1-[5-(4-Cyano-3-methoxy-phenyl)-8-methoxy-[1,2,4]triazolo[1,5-a]pyridin-2-yl]-cyclopropanecarboxylic acid benzylamide,
1-[8-Methoxy-5-(1-oxo-1,3-dihydro-isobenzofuran-5-yl)-[1,2,4]triazolo[1,5-a]pyridin-2-yl]-cyclopropanecarboxylic acid benzylamide,
1-[8-Methoxy-5-(1-oxo-indan-4-yl)-[1,2,4]triazolo[1,5-a]pyridin-2-yl]-cyclopropanecarboxylic acid isopropylamide,
1-[8-Methoxy-5-(1-oxo-indan-5-yl)-[1,2,4]triazolo[1,5-a]pyridin-2-yl]-cyclopropanecarboxylic acid isopropylamide,
1-[8-Methoxy-5-(1-oxo-indan-5-yl)-[1,2,4]triazolo[1,5-a]pyridin-2-yl]-cyclopropanecarboxylic acid benzylamide,
1-[8-Methoxy-5-(1-oxo-indan-4-yl)-[1,2,4]triazolo[1,5-a]pyridin-2-yl]-cyclopropanecarboxylic acid (2-methanesulfonyl-ethyl)-amide,
1-[8-Methoxy-5-(1-oxo-indan-5-yl)-[1,2,4]-triazolo[1,5-a]pyridin-2-yl]-cyclopropanecarboxylic acid (2-methanesulfonyl-ethyl)-amide,
1-[5-(5-Cyano-pyridin-3-yl)-8-methoxy-[1,2,4]triazolo[1,5-a]pyridin-2-yl]-cyclopropanecarboxylic acid cyclohexylmethyl-amide,
1-[5-(5-Cyano-pyridin-3-yl)-8-methoxy-[1,2,4]triazolo[1,5-a]pyridin-2-yl]-cyclopropanecarboxylic acid (2-methanesulfonyl-ethyl)-amide,
1-[8-Methoxy-5-(1-oxo-1,3-dihydro-isobenzofuran-5-yl)-[1,2,4]triazolo[1,5-a]pyridin-2-yl]-cyclopropanecarboxylic acid (2-dimethylsulfamoyl-ethyl)-amide,
1-[5-(3-Cyano-phenyl)-8-methoxy-[1,2,4]triazolo[1,5-a]pyridin-2-yl]-cyclopropanecarboxylic acid ethyl ester,
1-[5-(4-Cyano-phenyl)-8-methoxy-[1,2,4]triazolo[1,5-a]pyridin-2-yl]-cyclopropanecarboxylic acid ethyl ester,
1-[5-(3-Acetyl-phenyl)-8-methoxy-[1,2,4]triazolo[1,5-a]pyridin-2-yl]-cyclopropanecarboxylic acid ethyl ester,
1-[5-(3-Cyano-phenyl)-8-methoxy-[1,2,4]triazolo[1,5-a]pyridin-2-yl]-cyclopropanecarboxylic acid,
1-[5-(4-Cyano-phenyl)-8-methoxy-[1,2,4]triazolo[1,5-a]pyridin-2-yl]-cyclopropanecarboxylic acid,
1-[5-(3-Acetyl-phenyl)-8-methoxy-[1,2,4]triazolo[1,5-a]pyridin-2-yl]-cyclopropanecarboxylic acid,
1-[5-(3-Cyano-phenyl)-8-methoxy-[1,2,4]triazolo[1,5-a]pyridin-2-yl]-cyclopropanecarboxylic acid isopropylamide,
1-[5-(3-Cyano-phenyl)-8-methoxy-[1,2,4]triazolo[1,5-a]pyridin-2-yl]-cyclopropanecarboxylic acid (pyridin-3-ylmethyl)-amide,
3-{8-Methoxy-2-[1-(morpholine-4-carbonyl)-cyclopropyl]-[1,2,4]triazolo-[1,5-a]pyridin-5-yl}-benzonitrile,
1-[5-(3-Cyano-phenyl)-8-methoxy-[1,2,4]triazolo[1,5-a]pyridin-2-yl]-cyclopropanecarboxylic acid benzylamide,
1-[5-(3-Cyano-phenyl)-8-methoxy-[1,2,4]triazolo[1,5-a]pyridin-2-yl]-cyclopropanecarboxylic acid (2-sulfamoyl-ethyl)-amide,
1-[5-(3-Cyano-phenyl)-8-methoxy-[1,2,4]triazolo[1,5-a]pyridin-2-yl]-cyclopropanecarboxylic acid (2-methanesulfonyl-ethyl)-amide,
3-{8-Methoxy-2-[1-(pyrrolidine-1-carbonyl)-cyclopropyl]-[1,2,4]triazolo[1,5-a]pyridin-5-yl}-benzonitrile,
2-Methyl-acrylic acid 2-({1-[5-(3-cyano-phenyl)-8-methoxy-[1,2,4]triazolo[1,5-a]pyridin-2-yl]-cyclopropanecarbonyl}-amino)-ethyl ester,
1-[5-(3-Cyano-phenyl)-8-methoxy-[1,2,4]triazolo[1,5-a]pyridin-2-yl]-cyclopropanecarboxylic acid (2-methoxy-ethyl)-amide,
1-[5-(4-Cyano-phenyl)-8-methoxy-[1,2,4]triazolo[1,5-a]pyridin-2-yl]-cyclopropanecarboxylic acid (pyridin-3-ylmethyl)-amide,
4-{8-Methoxy-2-[1-(4-methyl-piperazine-1-carbonyl)-cyclopropyl]-[1,2,4]triazolo[1,5-a]pyridin-5-yl}-benzonitrile,
4-{8-Methoxy-2-[1-(morpholine-4-carbonyl)-cyclopropyl]-[1,2,4]triazolo[1,5-a]pyridin-5-yl}-benzonitrile,
1-[5-(4-Cyano-phenyl)-8-methoxy-[1,2,4]triazolo[1,5-a]pyridin-2-yl]-cyclopropanecarboxylic acid benzylamide,
1-[5-(4-Cyano-phenyl)-8-methoxy-[1,2,4]triazolo[1,5-a]pyridin-2-yl]-cyclopropanecarboxylic acid (2-sulfamoyl-ethyl)-amide,
1-[5-(4-Cyano-phenyl)-8-methoxy-[1,2,4]triazolo[1,5-a]pyridin-2-yl]-cyclopropanecarboxylic acid (2-methanesulfonyl-ethyl)-amide,
1-[5-(4-Cyano-phenyl)-8-methoxy-[1,2,4]triazolo[1,5-a]pyridin-2-yl]-cyclopropanecarboxylic acid isopropylamide,
1-[5-(4-Cyano-phenyl)-8-methoxy-[1,2,4]triazolo[1,5-a]pyridin-2-yl]-cyclopropanecarboxylic acid methylamide,
1-[5-(4-Cyano-phenyl)-8-methoxy-[1,2,4]triazolo[1,5-a]pyridin-2-yl]-cyclopropanecarboxylic acid ethylamide,
1-[5-(4-Cyano-phenyl)-8-methoxy-[1,2,4]triazolo[1,5-a]pyridin-2-yl]-cyclopropanecarboxylic acid propylamide,
1-[5-(4-Cyano-phenyl)-8-methoxy-[1,2,4]triazolo[1,5-a]pyridin-2-yl]-cyclopropanecarboxylic acid cyclopropylamide,
1-[5-(4-Cyano-phenyl)-8-methoxy-[1,2,4]triazolo[1,5-a]pyridin-2-yl]-cyclopropanecarboxylic acid isobutyl-amide,
1-[5-(4-Cyano-phenyl)-8-methoxy-[1,2,4]triazolo[1,5-a]pyridin-2-yl]-cyclopropanecarboxylic acid cyanomethyl-amide,
1-[5-(4-Cyano-phenyl)-8-methoxy-[1,2,4]triazolo[1,5-a]pyridin-2-yl]-cyclopropanecarboxylic acid (2-acetylamino-ethyl)-amide,
1-[5-(4-Cyano-phenyl)-8-methoxy-[1,2,4]triazolo[1,5-a]pyridin-2-yl]-cyclopropanecarboxylic acid (2-methanesulfonylamino-ethyl)-amide,
1-[5-(4-Cyano-phenyl)-8-methoxy-[1,2,4]triazolo[1,5-a]pyridin-2-yl]-cyclopropanecarboxylic acid (3-morpholin-4-yl-3-oxo-propyl)-amide,
1-[5-(4-Cyano-phenyl)-8-methoxy-[1,2,4]triazolo[1,5-a]pyridin-2-yl]-cyclopropanecarboxylic acid (2-dimethylsulfamoyl-ethyl)-amide,
1-[5-(4-Cyano-phenyl)-8-methoxy-[1,2,4]triazolo[1,5-a]pyridin-2-yl]-cyclopropanecarboxylic acid [2-(methanesulfonyl-methyl-amino)-ethyl]-amide,
1-[5-(3-Acetyl-phenyl)-8-methoxy-[1,2,4]triazolo[1,5-a]pyridin-2-yl]-cyclopropanecarboxylic acid (pyridin-3-ylmethyl)-amide,
1-(3-{8-Methoxy-2-[1-(4-methyl-piperazine-1-carbonyl)-cyclopropyl]-[1,2,4]triazolo[1,5-a]pyridin-5-yl}-phenyl)-ethanone,
1-(3-{8-Methoxy-2-[1-(morpholine-4-carbonyl)-cyclopropyl]-[1,2,4]triazolo[1,5-a]pyridin-5-yl}-phenyl)-ethanone,
1-[5-(3-Acetyl-phenyl)-8-methoxy-[1,2,4]triazolo[1,5-a]pyridin-2-yl]-cyclopropanecarboxylic acid benzylamide,
1-[5-(3-Acetyl-phenyl)-8-methoxy-[1,2,4]triazolo[1,5-a]pyridin-2-yl]-cyclopropanecarboxylic acid (2-sulfamoyl-ethyl)-amide,
1-[5-(3-Acetyl-phenyl)-8-methoxy-[1,2,4]triazolo[1,5-a]pyridin-2-yl]-cyclopropanecarboxylic acid (2-methanesulfonyl-ethyl)-amide,
2-Methyl-acrylic acid 2-({1-[5-(3-cyano-phenyl)-8-methoxy-[1,2,4]triazolo[1,5-a]pyridin-2-yl]-cyclopropanecarbonyl}-amino)-ethyl ester, 1-[5-(3-Cyano-phenyl)-8-methoxy-[1,2,4]triazolo[1,5-a]pyridin-2-yl]-cyclopropanecarboxylic acid (2-hydroxyethyl)-amide, Cyclohexyl-carbamic acid 1-[5-(5-cyano-pyridin-3-yl)-8-methoxy-[1,2,4]triazolo[1,5-a]pyridin-2-yl]-cyclopropylmethyl ester, Propyl-carbamic acid 1-[8-methoxy-5-(1-oxo-indan-5-yl)-[1,2,4]triazolo[1,5-a]pyridin-2-yl]-cyclopropylmethyl ester, Dimethyl-carbamic acid 1-[5-(4-cyano-3-methoxy-phenyl)-8-methoxy-[1,2,4]triazolo[1,5-a]pyridin-2-yl]-cyclopropylmethyl ester, Isopropyl-carbamic acid 1-[5-(5-cyano-pyridin-3-yl)-8-methoxy-[1,2,4]triazolo[1,5-a]pyridin-2-yl]-cyclopropylmethyl ester, Propyl-carbamic acid 1-[8-methoxy-5-(1-oxo-indan-4-yl)-[1,2,4]triazolo[1,5-a]pyridin-2-yl]-cyclopropylmethyl ester, Pyrrolidine-1-carboxylic acid 1-[5-(4-cyano-3-methoxy-phenyl)-8-methoxy-[1,2,4]triazolo[1,5-a]pyridin-2-yl]-cyclopropylmethyl ester, Isopropyl-carbamic acid 1-[5-(4-cyano-3-methoxy-phenyl)-8-methoxy-[1,2,4]triazolo[1,5-a]pyridin-2-yl]-cyclopropylmethyl ester, Propyl-carbamic acid 1-[5-(5-cyano-pyridin-3-yl)-8-methoxy-[1,2,4]triazolo[1,5-a]pyridin-2-yl]-cyclopropylmethyl ester, Propyl-carbamic acid 1-[5-(4-cyano-3-methoxy-phenyl)-8-methoxy-[1,2,4]triazolo[1,5-a]pyridin-2-yl]-cyclopropylmethyl ester, Pyrrolidine-1-carboxylic acid 1-[8-methoxy-5-(1-oxo-indan-5-yl)-[1,2,4]triazolo[1,5-a]pyridin-2-yl]-cyclopropylmethyl ester, Isopropyl-carbamic acid 1-[8-methoxy-5-(1-oxo-indan-5-yl)-[1,2,4]triazolo[1,5-a]pyridin-2-yl]-cyclopropylmethyl ester, Cyclohexyl-carbamic acid 1-[8-methoxy-5-(1-oxo-indan-4-yl)-[1,2,4]triazolo[1,5-a]pyridin-2-yl]-cyclopropylmethyl ester, Cyclohexyl-carbamic acid 1-[5-(4-cyano-3-methoxy-phenyl)-8-methoxy-[1,2,4]triazolo[1,5-a]pyridin-2-yl]-cyclopropylmethyl ester, Pyrrolidine-1-carboxylic acid 1-[5-(5-cyano-pyridin-3-yl)-8-methoxy-[1,2,4]triazolo[1,5-a]pyridin-2-yl]-cyclopropylmethyl ester, Dimethyl-carbamic acid 1-[8-methoxy-5-(1-oxo-indan-5-yl)-[1,2,4]triazolo[1,5-a]pyridin-2-yl]-cyclopropylmethyl ester, Dimethyl-carbamic acid 1-[5-(5-cyano-pyridin-3-yl)-8-methoxy-[1,2,4]triazolo[1,5-a]pyridin-2-yl]-cyclopropylmethyl ester, Diethyl-carbamic acid 1-[5-(4-cyano-3-methoxy-phenyl)-8-methoxy-[1,2,4]triazolo[1,5-a]pyridin-2-yl]-cyclopropylmethyl ester, Diethyl-carbamic acid 1-[8-methoxy-5-(1-oxo-indan-4-yl)-[1,2,4]triazolo[1,5-a]pyridin-2-yl]-cyclopropylmethyl ester, Diethyl-carbamic acid 1-[5-(5-cyano-pyridin-3-yl)-8-methoxy-[1,2,4]triazolo[1,5-a]pyridin-2-yl]-cyclopropylmethyl ester, 5-[2-(1-Hydroxymethyl-cyclopropyl)-8-methoxy-[1,2,4]triazolo[1,5-a]pyridin-5-yl]-nicotinonitrile, 4-(2-Cyclopropyl-5-methoxy-[1,2,4]triazolo[1,5-a]pyridin-8-yl)-2-methoxy-benzonitrile, 4-(2-Cyclopropyl-5-methoxy-[1,2,4]triazolo[1,5-a]pyridin-8-yl)-2-methyl-benzonitrile, 3-(2-Cyclopropyl-5-methoxy-[1,2,4]triazolo[1,5-a]pyridin-8-yl)-benzonitrile, 5-(2-Cyclopropyl-5-methoxy-[1,2,4]triazolo[1,5-a]pyridin-8-yl)-indan-1-one, 4-(2-Cyclopropyl-5-methoxy-[1,2,4]triazolo[1,5-a]pyridin-8-yl)-indan-1-one, 1-[8-(4-Cyano-3-methoxy-phenyl)-5-methoxy-[1,2,4]triazolo[1,5-a]pyridin-2-yl]-cyclopropanecarboxylic acid isopropylamide, 1-[5-Methoxy-8-(1-oxo-1,3-dihydro-isobenzofuran-5-yl)-[1,2,4]triazolo[1,5-a]pyridin-2-yl]-cyclopropanecarboxylic acid isopropylamide, 1-[5-Methoxy-8-(1-oxo-indan-5-yl)-[1,2,4]triazolo[1,5-a]pyridin-2-yl]-cyclopropanecarboxylic acid isopropylamide, 1-[5-Hydroxy-8-(1-oxo-indan-4-yl)-[1,2,4]triazolo[1,5-a]pyridin-2-yl]-cyclopropanecarboxylic acid isopropylamide, 1-[5-Methoxy-8-(1-oxo-indan-4-yl)-[1,2,4]triazolo[1,5-a]pyridin-2-yl]-cyclopropanecarboxylic acid (2-methanesulfonyl-ethyl)-amide, 1-[8-(5-Cyano-pyridin-3-yl)-5-methoxy-[1,2,4]triazolo[1,5-a]pyridin-2-yl]-cyclopropanecarboxylic acid (2-methanesulfonyl-ethyl)-amide, 1-[5-Methoxy-8-(1-oxo-indan-5-yl)-[1,2,4]triazolo[1,5-a]pyridin-2-yl]-cyclopropanecarboxylic acid isopropylamide, 1-[5-Methoxy-8-(1-oxo-indan-5-yl)-[1,2,4]triazolo[1,5-a]pyridin-2-yl]-cyclopropanecarboxylic acid isobutyl-amide, 1-[5-Methoxy-8-(1-oxo-1,3-dihydro-isobenzofuran-5-yl)-[1,2,4]triazolo[1,5-a]pyridin-2-yl]-cyclopropanecarboxylic acid isopropylamide, 1-[8-(4-Cyano-3-methoxy-phenyl)-5-methoxy-[1,2,4]triazolo[1,5-a]pyridin-2-yl]-cyclopropanecarboxylic acid isopropylamide, 1-[8-(4-Cyano-3-methoxy-phenyl)-5-methoxy-[1,2,4]triazolo[1,5-a]pyridin-2-yl]-cyclopropanecarboxylic acid (2-methanesulfonyl-ethyl)-amide, 1-[5-Methoxy-8-(1-oxo-indan-5-yl)-[1,2,4]triazolo[1,5-a]pyridin-2-yl]-cyclopropanecarboxylic acid (2-methanesulfonyl-ethyl)-amide, 1-[5-Methoxy-8-(1-oxo-1,3-dihydro-isobenzofuran-5-yl)-[1,2,4]triazolo[1,5-a]pyridin-2-yl]-cyclopropanecarboxylic acid (2-methanesulfonyl-ethyl)-amide, 1-[8-(4-Cyano-3-methoxy-phenyl)-5-methoxy-[1,2,4]triazolo[1,5-a]pyridin-2-yl]-cyclopropanecarboxylic acid isobutyl-amide, 1-[5-Hydroxy-8-(1-oxo-indan-5-yl)-[1,2,4]triazolo[1,5-a]pyridin-2-yl]-cyclopropanecarboxylic acid isopropylamide, 1-[8-Methoxy-5-(1-oxo-1,3-dihydro-isobenzofuran-5-yl)-[1,2,4]triazolo[1,5-a]pyridin-2-yl]-cyclopropanecarboxylic acid (2-methanesulfonyl-ethyl)-amide, 1-[8-Methoxy-5-(1-oxo-1,3-dihydro-isobenzofuran-5-yl)-[1,2,4]triazolo[1,5-a]pyridin-2-yl]-cyclopropanecarboxylic acid cyclohexylmethyl-amide, 1-[8-Methoxy-5-(1-oxo-1,3-dihydro-isobenzofuran-5-yl)-[1,2,4]triazolo[1,5-a]pyridin-2-yl]-cyclopropanecarboxylic acid (2-dimethylsulfamoyl-ethyl)-amide, Diethyl-carbamic acid 1-[8-methoxy-5-(1-oxo-indan-4-yl)-[1,2,4]triazolo[1,5-a]pyridin-2-yl]-cyclopropylmethyl ester, Dimethyl-carbamic acid 1-[8-methoxy-5-(1-oxo-1,3-dihydro-isobenzofuran-5-yl)-[1,2,4]triazolo[1,5-a]pyridin-2-yl]-cyclopropylmethyl ester, Diethyl-carbamic acid 1-[5-(5-cyano-pyridin-3-yl)-8-methoxy-[1,2,4]triazolo[1,5-a]pyridin-2-yl]-cyclopropylmethyl ester, Diethyl-carbamic acid 1-[5-(4-cyano-3-methoxy-phenyl)-8-methoxy-[1,2,4]triazolo[1,5-a]pyridin-2-yl]-cyclopropylmethyl ester, Cyclohexyl-carbamic acid 1-[8-methoxy-5-(1-oxo-1,3-dihydro-isobenzofuran-5-yl)-[1,2,4]triazolo[1,5-a]pyridin-2-yl]-cyclopropylmethyl ester, 4-[2-(1-Hydroxymethyl-cyclopropyl)-8-methoxy-[1,2,4]triazolo[1,5-a]pyridin-5-yl]-2-methoxy-benzonitrile, 4-[2-(1-Isobutoxymethyl-cyclopropyl)-8-methoxy-[1,2,4]triazolo[1,5-a]pyridin-5-yl]-2-methoxy-benzonitrile, 1-[5-(3-Cyano-phenyl)-8-methoxy-[1,2,4]triazolo[1,5-a]pyridin-2-yl]-cyclopropanecarboxylic acid isobutyl-amide, 1-[5-(3-Cyano-phenyl)-8-methoxy-[1,2,4]triazolo[1,5-a]pyridin-2-yl]-cyclopropanecarboxylic acid (2-methanesulfonylamino-ethyl)-amide, 1-[5-(3-Cyano-phenyl)-8-methoxy-[1,2,4]triazolo[1,5-a]pyridin-2-yl]-cyclopropanecarboxylic acid cyclopropylamide, 1-[5-(3-Cyano-phenyl)-8-methoxy-[1,2,4]triazolo[1,5-a]pyridin-2-yl]-cyclopropanecarboxylic acid cyclohexylmethyl-amide, 5-[2-(1-Isobutoxymethyl-cyclopropyl)-8-methoxy-[1,2,4]triazolo[1,5-a]pyridin-5-yl]-nicotinonitrile, 5-(2-Cyclopropyl-5-methoxy-[1,2,4]triazolo[1,5-a]pyridin-8-yl)-nicotinonitrile, 1-[5-(4-Cyano-phenyl)-8-methoxy-[1,2,4]triazolo[1,5-a]pyridin-2-yl]-cyclopropanecarboxylic acid (2-dimethylsulfamoyl-ethyl)-amide, 1-[5-(4-Cyano-phenyl)-8-methoxy-[1,2,4]triazolo[1,5-a]pyridin-2-yl]-cyclopropanecarboxylic acid [2-(methanesulfonyl-methyl-amino)-ethyl]-amide, 1-[5-(4-Cyano-3-methoxy-phenyl)-8-methoxy-[1,2,4]triazolo[1,5-a]pyridin-2-yl]-cyclopropanecarboxylic acid (2-dimethylsulfamoyl-ethyl)-amide, 1-[5-(5-Cyano-pyridin-3-yl)-8-methoxy-[1,2,4]triazolo[1,5-a]pyridin-2-yl]-cyclopropanecarboxylic acid (2-dimethylsulfamoyl-ethyl)-amide, 1-[8-Methoxy-5-(1-oxo-indan-5-yl)-[1,2,4]triazolo[1,5-a]pyridin-2-yl]-cyclopropanecarboxylic acid (2-dimethylsulfamoyl-ethyl)-amide, and pharmaceutically acceptable salts, hydrates, N-oxides or solvates thereof.

In one or more embodiments of the present invention, the compounds of general formula I have a molecular weight below 800 Dalton, such as below 750 Dalton, e.g. below 700 Dalton, or below 650, 600, 550, or 500 Dalton.

In one or more embodiments of the present invention, the compounds of formula I as defined above are useful in therapy, such as for the use in the treatment of dermal diseases or conditions or acute or chronic cutaneous wound disorders.

In one or more embodiments of the present invention, the dermal disease or condition is selected from the group consisting of proliferative and inflammatory skin disorders, psoriasis, cancer, epidermal inflammation, alopecia, skin atrophy, steroid induced skin atrophy, skin ageing, photo skin ageing, acne, dermatitis, atopic dermatitis, seborrheic dermatitis, contact dermatitis, urticaria, pruritis, and eczema.

The compounds of formula I may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline modifications and forms and also mixtures thereof.

Compounds of formula I may or may not comprise asymmetrically substituted (chiral) carbon atoms which give rise to the existence of isomeric forms, e.g. enantiomers and possibly diastereomers. The present invention relates to all such isomers, either in pure form or as mixtures thereof (e.g. racemates). Pure stereoisomeric forms of the compounds and the intermediates of this invention may be obtained by the application of procedures known in the art. The various isomeric forms may be separated by physical separation methods such as selective crystallization and chromatographic techniques, e.g. liquid chromatography using chiral stationary phases. Enantiomers may be separated from each other by the selective crystallization of their diastereomeric salts with optically active amines, such as l-ephedrine. Alternatively, enantiomers may be separated by chromatographic techniques using chiral stationary phases. Said pure stereoisomeric forms may also be derived from the corresponding pure stereoisomeric forms of the appropriate starting materials, provided that the reaction occurs stereoselectively or stereospecifically. Preferably, if a specific stereoisomer is desired, said compound will be synthesized by stereoselective or stereospecific methods of preparation. These methods will advantageously employ chiral pure starting materials.

Compounds of the invention, optionally in combination with other active compounds, may be useful for the treatment of dermal diseases or conditions, or acute or chronic cutaneous wound disorders, in particular for the treatment of proliferative and inflammatory skin disorders, psoriasis, cancer, epidermal inflammation, alopecia, skin atrophy, steroid induced skin atrophy, skin ageing, photo skin ageing, acne, dermatitis, atopic dermatitis, seborrheic dermatitis, contact dermatitis, urticaria, pruritis, and eczema.

Besides being useful for human treatment, the compounds of the present invention may also be useful for veterinary treatment of animals including mammals such as horses, cattle, sheep, pigs, dogs, and cats.

For use in therapy, compounds of the present invention are typically in the form of a pharmaceutical composition. The invention therefore relates to a pharmaceutical composition comprising a compound of formula I, optionally together with one or more other therapeutically active compound(s), together with a pharmaceutically acceptable excipient or vehicle. The excipient must be "acceptable" in the sense of being compatible with the other ingredients of the composition and not deleterious to the recipient thereof.

Conveniently, the active ingredient comprises from 0.05-99.9% by weight of the formulation.

In the form of a dosage unit, the compound may be administered one or more times a day at appropriate intervals, always depending, however, on the condition of the patient, and in accordance with the prescription made by the medical practitioner. Conveniently, a dosage unit of a formulation contain between 0.1 mg and 1000 mg, preferably between 1 mg and 100 mg, such as 5-50 mg of a compound of formula I.

A suitable dosage of the compound of the invention will depend, inter alia, on the age and condition of the patient, the severity of the disease to be treated and other factors well known to the practising physician. The compound may be administered either orally, parenterally or topically according to different dosing schedules, e.g. daily or with weekly intervals. In general a single dose will be in the range from 0.01 to 400 mg/kg body weight. The compound may be administered as a bolus (i.e. the entire daily dosis is administered at once) or in divided doses two or more times a day.

In the context of topical treatment it may be more appropriate to refer to a "usage unit", which denotes a single dose which is capable of being administered to a patient, and which may be readily handled and packed, remaining as a physically and chemically stable unit dose comprising either the active material as such or a mixture of it with solid or liquid pharmaceutical diluents or carriers.

The term "usage unit" in connection with topical use means a unitary, i.e. a single dose capable of being administered topically to a patient in an application per square centimeter of the infected area of from 0.1 mg to 10 mg and preferably from 0.2 mg to 1 mg of the active ingredient in question.

It is also envisaged that in certain treatment regimes, administration with longer intervals, e.g. every other day, every week, or even with longer intervals may be beneficial.

If the treatment involves administration of another therapeutically active compound it is recommended to consult Goodman & Gilman's The Pharmacological Basis of Therapeutics, 9$^{th}$ Ed., J. G. Hardman and L. E. Limbird (Eds.), McGraw-Hill 1995, for useful dosages of said compounds.

The administration of a compound of the present invention with one or more other active compounds may be either concomitantly or sequentially.

The formulations include e.g. those in a form suitable for oral (including sustained or timed release), rectal, parenteral (including subcutaneous, intraperitoneal, intramuscular, intraarticular and intravenous), transdermal, ophthalmic, topical, dermal, nasal or buccal administration. Topical administration of the claimed formulation is particularly suitable.

The formulations may conveniently be presented in dosage unit form and may be prepared by any of the methods well known in the art of pharmacy, e.g. as disclosed in Remington, The Science and Practice of Pharmacy, 20$^{th}$ ed., 2000. All methods include the step of bringing the active ingredient into association with the carrier, which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose, hydroxypropylmethylcellulose, hydroxypropylcellulose, carbomers and polyvinylpyrrolidone. The active ingredients may also be administered in the form of a bolus, electuary or paste.

A tablet may be made by compressing or moulding the active ingredient optionally with one or more accessory ingredients. Compressed tablets may be prepared by compressing, in a suitable machine, the active ingredient(s) in a free-flowing form such as a powder or granules, optionally mixed by a binder, such as e.g. lactose, glucose, starch, gelatine, acacia gum, tragacanth gum, sodium alginate, carboxymethylcellulose, methylcellulose, hydroxypropylmethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredient and suitable carrier moistened with an inert liquid diluent.

Formulations for rectal administration may be in the form of suppositories in which the compound of the present invention is admixed with low melting water soluble or insoluble solids such as cocoa butter, hydrogenated vegetable oils, polyethylene glycol or fatty acids esters of polyethylene glycols, while elixirs may be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution. The formulation may be conveniently sterilised by for instance filtration through a bacteria retaining filter, addition of sterilising agent to the formulation, irradiation of the formulation or heating of the formulation. Liposomal formulations as disclosed in e.g. Encyclopedia of Pharmaceutical Technology, vol. 9, 1994, are also suitable for parenteral administration.

Alternatively, the compounds of formula I may be presented as a sterile, solid preparation, e.g. a freeze-dried powder, which is readily dissolved in a sterile solvent immediately prior to use.

Transdermal formulations may be in the form of a plaster or a patch.

Formulations suitable for ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in Encyclopedia of Pharmaceutical Technology, vol. 2, 1989, may also be used to present the active ingredient for ophthalmic administration.

Formulations suitable for topical or ophthalmic administration include liquid or semi-liquid preparations such as liniments, lotions, gels, applicants, oil-in-water or water-in-oil emulsions such as creams, ointments or pastes; or solutions or suspensions such as drops. Compositions for ophthalmic treatment may preferably additionally contain a cyclodextrin.

For topical administration, the compound of formula I may typically be present in an amount of from 0.01 to 20% by weight of the composition, such as 0.1% to about 10%, but may also be present in an amount of up to about 50% of the composition.

Formulations suitable for nasal or buccal administration include powder, self-propelling and spray formulations, such as aerosols and atomisers. Such formulations are disclosed in greater detail in e.g. Modern Pharmaceutics, 2$^{nd}$ ed., G. S. Banker and C. T. Rhodes (Eds.), page 427-432, Marcel Dekker, New York; Modern Pharmaceutics, 3$^{th}$ ed., G. S. Banker and C. T. Rhodes (Eds.), page 618-619 and 718-721, Marcel Dekker, New York and Encyclopedia of Pharmaceutical Technology, vol. 10, J. Swarbrick and J. C. Boylan (Eds), page 191-221, Marcel Dekker, New York.

In addition to the aforementioned ingredients, the formulations of a compound of formula I may include one or more additional ingredients such as diluents, buffers, flavouring agents, colourant, surface active agents, thickeners, preservatives, e.g. methyl hydroxybenzoate (including anti-oxidants), emulsifying agents and the like.

When the active ingredient is administered in the form of salts with pharmaceutically acceptable non-toxic acids or bases, preferred salts are for instance easily water-soluble or slightly soluble in water, in order to obtain a particular and appropriate rate of absorption.

The pharmaceutical composition may additionally comprise one or more other active components conventionally used in the treatment of dermal disease or conditions, e.g. selected from the group consisting of glucocorticoids, vitamin D and vitamin D analogues, antihistamines, platelet activating factor (PAF) antagonists, anticholinergic agents, methylxanthines, β-adrenergic agents, COX-2 inhibitors, salicylates, indomethacin, flufenamate, naproxen, timegadine, gold salts, penicillamine, serum cholesterol lowering agents, retinoids, zinc salts, salicylazosulfapyridine and calcineurin inhibitors.

The term "compound of formula I" as used herein is intended to include compounds of formula Ia.

METHODS OF PREPARATION

The compounds of the present invention can be prepared in a number of ways well known to those skilled in the art of synthesis. The compounds of formula I may for example be prepared using the reactions and techniques outlined below together with methods known in the art of synthetic organic chemistry, or variations thereof as appreciated by those skilled in the art. Preferred methods include, but are not limited to, those described below. The reactions are carried out in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art of organic synthesis. Not all compounds falling into a given class may be compatible with some of the reaction conditions required in some of the methods described. Such restrictions to the substituents which are compatible with the reaction conditions will be readily apparent to one skilled in the art and alternative methods can be used.

Starting materials are either known or commercially available compounds or can be prepared by routine synthetic methods well known to a person skilled in the art.

General Procedures, Preparations and Examples $^1$H nuclear magnetic resonance (NMR) spectra were recorded at 300 MHz and $^{13}$C NMR spectra at 75.6 MHz or 151 MHz. Chemical shift values (δ, in ppm) are quoted in the specified solvent relative to internal tetramethylsilane (δ=0.00) or chloroform (δ=7.25) or deuteriochloroform (δ=76.81 for $^{13}$C NMR) standards. The value of a multiplet, either defined (doublet (d), triplet (t), quartet (q)) or not (m) at the approximate mid point is given unless a range is quoted. (bs) indicates a broad singlet. The organic solvents used were usually anhydrous. Chromatography was performed on Merck silica gel 60 (0.040-0.063 mm). The solvent ratios indicated refer to v:v unless otherwise noted.

The following abbreviations have been used throughout:
DCM dichloromethane
DMF N,N'-Dimethylformamide
DMSO dimethyl sulfoxide
Et ethyl
L liter
LDA lithium diisopropylamide
LiHMDS lithium hexamethyldisilazide
m milli
Me methyl
NMP N-methylpiperidinone
NMR nuclear magnetic resonance
Rt retention time
THF tetrahydrofuran
v volume
Preparative HPLC/MS Preparative HPLC/MS was performed on a Dionex APS-system with two Shimadzu PP150 prep. pumps and a Thermo MSQ Plus mass spectrometer. Column: Waters XTerra C-18, 150 mm×19 mm, 5 μm; solventsystem: A=water (0.1% formic acid) and B=acetonitrile (0.1% formic acid); flow rate=18 mL/min; method (10 min): Linear gradient method going from 10% B to 100% B in 6 minutes and staying at 100% B for another 2 minutes. The fractions were collected based on ion traces of relevant ions and PDA signal (240-400 nm).
Analytical HPLC/MS (A)

Analytical HPLC/MS was performed on a system consisting of a Waters 2795 HPLC, Micromass ZQ mass spectrometer, Waters 996 PDA. Column: Waters XTerra C-18, 50 mm×3.0 mm, 5 μm; solventsystem: A=water:acetonitrile 95:5 (0.05% formic acid) and B=acetonitrile (0.05% formic acid); flow rate=1.0 mL/min; method (8 min): Linear gradient method going from 10% B to 100% B in 6.0 minutes and staying at 100% B for 1 minute.
Analytical HPLC/MS (B)

Analytical HPLC/MS was performed on a Dionex APS-system with a P680A analytical pump and a Thermo MSQ Plus mass spectrometer. Column: Waters XTerra C-18, 150 mm×4.6 mm, 5 μm; solventsystem: A=water (0.1% formic acid) and B=acetonitrile (0.1% formic acid); flow rate=1.0 mL/min; method (10 min): Linear gradient method going from 10% B to 100% in 6.6 minutes and staying at 100% B for another 1.5 minutes.

General Procedure of Preparation:

The compounds of the invention can for example be prepared by the following general methods:
a) Reaction of Compounds of General Formula II

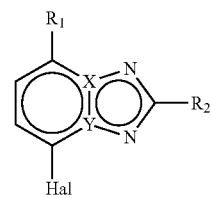

II wherein Hal is a halogen; R1, R2, X and Y is defined as described herein, with boronic acids (A-B(OH)$_2$) or boronic acid esters (A-B(OR)$_2$) under Suzuki conditions wherein A is defined as described herein under Suzuki conditions using a suitable catalyst (e.g. tetrakistriphenylphosphinepalladium, and a suitable base, such as potassium carbonate, sodium hydroxide, triethylamine, K$_3$PO$_4$ in a suitable solvent such as but not limited to DMF, NMP, 1,2-dimethoxyethane, THF, 1,4-dioxane, water or a mixture two or more of these, at temperatures from e.g. minus 78° C. to reflux.

b) Reaction of Compounds of General Formula II wherein Hal is a halogen; R1, R2, X and Y is defined as described herein, with nucleophilic hetorocycloalkyl systems (e.g. piperidine; A-H) potentially in the absence or presence of a suitable catalyst (e.g. tetrakistriphenylphosphine-palladium, and a suitable base, such as triethylamine in the presence or absence of a suitable solvent such as 2-propanol, ethyleneglycol, DMF, NMP, 1,2-dimethoxyethane, THF, 1,4-dioxane or a mixture of two or more of these at temperatures from e.g. minus 78° C. to reflux.

Starting materials of formula II are prepared according to standard procedures known to a chemist skilled in the art of organic synthesis. The 2-amino pyridines are N-aminated at the pyridine nitrogen using O-mesitylensulfonyl hydroxylamine and then treated with aldehydes to form the desired 1,2,4-triazolo-[1,5,a]-pyridine heterocycles according to known procedures as depicted in Scheme 1 and Scheme 2 (Tet. Lett. (2003), 44, 1675-78).

Scheme 1

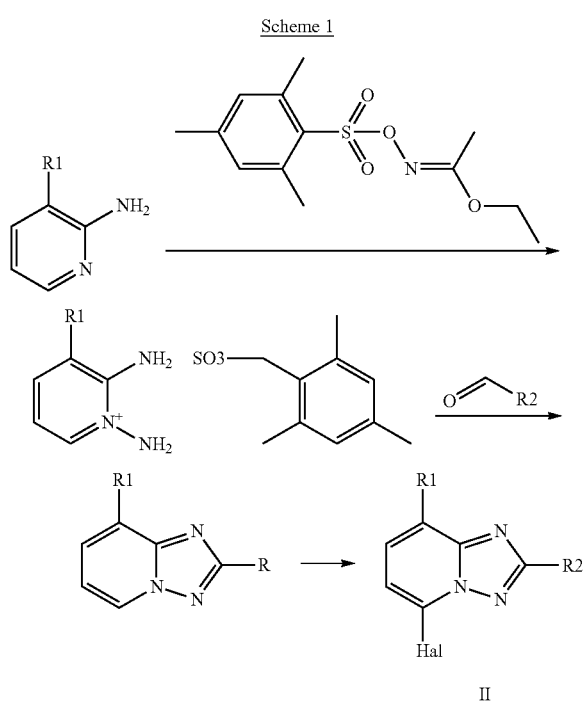

Scheme 2

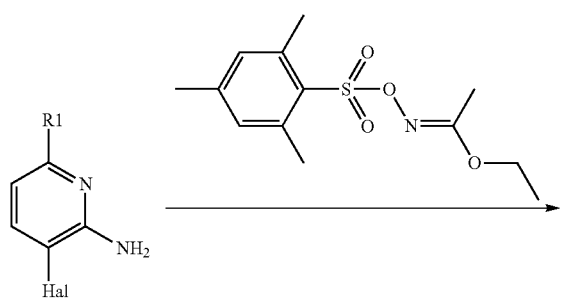

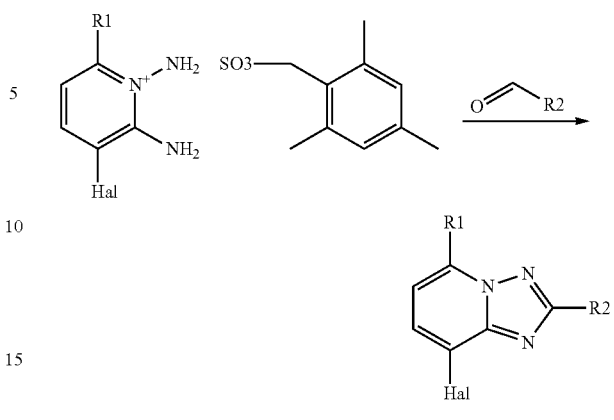

c) Reaction of Compounds of General Formula III

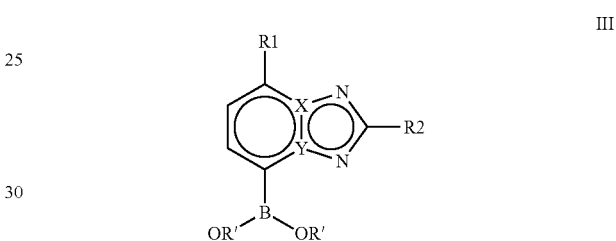

wherein R' is hydrogen or alkyl; R1, R2, X and Y is defined as described herein, with halides (A-Hal) wherein A is defined as described herein under Suzuki conditions using a suitable catalyst (e.g. tetrakistriphenylphosphinepalladium), and a suitable base, such as potassium carbonate, sodium hydroxide, triethylamine, $K_3PO_4$ in a suitable solvent such as but not limited to DMF, NMP, 1,2-dimethoxyethane, THF, 1,4-dioxane, water or a mixture two or more of these, at temperatures from e.g. minus 78° C. to reflux.

d) Reaction of Compounds of General Formula IV

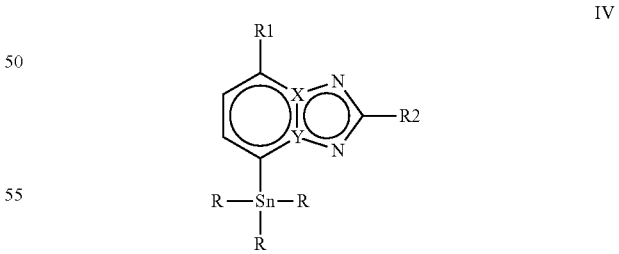

wherein R is alkyl; R1, R2, X and Y is defined as described herein, with halides (A-Hal) wherein A is defined as described herein under Stille conditions using a suitable catalyst (e.g. tetrakistriphenylphosphinepalladium or $Pd_2(dba)_3$ and $P(furyl)_3$), in a suitable solvent such as but not limited to toluene, benzene, 1,2-dimethoxyethane, THF, 1,4-dioxane, acetonitrile, DMF or a mixture two or more of these, at temperatures from e.g. minus 78° C. to reflux.

Preparation 1 (Compound 301)

2-Cyclopropyl-8-methoxy-[1,2,4]triazolo[1,5-a]pyridine

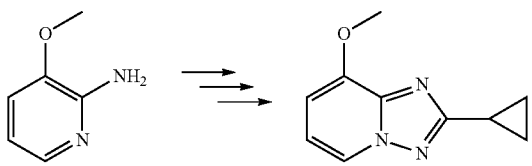

Ethyl O-mesitylsulfonylacetohydroxamate (22.7 g, 77.1 mmol, 97% pure) and dioxane (14.8 mL) were mixed under Argon. The suspension was cooled on ice and treated with 70% HClO$_4$ (8.68 mL). After 10 min. at 0° C. ice-cooled water (130 mL) was added and the white precipitate was filtered and washed with additional ice-cooled water. The precipitate was re-dissolved in DCM (140 mL). Excess of water was decanted and the DCM was dried with Na$_2$SO$_4$. After filtration the DCM solution was used directly to the next step. The solution was slowly (20 min) added to a cold (5° C.) solution of 2-amino-3-methoxy-pyridine (7.97 g, 64.2 mmol) in DCM (100 mL). The brown-yellow suspension was stirred at rt for 120 minutes and then treated with tert-butyl methyl ether (120 mL). The white precipitate formed was filtered and washed with DCM:tert-butyl methyl ether (1:1) to provide 19.2 g of a off-white solid. 12.2 g of the product was re-dissolved in dioxane (120 mL), under argon, and treated with cyclopropane carboxaldehyde (3.34 mL) and heated to 90° C. for 2.5 hours. Additional cyclopropane carboxaldehyde (1.11 mL) was added. Heating was continued for another 4 hours. The reaction mixture was cooled to 0° C. and treated with 1N KOH in MeOH (36 mL) and left at rt for 17 hours. The solvent was evaporated in vacuo and a NaCl solution was added to the product. The product was extracted with DCM and the combined organic phases was dried over Na$_2$SO$_4$, filtered and concentrated in vacuo. The product was purified by flash chromatography on silica using DCM-EtOAc as eluent. 2-Cyclopropyl-8-methoxy-[1,2,4]triazolo[1,5-a]pyridine was obtained as a light yellow solid (5.15 g, 76%).

$^1$H NMR (300 MHz, CDCl$_3$) δ 8.10 (dd, 1H), 6.81 (bt, 1H), 6.71 (bd, 1H), 4.01 (s, 3H), 2.22 (m, 1H), 1.18 (m, 2H), 1.04 (m, 2H)

LC/MS (System A): (m/z) 190.3 (MH$^+$); Rt=2.01 min; purity (UV)=100%

Preparation 2 (Compound 302)

2-Cyclopropyl-5-iodo-8-methoxy-[1,2,4]triazolo[1,5-a]pyridine

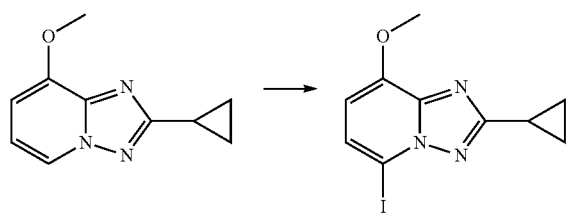

Compound 301 (5.54 g, 29.3 mmol) and N-iodosuccinimide (6.94 g, 29.3 mmol) was added BF$_3$×2H$_2$O (14.9 ml, 234 mmol) with cooling (0° C.) under argon. The suspension was stirred for 20 hours at r.t and added additional N-iodosuccinimide (3.48 g, 17.4 mmol). After additional 30 hours the susepension was slowly added to a mixture of sat. NaHCO$_3$ (400 mL) and DCM (250 mL). The organic phase was washed with a solution of Na$_2$S$_2$O$_3$ and the aquous pase was extracted with DCM (2×250 mL). The combined organic phases was dried over Na$_2$SO$_4$, filtered and concentrated in vacuo. The product was purified by flash chromatography on silica using DCM-EtOAc as eluent. 2-Cyclopropyl-5-iodo-8-methoxy-[1,2,4]triazolo[1,5-a]pyridine was obtained as a yellow-green solid (7.75 g, 84%).

$^1$H NMR (300 MHz, CDCl$_3$) δ 7.26 (d, 1H), 6.58 (d, 1H), 4.01 (s, 3H), 2.29 (m, 1H), 1.22 (m, 2H), 1.04 (m, 2H)

LC/MS (system A): (m/z) 316.4 (MH+); Rt=2.87 min; purity (UV) ~80%

Example 1

Procedure for the Parallel Synthesis of Compounds 101-142

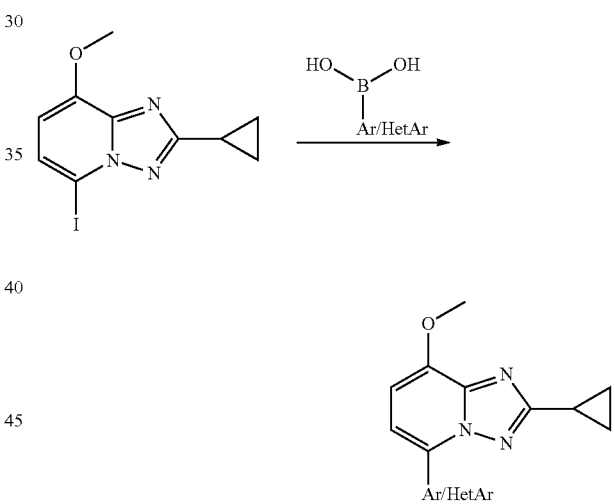

To a solution of 2-cyclopropyl-5-iodo-8-methoxy-[1,2,4]triazolo[1,5-a]pyridine (15.8 mg, 0.05 mmol) in 300 μl 1,2-dimethoxyethane under argon was added K$_2$CO$_3$ (100 μL, 1 N in H$_2$O, 0.1 mmol or alternatively 150 μL in cases where the boronic acid building block contains an acidic proton). The mixture was added the boronic acid (0.0625 mmol) and tetrakistriphenylphosphine paladium (2.9 mg, 0.0025 mmol) and heated to 80° C. in a closed reaction vessel for 3 days.

Brine (2 mL) was added to the reaction mixture. 4 N HCl (75 μL) were added to the reactions where 150 μL K$_2$CO$_3$ were used. The reaction mixture was extracted with 3 mL dichloromethane and the phases were separated using a phase separation cartridge (Chromabond, PTS). The organic phase was concentrated in vacuo and the residue was dissolved in 350 μL N,N-dimethylformamide and purified by preparative HPLC/MS.

| Compound | Name | structure | HPLC-MS (M + 1) | HPLC-MS Rt [min] | HPLC-MS system |
|---|---|---|---|---|---|
| 101 | 2-Cyclopropyl-8-methoxy-5-(3-acetyl-phenyl)-[1,2,4]triazolo[1,5-a]pyridine | 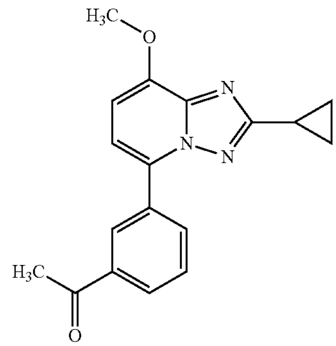 [SMILES: COc1ccc(-c2cccc(C(C)=O)c2)n2nc(C3CC3)nc12] | 308.3 | 3.2 | A |
| 102 | 2-Cyclopropyl-8-methoxy-5-phenyl-[1,2,4]triazolo[1,5-a]pyridine | 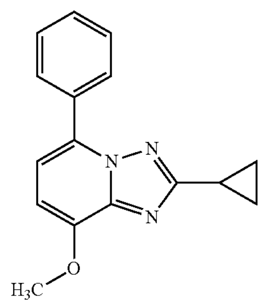 [SMILES: COc1ccc(-c2ccccc2)n2nc(C3CC3)nc12] | 266.2 | 5.7 | B |
| 103 | 2-Cyclopropyl-8-methoxy-5-(4-methoxy-phenyl)-[1,2,4]triazolo[1,5-a]pyridine | 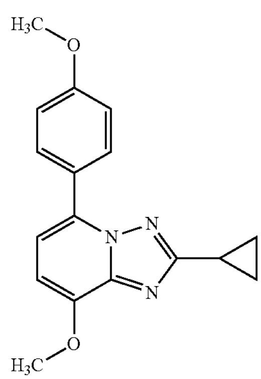 [SMILES: COc1ccc(-c2ccc(OC)c3nc(C4CC4)nn23)cc1] | 296.1 | 5.7 | B |
| 104 | 2-Cyclopropyl-8-methoxy-5-(4-trifluoromethyl-phenyl)-[1,2,4]triazolo[1,5-a]pyridine | 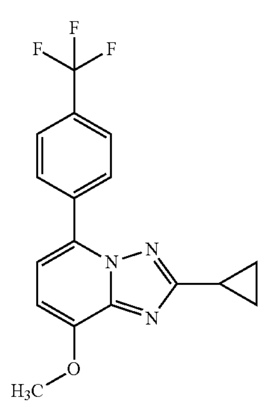 [SMILES: COc1ccc(-c2ccc(C(F)(F)F)cc2)n2nc(C3CC3)nc12] | 334.1 | 6.2 | B |

| Compound | Name | structure | HPLC-MS (M + 1) | HPLC-MS Rt [min] | HPLC-MS system |
|---|---|---|---|---|---|
| 105 | 2-Cyclopropyl-5-(3,4-dimethoxy-phenyl)-8-methoxy-[1,2,4]triazolo[1,5-a]pyridine | 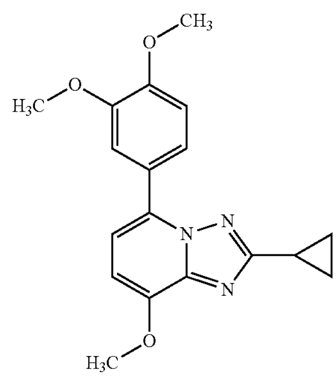 [SMILES: COc1ccc(-c2ccc(OC)c3nc(C4CC4)nn23)cc1OC] | 326.1 | 5.3 | B |
| 106 | 2-Cyclopropyl-8-methoxy-5-thiophen-2-yl-[1,2,4]triazolo[1,5-a]pyridine | 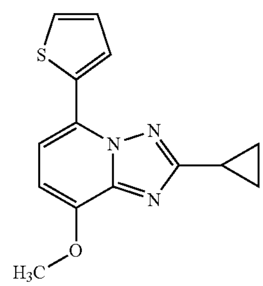 [SMILES: COc1ccc(-c2cccs2)n2nc(C3CC3)nc12] | 272.1 | 6 | B |
| 107 | N-[3-(2-Cyclopropyl-8-methoxy-[1,2,4]triazolo[1,5-a]pyridin-5-yl)-phenyl]-acetamide | 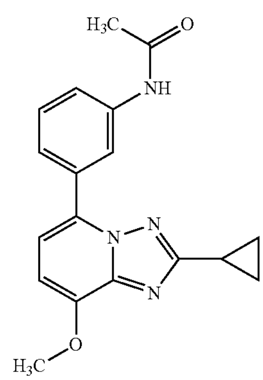 [SMILES: COc1ccc(-c2cccc(NC(C)=O)c2)n2nc(C3CC3)nc12] | 323.1 | 4.8 | B |
| 108 | 2-Cyclopropyl-8-methoxy-5-(3-trifluoromethoxy-phenyl)-[1,2,4]triazolo[1,5-a]pyridine | 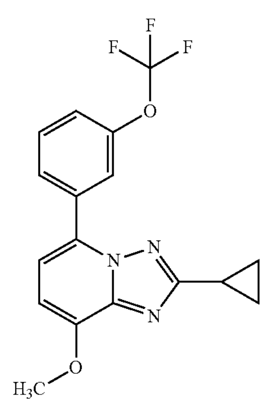 [SMILES: COc1ccc(-c2cccc(OC(F)(F)F)c2)n2nc(C3CC3)nc12] | 350.0 | 6.2 | B |

-continued

| Compound | Name | structure | HPLC-MS (M + 1) | HPLC-MS Rt [min] | HPLC-MS system |
|---|---|---|---|---|---|
| 109 | 2-Cyclopropyl-8-methoxy-5-(3-methoxy-phenyl)-[1,2,4]triazolo[1,5-a]pyridine | 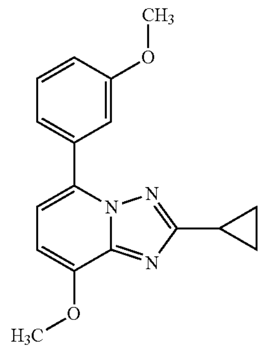 [SMILES: COc1cccc(-c2ccc(OC)c3nc(C4CC4)nn23)c1] | 296.1 | 5.7 | B |
| 110 | 1-[5-(2-Cyclopropyl-8-methoxy-[1,2,4]triazolo[1,5-a]pyridin-5-yl)-thiophen-2-yl]-ethanone | 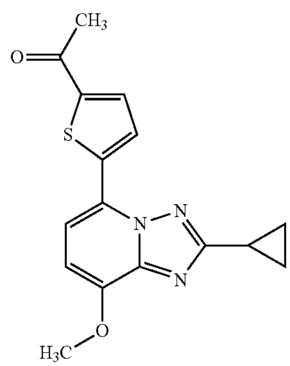 [SMILES: COc1ccc(-c2ccc(C(C)=O)s2)n2nc(C3CC3)nc12] | 314.1 | 5.6 | B |
| 111 | 2-Cyclopropyl-8-methoxy-5-pyrimidin-5-yl-[1,2,4]triazolo[1,5-a]pyridine | 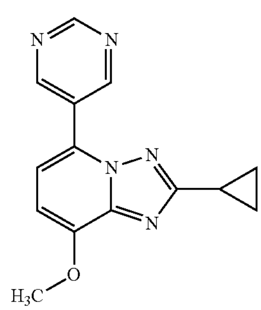 [SMILES: COc1ccc(-c2cncnc2)n2nc(C3CC3)nc12] | 268.2 | 4.4 | B |
| 112 | 2-Cyclopropyl-5-(3-methanesulfonyl-phenyl)-8-methoxy-[1,2,4]triazolo[1,5-a]pyridine | 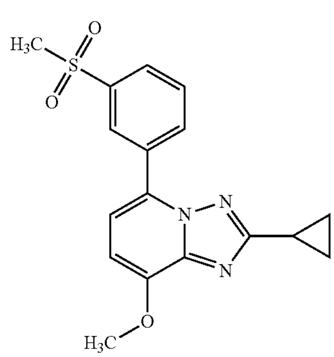 [SMILES: COc1ccc(-c2cccc(S(C)(=O)=O)c2)n2nc(C3CC3)nc12] | 344.1 | 5 | B |

| Compound | Name | structure | HPLC-MS (M + 1) | HPLC-MS Rt [min] | HPLC-MS system |
|---|---|---|---|---|---|
| 113 | N-[3-(2-Cyclopropyl-8-methoxy-[1,2,4]triazolo[1,5-a]pyridin-5-yl)-phenyl]-methanesulfonamide | 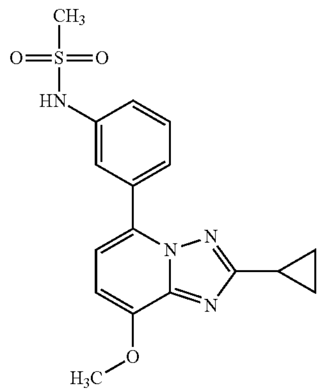 [SMILES: COc1ccc(-c2cccc(NS(C)(=O)=O)c2)n2nc(C3CC3)nc12] | 359.0 | 5 | B |
| 114 | 3-(2-Cyclopropyl-8-methoxy-[1,2,4]triazolo[1,5-a]pyridin-5-yl)-N-methyl-benzamide | 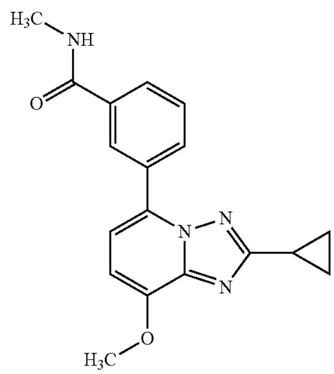 [SMILES: CNC(=O)c1cccc(-c2ccc(OC)c3nc(C4CC4)nn23)c1] | 323.0 | 4.7 | B |
| 115 | 2-Cyclopropyl-8-methoxy-5-(4-acetyl-phenyl)-[1,2,4]triazolo[1,5-a]pyridine | 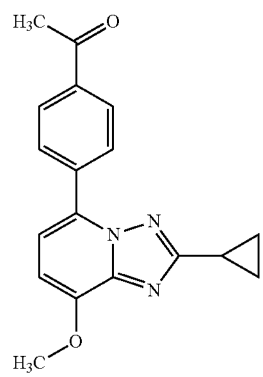 [SMILES: COc1ccc(-c2ccc(C(C)=O)cc2)n2nc(C3CC3)nc12] | 308.1 | 5.4 | B |
| 116 | N-[4-(2-Cyclopropyl-8-methoxy-[1,2,4]triazolo[1,5-a]pyridin-5-yl)-phenyl]-acetamide | 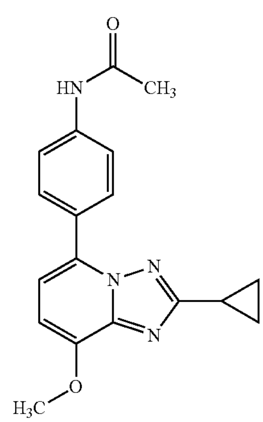 [SMILES: COc1ccc(-c2ccc(NC(C)=O)cc2)n2nc(C3CC3)nc12] | 323.1 | 4.8 | B |

-continued

| Compound | Name | structure | HPLC-MS (M + 1) | HPLC-MS Rt [min] | HPLC-MS system |
|---|---|---|---|---|---|
| 117 | 3-(2-Cyclopropyl-8-methoxy-[1,2,4]triazolo[1,5-a]pyridin-5-yl)-benzoic acid methyl ester | 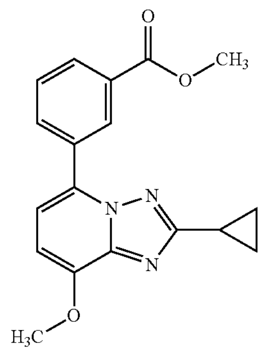 [SMILES: COC(=O)c1cccc(-c2ccc(OC)c3nc(C4CC4)nn23)c1] | 324.1 | 5.7 | B |
| 118 | 2-Cyclopropyl-8-methoxy-5-pyridin-3-yl-[1,2,4]triazolo[1,5-a]pyridine | 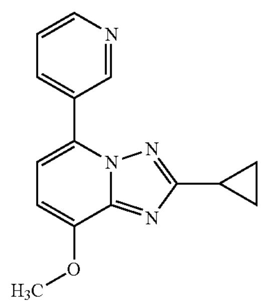 [SMILES: COc1ccc(-c2cccnc2)n2nc(C3CC3)nc12] | 267.2 | 4 | B |
| 119 | 4-(2-Cyclopropyl-8-methoxy-[1,2,4]triazolo[1,5-a]pyridin-5-yl)-benzoic acid methyl ester | 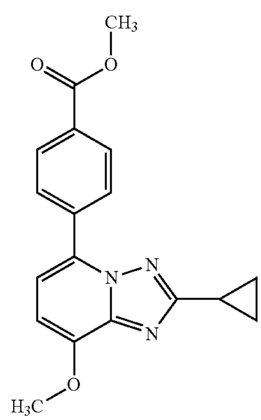 [SMILES: COC(=O)c1ccc(-c2ccc(OC)c3nc(C4CC4)nn23)cc1] | 324.1 | 5.7 | B |
| 120 | 2-Cyclopropyl-5-(4-methanesulfonyl-phenyl)-8-methoxy-[1,2,4]triazolo[1,5-a]pyridine | 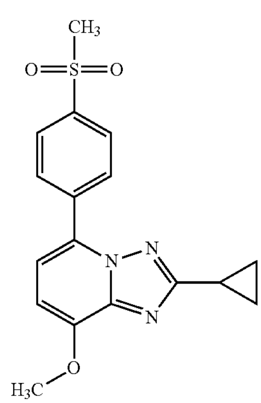 [SMILES: COc1ccc(-c2ccc(S(C)(=O)=O)cc2)n2nc(C3CC3)nc12] | 344.1 | 5 | B |

-continued
| Compound | Name | structure | HPLC-MS (M + 1) | HPLC-MS Rt [min] | HPLC-MS system |
|---|---|---|---|---|---|
| 121 | 2-Cyclopropyl-5-(2-fluoro-phenyl)-8-methoxy-[1,2,4]triazolo[1,5-a]pyridine | 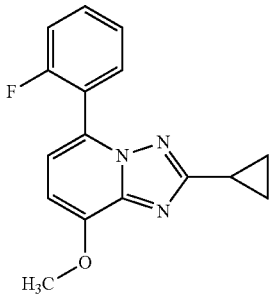 [SMILES: COc1ccc(-c2ccccc2F)n2nc(C3CC3)nc12] | 284.1 | 5.5 | B |
| 122 | 2-Cyclopropyl-8-methoxy-5-[4-(2-methoxy-ethoxy)-phenyl]-[1,2,4]triazolo[1,5-a]pyridine | 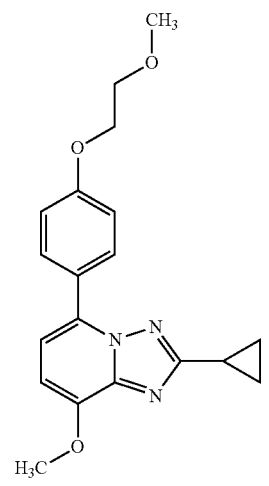 [SMILES: COCCOc1ccc(-c2ccc(OC)c3nc(C4CC4)nn23)cc1] | 340.1 | 5.5 | B |
| 123 | 4-(2-Cyclopropyl-8-methoxy-[1,2,4]triazolo[1,5-a]pyridin-5-yl)-benzamide | 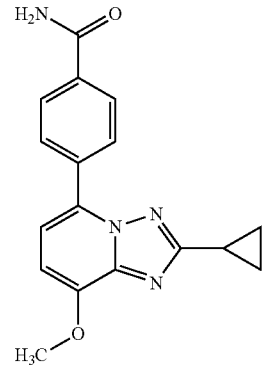 | 309.1 | 4.4 | B |

| Compound | Name | structure | HPLC-MS (M + 1) | HPLC-MS Rt [min] | HPLC-MS system |
|---|---|---|---|---|---|
| 124 | 5-(3-Butoxy-phenyl)-2-cyclopropyl-8-methoxy-[1,2,4]triazolo[1,5-a]pyridine | 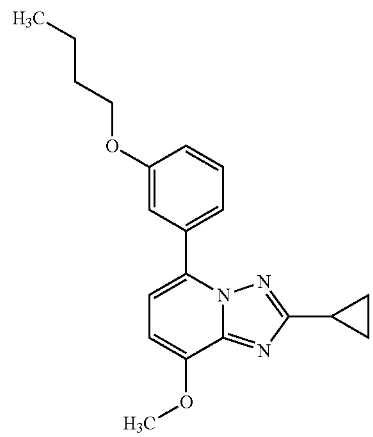 [SMILES: CCCCOc1cccc(-c2ccc(OC)c3nc(C4CC4)nn23)c1] | 338.1 | 6.5 | B |
| 125 | 2-Cyclopropyl-5-(3-fluoro-phenyl)-8-methoxy-[1,2,4]triazolo[1,5-a]pyridine | 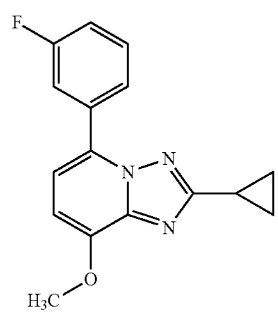 [SMILES: COc1ccc(-c2cccc(F)c2)n2nc(C3CC3)nc12] | 284.1 | 5.8 | B |
| 126 | 2-Cyclopropyl-8-methoxy-5-pyridin-4-yl-[1,2,4]triazolo[1,5-a]pyridine | 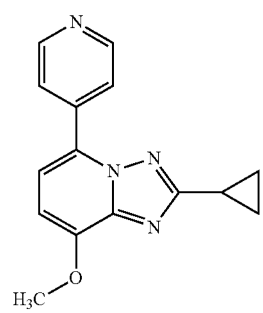 [SMILES: COc1ccc(-c2ccncc2)n2nc(C3CC3)nc12] | 267.2 | 3.6 | B |
| 127 | 2-Cyclopropyl-5-(2,4-dichloro-phenyl)-8-methoxy-[1,2,4]triazolo[1,5-a]pyridine | 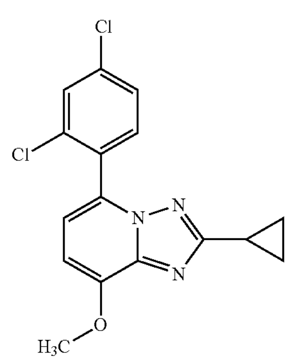 [SMILES: COc1ccc(-c2ccc(Cl)cc2Cl)n2nc(C3CC3)nc12] | 334.0 | 6.1 | B |

-continued

| Compound | Name | structure | HPLC-MS (M + 1) | HPLC-MS Rt [min] | HPLC-MS system |
|---|---|---|---|---|---|
| 128 | 2-Cyclopropyl-8-methoxy-5-[4-(morpholine-4-sulfonyl)-phenyl]-[1,2,4]triazolo[1,5-a]pyridine | 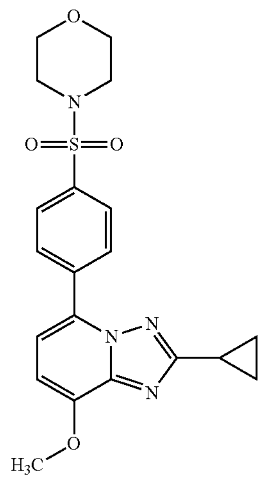 [SMILES: COc1ccc(-c2ccc(S(=O)(=O)N3CCOCC3)cc2)n2nc(C3CC3)nc12] | 415.0 | 5.4 | B |
| 129 | N-[4-(2-Cyclopropyl-8-methoxy-[1,2,4]triazolo[1,5-a]pyridin-5-yl)-benzyl]-acetamide | 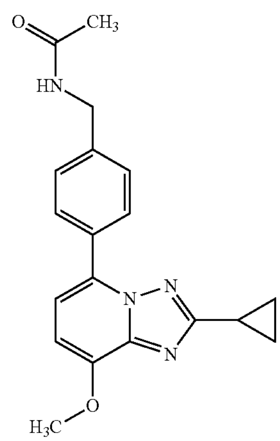 [SMILES: COc1ccc(-c2ccc(CNC(C)=O)cc2)n2nc(C3CC3)nc12] | 337.1 | 4.6 | B |
| 130 | N-[4-(2-Cyclopropyl-8-methoxy-[1,2,4]triazolo[1,5-a]pyridin-5-yl)-benzyl]-methanesulfonamide | 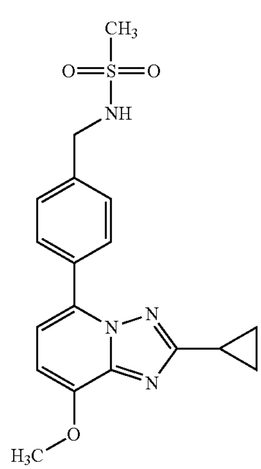 [SMILES: COc1ccc(-c2ccc(CNS(C)(=O)=O)cc2)n2nc(C3CC3)nc12] | 373.1 | 4.9 | B |

-continued

| Compound | Name | structure | HPLC-MS (M + 1) | HPLC-MS Rt [min] | HPLC-MS system |
|---|---|---|---|---|---|
| 131 | 2-Cyclopropyl-5-(4-fluoro-phenyl)-8-methoxy-[1,2,4]triazolo[1,5-a]pyridine | 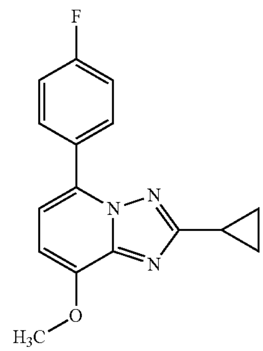 [SMILES: COc1ccc(-c2ccc(F)cc2)n2nc(C3CC3)nc12] | 284.1 | 5.8 | B |
| 132 | 4-(2-Cyclopropyl-8-methoxy-[1,2,4]triazolo[1,5-a]pyridin-5-yl)-benzonitrile | 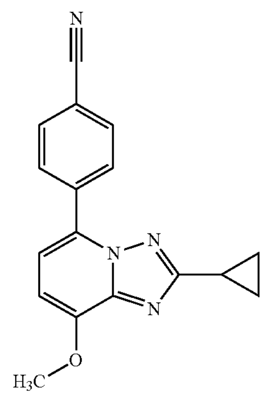 [SMILES: COc1ccc(-c2ccc(C#N)cc2)n2nc(C3CC3)nc12] | 291.1 | 5.5 | B |
| 133 | 3-[4-(2-Cyclopropyl-8-methoxy-[1,2,4]triazolo[1,5-a]pyridin-5-yl)-phenyl]-propionic acid methyl ester | 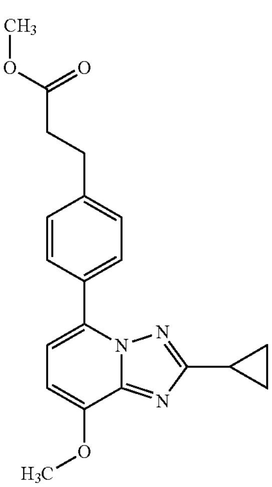 [SMILES: COC(=O)CCc1ccc(-c2ccc(OC)c3nc(C4CC4)nn23)cc1] | 352.3 | 3.8 | A |

-continued

| Compound | Name | structure | HPLC-MS (M + 1) | HPLC-MS Rt [min] | HPLC-MS system |
|---|---|---|---|---|---|
| 134 | 4-(2-Cyclopropyl-8-methoxy-[1,2,4]triazolo[1,5-a]pyridin-5-yl)-N-(2-hydroxy-ethyl)-benzenesulfonamide | 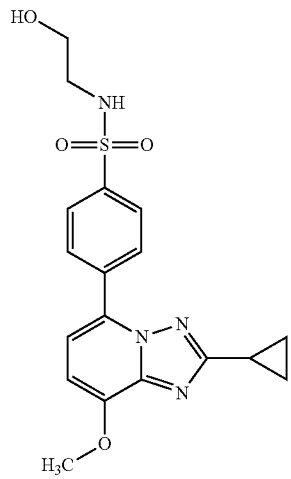 [SMILES: COc1ccc(-c2ccc(S(=O)(=O)NCCO)cc2)n2nc(C3CC3)nc12] | 389.3 | 2.6 | A |
| 135 | 3-(2-Cyclopropyl-8-methoxy-[1,2,4]triazolo[1,5-a]pyridin-5-yl)-benzonitrile | 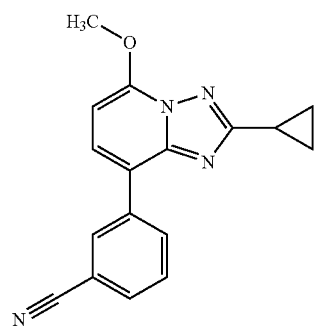 [SMILES: COc1ccc(-c2cccc(C#N)c2)c2nc(C3CC3)nn12] | 291.4 | 3.4 | A |
| 136 | 3-(2-Cyclopropyl-8-methoxy-[1,2,4]triazolo[1,5-a]pyridin-5-yl)-benzoic acid | 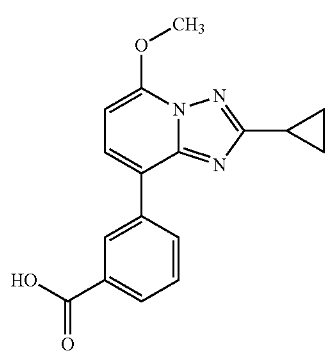 [SMILES: COc1ccc(-c2cccc(C(=O)O)c2)c2nc(C3CC3)nn12] | 310.5 | 2.9 | A |
| 137 | [3-(2-Cyclopropyl-8-methoxy-[1,2,4]triazolo[1,5-a]pyridin-5-yl)-phenyl]-methanol | 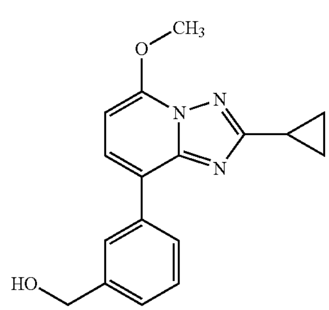 [SMILES: COc1ccc(-c2cccc(CO)c2)c2nc(C3CC3)nn12] | 296.3 | 2.7 | A |

-continued

| Compound | Name | structure | HPLC-MS (M + 1) | HPLC-MS Rt [min] | HPLC-MS system |
|---|---|---|---|---|---|
| 138 | 3-(2-Cyclopropyl-8-methoxy-[1,2,4]triazolo[1,5-a]pyridin-5-yl)-N,N-dimethyl-benzamide | 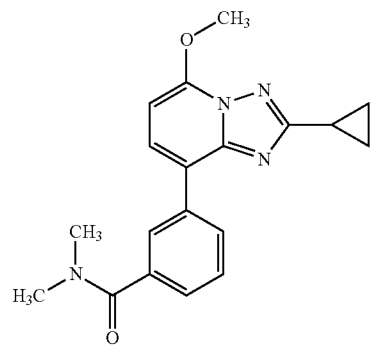 [SMILES: COc1ccc(-c2cccc(C(=O)N(C)C)c2)c2nc(C3CC3)nn12] | 337.4 | 2.7 | A |
| 139 | 3-(2-Cyclopropyl-8-methoxy-[1,2,4]triazolo[1,5-a]pyridin-5-yl)-benzamide | 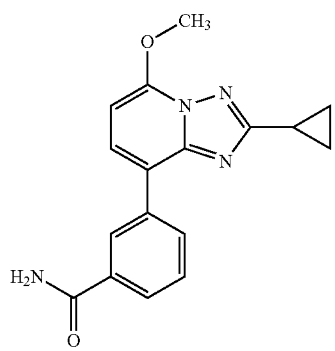 [SMILES: COc1ccc(-c2cccc(C(N)=O)c2)c2nc(C3CC3)nn12] | 309.4 | 2.4 | A |
| 140 | 4-(2-Cyclopropyl-8-methoxy-[1,2,4]triazolo[1,5-a]pyridin-5-yl)-benzoic acid | 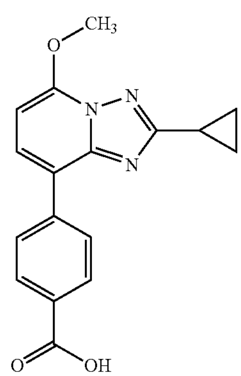 [SMILES: COc1ccc(-c2ccc(C(=O)O)cc2)c2nc(C3CC3)nn12] | 310.5 | 2.8 | A |
| 141 | 4-(2-Cyclopropyl-8-methoxy-[1,2,4]triazolo[1,5-a]pyridin-5-yl)-N,N-dimethyl-benzamide | 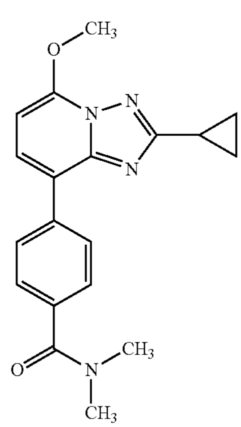 [SMILES: COc1ccc(-c2ccc(C(=O)N(C)C)cc2)c2nc(C3CC3)nn12] | 337.5 | 2.7 | A |

| Compound | Name | structure | HPLC-MS (M + 1) | HPLC-MS Rt [min] | HPLC-MS system |
|---|---|---|---|---|---|
| 142 | 4-(2-Cyclopropyl-8-methoxy-[1,2,4]triazolo[1,5-a]pyridin-5-yl)-N-methyl-benzamide | 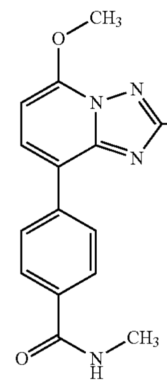 | 323.5 | 2.5 | A |

Example 2

2-Cyclopropyl-8-methoxy-5-piperidin-1-yl-[1,2,4]triazolo[1,5-a]pyridine (Compound 143)

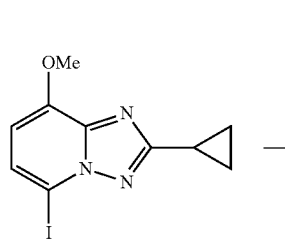

Copper iodide (1.0 mg, 0.005 mmol) and potassium phosphate (42.5 mg, 0.200 mmol), kept under argon, was added 2-propanol (200 μL), ethylene glycol (12.4 mg, 0.200 mmol), piperidine (10.1 mg, 0.12 mmol) and 2-cyclopropyl-5-iodo-8-methoxy-[1,2,4]triazolo[1,5-a]pyridine (31.5 mg, 0.100 mmol). The resulting suspension was heated to 80° C. for 4 days. The mixture was allowed to reach room temperature before it was extracted with dichloromethane (3 mL). The organic phase was washed with brine, dried ($Na_2SO_4$) and filtered before it was concentrated in vacuo. The crude product was purified by flash column chromatography ($SiO_2$, 20% EtOAc in toluene to 40% EtOAc in toluene) to give 2-cyclopropyl-8-methoxy-5-piperidin-1-yl-[1,2,4]triazolo[1,5-a]pyridine (2.2 mg.

$^1$H NMR (300 MHz, $CDCl_3$) δ 6.97 (d, 1H), 6.32 (d, 1H), 3.87 (s, 3H), 3.18 (m, 4H), 2.16 (m, 1H), 1.75-1.55 (m, 6H), 1.05-0.90 (m, 4H)

LC/MS (System A): (m/z) 273.5 (MH+); Rt=3.59 min.

Example 3

1-[3-(2-Cyclopropyl-8-hydroxy-[1,2,4]triazolo[1,5-a]pyridin-5-yl)-phenyl]-ethanone (Compound 144)

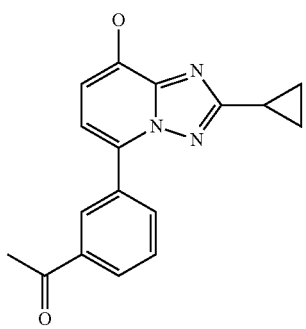 [SMILES: CC(=O)c1cccc(-c2ccc(O)c3nc(C4CC4)nn23)c1]

In a screw cap vessel Compound 101 (30.7 mg, 0.10 mmol) was dissolved in DMF (0.70 mL) under argon. Tert-dodecyl mercaptan (0.41 g, 2.0 mmol) and $K_2CO_3$ (0.138 g, 1.0 mmol) were added. The suspension was shaken at 140° C. for 16 h and the suspension was poured onto $H_2O$. pH was adjusted to 6 with 2 N HCl and the mixture was extracted with $CH_2Cl_2$. The organic phase was washed with brine, dried ($Na_2SO_4$), filtered and concentrated. The crude product was purified by flash chromatography, CH2Cl2:MeOH 99.5:0.5->97.5:2.5. This afforded the title compound as a slightly coloured solid.

1H NMR (600 MHz, DMSO-SPE) δ 8.51 (t, J=1.7 Hz, 1H), 8.20-8.17 (m, 1H), 8.10-8.06 (m, 1H), 7.69 (dd, J=9.7, 5.9 Hz, 1H), 7.36 (d, J=8.2 Hz, 1H), 7.22-7.19 (m, 1H), 4.02 (s, 3H), 3.49 (s, 2H), 3.41-3.36 (m, 2H), 2.65 (s, 3H), 2.20 (s, 2H), 2.07 (s, 2H), 2.01 (s, 3H), 1.47 (dd, J=7.1, 4.2 Hz, 2H), 1.39 (dd, J=7.1, 4.1 Hz, 2H).

Preparation 3

(2-cyclopropyl-8-methoxy-[1,2,4]triazolo[1,5-a]pyridin-5-yl)boronic acid (Compound 303)

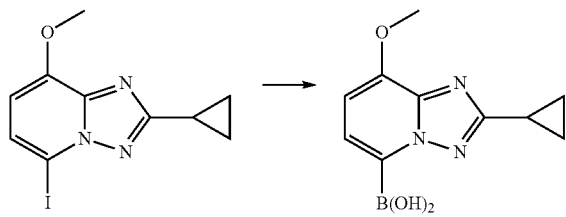 [SMILES: COc1ccc(I)n2nc(C3CC3)nc12 ; COc1ccc(B(O)O)n2nc(C3CC3)nc12]

In a two-necked flask under argon compound 302 (0.16 g, 0.50 mmol) was dissolved in dry THF (2 mL). The solution was cooled to −78° C. iPrMgCl*LiCl (1.0M in THF, 0.5 mL, 0.5 mmol) was added dropwise over 5 min. Stirring for 20 min at −70° C. Trimethylborate (0.070 mL, 0.63 mmol) was added and the solution was stirred at RT for 1 h. 4 N HCl in dioxin (0.5 mL) was added. The suspension was concentrated, suspended in toluene and concentrated again. The crude product was dissolved in 2 N NaOH (10 mL) and washed with EtOAc. 4 N HCl (6 mL) was added to the aqueous phase to pH 1. The aqueous phase was extracted with $CH_2Cl_2$+5% EtOH (×3), dried (Na2SO4), filtered and concentrated. This provided compound 303 as a solid.

Example 4

2-(2-Cyclopropyl-8-methoxy-[1,2,4]triazolo[1,5-a]pyridin-5-yl)-isonicotinonitrile (Compound 145)

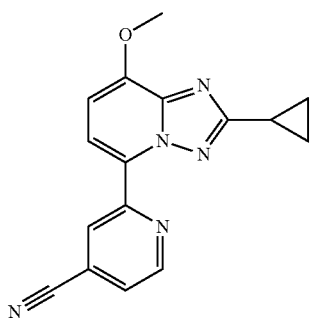 [SMILES: COc1ccc(-c2cc(C#N)ccn2)n2nc(C3CC3)nc12]

In a screw cap vial (2-cyclopropyl-8-methoxy-[1,2,4]triazolo[1,5-a]pyridin-5-yl)boronic acid, compound 303, (26 mg, 0.1 mmol) was dissolved in DME (0.6 mL) and 1 M $K_2CO_3$ (0.2 mL) under argon. 2-Bromo-isonicotinonitrile (18 mg, 0.1 mmol) and Pd(PPh$_3$)$_4$ (6 mg, 0.005 mmol) were added. The suspension was shaken at 80° C. for 17 h after which brine was added, and the aqueous phase was extracted with DCM (×3). The combined organic phases were dried, filtered and concentrated. The crude product was purified by flash chromatography, eluent TBME:heptane 4:1->9:1. This afforded the title compound as a solid 1H NMR (300 MHz, DMSO) δ 9.23-9.09 (m, 1H), 9.00 (dd, J=4.9, 0.8 Hz, 1H), 7.95 (dd, J=4.9, 1.5 Hz, 1H), 7.90 (d, J=8.3 Hz, 1H), 7.24 (d, J=8.4 Hz, 1H), 4.03 (s, 3H), 2.29 (tt, J=8.1, 5.0 Hz, 1H), 1.18-0.87 (m, 4H).

Preparation 4

1-(8-Methoxy-[1,2,4]triazolo[1,5-a]pyridin-2-yl)-cyclopropanecarboxylic acid ethyl ester (Compound 304)

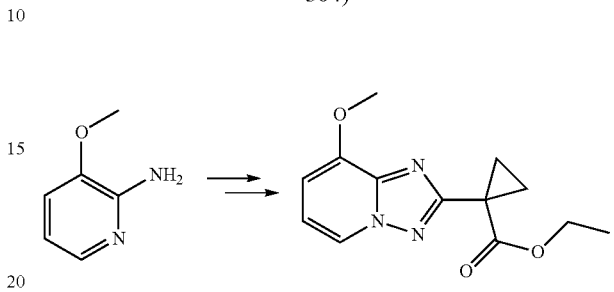

Under an argon atmosphere 1-Hydroxymethyl-cyclopropanecarboxylic acid ethyl ester (5.0 g, 34.7 mmol) was dissolved in DCM (200 mL). NaHCO$_3$ (11.7 g, 139 mmol) and Dess Martin periodinane (29.4 g, 69.4 mmol) were added. The suspension was stirred at rt for 30 min. A 1:1 solution of saturated Na$_2$S$_2$O$_3$ and saturated NaHCO$_3$ (200 mL) was added while keeping the temperature at 20° C. The mixture was stirred for 20 min followed by extraction with DCM (×2). The combined organic phases were dried (Na$_2$SO$_4$), filtered and concentrated to afford a crude product of 1-formyl-cyclopropanecarboxylic acid ethyl ester (5.1 g) which was used directly in the next step.

Ethyl O-mesitylsulfonylacetohydroxamate (22.7 g, 77.1 mmol, 97% pure) and dioxane (14.8 mL) were mixed under Argon. The suspension was cooled on ice and treated with 70% HClO$_4$ (8.68 mL). After 10 min. at 0° C. ice-cooled water (130 mL) was added and the white precipitate was filtered and washed with additional ice-cooled water. The precipitate was re-dissolved in DCM (140 mL). Excess of water was decanted and the DCM was dried with Na$_2$SO$_4$. After filtration the DCM solution was used directly to the next step. The solution was slowly (20 min) added to a cold (5° C.) solution of 2-amino-3-methoxy-pyridine (7.97 g, 64.2 mmol) in DCM (100 mL). The brown-yellow suspension was stirred at rt for 120 minutes and then treated with tert-butyl methyl ether (120 mL). The white precipitate formed was filtered and washed with DCM:tert-butyl methyl ether (1:1) to provide 19.2 g of a off-white solid (2,4,6-Trimethyl-benzenesulfonate-1,2-diamino-3-methoxy-pyridinium).

6.11 g (18 mmol) of the product was re-dissolved in dioxane (60 mL), under argon, and treated with 1-formyl-cyclopropanecarboxylic acid ethyl ester (5.1 g, 27 mmol) and heated to 90° C. for 17 hours. The reaction mixture was cooled to rt and treated with 1N KOH in MeOH (18 mL) and left at rt for 24 hours. The solvent was evaporated in vacuo and a NaCl solution was added to the product. The product was extracted with DCM and the combined organic phases was dried over Na$_2$SO$_4$, filtered and concentrated in vacuo. The product was purified by flash chromatography on silica using DCM-EtOAc as eluent. The title compound was obtained as a light yellow solid (4.15 g).

1H NMR (300 MHz, CDCl3) δ 8.17 (dd, J=6.8, 0.8 Hz, 1H), 6.89 (dd, J=7.8, 6.8 Hz, 1H), 6.79-6.70 (m, 1H), 4.18 (q, J=7.1, 2H), 4.03 (s, 3H), 1.72 (dt, J=6.7, 3.5 Hz, 2H), 1.62-1.52 (m, 2H), 1.20 (t, J=7.1 Hz, 3H).

Preparation 5

1-(5-Iodo-8-methoxy-[1,2,4]triazolo[1,5-a]pyridin-2-yl)-cyclopropanecarboxylic acid ethyl ester (Compound 305)

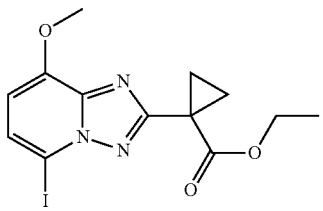 [SMILES: CCOC(=O)C1(c2nc3c(OC)ccc(I)n3n2)CC1]

Under an argon atmosphere 1-(8-Methoxy-[1,2,4]triazolo[1,5-a]pyridin-2-yl)-cyclopropanecarboxylic acid ethyl ester (4.1 g, 13.7 mmol) was mixed with N-iodosuccinimide (4.9 g, 21.9 mmol). BF$_3$*2H$_2$O (7.0 mL, 110 mmol) was added at 20° C. The dark suspension was stirred at rt for 24 h. NIS (2.5 g) and BF$_3$*2H$_2$O (2.0 mL) were added and the suspension was stirred for 24H. NIS (2.5 g) and BF$_3$*2H$_2$O (2.0 mL) were added and the suspension was stirred for another 24 h after which it was poured onto a 1:1 solution of saturated Na$_2$S$_2$O$_3$ and saturated NaHCO$_3$ (300 mL). The aqueous phase was extracted with DCM and the combined organic phases were washed with brine, dried over Na$_2$SO$_4$, filtered and concentrated in vacuo. The crude product was purified by flash chromatography on silica using DCM-EtOAc as eluent. The title compound was obtained as a colourless solid (4.1 g).

1H NMR (300 MHz, CDCl3) δ 7.33 (d, J=8.1 Hz, 1H), 6.62 (d, J=8.1 Hz, 1H), 4.16 (q, J=7.1 Hz, 2H), 4.02 (s, 3H), 1.73 (dd, J=7.5, 4.3 Hz, 2H), 1.63-1.54 (m, 2H), 1.20 (t, J=7.1 Hz, 3H).

Example 5

1-[5-(4-Cyano-phenyl)-8-methoxy-[1,2,4]triazolo[1,5-a]pyridin-2-yl]-cyclopropanecarboxylic acid ethyl ester (Compound 146)

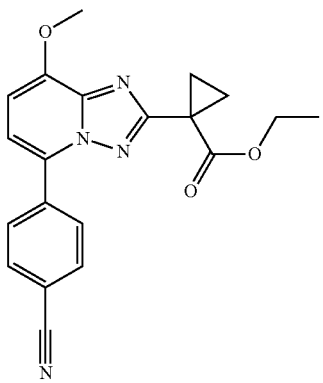 [SMILES: CCOC(=O)C1(c2nc3c(OC)ccc(-c4ccc(C#N)cc4)n3n2)CC1]

Under an argon atmosphere 1-(5-Iodo-8-methoxy-[1,2,4]triazolo[1,5-a]pyridin-2-yl)-cyclopropanecarboxylic acid ethyl ester (0.50 g, 1.3 mmol) was dissolved in DME (7.8 mL). 1M K$_2$CO$_3$ in H2O (2.6 mL) was added, followed by the addition of 4-CN-phenyl boronic acid (0.38 g, 2.6 mmol) and Pd(PPh$_3$)$_4$ (75.1 mg, 0.065 mmol). The reaction mixture was stirred at 80° C. for 17 h and the cooled to rt. The suspension was poured onto brine and the aqueous phase was extracted with DCM. The combined organic phases were dried over Na$_2$SO$_4$, filtered and concentrated in vacuo. The crude product was purified by flash chromatography on silica using DCM:EtOAc 20:1->10:1 as eluent. The title compound was obtained as a slightly coloured solid.

1H NMR (300 MHz, CDCl3) δ 8.12-8.05 (m, 2H), 7.82-7.75 (m, 2H), 7.07 (d, J=8.1 Hz, 1H), 6.89 (t, J=6.3 Hz, 1H), 4.17 (q, J=7.2 Hz, 2H), 4.09 (s, 3H), 1.72 (dt, J=6.8, 3.6 Hz, 2H), 1.62-1.54 (m, 2H), 1.22 (t, J=7.1 Hz, 3H).

Example 6

1-[5-(4-Cyano-phenyl)-8-methoxy-[1,2,4]triazolo[1,5-a]pyridin-2-yl]-cyclopropanecarboxylic acid (Compound 147)

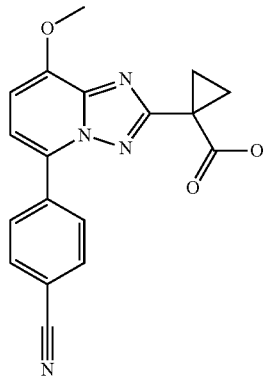 [SMILES: COc1ccc(-c2ccc(C#N)cc2)n2nc(C3(C(=O)O)CC3)nc12]

1-[5-(4-Cyano-phenyl)-8-methoxy-[1,2,4]triazolo[1,5-a]pyridin-2-yl]-cyclopropanecarboxylic acid ethyl ester (0.39 g, 1.08 mmol) was suspended in 1,4-dioxan (10 mL) and aq. LiOH (68 mg, 1.6 mmol in 1.6 mL H$_2$O) and stirred at it for 17 h. The mixture was concentrated in vacuo. The crude was suspended in H$_2$O (3 mL) and 4N HCl (0.6 mL) was added. The aqueous phase was extracted with DCM (×3). The combined organic phases were dried over Na$_2$SO$_4$, filtered and concentrated in vacuo. This afforded the title compound as a slightly coloured solid.

1H NMR (300 MHz, CDCl3) δ 8.02-7.92 (m, 2H), 7.87-7.77 (m, 2H), 7.14 (d, J=8.3 Hz, 1H), 7.01 (d, J=8.2 Hz, 1H), 4.12 (s, 3H), 1.99 (dd, J=7.8, 3.5 Hz, 2H), 1.78 (dd, J=7.6, 3.8 Hz, 2H).

Example 7

1-[5-(4-Cyano-phenyl)-8-methoxy-[1,2,4]triazolo[1,5-a]pyridin-2-yl]-cyclopropanecarboxylic acid amide (Compound 148)

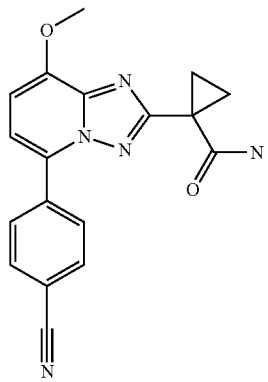 [SMILES: COc1ccc(-c2ccc(C#N)cc2)n2nc(C3(C(N)=O)CC3)nc12]

1-[5-(4-Cyano-phenyl)-8-methoxy-[1,2,4]triazolo[1,5-a]pyridin-2-yl]-cyclopropanecarboxylic acid (27 mg, 0.08 mmol) was dissolved in DCM (0.3 mL). Oxalyl chloride (0.008 mL, 0.09 mmol) and drop of DMF was added. Stirring for 5 min. Oxalyl chloride (0.003 mL) was added. After 20 min the suspension was concentrated and re-suspended in dioxan (0.3 mL). Aq. NH₃ (25%, 0.1 mL) was added. The suspension was stirred at rt for 2 h after which it was concentrated in vacuo. The crude product was mixed with aq. Na₂CO₃ and the aqueous phase was extracted with DCM (×3). The combined organic phases were dried over Na₂SO₄, filtered and concentrated in vacuo. The title compound was obtained as a slightly coloured solid.

1H NMR (300 MHz, DMSO) δ 8.21-8.12 (m, 2H), 8.04-7.98 (m, 2H), 7.95 (s, 1H), 7.41 (d, J=8.2 Hz, 1H), 7.35 (s, 1H), 7.24 (d, J=8.3 Hz, 1H), 4.04 (s, 3H), 1.50 (dd, J=6.9, 3.5 Hz, 2H), 1.37 (dd, J=7.0, 3.5 Hz, 2H).

Preparation 6

1-(5-Iodo-8-methoxy-[1,2,4]triazolo[1,5-a]pyridin-2-yl)-cyclopropanecarboxylic acid (Compound 306)

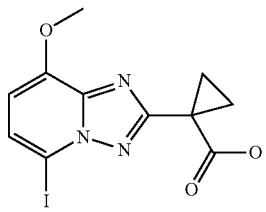 [SMILES: COc1ccc(I)n2nc(C3(C(=O)O)CC3)nc12]

1-(5-Iodo-8-methoxy-[1,2,4]triazolo[1,5-a]pyridin-2-yl)-cyclopropanecarboxylic acid ethyl ester (compound 305) (0.06 g, 0.16 mmol) was suspended in 1,4-dioxan (1.4 mL) and LiOH (0.01 g, 0.23 mmol) in H₂O (0.23 mL) was added. The suspension was stirred for 15 h. The mixture was concentrated in vacuo. H₂O and 4N HCL (0.085 mL) was added. Brine was added and the aqueous phase was extracted with DCM (×3). The combined organic phases were dried over Na₂SO₄, filtered and concentrated in vacuo. The title compound was obtained as a slightly coloured solid.

Preparation 7

1-(5-Iodo-8-methoxy-[1,2,4]triazolo[1,5-a]pyridin-2-yl)-cyclopropanecarboxylic acid isopropylamide (Compound 307)

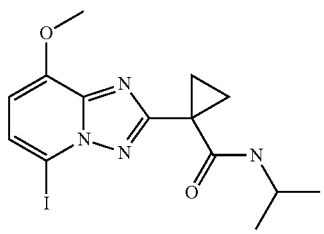 [SMILES: COc1ccc(I)n2nc(C3(C(=O)NC(C)C)CC3)nc12]

Under an argon atmosphere 1-(5-Iodo-8-methoxy-[1,2,4]triazolo[1,5-a]pyridin-2-yl)-cyclopropanecarboxylic acid (compound 306) (0.05 g, 0.14 mmol) was dissolved in DMF (0.5 mL) and Et₃N (0.058 mL, 0.42 mmol). HATU (0.082 g, 0.21 mmol) and isopropyl amine (0.018 mL, 0.21 mmol) were added. The solution was stirred at rt for 2 h. H₂O was added and the aqueous phase was extracted with EtOAc (×3). The combined organic phases were washed with H₂O and brine and dried over Na₂SO₄, filtered and concentrated in vacuo. The crude product was purified by flash chromatography on silica using DCM:EtOAc 9:1->3:1 as eluent. The title compound was obtained as a solid.

1H NMR (300 MHz, CDCl3) δ 9.00 (bs, 1H), 7.34 (d, J=8.1 Hz, 1H), 6.66 (d, J=8.1 Hz, 1H), 4.25-4.10 (m, 1H), 4.04 (s, 3H), 1.88-1.81 (m, 2H), 1.71-1.64 (m, 2H), 1.29 (d, J=6.9 Hz, 3H), 1.26 (d, J=6.9 Hz, 3H).

Example 8

1-[5-(5-Cyano-pyridin-3-yl)-8-methoxy-[1,2,4]triazolo[1,5-a]pyridin-2-yl]-cyclopropanecarboxylic acid isopropylamide (Compound 149)

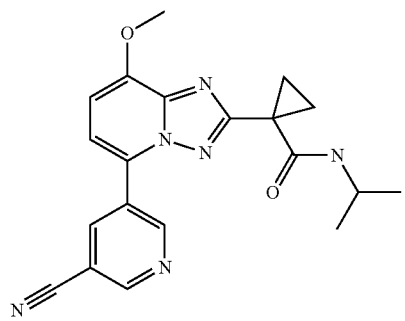 [SMILES: COc1ccc(-c2cncc(C#N)c2)n2nc(C3(C(=O)NC(C)C)CC3)nc12]

Under an argon atmosphere 1-(5-Iodo-8-methoxy-[1,2,4]triazolo[1,5-a]pyridin-2-yl)-cyclopropanecarboxylic acid isopropylamide (compound 307) (0.022 g, 0.055 mmol) was dissolved in DME (0.33 mL) and 1 M K₂CO₃ (0.11 mL). 5-CN-3-pyridinyl boronic acid (0.016 g, 0.11 mmol) was added followed by Pd(PPh₃)₄ (0.003 g, 0.003 mmol). The mixture was shaken at 80° C. for 20 h. Brine was added and aqueous phase was extracted with DCM (×3). The combined organic phases were dried over Na₂SO₄, filtered and concentrated in vacuo. The crude product was purified by flash chromatography on silica using DCM:EtOAc 3:7->15:85 as eluent. The title compound was obtained as a solid.

1H NMR (300 MHz, DMSO) δ 9.42 (d, J=2.2 Hz, 1H), 9.14 (d, J=2.0 Hz, 1H), 8.90 (t, J=2.1 Hz, 1H), 8.29 (d, J=7.5 Hz, 1H), 7.54-7.48 (m, 1H), 7.28 (d, J=8.3 Hz, 1H), 4.05 (s, 3H), 3.96 (td, J=13.2, 6.5 Hz, 1H), 1.52 (dd, J=6.9, 3.5 Hz, 2H), 1.41 (dd, J=7.0, 3.4 Hz, 2H), 1.10 (d, J=6.6 Hz, 6H).

Preparation 8

[1-(5-Iodo-8-methoxy-[1,2,4]triazolo[1,5-a]pyridin-2-yl)-cyclopropyl]-methanol (Compound 308)

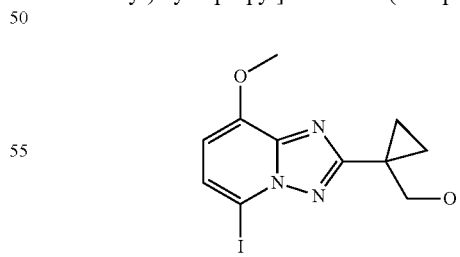

To a solution of 1-(tert-Butyl-diphenyl-silanyloxymethyl)-cyclopropanecarbaldehyde (7.0 g, 20.71 mmol) in dioxane (175 ml) was added 2,4,6-Trimethyl-benzenesulfonate1,2-diamino-3-methoxy-pyridinium (6.9 g, 20.71 mmol, prepared as described in the preparation of compound 304) under N₂ atmosphere and the reaction mixture was heated to reflux. After 24 h, the reaction mixture was cooled to RT and after removing the N₂ atmosphere, 1M KOH (20.71 mmol, 20 ml) was added slowly. The reaction mixture was stirred further. After 1 h, the reaction mixture was concentrated and the residue was dissolved in EtOAc. The organic phase was washed with water, dried over anhyd. Na₂SO₄ and concentrated under reduced pressure. The residue obtained was purified by column chromatography to afford 2-(1-((tert-butyldiphenylsilyloxy)methyl)cyclopropyl)-8-methoxy-[1,2,4]triazolo[1,5-a]pyridine (4.5 g, 47%) as a solid.

To a solution of 2-(1-((tert-butyldiphenylsilyloxy)methyl)cyclopropyl)-8-methoxy-[1,2,4]triazolo[1,5-a]pyridine (4.5 g, 9.84 mmol) in dry THF (40 ml) was added TBAF (38.38 mmol, 1M in THF) at RT and the mixture was stirred further. After 16 h, the reaction mixture was diluted with water and extracted with EtOAc. The combined organic phase was dried over anhyd. Na₂SO₄ and concentrated under reduced pressure. The residue obtained was purified by column chromatography to afford (1-(8-methoxy-[1,2,4]triazolo[1,5-a]pyridin-2-yl)cyclopropyl)methanol (1.7 g, 79%) as a solid.

A mixture of (1-(8-methoxy-[1,2,4]triazolo[1,5-a]pyridin-2-yl)cyclopropyl)methanol (1.7 g, 7.76 mmol) and N-iodosuccinimide (1.7 g, 7.76 mmol) was treated with BF₃.2H₂O (8.5 g, 77.6 mmol, 5.3 ml) at RT. After 24 h, the reaction mixture was poured into a 1:1 mixture of the aq. solutions of NaHCO₃ (1 M) and Na₂S₂O₃ (1 M) and extracted with DCM. The combined organic phase was washed with H₂O, over anhyd. Na₂SO₄ and concentrated under reduced pressure. The residue obtained was purified by column chromatography to afford (1-(5-iodo-8-methoxy-[1,2,4]triazolo[1,5-a]pyridin-2-yl)cyclopropyl)methanol (1.4 g, 52%) as a solid.

1H NMR (300 MHz, dmso) δ 7.47 (d, J=8.2 Hz, 1H), 6.89 (d, J=8.2 Hz, 1H), 4.63 (t, J=5.8 Hz, 1H), 3.93 (s, 3H), 3.90 (m, 2H), 1.09 (t, J=5.0 Hz, 2H), 1.03 (t, J=5.0 Hz, 2H).

Example 9

3-[2-(1-Hydroxymethyl-cyclopropyl)-8-methoxy-[1,2,4]triazolo[1,5-a]pyridin-5-yl]-benzonitrile (Compound 150)

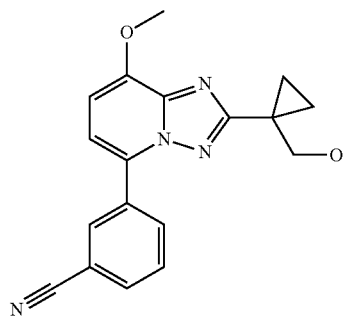 [SMILES: COc1ccc(-c2cccc(C#N)c2)n2nc(C3(CO)CC3)nc12]

[1-(5-Iodo-8-methoxy-[1,2,4]triazolo[1,5-a]pyridin-2-yl)-cyclopropyl]-methanol (compound 308)(0.24 g, 0.07 mmol) was dissolved in DME (4.5 mL) and 1 M K₂CO₃ (1.4 mL). 5-CN-3-pyridinyl boronic acid (0.21 g, 1.4 mmol) was added followed by Pd(PPh₃)₄ (0.04 g, 0.035 mmol). The mixture was shaken at 80° C. for 18 h. Brine was added and aqueous phase was extracted with DCM (×3). The combined organic phases were dried over Na₂SO₄, filtered and concentrated in vacuo. The crude product was purified by flash chromatography on silica using DCM:MeOH 99:1 as eluent. The impure product was suspended in 2-propanol and filtered to provide the title compound as a solid.

1H NMR (300 MHz, DMSO) δ 8.45 (t, J=1.5 Hz, 1H), 8.38-8.31 (m, 1H), 7.95 (dt, J=7.7, 1.2 Hz, 1H), 7.75 (t, J=8.0 Hz, 1H), 7.36 (d, J=8.1 Hz, 1H), 7.16 (d, J=8.3 Hz, 1H), 4.61 (t, J=5.7 Hz, 1H), 4.01 (s, 3H), 3.89 (d, J=5.4 Hz, 2H), 1.10 (dd, J=6.3, 3.9 Hz, 2H), 1.03 (dd, J=6.3, 3.8 Hz, 2H).

Example 10

Pyrrolidine-1-carboxylic acid 1-[5-(3-cyano-phenyl)-8-methoxy-[1,2,4]triazolo[1,5-a]pyridin-2-yl]-cyclopropylmethyl ester (Compound 151)

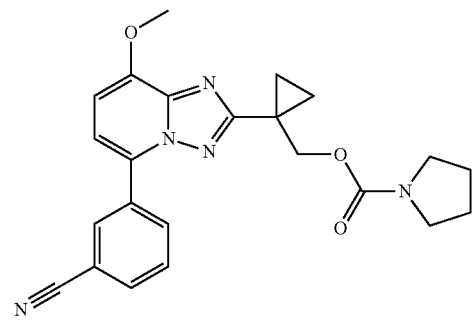

Under an argon atmosphere 3-[2-(1-Hydroxymethyl-cyclopropyl)-8-methoxy-[1,2,4]triazolo[1,5-a]pyridin-5-yl]-benzonitrile (compound 150) (0.03 g, 0.08 mmol) was dissolved in DMF (0.5 mL). NaH (0.02 g, 0.48 mmol) was added and the suspension was heated at 65° C. for 1 h after which 1-pyrrolidine carbonylchloride (0.088 mL, 0.8 mmol) was added. Stirring was performed at 65° C. for 1 h. The reaction mixture was cooled and aq. NaHCO₃ and H₂O was added. The aqueous phase was extracted with EtOAc (×2). The combined organic phases were dried over Na₂SO₄, filtered and concentrated in vacuo. The crude product was purified by flash chromatography on silica using DCM:MeOH 99:1 as eluent to afford the title compound as a solid.

1H NMR (300 MHz, DMSO) δ 8.43 (d, J=1.4 Hz, 1H), 8.33 (d, J=8.1 Hz, 1H), 7.95 (d, J=7.8 Hz, 1H), 7.73 (t, J=7.9 Hz, 1H), 7.37 (d, J=8.2 Hz, 1H), 7.18 (d, J=8.2 Hz, 1H), 4.41 (s, 2H), 4.01 (s, 3H), 3.19 (d, J=18.8 Hz, 4H), 1.72 (t, J=6.5 Hz, 4H), 1.26 (dd, J=6.4, 4.1 Hz, 2H), 1.15 (dd, J=6.5, 4.1 Hz, 2H).

Example 11

Isopropyl-carbamic acid 1-[5-(3-cyano-phenyl)-8-methoxy-[1,2,4]triazolo[1,5-a]pyridin-2-yl]-cyclopropylmethyl ester (Compound 152)

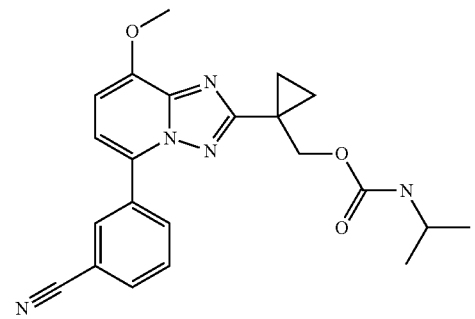 [SMILES: COc1ccc(-c2cccc(C#N)c2)n2nc(C3(COC(=O)NC(C)C)CC3)nc12]

Under an argon atmosphere 3-[2-(1-Hydroxymethyl-cyclopropyl)-8-methoxy-[1,2,4]triazolo[1,5-a]pyridin-5-yl]-benzonitrile (compound 150) (0.03 g, 0.08 mmol) was dissolved in CH$_3$CN (1 mL). Et$_3$N (0.005 mL) and isopropyl isocyanate (0.04 mL) were added and the reaction mixture was shaken at 65° C. for 20 H. Et$_3$N (0.005 mL) and isopropyl isocyanate (0.04 mL) were added again and the reaction mixture was shaken at 65° C. for another 24 H. The solvent was evaporated and the crude product was purified by flash chromatography on silica using DCM:MeOH 99:1 as eluent to afford the title compound as a solid.

1H NMR (300 MHz, DMSO) δ 8.41 (s, 1H), 8.37 (d, J=8.1 Hz, 1H), 7.95 (d, J=7.8 Hz, 1H), 7.72 (t, J=7.9 Hz, 1H), 7.39 (d, J=8.2 Hz, 1H), 7.18 (d, J=8.3 Hz, 1H), 6.93 (d, J=7.6 Hz, 1H), 4.40 (s, 2H), 4.01 (s, 3H), 3.65-3.48 (m, 1H), 1.25 (dd, J=6.3, 4.1 Hz, 2H), 1.12 (dd, J=6.4, 4.0 Hz, 2H), 0.98 (d, J=6.5 Hz, 6H).

Example 12

3-[2-(1-Benzyloxymethyl-cyclopropyl)-8-methoxy-[1,2,4]-triazolo[1,5-a]pyridin-5-yl]-benzonitrile (Compound 153)

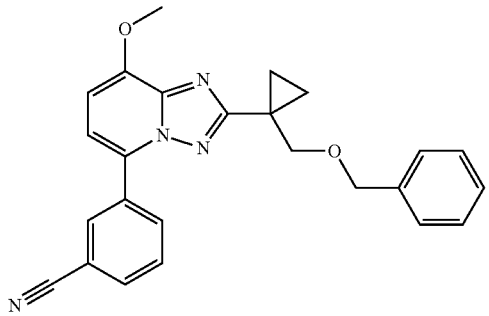 [SMILES: COc1ccc(-c2cccc(C#N)c2)n2nc(C3(COCc4ccccc4)CC3)nc12]

Under an argon atmosphere [1-(5-Iodo-8-methoxy-[1,2,4]triazolo[1,5-a]pyridin-2-yl)-cyclopropyl]-methanol (compound 150)(0.033 g, 0.06 mmol) was dissolved in DMF (0.5 mL). NaH (0.014 g, 0.36 mmol) was added and the suspension was heated at 65° C. for 1 h after which benzyl bromide (0.071 mL, 0.6 mmol) was added. The reaction mixture was stirred at 65° C. for 30 min after which is was cooled to rt. Aq. NaHCO$_3$ and H$_2$O was added. The aqueous phase was extracted with EtOAc (×2). The combined organic phases were dried over Na$_2$SO$_4$, filtered and concentrated in vacuo. The crude product was purified by flash chromatography on silica using DCM:MeOH 99:1 as eluent to afford the title compound as a solid.

1H NMR (300 MHz, DMSO) δ 8.47 (t, J=1.5 Hz, 1H), 8.37-8.28 (m, 1H), 8.00-7.90 (m, 1H), 7.72 (t, J=7.9 Hz, 1H), 7.37 (d, J=8.2 Hz, 1H), 7.29-7.22 (m, 5H), 7.17 (d, J=8.3 Hz, 1H), 4.55 (s, 2H), 4.01 (s, 3H), 3.97-3.80 (m, 2H), 1.27-1.15 (m, 2H), 1.07 (dd, J=6.4, 3.9 Hz, 2H).

Preparation 9

C-[1-(8-Methoxy-[1,2,4]triazolo[1,5-a]pyridin-2-yl)-cyclopropyl]-methylamine (Compound 309)

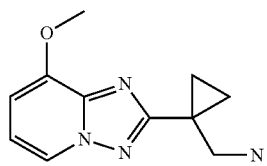 [SMILES: COc1cccn2nc(C3(CN)CC3)nc12]

Under an argon atmosphere 1-(tert-Butoxycarbonylaminomethyl)-cyclopropanecarboxylic acid (3.23 g, 15.0 mmol) was dissolved in THF (50 mL) and cooled to −70 C. Borane tetrahydrofurane complex (1 M in THF, 22.5 mL, 22.5 mmol) was added at −70 C. The mixture was then stirred at 0 C for 2.5 h after which borane tetrahydrofurane complex (1 M in THF, 7.5 mL, 7.5 mmol) was added at 0 C. The mixture was stirred at RT for 1.5 h. Aq. NH$_4$Cl (50 mL) was added at 20 C and the aqueous phase was extracted with EtOAc (×3). The combined organic phases were dried over Na$_2$SO$_4$, filtered and concentrated in vacuo to afford (1-Hydroxymethyl-cyclopropylmethyl)-carbamic acid tert-butyl ester (2.6 g) as an oil.

Under an argon atmosphere oxalyl chloride (1.17 mL, 13.8 mmol) was dissolved in DCM (30 mL) and cooled to −70 C. DMSO (1.95 mL, 27.6 mmol) in DCM (2.5 mL) was added over 5 min and stirred for 10 min. (1-Hydroxymethyl-cyclopropylmethyl)-carbamic acid tert-butyl ester (2.6 g, 12 mmol) in DCM (8.5 mL) was added at −70 C over 5 min and the mixture was stirred for 30 min. Et$_3$N (6.4 mL, 45.6 mmol) was added over 5 min and the temperature was allowed to reach RT over 1 h. H$_2$O was added and the aqueous phase was extracted with DCM (×2). The combined organic phases were washed with brine, dried over Na$_2$SO$_4$, filtered and concentrated in vacuo. The crude product was purified by flash chromatography on silica using heptane:EtOAc 1:15 as eluent to afford (1-Formyl-cyclopropylmethyl)-carbamic acid tert-butyl ester (0.65 g) as an oil.

Under an argon atmosphere (1-Formyl-cyclopropylmethyl)-carbamic acid tert-butyl ester (0.63 g, 3.19 mmol) was dissolved in dioxane (8.2 mL) and 2,4,6-Trimethyl-benzenesulfonate1,2-diamino-3-methoxy-pyridinium (0.73 g, 2.13 mmol, preparation as described for compound 304) was added. The suspension was heated to 90° C. for 4 days. The reaction mixture was cooled to rt and treated with 1N KOH in MeOH (2.13 mL) and stirred at rt for 24 hours. The solvent was evaporated in vacuo and a NaCl solution was added to the product. The product was extracted with DCM and the combined organic phases was dried over Na$_2$SO$_4$, filtered and concentrated in vacuo. The product was purified by flash chromatography on silica using Toluene:EtOAc 85:15->70:30 as eluent to afford [1-(8-Methoxy-[1,2,4]triazolo[1,5-a]pyridin-2-yl)-cyclopropylmethyl]-carbamic acid tert-butyl ester (0.37 g) as a solid.

Under an argon atmosphere [1-(8-Methoxy-[1,2,4]triazolo[1,5-a]pyridin-2-yl)-cyclopropylmethyl]-carbamic acid tert-butyl ester (0.37 g, 1.16 mmol) was mixed with N-iodosuccinimide (0.42 g, 1.9 mmol). BF$_3$*2H$_2$O (0.6 mL, 9.3 mmol) was added at 20° C. The dark suspension was stirred at rt for 24 h after which it was poured onto a 1:1 solution of saturated Na$_2$S$_2$O$_3$ and saturated NaHCO$_3$ (30 mL). The aqueous phase was extracted with DCM and the combined organic phases were washed with brine, dried over Na$_2$SO$_4$, filtered and concentrated in vacuo. The crude product was purified by flash chromatography on silica using DCM:MeOH:NH3 95:5:0.5 as the eluent to afford the boc-deprotected compound C-[1-(8-Methoxy-[1,2,4]triazolo[1,5-a]pyridin-2-yl)-yclopropyl]-methylamine.

1H NMR (300 MHz, DMSO) δ 8.47-8.36 (m, 1H), 7.04-6.93 (m, 2H), 3.95 (s, 3H), 2.96 (s, 2H), 1.11 (dd, J=6.4, 3.8 Hz, 2H), 0.98 (dd, J=6.4, 3.8 Hz, 2H).

Example 13

N-{1-[5-(3-Cyano-phenyl)-8-methoxy-[1,2,4]triazolo[1,5-a]pyridin-2-yl]-cyclopropylmethyl}-isobutyramide (Compound 154)

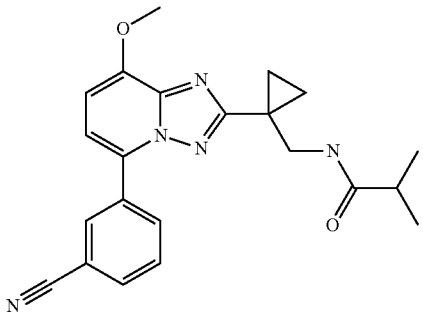 [SMILES: COc1ccc(-c2cccc(C#N)c2)n2nc(C3(CNC(=O)C(C)C)CC3)nc12]

Under an argon atmosphere C-[1-(8-Methoxy-[1,2,4]triazolo[1,5-a]pyridin-2-yl)-cyclopropyl]-methylamine (0.05 g, 0.23 mmol) was dissolved in THF (1 mL) and Et₃N (0.048 mL, 0.35 mmol). Isobutyryl chloride (0.03 mL, 0.29 mmol) was added. Stirring for 30 min. Aq. NaHCO₃ and H₂O was added. The aqueous phase was extracted with DCM (×3). The combined organic phases were dried over Na₂SO₄, filtered and concentrated in vacuo to afford N-[1-(8-Methoxy-[1,2,4]triazolo[1,5-a]pyridin-2-yl)-cyclopropylmethyl]-isobutyramide as a solid.

Under an argon atmosphere N-[1-(8-Methoxy-[1,2,4]triazolo[1,5-a]pyridin-2-yl)-cyclopropylmethyl]-isobutyramide (0.063 g, 0.22 mmol) was mixed with N-iodosuccinimide (0.15 g, 0.65 mmol). BF₃*2H₂O (0.47 mL, 7.4 mmol) was added at 0° C. The dark suspension was stirred at rt for 3 h after which it was poured onto a 1:1 solution of saturated Na₂S₂O₃ and saturated NaHCO₃ (20 mL). The aqueous phase was extracted with DCM (×2) and the combined organic phases were washed with brine, dried over Na₂SO₄, filtered and concentrated in vacuo. The crude product was purified by flash chromatography on silica using EtOAc:Toluene 3:1->7:1 as the eluent to afford N-[1-(5-Iodo-8-methoxy-[1,2,4]triazolo[1,5-a]pyridin-2-yl)-cyclopropylmethyl]-isobutyramide as a solid.

In a screw cap vial N-[1-(5-Iodo-8-methoxy-[1,2,4]triazolo[1,5-a]pyridin-2-yl)-cyclopropylmethyl]-isobutyramide (0.03 g, 0.07 mmol) was dissolved in DME (0.45 mL) and 1 M K₂CO₃ (0.14 mL) under argon. 3-cyanophenyl boronic acid (0.021 g, 0.15 mmol) and Pd(PPh₃)₄ (4 mg, 0.004 mmol) were added. The suspension was shaken at 80° C. for 17 h after which brine was added, and the aqueous phase was extracted with DCM (×3). The combined organic phases were dried, filtered and concentrated. The crude product was purified by flash chromatography, eluent toluene:EtOAc 1:7->0:100. This afforded the title compound as an oil.

1H NMR (300 MHz, DMSO) δ 8.45 (t, J=1.6 Hz, 1H), 8.37 (ddd, J=8.0, 1.8, 1.2 Hz, 1H), 7.98-7.91 (m, 1H), 7.74 (t, J=8.1 Hz, 1H), 7.67-7.60 (m, 2H), 7.37 (d, J=8.3 Hz, 1H), 7.18 (d, J=8.3 Hz, 1H), 4.01 (s, 3H), 3.66 (d, J=5.8 Hz, 2H), 2.43-2.32 (m, 1H), 1.12 (t, J=3.0 Hz, 2H), 0.99 (dd, J=6.7, 4.2 Hz, 2H), 0.95 (d, J=6.9 Hz, 6H).

Example 14

{1-[5-(3-Cyano-phenyl)-8-methoxyl-[1,2,4]triazolo[1,5-a]pyridin-2-yl]-cyclopropylmethyl}-carbamic acid cyclopentyl ester (Compound 155)

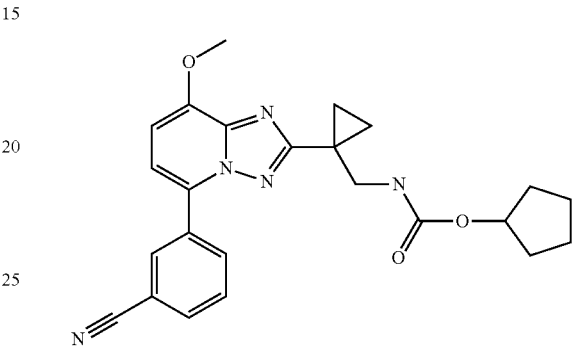

Under an argon atmosphere C-[1-(8-Methoxy-[1,2,4]triazolo[1,5-a]pyridin-2-yl)-cyclopropyl]-methylamine (0.063 g, 0.29 mmol) was dissolved in THF (1 mL) and Et₃N (0.06 mL, 0.43 mmol). Cyclopentyl chloroformate (0.053 g, 036 mmol) was added. Stirring was performed at RT for 24 h. Aq. NaHCO₃ and H₂O were added. The aqueous phase was extracted with DCM (×3). The combined organic phases were dried over Na₂SO₄, filtered and concentrated in vacuo. The crude product was purified by flash chromatography using toluene:EtOAc 2:1->1:1 as the eluent to afford [1-(8-Methoxy-[1,2,4]triazolo[1,5-a]pyridin-2-yl)-cyclopropylmethyl]-carbamic acid cyclopentyl ester.

Under an argon atmosphere [1-(8-Methoxy-[1,2,4]triazolo[1,5-a]pyridin-2-yl)-cyclopropylmethyl]-carbamic acid cyclopentyl ester was mixed with N-iodosuccinimide. BF₃*2H₂O was added at 0° C. The dark suspension was stirred at rt for 3 h after which it was poured onto a 1:1 solution of saturated Na₂S₂O₃ and saturated NaHCO₃ (20 mL). The aqueous phase was extracted with DCM (×2) and the combined organic phases were washed with brine, dried over Na₂SO₄, filtered and concentrated in vacuo. The crude product was purified by flash chromatography on silica to afford [1-(5-Iodo-8-methoxy-[1,2,4]triazolo[1,5-a]pyridin-2-yl)-cyclopropylmethyl]-carbamic acid cyclopentyl ester.

In a screw cap vial [1-(5-Iodo-8-methoxy-[1,2,4]triazolo[1,5-a]pyridin-2-yl)-cyclopropylmethyl]-carbamic acid cyclopentyl ester was dissolved in DME (0.45 mL) and 1 M K₂CO₃ (0.14 mL) under argon. 3-cyanophenyl boronic acid (0.021 g, 0.15 mmol) and Pd(PPh₃)₄ (4 mg, 0.004 mmol) were added. The suspension was shaken at 80° C. for 17 h after which brine was added, and the aqueous phase was extracted with DCM (×3). The combined organic phases were dried, filtered and concentrated. The crude product was purified by flash chromatography using EtOAc:toluene 1:1->2:1 as the eluent to afford the title compound as an oil.

1H NMR (300 MHz, DMSO) δ 8.41 (d, J=1.5 Hz, 1H), 8.36-8.27 (m, 1H), 8.01-7.90 (m, 1H), 7.75 (t, J=7.9 Hz, 1H), 7.34 (d, J=8.1 Hz, 1H), 7.18 (d, J=8.3 Hz, 1H), 5.92 (t, J=5.9

Hz, 1H), 4.01 (s, 3H), 3.61 (d, J=5.9 Hz, 2H), 3.21-3.08 (m, 4H), 1.76 (dd, J=8.0, 5.2 Hz, 4H), 1.15-0.97 (m, 4H).

Example 15

Pyrrolidine-1-carboxylic acid {1-[5-(3-cyano-phenyl)-8-methoxy-[1,2,4]triazolo[1,5-a]pyridin-2-yl]-cyclopropylmethyl}-amide (Compound 156)

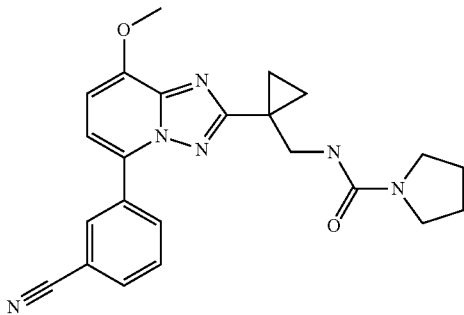 [SMILES: COc1ccc(-c2cccc(C#N)c2)n2nc(C3(CNC(=O)N4CCCC4)CC3)nc12]

Under an argon atmosphere C-[1-(8-Methoxy-[1,2,4]triazolo[1,5-a]pyridin-2-yl)-cyclopropyl]-methylamine (0.050 g, 0.23 mmol) was dissolved in THF (1 mL) and Et₃N (0.048 mL, 0.35 mmol). 1-Pyrrolidinecarbonyl chloride (0.032 mL, 0.29 mmol) was added. Stirring was performed at RT for 24 h. Aq. NaHCO₃ and H₂O were added. The aqueous phase was extracted with DCM (×3). The combined organic phases were dried over Na₂SO₄, filtered and concentrated in vacuo to afford Pyrrolidine-1-carboxylic acid [1-(8-methoxy-[1,2,4]triazolo[1,5-a]pyridin-2-yl)-cyclopropylmethyl]-amide as a crude product.

Under an argon atmosphere Pyrrolidine-1-carboxylic acid [1-(8-methoxy-[1,2,4]triazolo[1,5-a]pyridin-2-yl)-cyclopropylmethyl]-amide (0.085 g, 0.23 mmol) was mixed with N-iodosuccinimide (0.16 g, 0.69 mmol). BF₃*2H₂O (0.5 mL, 7.8 mmol) was added at 0° C. The dark suspension was stirred at rt for 4 h after which N-iodosuccinimide (0.08 g1) and BF₃*2H₂O (0.25 mLl) were added. The suspension was stirred for 24 h all together after which it was poured onto a 1:1 solution of saturated Na₂S₂O₃ and saturated NaHCO₃ (30 mL). The aqueous phase was extracted with DCM (×2) and the combined organic phases were washed with brine, dried over Na₂SO₄, filtered and concentrated in vacuo. The crude product was purified by flash chromatography on silica using DCM:MeOH 97:3 as the eluent to afford Pyrrolidine-1-carboxylic acid [1-(5-iodo-8-methoxy-[1,2,4]triazolo[1,5-a]pyridin-2-yl)-cyclopropylmethyl]-amide.

In a screw cap vial pyrrolidine-1-carboxylic acid [1-(5-iodo-8-methoxy-[1,2,4]triazolo[1,5-a]pyridin-2-yl)-cyclopropylmethyl]-amide was dissolved in DME (0.45 mL) and 1 M K₂CO₃ (0.14 mL) under argon. 3-cyanophenyl boronic acid (0.021 g, 0.15 mmol) and Pd(PPh₃)₄ (4 mg, 0.004 mmol) were added. The suspension was shaken at 80° C. for 17 h after which brine was added, and the aqueous phase was extracted with DCM (×3). The combined organic phases were dried, filtered and concentrated. The crude product was purified by flash chromatography using DCM:MeOH 97:3 as the eluent to afford the amorphous title compound.

1H NMR (300 MHz, DMSO) δ 8.41 (t, J=1.4 Hz, 1H), 8.32 (ddd, J=8.0, 1.7, 1.2 Hz, 1H), 8.00-7.92 (m, 1H), 7.74 (t, J=8.0 Hz, 1H), 7.34 (d, J=8.2 Hz, 1H), 7.18 (d, J=8.2 Hz, 1H), 5.91 (t, J=5.9 Hz, 1H), 4.01 (s, 3H), 3.61 (d, J=6.0 Hz, 2H), 3.20-3.10 (m, 4H), 1.79-1.71 (m, 4H), 1.14-0.99 (m, 4H).

Preparation 10

2-Cyclopropyl-8-methoxy-5-trimethylstannanyl-[1,2,4]-triazolo[1,5-a]pyridine (Compound 310)

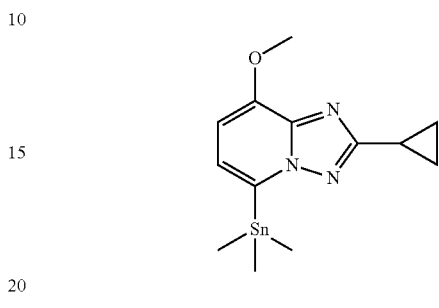

Under an argon atmosphere Hexamethyl distannane (0.63 g, 1.9 mmol) was dissolved in toluene (9 mL). 2-Cyclopropyl-5-iodo-8-methoxy-[1,2,4]triazolo[1,5-a]pyridine (0.49 g, 1.5 mmol) was added followed by addition of (PPh₃)₂Pd(OAc)₂ (0.041 g, 0.055 mmol). The dark suspension was stirred at 100° C. for 1 h. KF (10% in H₂O, 4.2 mL) was added at rt and the mixture was stirred for 2 h at rt. The mixture was filtered through Hyflo and washed with toluene. The filtrate was extracted with toluene (×2). The combined organic phases were dried over Na₂SO₄, filtered and concentrated in vacuo. The crude product was purified by flash chromatography on silica using toluene:EtOAc 10:1 as eluent. The title compound was obtained as an oil.

Example 17

6-(2-Cyclopropyl-8-methoxyl-[1,2,4]triazolo[1,5-a]pyridin-5-yl)-5-methyl-4,5-dihydro-2H-pyridazin-3-one (Compound 158)

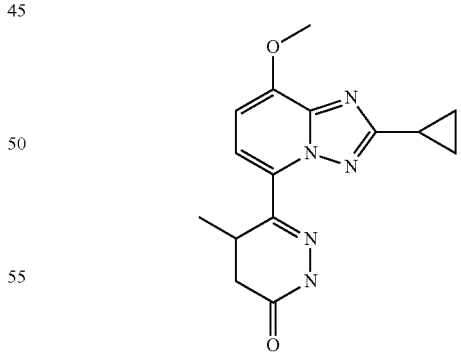

Under an argon atmosphere 2-Cyclopropyl-8-methoxy-5-trimethylstannanyl-[1,2,4]triazolo[1,5-a]pyridine (compound 310) (1.33 g, 3.8 mmol) was dissolved in toluene (20 mL). Propionyl chloride (0.39 g, 4.2 mmol) and Pd₂(dba)₃ (0.087 g, 0.095 mmol) were added. The solution was heated at 70 C for 2.5 h after which aq. NaHCO₃ was added. The aqueous phase was extracted with ÉtOAc (×3). The combined organic phases were dried over Na₂SO₄, filtered and concentrated in vacuo. The crude product was purified by flash chromatography using toluene:EtOAc 8:2->7:3 as the eluent to afford 1-(2-Cyclopropyl-8-methoxy-[1,2,4]triazolo[1,5-] pyridin-5-yl)-propan-1-one as a solid.

Under an argon atmosphere 1-(2-Cyclopropyl-8-methoxy-[1,2,4]triazolo[1,5-]pyridin-5-yl)-propan-1-one (0.42 g, 1.7 mmol) was dissolved in THF (5.0 mL). The solution was cooled to −70 C and Lithium-bis(trimethylsilyl)amide (1M in THF, 1.96 mL, 1.96 mmol) was added over 3 min. The cooling bath was removed and the suspension was stirred at RT for 40 min. The suspension was cooled to −70 C and tButylbromoacetate (0.29 mL, 1.96 mmol) was added. The solution was stirred at RT for 22 h and aq. NH$_4$Cl was added. The aqueous phase was extracted with EtOAc (×2). The combined organic phases were washed with brine, dried over Na$_2$SO$_4$, filtered and concentrated in vacuo. The crude product was purified by flash chromatography using toluene:EtOAc 85:15 as the eluent to afford 4-(2-Cyclopropyl-8-methoxy-[1,2,4]triazolo[1,5-a]pyridin-5-yl)-3-methyl-4-oxo-butyric acid tert-butyl ester.

Under an argon atmosphere 4-(2-Cyclopropyl-8-methoxy-[1,2,4]triazolo[1,5-a]pyridin-5-yl)-3-methyl-4-oxo-butyric acid tert-butyl ester (0.29 g) was dissolved in Trifluoroacetic acid (0.6 mL) and stirred at RT for 2 h after which the mixture was concentrated in vacuo. The crude product was suspended in 1 N NaOH (5 mL) and washed with Et$_2$O (×2). The aqueous phase was adjusted to pH 1 with 4N HCl (1.5 mL) The aqueous phase was extracted with DCM (×2). The combined organic phases were dried over Na$_2$SO$_4$, filtered and concentrated in vacuo to afford 4-(2-Cyclopropyl-8-methoxy-[1,2,4]triazolo[1,5-a]pyridin-5-yl)-3-methyl-4-oxo-butyric acid as a crude product.

Under an argon atmosphere 4-(2-Cyclopropyl-8-methoxy-[1,2,4]triazolo[1,5-a]pyridin-5-yl)-3-methyl-4-oxo-butyric acid (0.1 g, ca. 0.33 mmol) was dissolved in EtOH (1.5 mL). AcOH (0.11 mL, 1.98 mmol) and NH2NH2*H2O (0.048 mL, 0.99 mmol) were added. The solution was heated at reflux for 17 h after which it was concentrated in vacuo and co-concentrated with toluene. Aq. NaHCO$_3$ was added and the aqueous phase was extracted with EtOAc (×2). The combined organic phases were dried over Na$_2$SO$_4$, filtered and concentrated in vacuo. The crude product was purified by flash chromatography using EtOAc as the eluent to afford the title compound as a solid.

1H NMR (300 MHz, DMSO) δ 11.17 (s, 1H), 7.16 (d, J=8.1 Hz, 1H), 7.09 (d, J=8.2 Hz, 1H), 3.98 (s, 3H), 3.66-3.50 (m, 1H), 2.72 (dd, J=16.7, 6.7 Hz, 1H), 2.34 (dd, J=16.8, 5.1 Hz, 1H), 2.22-2.10 (m, 1H), 1.10-1.00 (m, 5H), 0.99-0.92 (m, 2H).

General Procedure 1

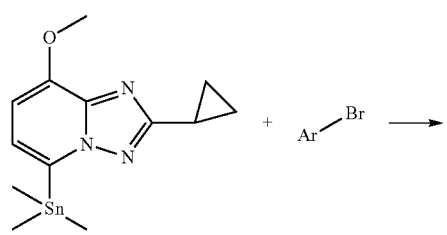

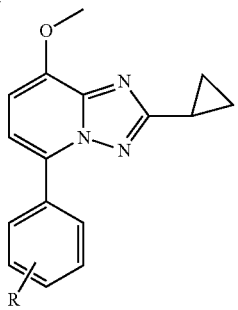

Under an argon atmosphere compound 310 (25 mg, 0.07 mmol) was dissolved in toluene (0.8 mL). Aryl bromide or heteroaryl bromide (0.085 mmol) was added followed by addition of Pd(PPh$_3$)$_4$ (3 mg, 0.003 mmol). The mixture was shaken at 100° C. for 24 h. The reaction mixture was cooled and filtered through decalite and the filter was washed with 0.5 mL toluene. The filtrate was purified by preparative HPLC/MS to afford the title compound.

Example 18

Compounds 159-171 were prepared according to General Procedure 1.

5-(2-Cyclopropyl-8-methoxy-[1,2,4]triazolo[1,5-a] pyridin-5-yl)-nicotinonitrile (Compound 159)

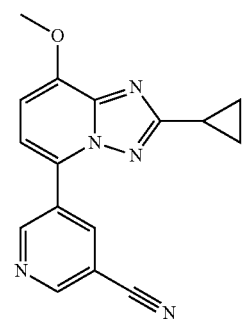 [SMILES: COc1ccc(-c2cncc(C#N)c2)n2nc(C3CC3)nc12]

1H NMR (300 MHz, DMSO) δ 9.41 (d, J=2.2 Hz, 1H), 9.11 (d, J=1.9 Hz, 1H), 8.89 (t, J=2.1 Hz, 1H), 7.44 (d, J=8.2 Hz, 1H), 7.19 (d, J=8.3 Hz, 1H), 4.01 (s, 3H), 2.29-2.10 (m, 1H), 1.12-0.89 (m, 4H).

5-(2-Cyclopropyl-8-methoxy-[1,2,4]triazolo[1,5-a] pyridin-5-yl)-indan-1-one (Compound 160)

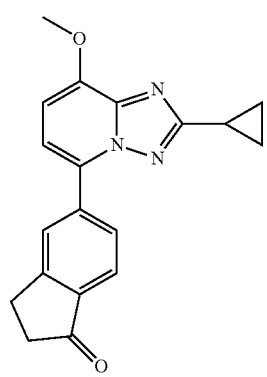 [SMILES: COc1ccc(-c2ccc3c(c2)CCC3=O)n2nc(C3CC3)nc12]

1H NMR (300 MHz, DMSO) δ 8.13 (s, 1H), 7.96 (d, J=8.1 Hz, 1H), 7.77 (d, J=8.0 Hz, 1H), 7.28 (d, J=8.1 Hz, 1H), 7.15 (d, J=8.3 Hz, 1H), 4.00 (s, 3H), 3.25-3.10 (m, 2H), 2.78-2.62 (m, 2H), 2.16 (tt, J=8.1, 5.0 Hz, 1H), 1.11-0.88 (m, 4H).

4-(2-Cyclopropyl-8-methoxyl-[1,2,4]triazolo[1,5-a]pyridin-5-yl)-2-methyl-benzonitrile (Compound 161)

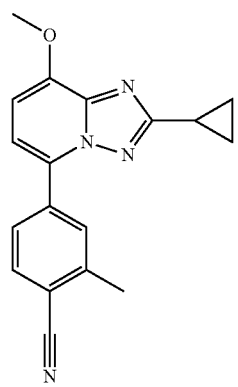 [SMILES: COc1ccc(-c2ccc(C#N)c(C)c2)n2nc(C3CC3)nc12]

1H NMR (300 MHz, DMSO) δ 8.01 (s, 1H), 8.01-7.96 (m, 1H), 7.92 (d, J=8.1 Hz, 1H), 7.29 (d, J=8.3 Hz, 1H), 7.19-7.09 (m, 1H), 3.99 (d, J=4.4 Hz, 3H), 2.57 (s, 3H), 2.16 (tt, J=8.1, 5.0 Hz, 1H), 1.09-0.91 (m, 4H).

4-(2-Cyclopropyl-8-methoxyl-[1,2,4]triazolo[1,5-a]pyridin-5-yl)-indan-1-one (Compound 162)

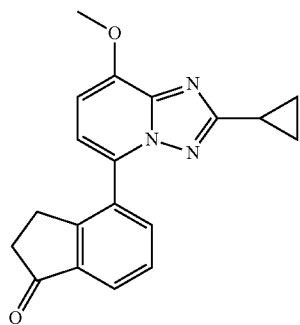 [SMILES: COc1ccc(-c2cccc3c2CCC3=O)n2nc(C3CC3)nc12]

1H NMR (300 MHz, CDCl3) δ 7.91 (dd, J=7.6, 0.9 Hz, 1H), 7.75 (dd, J=7.4, 1.1 Hz, 1H), 7.53 (t, J=7.6 Hz, 1H), 6.84 (s, 2H), 4.08 (s, 3H), 3.08-2.98 (m, 2H), 2.76-2.65 (m, 2H), 2.19 (tt, J=8.4, 4.9 Hz, 1H), 1.22-1.13 (m, 2H), 1.05-0.98 (m, 2H).

3-(2-Cyclopropyl-8-methoxy-[1,2,4]triazolo[1,5-a]pyridin-5-yl)-5-fluoro-benzonitrile (Compound 164)

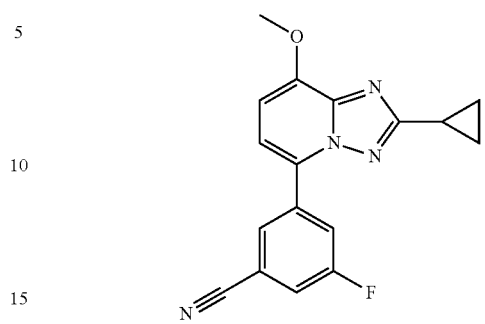

1H NMR (300 MHz, DMSO) δ 8.32 (t, J=1.4 Hz, 1H), 8.27 (ddd, J=10.2, 2.3, 1.6 Hz, 1H), 7.98 (ddd, J=8.4, 2.5, 1.3 Hz, 1H), 7.41 (d, J=8.1 Hz, 1H), 7.16 (d, J=8.3 Hz, 1H), 4.01 (s, 3H), 2.20 (tt, J=8.2, 4.9 Hz, 1H), 1.10-0.90 (m, 4H).

4-(2-Cyclopropyl-8-methoxyl-[1,2,4]-triazolo[1,5-a]pyridin-5-yl)-2-fluoro-benzonitrile (Compound 165)

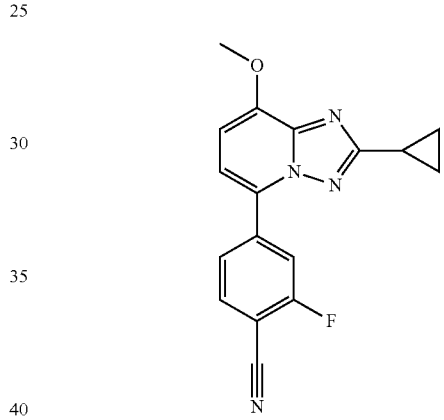

1H NMR (300 MHz, DMSO) δ 8.26-8.17 (m, 1H), 8.13-8.06 (m, 2H), 7.44 (d, J=8.3 Hz, 1H), 7.17 (d, J=8.3 Hz, 1H), 4.01 (s, 3H), 2.24-2.14 (tt, J=8.1, 5.0 Hz, 1H), 1.11-0.90 (m, 4H).

4-(2-Cyclopropyl-8-methoxy-[1,2,4]triazolo[1,5-a]pyridin-5-yl)-2-methoxy-benzonitrile (Compound 166)

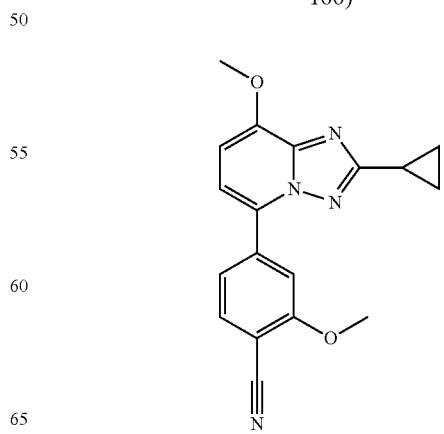

1H NMR (300 MHz, DMSO) δ 7.88 (d, J=8.1 Hz, 1H), 7.83 (d, J=1.2 Hz, 1H), 7.73-7.68 (m, 1H), 7.39 (d, J=8.1 Hz, 1H), 7.16 (d, J=8.3 Hz, 1H), 4.01 (d, J=0.9 Hz, 6H), 2.18 (tt, J=8.2, 5.0 Hz, 1H), 1.09-0.91 (m, 4H).

5-(2-Cyclopropyl-8-methoxy-[1,2,4]triazolo[1,5-a]pyridin-5-yl)-3H-isobenzofuran-1-one (Compound 167)

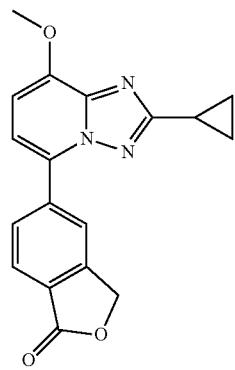 [SMILES: COc1ccc(-c2ccc3c(c2)COC3=O)n2nc(C3CC3)nc12]

1H NMR (300 MHz, DMSO) δ 8.24 (s, 1H), 8.15-8.09 (m, 1H), 7.99 (d, J=8.1 Hz, 1H), 7.30 (d, J=8.2 Hz, 1H), 7.17 (d, J=8.2 Hz, 1H), 5.51 (s, 2H), 4.01 (s, 3H), 2.26-2.05 (m, 1H), 1.14-0.85 (m, 4H).

3-(2-Cyclopropyl-8-methoxy-[1,2,4]triazolo[1,5-a]pyridin-5-yl)-5-hydroxymethyl-benzonitrile (Compound 168)

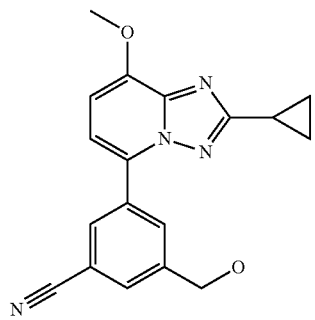 [SMILES: COc1ccc(-c2cc(C#N)cc(CO)c2)n2nc(C3CC3)nc12]

1H NMR (300 MHz, DMSO) δ 8.53 (s, 1H), 8.28 (s, 1H), 8.19 (s, 1H), 7.85 (s, 1H), 7.29 (d, J=8.1 Hz, 1H), 7.18 (d, J=6.9 Hz, 1H), 4.65 (s, 2H), 4.00 (s, 3H), 2.25-2.10 (m, 1H), 1.07-0.93 (m, 4H).

3-(2-Cyclopropyl-8-methoxy-[1,2,4]triazolo[1,5-a]pyridin-5-yl)-5-methoxy-benzonitrile (Compound 169)

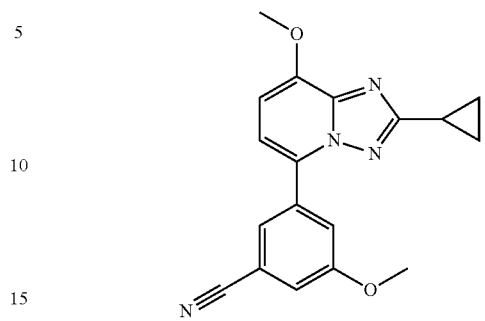

1H NMR (300 MHz, DMSO) δ 7.97 (t, J=1.3 Hz, 1H), 7.88 (dd, J=2.5, 1.6 Hz, 1H), 7.56 (dd, J=2.5, 1.3 Hz, 1H), 7.34 (d, J=8.2 Hz, 1H), 7.14 (d, J=8.2 Hz, 1H), 4.00 (s, 3H), 3.90 (s, 3H), 2.18 (dq, J=8.2, 4.9 Hz, 1H), 1.02 (dt, J=7.7, 2.5 Hz, 2H), 0.99-0.95 (m, 2H).

4-(2-Cyclopropyl-8-methoxy-[1,2,4]triazolo[1,5-a]pyridin-5-yl)-3H-isobenzofuran-1-one (Compound 170)

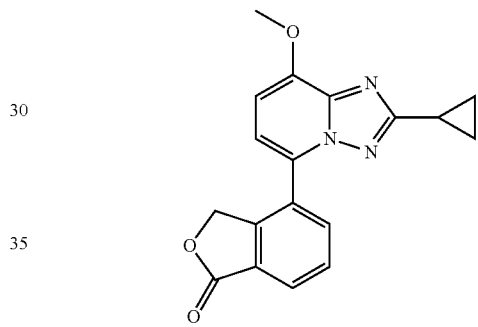

Purification: During the reaction a solid precipitated. The solid was filtered and the solid was purified by preparative HPLC/MS.

1H NMR (300 MHz, DMSO) δ 8.12 (dd, J=7.6, 0.8 Hz, 1H), 8.02 (d, J=7.0 Hz, 1H), 7.79 (t, J=7.6 Hz, 1H), 7.25 (d, J=8.1 Hz, 1H), 7.15 (d, J=8.1 Hz, 1H), 5.47 (s, 2H), 4.01 (s, 3H), 2.25-2.10 (m, 1H), 1.08-0.85 (m, 4H).

5-(2-Cyclopropyl-8-methoxy-[1,2,4]triazolo[1,5-a]pyridin-5-yl)-2,3-dihydro-isoindol-1-one (Compound 171)

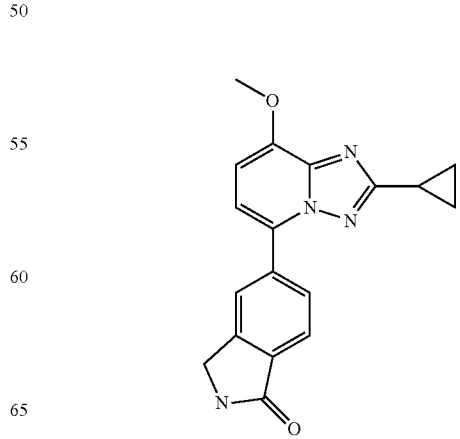

Purification: During the reaction a solid precipitated. The solid was filtered and the solid was purified by preparative HPLC/MS.

1H NMR (300 MHz, DMSO) δ 8.67 (s, 1H), 8.12 (s, 1H), 8.05-7.97 (m, 1H), 7.81 (d, J=8.0 Hz, 1H), 7.24 (d, J=8.2 Hz, 1H), 7.15 (d, J=8.2 Hz, 1H), 4.47 (s, 2H), 4.00 (s, 3H), 2.22-2.09 (m, 1H), 1.08-0.89 (m, 4H).

General Procedure 2

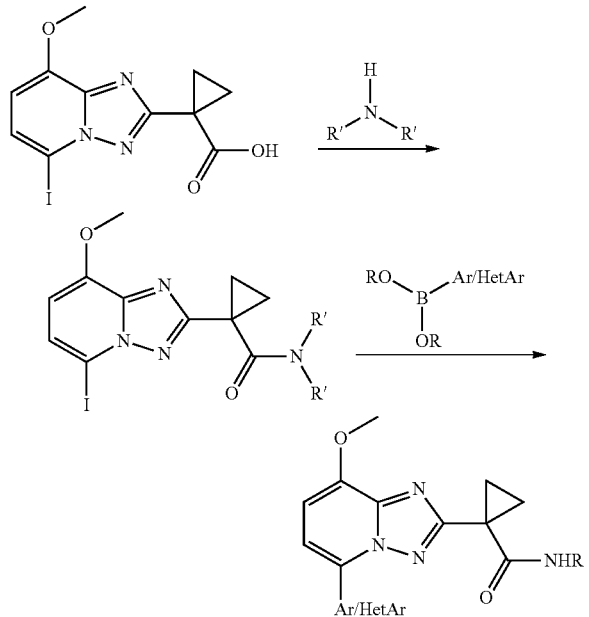

Under an argon atmosphere 1-(5-Iodo-8-methoxy-[1,2,4]triazolo[1,5-a]pyridin-2-yl)-cyclopropanecarboxylic acid, compound 306, (0.075 g, 0.20 mmol) was dissolved in DMF (0.7 mL). Et$_3$N (0.086 mL, 0.6 mmol) and HATU (0.12 g, 0.3 mmol) were added. The amine (0.3 mmol) was added and the mixture was shaken at RT for 2H. The solvent was concentrated in vacuo and qq. NaHCO$_3$ (1 mL) was added. The aqueous phase was shaken with DCM (1.5 mL) and the phases were separated using a phase separation cartridge (Chromabond, PTS). The organic phase was concentrated and the crude product was used directly in the next step.

Under an argon atmosphere the crude iodide (ca. 0.03 mmol) from above was dissolved in 1,4-dioxan (0.5 mL) and H$_2$O (0.25 mL). Argon was purged through the mixture. Boronic acid or boronic acid ester (3 eq) and K$_3$PO$_4$ (3.5 eq) were added, followed by the addition of Pd$_2$(dba)$_3$ (0.01 eq) and PCy$_3$ (0.02 eq). The mixture was heated in a microwave oven at 100° C. for 5 min. The reaction mixture was filtered and the filtrate was purified by preparative HPLC/MS.

Example 19

Compounds 172-178 and 180-186 were prepared according to the General Procedure 2.

General Procedure 3

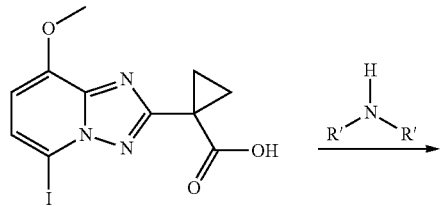

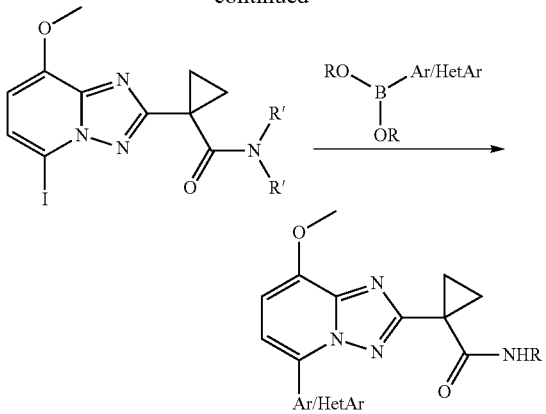

Under an argon atmosphere 1-(5-Iodo-8-methoxy-[1,2,4]triazolo[1,5-a]pyridin-2-yl)-cyclopropanecarboxylic acid, compound 306, (0.075 g, 0.20 mmol) was dissolved in DMF (0.7 mL). Et$_3$N (0.086 mL, 0.6 mmol) and HATU (0.12 g, 0.3 mmol) were added. The amine (0.3 mmol) was added and the mixture was shaken at RT for 2H. The solvent was concentrated in vacuo and qq. NaHCO$_3$ (1 mL) was added. The aqueous phase was shaken with DCM (1.5 mL) and the phases were separated using a phase separation cartridge (Chromabond, PTS). The organic phase was concentrated and the crude product was used directly in the next step.

Under argon atmosphere the crude iodide (ca. 0.03 mmol) from above was dissolved in DME (0.8 mL) and aq. K$_2$CO$_3$ (1M, 0.1 mL, 0.1 mmol). Argon was purged through the mixture. Boronic acid or boronic acid ester (3 eq) was added followed by the addition of Pd(PPh$_3$)$_4$ (0.002 g, 0.002 mmol). The mixture was heated at 80° C. overnight. The reaction mixture was filtered and the filtrate was purified by preparative HPLC/MS.

Example 20

Compounds 179 and 187 were prepared according to General Procedure 3.

1-[8-Methoxy-5-(1-oxo-indan-4-yl)-[1,2,4]triazolo[1,5-a]pyridin-2-yl]-cyclopropanecarboxylic acid benzylamide (Compound 172)

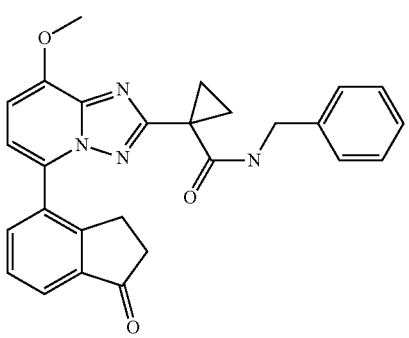 [SMILES: COc1ccc(-c2cccc3c2CCC3=O)n2nc(C3(C(=O)NCc4ccccc4)CC3)nc12]

1H NMR (300 MHz, DMSO) δ 8.72 (s, 1H), 7.93 (d, J=7.5 Hz, 1H), 7.78 (d, J=7.7 Hz, 1H), 7.53 (t, J=7.5 Hz, 1H), 7.27-7.15 (m, 6H), 4.32 (d, J=6.0 Hz, 2H), 4.04 (s, 3H), 3.05-2.95 (s, 2H), 2.61-2.54 (m, 2H), 1.50 (dd, J=7.0, 3.5 Hz, 2H), 1.36 (dd, J=7.1, 3.6 Hz, 2H).

1-[5-(5-Cyano-pyridin-3-yl)-8-methoxy-[1,2,4]triazolo[1,5-a]pyridin-2-yl]-cyclopropanecarboxylic acid benzylamide (Compound 173)

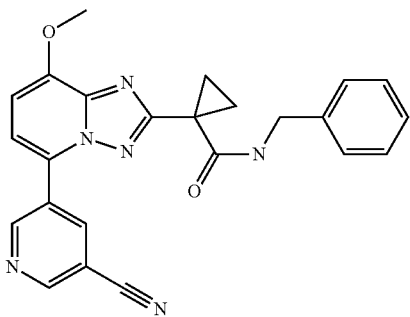 [SMILES: COc1ccc(-c2cncc(C#N)c2)n2nc(C3(C(=O)NCc4ccccc4)CC3)nc12]

1H NMR (300 MHz, DMSO) δ 9.43 (d, J=2.2 Hz, 1H), 9.12 (d, J=1.9 Hz, 1H), 8.90 (t, J=2.0 Hz, 1H), 8.67 (t, J=5.8 Hz, 1H), 7.52 (d, J=8.2 Hz, 1H), 7.38-7.14 (m, 6H), 4.36 (d, J=5.9 Hz, 2H), 4.04 (s, 3H), 1.53 (dd, J=6.9, 3.5 Hz, 2H), 1.40 (dd, J=7.0, 3.5 Hz, 2H).

1-[5-(4-Cyano-3-methoxy-phenyl)-8-methoxy-[1,2,4]triazolo[1,5-a]pyridin-2-yl]-cyclopropanecarboxylic acid cyclohexylmethyl-amide (Compound 174)

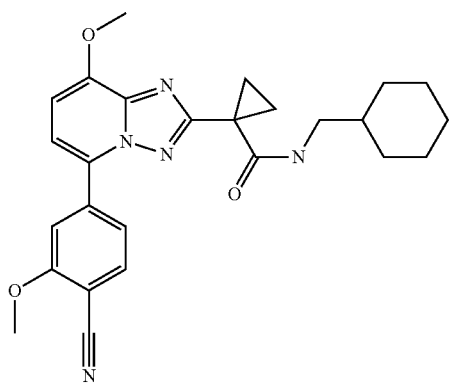 [SMILES: COc1cc(-c2ccc(OC)c3nc(C4(C(=O)NCC5CCCCC5)CC4)nn23)ccc1C#N]

1H NMR (300 MHz, DMSO) δ 8.64 (s, 1H), 7.88 (d, J=8.1 Hz, 1H), 7.80 (s, 1H), 7.67 (dd, J=8.1, 1.4 Hz, 1H), 7.44 (d, J=8.2 Hz, 1H), 7.25 (d, J=8.3 Hz, 1H), 4.04 (s, 3H), 3.99 (s, 3H), 3.01 (t, J=6.2 Hz, 2H), 1.9-0.7 (m, 15H).

1-[5-(4-Cyano-3-methoxy-phenyl)-8-methoxy-[1,2,4]triazolo[1,5-a]pyridin-2-yl]-cyclopropanecarboxylic acid isopropylamide (Compound 175)

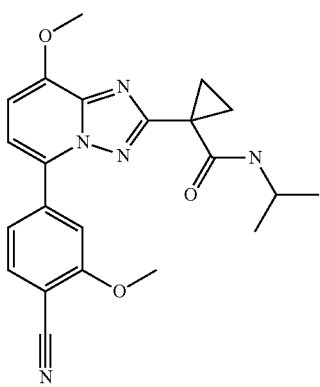 [SMILES: COc1cc(-c2ccc(OC)c3nc(C4(C(=O)NC(C)C)CC4)nn23)ccc1C#N]

1H NMR (300 MHz, DMSO) δ 8.49 (d, J=7.3 Hz, 1H), 7.88 (d, J=8.0 Hz, 1H), 7.79-7.66 (m, 2H), 7.46 (d, J=8.3 Hz, 1H), 7.25 (d, J=8.3 Hz, 1H), 4.05 (s, 3H), 4.00 (s, 3H), 4.00-3.85 (m, 1H), 1.52 (d, J=3.5 Hz, 2H), 1.41 (d, J=3.6 Hz, 2H), 1.06 (d, J=6.9 Hz, 6H).

1-[8-Methoxy-5-(1-oxo-indan-4-yl)-[1,2,4]triazolo[1,5-a]pyridin-2-yl]-cyclopropanecarboxylic acid cyclohexylmethyl-amide (Compound 176)

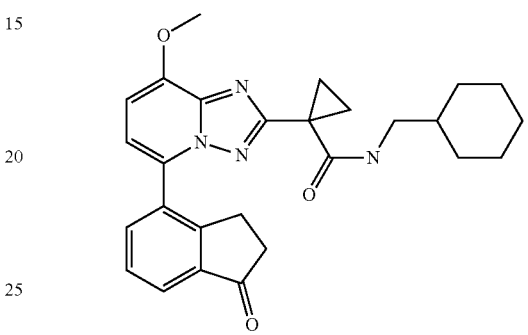

1H NMR (300 MHz, DMSO) δ 8.57 (s, 1H), 7.94 (d, J=7.8 Hz, 1H), 7.82 (d, J=7.4 Hz, 1H), 7.61 (t, J=7.5 Hz, 1H), 7.25 (s, 2H), 4.05 (s, 3H), 2.96 (dd, J=13.6, 6.9 Hz, 4H), 2.69-2.60 (m, 2H), 1.52 (d, J=19.2 Hz, 8H), 1.38 (d, J=3.6 Hz, 2H), 1.26 (s, 1H), 1.13-0.92 (m, 4H), 0.75 (d, J=10.9 Hz, 2H).

1-[5-(4-Cyano-3-methoxy-phenyl)-8-methoxy-[1,2,4]triazolo[1,5-a]pyridin-2-yl]-cyclopropanecarboxylic acid (2-methanesulfonyl-ethyl)-amide (Compound 177)

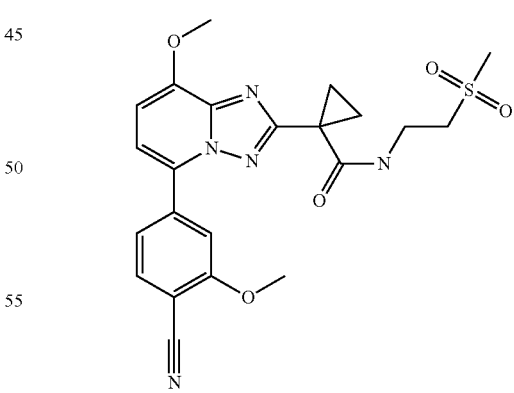

1H NMR (300 MHz, DMSO) δ 8.41 (t, J=5.6 Hz, 1H), 7.89 (d, J=8.1 Hz, 1H), 7.83 (d, J=1.2 Hz, 1H), 7.73 (dd, J=8.1, 1.4 Hz, 1H), 7.49 (d, J=8.2 Hz, 1H), 7.25 (d, J=8.3 Hz, 1H), 4.05 (s, 3H), 3.99 (s, 3H), 3.56 (q, J=6.4 Hz, 2H), 3.31-3.23 (m, 2H), 2.98 (s, 3H), 1.52 (dd, J=7.0, 3.6 Hz, 2H), 1.38 (dd, J=7.1, 3.6 Hz, 2H).

1-[5-(4-Cyano-3-methoxy-phenyl)-8-methoxy-[1,2,4]triazolo[1,5-a]pyridin-2-yl]-cyclopropanecarboxylic acid benzylamide (Compound 178)

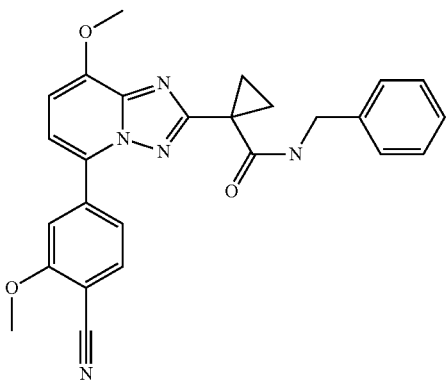 [SMILES: COc1cc(-c2ccc(OC)c3nc(C4(C(=O)NCc5ccccc5)CC4)nn23)ccc1C#N]

1H NMR (300 MHz, DMSO) δ 8.79 (t, J=5.8 Hz, 1H), 7.80 (d, J=1.1 Hz, 1H), 7.75 (d, J=8.1 Hz, 1H), 7.65 (dd, J=8.1, 1.3 Hz, 1H), 7.45 (d, J=8.2 Hz, 1H), 7.32-7.19 (m, 6H), 4.37 (d, J=5.9 Hz, 2H), 4.04 (s, 3H), 3.92 (s, 3H), 1.55 (dd, J=7.0, 3.5 Hz, 2H), 1.42 (dd, J=7.0, 3.6 Hz, 2H).

1-[8-Methoxy-5-(1-oxo-1,3-dihydro-isobenzofuran-5-yl)-[1,2,4]triazolo[1,5-a]pyridin-2-yl]-cyclopropanecarboxylic acid benzylamide (Compound 179)

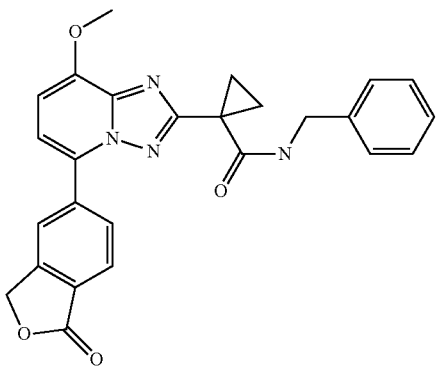

1H NMR (300 MHz, DMSO) δ 8.77 (d, J=5.8 Hz, 1H), 8.19 (s, 1H), 8.12 (d, J=8.1 Hz, 1H), 7.88 (d, J=8.0 Hz, 1H), 7.38 (d, J=8.1 Hz, 1H), 7.28-7.17 (m, 6H), 5.37 (s, 2H), 4.38 (d, J=5.9 Hz, 2H), 4.04 (s, 3H), 1.55 (dd, J=6.9, 3.6 Hz, 2H), 1.43 (dd, J=7.0, 3.6 Hz, 2H).

1-[8-Methoxy-5-(1-oxo-indan-4-yl)-[1,2,4]triazolo[1,5-a]pyridin-2-yl]-cyclopropanecarboxylic acid isopropylamide (Compound 180)

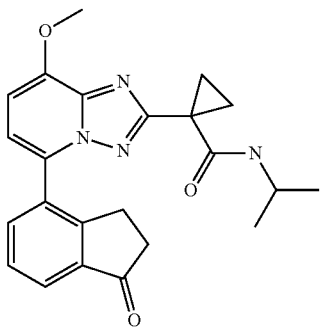 [SMILES: COc1ccc(-c2cccc3c2CCC3=O)n2nc(C3(C(=O)NC(C)C)CC3)nc12]

1H NMR (300 MHz, DMSO) δ 8.46 (d, J=7.1 Hz, 1H), 7.98 (d, J=7.4 Hz, 1H), 7.82 (d, J=7.5 Hz, 1H), 7.62 (t, J=7.5 Hz, 1H), 7.28 (d, J=8.2 Hz, 1H), 7.24 (d, J=8.2 Hz, 1H), 4.05 (s, 3H), 3.85 (dd, J=13.7, 6.7 Hz, 1H), 3.05-2.97 (m, 2H), 2.69-2.60 (m, 2H), 1.50 (dd, J=6.9, 3.4 Hz, 2H), 1.39 (dd, J=7.0, 3.4 Hz, 2H), 0.94 (d, J=6.6 Hz, 6H).

1-[8-Methoxy-5-(1-oxo-indan-5-yl)-[1,2,4]triazolo[1,5-a]pyridin-2-yl]-cyclopropanecarboxylic acid isopropylamide (Compound 181)

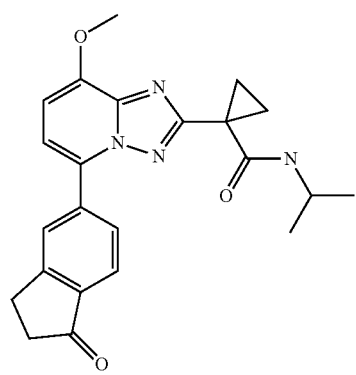 [SMILES: COc1ccc(-c2ccc3c(c2)CCC3=O)n2nc(C3(C(=O)NC(C)C)CC3)nc12]

1H NMR (300 MHz, DMSO) δ 8.43 (d, J=7.5 Hz, 1H), 8.13 (s, 1H), 8.01 (d, J=7.9 Hz, 1H), 7.76 (d, J=8.0 Hz, 1H), 7.38 (d, J=8.1 Hz, 1H), 7.25 (d, J=8.3 Hz, 1H), 4.04 (s, 3H), 3.95 (dd, J=13.9, 6.8 Hz, 1H), 3.23-3.15 (m, 2H), 2.76-2.66 (m, 2H), 1.52 (dd, J=6.9, 3.4 Hz, 2H), 1.41 (dd, J=6.9, 3.4 Hz, 2H), 1.08 (d, J=6.5 Hz, 6H).

1-[8-Methoxy-5-(1-oxo-indan-5-yl)-[1,2,4]triazolo[1,5-a]pyridin-2-yl]-cyclopropanecarboxylic acid benzylamide (Compound 182)

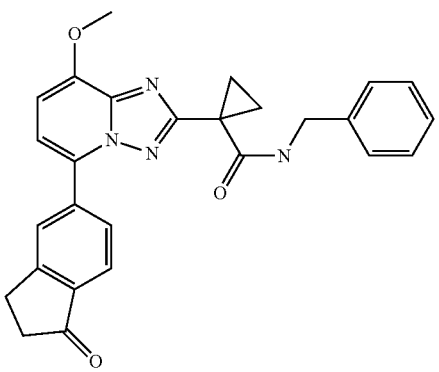 [SMILES: COc1ccc(-c2ccc3c(c2)CCC3=O)n2nc(C3(C(=O)NCc4ccccc4)CC3)nc12]

1H NMR (300 MHz, DMSO) δ 8.80 (t, J=5.7 Hz, 1H), 8.11 (s, 1H), 7.95 (d, J=8.1 Hz, 1H), 7.67 (d, J=8.0 Hz, 1H), 7.37 (d, J=8.1 Hz, 1H), 7.30-7.13 (m, 6H), 4.38 (d, J=5.9 Hz, 2H), 4.04 (d, J=6.2 Hz, 3H), 3.14-3.00 (m, 2H), 2.67 (dd, J=6.7, 4.9 Hz, 2H), 1.55 (dd, J=6.8, 3.6 Hz, 2H), 1.42 (dd, J=6.9, 3.5 Hz, 2H).

77

1-[8-Methoxy-5-(1-oxo-indan-4-yl)-[1,2,4]triazolo[1,5-a]pyridin-2-yl]-cyclopropanecarboxylic acid (2-methanesulfonyl-ethyl)-amide (Compound 183)

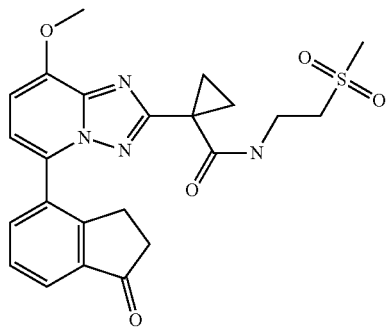 [SMILES: COc1ccc(-c2cccc3c2CCC3=O)n2nc(C3(C(=O)NCCS(C)(=O)=O)CC3)nc12]

1H NMR (300 MHz, DMSO) δ 8.33 (t, J=5.6 Hz, 1H), 7.97 (dd, J=7.4, 1.1 Hz, 1H), 7.81 (d, J=7.6 Hz, 1H), 7.62 (t, J=7.5 Hz, 1H), 7.27 (d, J=8.2 Hz, 1H), 7.24 (d, J=8.2 Hz, 1H), 4.05 (s, 3H), 3.59-3.47 (m, 2H), 3.21 (t, J=6.7 Hz, 2H), 3.07-2.96 (m, 2H), 2.93 (s, 3H), 2.66 (dd, J=6.6, 4.7 Hz, 2H), 1.47 (dd, J=6.9, 3.6 Hz, 2H), 1.32 (dd, J=7.0, 3.6 Hz, 2H).

1-[8-Methoxy-5-(1-oxo-indan-5-yl)-[1,2,4]triazolo[1,5-a]pyridin-2-yl]-cyclopropanecarboxylic acid (2-methanesulfonyl-ethyl)-amide (Compound 184)

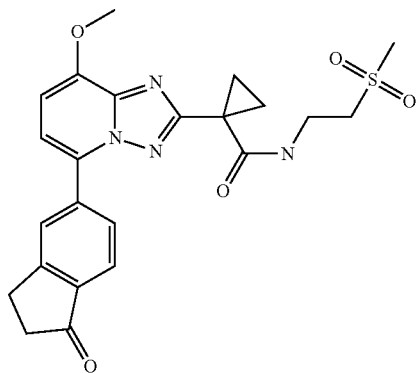 [SMILES: COc1ccc(-c2ccc3c(c2)CCC3=O)n2nc(C3(C(=O)NCCS(C)(=O)=O)CC3)nc12]

1H NMR (300 MHz, DMSO) δ 8.40 (t, J=6.0 Hz, 1H), 8.15 (s, 1H), 8.00 (d, J=8.1 Hz, 1H), 7.79 (d, J=8.1 Hz, 1H), 7.40 (d, J=8.2 Hz, 1H), 7.25 (d, J=8.3 Hz, 1H), 4.04 (s, 3H), 3.62-3.51 (m, 2H), 3.40-3.25 (m, 2H), 3.26-3.18 (m, 2H), 2.97 (s, 3H), 2.76-2.68 (m, 2H), 1.51 (dd, J=6.9, 3.6 Hz, 2H), 1.38 (dd, J=7.0, 3.6 Hz, 2H).

78

1-[5-(5-Cyano-pyridin-3-yl)-8-methoxy-[1,2,4]triazolo[1,5-a]pyridin-2-yl]-cyclopropanecarboxylic acid cyclohexylmethyl-amide (Compound 185)

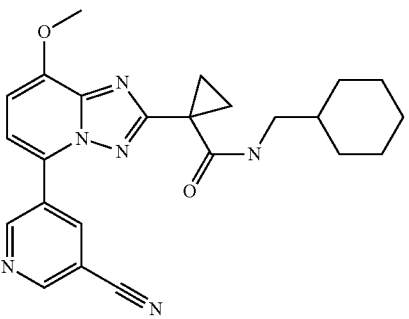 [SMILES: COc1ccc(-c2cncc(C#N)c2)n2nc(C3(C(=O)NCC4CCCCC4)CC3)nc12]

1H NMR (300 MHz, DMSO) δ 9.40 (d, J=2.1 Hz, 1H), 9.14 (d, J=1.9 Hz, 1H), 8.90 (t, J=2.0 Hz, 1H), 8.45 (d, J=5.4 Hz, 1H), 7.51 (d, J=8.1 Hz, 1H), 7.28 (d, J=8.3 Hz, 1H), 4.05 (s, 3H), 3.01 (t, J=6.3 Hz, 2H), 1.72-1.34 (m, 10H), 1.12 (t, J=10.2 Hz, 3H), 0.86 (t, J=10.8 Hz, 2H).

1-[5-(5-Cyano-pyridin-3-yl)-8-methoxy-[1,2,4]triazolo[1,5-a]pyridin-2-yl]-cyclopropanecarboxylic acid (2-methanesulfonyl-ethyl)-amide (Compound 186)

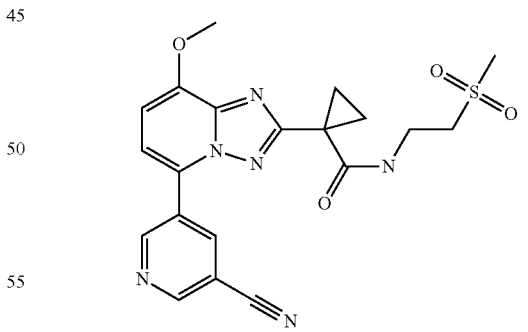

1H NMR (300 MHz, DMSO) δ 9.44 (d, J=2.1 Hz, 1H), 9.12 (d, J=1.8 Hz, 1H), 8.91 (t, J=2.0 Hz, 1H), 8.34 (t, J=5.6 Hz, 1H), 7.55 (d, J=8.1 Hz, 1H), 7.29 (d, J=8.2 Hz, 1H), 4.05 (s, 3H), 3.63-3.49 (m, 2H), 3.29-3.22 (m, 2H), 2.98 (s, 3H), 1.55-1.48 (m, 2H), 1.43-1.34 (m, 2H).

1-[8-Methoxy-5-(1-oxo-1,3-dihydro-isobenzofuran-5-yl)-[1,2,4]triazolo[1,5-a]pyridin-2-yl]-cyclopropanecarboxylic acid (2-dimethylsulfamoyl-ethyl)-amide (Compound 187)

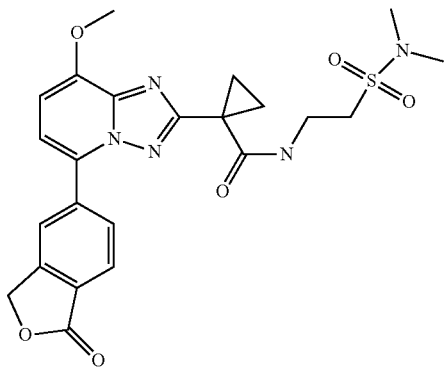 [SMILES: COc1ccc(-c2ccc3c(c2)COC3=O)n2nc(C3(C(=O)NCCS(=O)(=O)N(C)C)CC3)nc12]

1H NMR (300 MHz, DMSO) δ 8.42 (t, J=5.8 Hz, 1H), 8.26 (s, 1H), 8.18 (d, J=8.1 Hz, 1H), 8.01 (d, J=8.1 Hz, 1H), 7.42 (m, 1H), 7.27 (m, 1H), 5.52 (s, 2H), 4.04 (s, 3H), 3.53 (dd, J=12.9, 6.8 Hz, 2H), 3.17 (t, J=7.0 Hz, 2H), 2.77-2.70 (m, 7H), 1.52 (dd, J=7.0, 3.6 Hz, 2H), 1.40 (dd, J=7.1, 3.6 Hz, 2H).

Example 21

1-[5-(3-Cyano-phenyl)-8-methoxy-[1,2,4]triazolo[1,5-a]pyridin-2-yl]-cyclopropanecarboxylic acid ethyl ester (Compound 188)

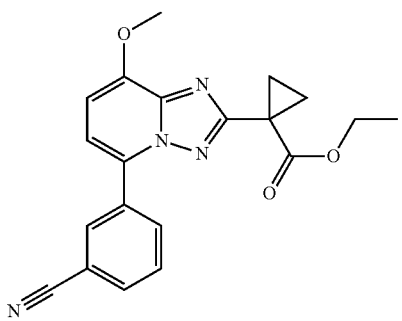 [SMILES: CCOC(=O)C1(c2nc3c(OC)ccc(-c4cccc(C#N)c4)n3n2)CC1]

Under an argon atmosphere 1-(5-Iodo-8-methoxy-[1,2,4]triazolo[1,5-a]pyridin-2-yl)-cyclopropanecarboxylic acid ethyl ester) (compound 305)(0.5 g, 1.3 mmol) was dissolved in 1,4-dioxan (2.8 mL) and H₂O (1.4 mL). Argon was purged through the mixture. 3-CN-phenyl boronic acid (0.19 g, 1.3 mmol) and K₃PO₄ (0.96 g, 4.5 mmol) were added, followed by the addition of Pd₂(dba)₃ (12 mg, 0.013 mmol)) and PCy₃ (9 mg, 0.03 mmol). The mixture was heated in a microwave oven at 145° C. for 30 min. The reaction mixture was filtered, concentrated and purified by flash chromatography using P.ether:EtOAc 2:1->1:5 as the eluent. This afforded the title compound as a solid.

1H NMR (300 MHz, CDCl3) δ 8.25 (t, J=1.4 Hz, 1H), 8.21-8.15 (m, 1H), 7.74 (dt, J=7.7, 1.3 Hz, 1H), 7.62 (t, J=7.8 Hz, 1H), 7.03 (d, J=8.1 Hz, 1H), 6.88 (d, J=8.1 Hz, 1H), 4.19 (q, J=7.1 Hz, 2H), 4.09 (s, 3H), 1.72 (dd, J=7.4, 4.3 Hz, 2H), 1.60-1.56 (m, 2H), 1.27-1.19 (m, 3H).

Example 22(Compound 190)

1-[5-(3-Acetyl-phenyl)-8-methoxy-[1,2,4]triazolo[1,5-a]pyridin-2-yl]-cyclopropanecarboxylic acid ethyl ester

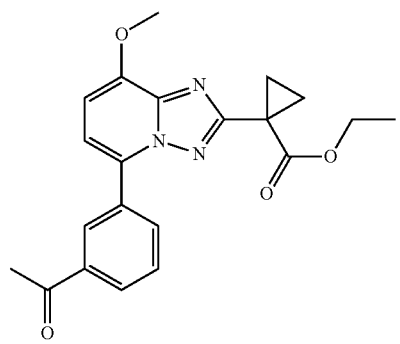 [SMILES: CCOC(=O)C1(c2nc3c(OC)ccc(-c4cccc(C(C)=O)c4)n3n2)CC1]

The title compound was prepared according to the method described for compound 188.

1H NMR (300 MHz, CDCl3) δ 8.50 (d, J=1.6 Hz, 1H), 8.24-8.12 (m, 1H), 8.10-8.00 (m, 1H), 7.61 (t, J=7.8 Hz, 1H), 7.06 (d, J=8.1 Hz, 1H), 6.88 (d, J=8.1 Hz, 1H), 4.22-4.13 (m, 2H), 4.08 (s, 3H), 2.67 (s, 3H), 1.71 (dd, J=7.4, 4.2 Hz, 2H), 1.62-1.56 (m, 2H), 1.19 (t, J=7.0 Hz, 3H).

Example 23

1-[5-(3-Cyano-phenyl)-8-methoxy-[1,2,4]triazolo[1,5-a]pyridin-2-yl]-cyclopropanecarboxylic acid (Compound 191)

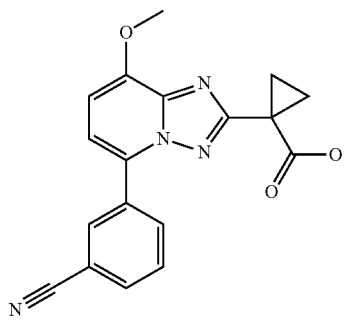 [SMILES: COc1ccc(-c2cccc(C#N)c2)n2nc(C3(C(=O)O)CC3)nc12]

1-[5-(3-Cyano-phenyl)-8-methoxy-[1,2,4]triazolo[1,5-a]pyridin-2-yl]-cyclopropanecarboxylic acid ethyl ester (compound 188) (0.32 g, 0.88 mmol) was dissolved in 1,4-dioxan (10 mL) by heating. LiOH (0.06 g, 1.4 mmol) in H₂O (2.5 mL) was added at RT. The suspension was stirred at RT overnight. The reaction mixture was concentrated in vacuo and H2O was added. The aqueous phase was washed with EtOAc and acidified with 4N HCl to pH 1. The aqueous phase was extracted with DCM (×2) and dried over MgSO₄, filtered and concentrated in vacuo. This afforded the title compound as a solid.

1H NMR (300 MHz, CDCl3) δ 8.14-8.05 (m, 2H), 7.78 (dt, J=7.7, 1.3 Hz, 1H), 7.70-7.59 (m, 1H), 7.11 (d, J=8.1 Hz, 1H), 7.05-6.96 (m, 1H), 4.12 (s, 3H), 1.99 (dd, J=7.9, 3.6 Hz, 2H), 1.78 (dd, J=7.9, 3.6 Hz, 2H).

Example 24

1-[5-(3-Acetyl-phenyl)-8-methoxyl-[1,2,4]triazolo[1,5-a]pyridin-2-yl]-cyclopropanecarboxylic acid (Compound 193)

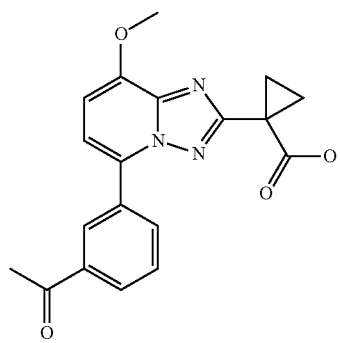 [SMILES: COc1ccc(-c2cccc(C(C)=O)c2)n2nc(C3(C(=O)O)CC3)nc12]

The title compound was prepared according to the method described for compound 191.

1H NMR (300 MHz, CDCl3) δ 13.93 (s, 1H), 8.44 (d, J=1.6 Hz, 1H), 8.06 (ddd, J=9.1, 8.4, 1.2 Hz, 2H), 7.64 (t, J=7.8 Hz, 1H), 7.14 (d, J=8.2 Hz, 1H), 7.01 (d, J=8.1 Hz, 1H), 4.11 (s, 3H), 2.67 (s, 3H), 1.98 (dd, J=7.8, 3.5 Hz, 2H), 1.80 (dd, J=7.6, 3.8 Hz, 2H).

Example 25

1-[5-(3-Cyano-phenyl)-8-methoxyl-[1,2,4]triazolo[1,5-a]pyridin-2-yl]-cyclopropanecarboxylic acid isopropylamide (Compound 194)

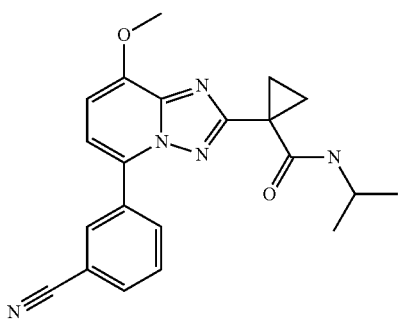 [SMILES: COc1ccc(-c2cccc(C#N)c2)n2nc(C3(C(=O)NC(C)C)CC3)nc12]

Under an argon atmosphere 1-[5-(3-Cyano-phenyl)-8-methoxy-[1,2,4]triazolo[1,5-a]pyridin-2-yl]-cyclopropanecarboxylic acid) (compound 191) (0.026 g, 0.08 mmol) was dissolved in DMF (0.25 mL). Et3N (0.23 mL, 0.6 mmol) and HATU (0.043 g, 0.11 mmol) were added. Isopropyl amine (0.01 mL, 0.11 mmol) was added and the mixture was shaken at RT overnight. H2O was added and the aqueous phase was extracted with EtOAc (×3), the organic phases were washed with brine, dried over MgSO4, filtered and concentrated in vacuo. Purification by flash chromatography, MeOH:DCM 2:98->4:96, afforded the title compound as a solid.

1H NMR (300 MHz, CDCl3) δ 8.72 (d, J=6.4 Hz, 1H), 8.15 (d, J=7.9 Hz, 2H), 7.79 (dd, J=7.7, 1.1 Hz, 1H), 7.66 (t, J=7.7 Hz, 1H), 7.03 (d, J=8.1 Hz, 1H), 6.93 (d, J=8.2 Hz, 1H), 4.20-4.04 (m, 1H), 4.11 (s, 2H), 1.83 (dd, J=6.8, 2.7 Hz, 2H), 1.69-1.63 (m, 2H), 1.15 (d, J=6.5 Hz, 6H).

General Procedure 4

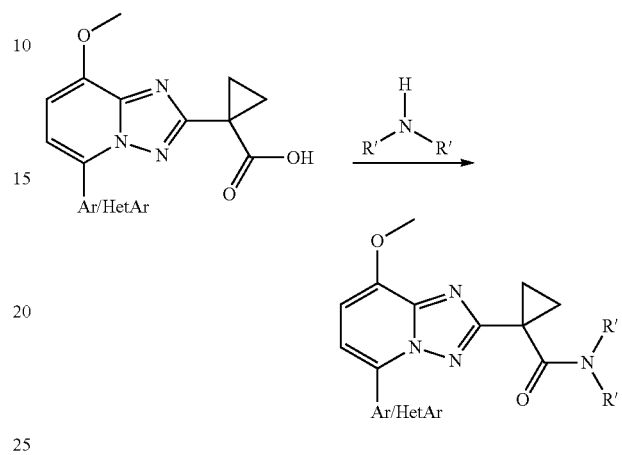

Under an argon atmosphere the carboxylic acid (0.04 mmol) was dissolved in DMF (0.25 mL). Et3N (0.016 mL, 0.12 mmol or 0.025 mL, 0.18 mmol of the amine was an HCl salt) and HATU (0.022 g, 0.06 mmol) were added. The amine (0.06 mmol) was added and the mixture was shaken at RT overnight. The reaction mixture was filtered on a micro filter plate and washed with DMF (0.05 mL) and purified by HPLC.

Example 26

Compounds 195-199 were prepared according to General Procedure 4 using compound 191 (1-[5-(3-Cyano-phenyl)-8-methoxy-[1,2,4]triazolo[1,5-a]pyridin-2-yl]-cyclopropanecarboxylic acid) as starting material.

1-[5-(3-Cyano-phenyl)-8-methoxy-[1,2,4]triazolo[1,5-a]pyridin-2-yl]-cyclopropanecarboxylic acid (pyridin-3-ylmethyl)-amide (Compound 195)

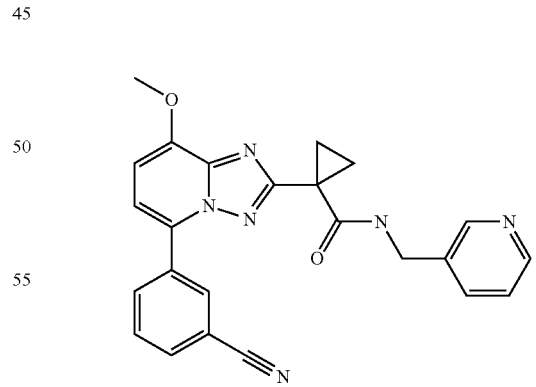

1H NMR (600 MHz, DMSO) δ 8.69 (t, J=6.0 Hz, 1H), 8.49 (d, J=1.9 Hz, 1H), 8.45 (dd, J=4.8, 1.6 Hz, 1H), 8.41 (t, J=1.6 Hz, 1H), 8.31 (ddd, J=8.0, 1.6, 1.2 Hz, 1H), 7.97-7.93 (m, 1H), 7.69 (t, J=7.9 Hz, 1H), 7.65 (dt, J=7.8, 1.9 Hz, 1H), 7.41 (d, J=8.1 Hz, 1H), 7.30 (ddd, J=7.7, 4.8, 0.5 Hz, 1H), 7.26-7.22 (m, 1H), 4.39 (d, J=6.0 Hz, 2H), 4.03 (s, 3H), 1.52 (dd, J=7.1, 3.5 Hz, 2H), 1.40 (dd, J=7.2, 3.5 Hz, 2H).

3-{8-Methoxy-2-[1-(morpholine-4-carbonyl)-cyclopropyl]-[1,2,4]triazolo-[1,5-a]pyridin-5-yl}-benzonitrile (Compound 196)

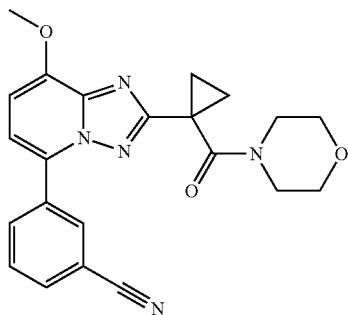

1H NMR (600 MHz, DMSO) δ 8.45 (t, J=1.6 Hz, 1H), 8.27 (ddd, J=8.0, 1.6, 1.2 Hz, 1H), 8.02-7.95 (m, 1H), 7.76 (t, J=7.9 Hz, 1H), 7.41 (d, J=8.2 Hz, 1H), 7.27-7.12 (m, 1H), 4.02 (s, 3H), 3.55 (d, J=10.6 Hz, 4H), 3.42 (s, 4H), 1.49-1.46 (m, 2H), 1.45-1.41 (m, 2H).

1-[5-(3-Cyano-phenyl)-8-methoxyl-[1,2,4]triazolo[1,5-a]pyridin-2-yl]-cyclopropanecarboxylic acid benzylamide (Compound 197)

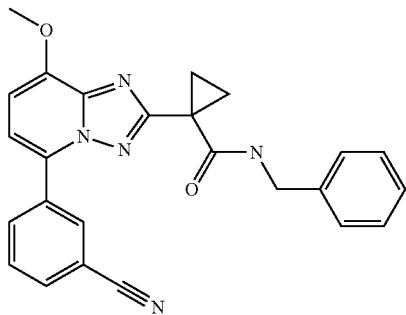 [SMILES: COc1ccc(-c2cccc(C#N)c2)n2nc(C3(C(=O)NCc4cccnc4)CC3)nc12]

1H NMR (600 MHz, DMSO) a 8.73 (t, J=5.9 Hz, 1H), 8.41 (t, J=1.6 Hz, 1H), 8.30 (ddd, J=8.0, 1.6, 1.2 Hz, 1H), 7.98-7.92 (m, 1H), 7.66 (t, J=7.9 Hz, 1H), 7.40 (d, J=8.1 Hz, 1H), 7.32-7.17 (m, 6H), 4.37 (d, J=6.0 Hz, 2H), 4.03 (s, 3H), 1.53 (dd, J=7.1, 3.4 Hz, 2H), 1.41 (dd, J=7.2, 3.4 Hz, 2H).

1-[5-(3-Cyano-phenyl)-8-methoxyl-[1,2,4]triazolo[1,5-a]pyridin-2-yl]-cyclopropanecarboxylic acid (2-sulfamoyl-ethyl)-amide (Compound 198)

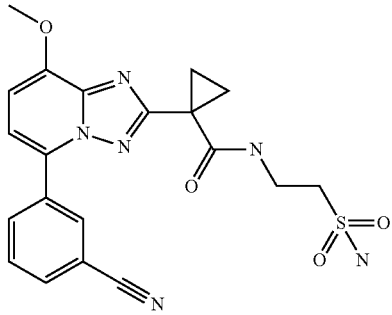 [SMILES: COc1ccc(-c2cccc(C#N)c2)n2nc(C3(C(=O)NCCS(N)(=O)=O)CC3)nc12]

1H NMR (600 MHz, DMSO) δ 8.43-8.33 (m, 2H), 8.28 (t, J=5.8 Hz, 1H), 7.97 (dt, J=7.8, 1.3 Hz, 1H), 7.77 (t, J=7.7 Hz, 1H), 7.44 (d, J=8.2 Hz, 1H), 7.31-7.17 (m, 1H), 6.89 (s, 2H), 4.04 (s, 3H), 3.59-3.45 (m, 2H), 3.13 (dd, J=8.0, 6.5 Hz, 2H), 1.57-1.44 (m, 2H), 1.42-1.26 (m, 2H).

1-[5-(3-Cyano-phenyl)-8-methoxy-[1,2,4]triazolo[1,5-a]pyridin-2-yl]-cyclopropanecarboxylic acid (2-methanesulfonyl-ethyl)-amide (Compound 199)

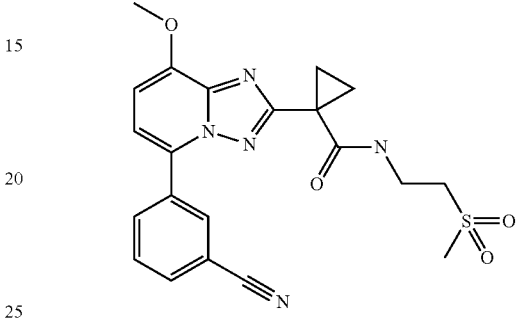

1H NMR (300 MHz, CDCl3) δ 9.35 (s, 1H), 8.20-8.11 (m, 2H), 7.78 (dt, J=7.7, 1.3 Hz, 1H), 7.70 (t, J=7.8 Hz, 1H), 7.06 (d, J=8.1 Hz, 1H), 6.94 (d, J=8.2 Hz, 1H), 4.11 (s, 3H), 3.84 (dd, J=12.3, 6.0 Hz, 2H), 3.32 (t, J=6.2 Hz, 2H), 2.95 (s, 3H), 1.83 (dd, J=7.3, 3.6 Hz, 2H), 1.68 (dd, J=7.4, 3.7 Hz, 2H).

Example 27

Compounds 200-202 were prepared according to General Procedure 4 using compound 191 (1-[5-(3-Cyano-phenyl)-8-methoxy-[1,2,4]triazolo[1,5-a]pyridin-2-yl]-cyclopropanecarboxylic acid) as starting material. The reaction mixtures were worked up by adding $H_2O$ (4 mL) to the reaction mixture the aqueous phase was extracted with DCM. The organic phase was dried ($MgSO_4$), filtered and concentrated and purified by flash chromatography.

3-{8-Methoxy-2-[1-(pyrrolidine-1-carbonyl)-cyclopropyl]-[1,2,4]triazolo[1,5-a]pyridin-5-yl}-benzonitrile (Compound 200)

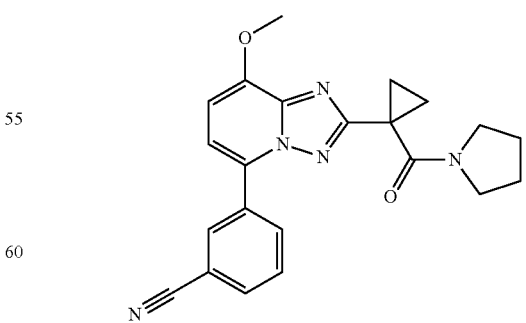

1H NMR (300 MHz, CDCl3) δ 8.26 (t, J=1.6 Hz, 1H), 8.16-8.10 (m, 1H), 7.72 (dt, J=7.8, 1.4 Hz, 1H), 7.59 (t, J=7.9 Hz, 1H), 7.03 (d, J=8.1 Hz, 1H), 6.92-6.82 (m, 1H), 4.08 (s,

3H), 3.59 (t, J=6.7 Hz, 2H), 3.37 (t, J=6.4 Hz, 2H), 1.96-1.76 (m, 4H), 1.70-1.64 (m, 2H), 1.59-1.50 (m, 2H).

2-Methyl-acrylic acid 2-({1-[5-(3-cyano-phenyl)-8-methoxy-[1,2,4]triazolo[1,5-a]pyridin-2-yl]-cyclopropanecarbonyl}-amino)-ethyl ester (Compound 201)

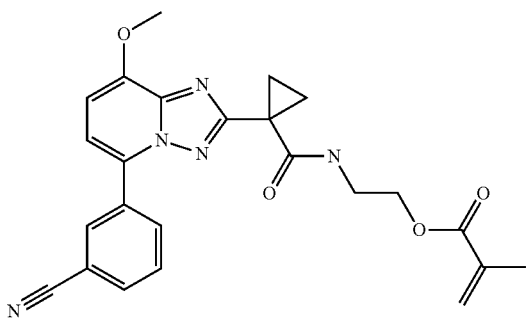 [SMILES: C=C(C)C(=O)OCCNC(=O)C1(c2nc3c(OC)ccc(-c4cccc(C#N)c4)n3n2)CC1]

1H NMR (300 MHz, CDCl3) δ 9.21 (t, J=5.3 Hz, 1H), 8.21-8.12 (m, 2H), 7.77 (ddd, J=7.7, 3.5, 2.1 Hz, 1H), 7.69-7.61 (m, 1H), 7.07 (dd, J=8.1, 2.4 Hz, 1H), 6.94 (dd, J=8.0, 3.6 Hz, 1H), 6.04 (dd, J=1.5, 0.9 Hz, 1H), 5.49 (p, J=1.5 Hz, 1H), 4.29-4.21 (m, 2H), 4.10 (d, J=4.3 Hz, 3H), 3.75-3.65 (m, 2H), 1.90-1.86 (m, 3H), 1.83 (dd, J=7.4, 3.4 Hz, 2H), 1.66-1.59 (m, 2H).

1-[5-(3-Cyano-phenyl)-8-methoxy-[1,2,4]triazolo[1,5-a]pyridin-2-yl]-cyclopropanecarboxylic acid (2-methoxy-ethyl)-amide (Compound 202)

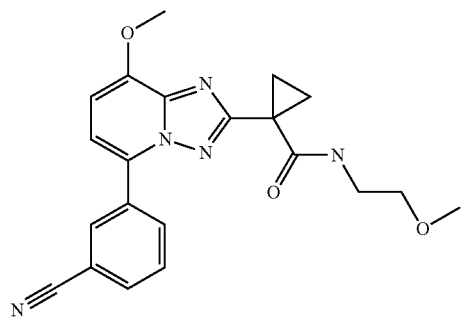 [SMILES: COCCNC(=O)C1(c2nc3c(OC)ccc(-c4cccc(C#N)c4)n3n2)CC1]

1H NMR (300 MHz, CDCl3) δ 9.09 (s, 1H), 8.23-8.17 (m, 1H), 8.17-8.11 (m, 1H), 7.77 (dt, J=7.7, 1.2 Hz, 1H), 7.65 (dd, J=11.9, 4.3 Hz, 1H), 7.05 (d, J=8.1 Hz, 1H), 6.97-6.89 (m, 1H), 4.11 (s, 3H), 3.62-3.52 (m, 2H), 3.49 (dd, J=8.1, 3.3 Hz, 2H), 3.27 (s, 3H), 1.83 (dd, J=7.5, 3.5 Hz, 2H), 1.65 (dd, J=7.5, 3.5 Hz, 2H).

Example 28

Compounds 203-209 were prepared according to General Procedure 4 using compound 147 1-[5-(4-Cyano-phenyl)-8-methoxy-[1,2,4]triazolo[1,5-a]pyridin-2-yl]-cyclopropanecarboxylic acid) as the starting compound:

1-[5-(4-Cyano-phenyl)-8-methoxy-[1,2,4]triazolo[1,5-a]pyridin-2-yl]-cyclopropanecarboxylic acid (pyridin-3-ylmethyl)-amide (Compound 203)

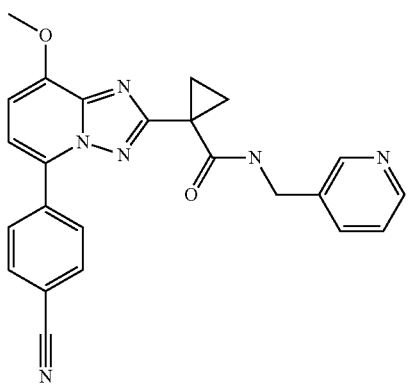 [SMILES: COc1ccc(-c2ccc(C#N)cc2)n2nc(C3(C(=O)NCc4cccnc4)CC3)nc12]

1H NMR (600 MHz, DMSO) δ 8.64 (t, J=5.9 Hz, 1H), 8.50 (d, J=1.9 Hz, 1H), 8.47 (dd, J=4.8, 1.6 Hz, 1H), 8.18-8.08 (m, 2H), 7.96-7.89 (m, 2H), 7.66 (dt, J=7.8, 2.0 Hz, 1H), 7.41 (d, J=8.2 Hz, 1H), 7.35-7.28 (m, 1H), 7.27-7.20 (m, 1H), 4.38 (d, J=5.9 Hz, 2H), 4.03 (s, 3H), 1.52 (dd, J=7.1, 3.5 Hz, 2H), 1.39 (dd, J=7.2, 3.5 Hz, 2H).

4-{8-Methoxy-2-[1-(4-methyl-piperazine-1-carbonyl)-cyclopropyl]-[1,2,4]triazolo[1,5-a]pyridin-5-yl}-benzonitrile (Compound 204)

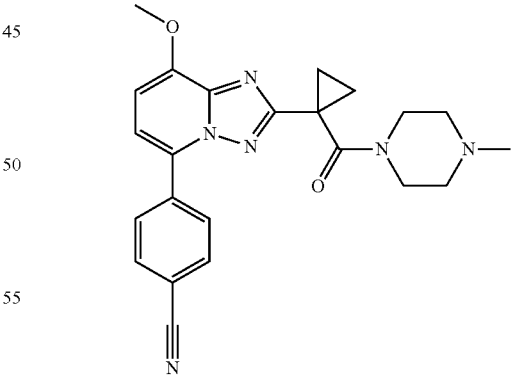

1H NMR (600 MHz, DMSO) δ 8.21-8.13 (m, 2H), 8.05-7.98 (m, 2H), 7.40 (d, J=8.2 Hz, 1H), 7.26-7.17 (m, 1H), 4.02 (s, 3H), 3.51 (s, 2H), 3.40-3.36 (m, 2H), 2.25 (s, 2H), 2.07 (s, 2H), 2.04 (s, 3H), 1.46 (dd, J=7.1, 4.2 Hz, 2H), 1.40 (dd, J=7.1, 4.1 Hz, 2H).

4-{8-Methoxy-2-[1-(morpholine-4-carbonyl)-cyclopropyl]-[1,2,4]triazolo[1,5-a]pyridin-5-yl}-benzonitrile (Compound 205)

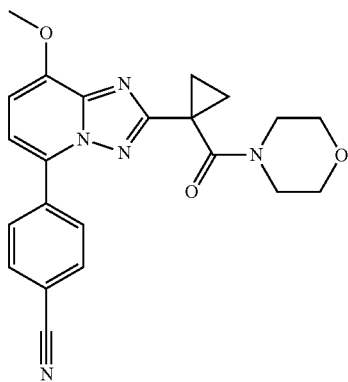 [SMILES: COc1ccc(-c2ccc(C#N)cc2)n2nc(C3(C(=O)N4CCOCC4)CC3)nc12]

1H NMR (600 MHz, DMSO) δ 8.22-8.13 (m, 2H), 8.06-8.00 (m, 2H), 7.41 (d, J=8.2 Hz, 1H), 7.26-7.17 (m, 1H), 4.02 (s, 3H), 3.54 (d, J=10.5 Hz, 4H), 3.46-3.35 (m, 4H), 1.47 (dd, J=7.1, 4.2 Hz, 2H), 1.43 (dd, J=7.1, 4.2 Hz, 2H).

1-[5-(4-Cyano-phenyl)-8-methoxy-[1,2,4]triazolo[1,5-a]pyridin-2-yl]-cyclopropanecarboxylic acid benzylamide (Compound 206)

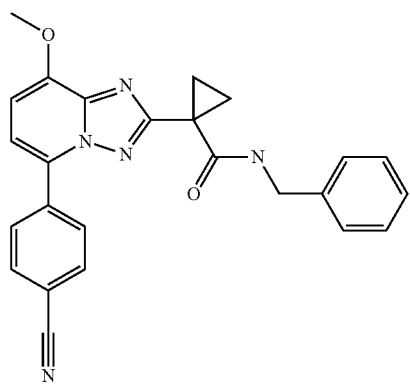 [SMILES: COc1ccc(-c2ccc(C#N)cc2)n2nc(C3(C(=O)NCc4ccccc4)CC3)nc12]

1H NMR (600 MHz, DMSO) δ 8.71 (t, J=5.9 Hz, 1H), 8.16-8.07 (m, 2H), 7.92-7.81 (m, 2H), 7.40 (d, J=8.2 Hz, 1H), 7.24-7.22 (m, 1H), 4.37 (d, J=5.9 Hz, 2H), 4.03 (s, 3H), 1.54 (dd, J=7.1, 3.4 Hz, 2H), 1.41 (dd, J=7.2, 3.4 Hz, 2H).

1-[5-(4-Cyano-phenyl)-8-methoxy-[1,2,4]triazolo[1,5-a]pyridin-2-yl]-cyclopropanecarboxylic acid (2-sulfamoyl-ethyl)-amide (Compound 207)

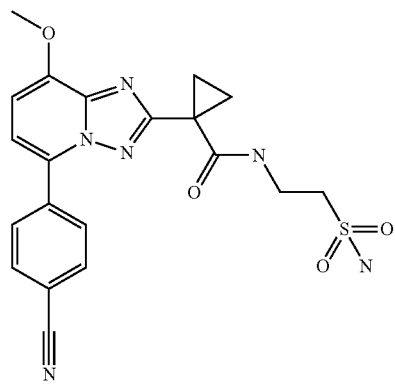 [SMILES: COc1ccc(-c2ccc(C#N)cc2)n2nc(C3(C(=O)NCCS(N)(=O)=O)CC3)nc12]

1H NMR (600 MHz, DMSO) δ 8.27 (t, J=5.7 Hz, 1H), 8.23-8.18 (m, 2H), 8.04-7.99 (m, 2H), 7.44 (d, J=8.2 Hz, 1H), 7.25 (d, J=8.3 Hz, 1H), 6.92 (s, 2H), 4.04 (s, 3H), 3.59-3.48 (m, 2H), 3.14 (dd, J=7.9, 6.5 Hz, 2H), 1.50 (dd, J=7.1, 3.5 Hz, 2H), 1.37 (dd, J=7.2, 3.5 Hz, 2H).

1-[5-(4-Cyano-phenyl)-8-methoxy-[1,2,4]triazolo[1,5-a]pyridin-2-yl]-cyclopropanecarboxylic acid (2-methanesulfonyl-ethyl)-amide (Compound 208)

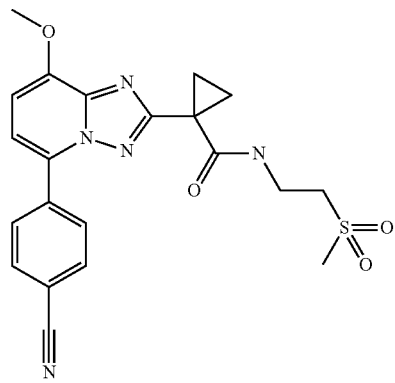 [SMILES: COc1ccc(-c2ccc(C#N)cc2)n2nc(C3(C(=O)NCCS(C)(=O)=O)CC3)nc12]

1H NMR (600 MHz, DMSO) δ 8.35 (t, J=5.7 Hz, 1H), 8.22-8.17 (m, 2H), 8.06-7.99 (m, 2H), 7.44 (d, J=8.2 Hz, 1H), 7.25 (d, J=8.3 Hz, 1H), 4.05 (d, J=15.5 Hz, 3H), 3.55 (dd,

J=12.6, 6.6 Hz, 2H), 3.27 (t, J=6.7 Hz, 2H), 2.98 (s, 3H), 1.51 (dd, J=7.1, 3.5 Hz, 2H), 1.37 (dd, J=7.2, 3.5 Hz, 2H).

1-[5-(4-Cyano-phenyl)-8-methoxy-[1,2,4]triazolo[1,5-a]pyridin-2-yl]-cyclopropanecarboxylic acid isopropylamide (Compound 209)

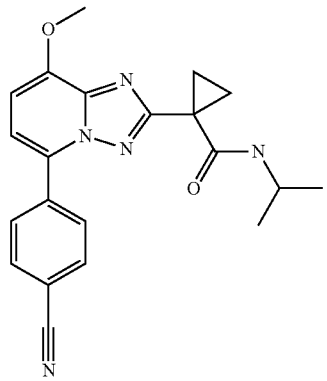 [SMILES: COc1ccc(-c2ccc(C#N)cc2)n2nc(C3(C(=O)NC(C)C)CC3)nc12]

1H NMR (300 MHz, CDCl3) δ 8.73 (m, H), 8.06-7.99 (m, 2H), 7.85-7.78 (m, 2H), 7.07 (d, J=8.1 Hz, 1H), 6.93 (d, J=8.2 Hz, 1H), 4.20-4.05 (m, 4H), 1.83 (m, 2H), 1.71-1.57 (m, 2H), 1.16 (s, 3H), 1.14 (s, 3H).

Example 29

Compounds 210-220 were prepared according to general procedure 4 using compound 192 (1-[5-(4-Cyano-phenyl)-8-methoxy-[1,2,4]triazolo[1,5-a]pyridin-2-yl]-cyclopropanecarboxylic acid) as the starting compound. The reaction mixtures were worked up by adding H₂O (4 mL) to the reaction mixture or adding aq. Na₂CO₃ for the reactions run with HCl salts of the amine. The aqueous phase was extracted with DCM (2×4 mL). The organic phase was put on a separation cartridge (Chromabond, PTS), concentrated and purified by preparative HPLC/MS.

1-[5-(4-Cyano-phenyl)-8-methoxy-[1,2,4]triazolo[1,5-a]pyridin-2-yl]-cyclopropanecarboxylic acid methylamide (Compound 210)

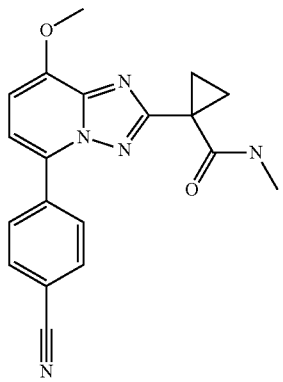 [SMILES: CNC(=O)C1(c2nc3c(OC)ccc(-c4ccc(C#N)cc4)n3n2)CC1]

1H NMR (300 MHz, CDCl3) δ 8.81 (s, 1H), 8.09-7.95 (m, 2H), 7.86-7.74 (m, 2H), 7.09 (d, J=8.2 Hz, 1H), 7.00-6.86 (m, 1H), 4.11 (s, 3H), 2.90 (d, J=4.8 Hz, 3H), 1.83 (dd, J=7.5, 3.4 Hz, 2H), 1.60 (dd, J=7.4, 3.5 Hz, 2H).

1-[5-(4-Cyano-phenyl)-8-methoxy-[1,2,4]triazolo[1,5-a]pyridin-2-yl]-cyclopropanecarboxylic acid ethylamide (Compound 211)

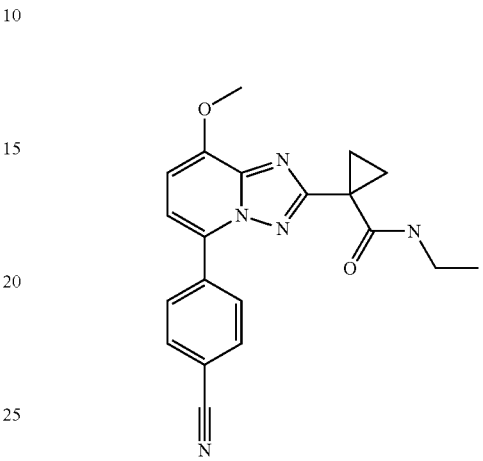

1H NMR (300 MHz, CDCl3) δ 8.79 (s, 1H), 8.05-7.99 (m, 2H), 7.86-7.79 (m, 2H), 7.08 (d, J=8.2 Hz, 1H), 6.94 (d, J=8.2 Hz, 1H), 4.11 (s, 3H), 3.37 (qd, J=7.3, 5.3 Hz, 2H), 1.83 (dd, J=7.4, 3.4 Hz, 2H), 1.63 (dd, J=7.4, 3.4 Hz, 3H), 1.16 (t, J=7.3 Hz, 3H).

1-[5-(4-Cyano-phenyl)-8-methoxy-[1,2,4]triazolo[1,5-a]pyridin-2-yl]-cyclopropanecarboxylic acid propylamide (Compound 212)

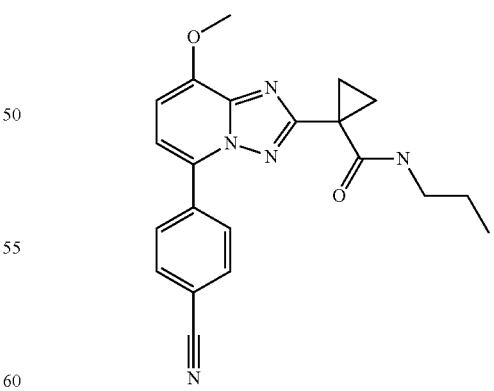

1H NMR (300 MHz, CDCl3) δ 8.87 (s, 1H), 8.08-7.92 (m, 2H), 7.87-7.73 (m, 2H), 7.06 (d, J=8.1 Hz, 1H), 6.93 (d, J=8.2 Hz, 1H), 4.11 (s, 3H), 3.30 (td, J=7.0, 5.5 Hz, 2H), 3.30 (td,

J=7.0, 5.5 Hz, 2H), 1.88-1.75 (m, 2H), 1.64 (dd, J=7.5, 3.4 Hz, 2H), 1.60-1.46 (m, 2H), 0.90 (t, J=7.4 Hz, 3H).

1-[5-(4-Cyano-phenyl)-8-methoxy-[1,2,4]triazolo[1,5-a]pyridin-2-yl]-cyclopropanecarboxylic acid cyclopropylamide (Compound 213)

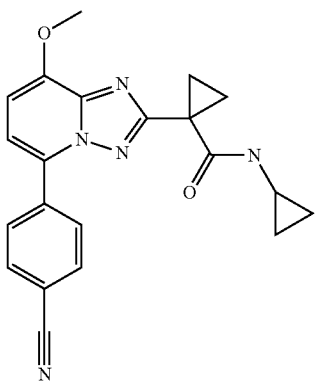 [SMILES: COc1ccc(-c2ccc(C#N)cc2)n2nc(C3(C(=O)NC4CC4)CC3)nc12]

1H NMR (300 MHz, CDCl3) δ 8.96 (s, 1H), 8.04-7.96 (m, 2H), 7.87-7.77 (m, 2H), 7.07 (d, J=8.1 Hz, 1H), 6.93 (d, J=8.2 Hz, 1H), 4.11 (s, 3H), 2.83 (dq, J=11.0, 3.7 Hz, 1H), 1.85 (dd, J=7.5, 3.3 Hz, 2H), 1.64 (dd, J=7.5, 3.3 Hz, 2H), 0.87-0.70 (m, 2H), 0.52-0.38 (m, 2H).

1-[5-(4-Cyano-phenyl)-8-methoxy-[1,2,4]triazolo[1,5-a]pyridin-2-yl]-cyclopropanecarboxylic acid isobutyl-amide (Compound 214)

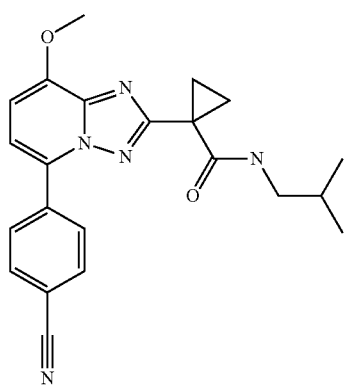 [SMILES: COc1ccc(-c2ccc(C#N)cc2)n2nc(C3(C(=O)NCC(C)C)CC3)nc12]

1H NMR (300 MHz, CDCl3) δ 8.96 (s, 1H), 8.06-7.95 (m, 2H), 7.85-7.73 (m, 2H), 7.06 (d, J=8.1 Hz, 1H), 6.93 (d, J=8.1 Hz, 1H), 4.11 (s, 3H), 3.16 (dd, J=6.7, 5.6 Hz, 2H), 1.83 (dd,

J=7.4, 3.4 Hz, 2H), 1.80-1.69 (m, 1H), 1.65 (dd, J=7.4, 3.4 Hz, 3H), 0.88 (d, J=6.7 Hz, 6H).

1-[5-(4-Cyano-phenyl)-8-methoxy-[1,2,4]triazolo[1,5-a]pyridin-2-yl]-cyclopropanecarboxylic acid cyanomethyl-amide (Compound 215)

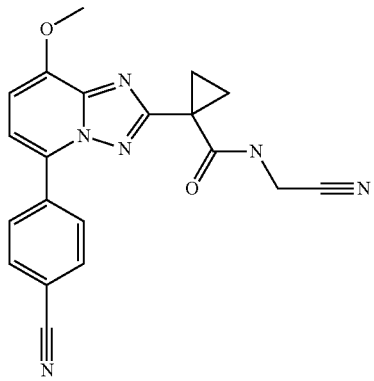 [SMILES: COc1ccc(-c2ccc(C#N)cc2)n2nc(C3(C(=O)NCC#N)CC3)nc12]

1H NMR (300 MHz, CDCl3) δ 9.74 (t, J=5.2 Hz, 1H), 8.07-7.94 (m, 2H), 7.92-7.78 (m, 2H), 7.11 (d, J=8.1 Hz, 1H), 6.97 (d, J=8.2 Hz, 1H), 4.30 (d, J=5.6 Hz, 2H), 4.12 (s, 3H), 1.89 (dd, J=7.5, 3.6 Hz, 2H), 1.72 (dd, J=7.5, 3.7 Hz, 2H).

1-[5-(4-Cyano-phenyl)-8-methoxy-[1,2,4]triazolo[1,5-a]pyridin-2-yl]-cyclopropanecarboxylic acid (2-acetylamino-ethyl)-amide (Compound 216)

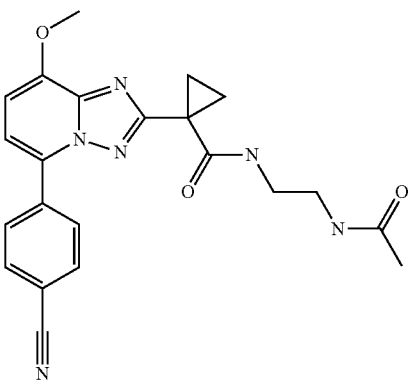 [SMILES: COc1ccc(-c2ccc(C#N)cc2)n2nc(C3(C(=O)NCCNC(C)=O)CC3)nc12]

1H NMR (300 MHz, CDCl3) δ 9.16 (d, J=5.6 Hz, 1H), 8.06-7.98 (m, 2H), 7.83 (d, J=8.6 Hz, 2H), 7.10 (d, J=8.2 Hz, 1H), 6.96 (d, J=8.2 Hz, 1H), 6.50 (s, 1H), 4.11 (s, 3H), 3.51

(dd, J=11.7, 5.6 Hz, 2H), 3.41 (dd, J=11.1, 5.3 Hz, 2H), 1.95 (s, 3H), 1.81 (dd, J=7.4, 3.6 Hz, 2H), 1.64 (dd, J=7.4, 3.6 Hz, 2H).

1-[5-(4-Cyano-phenyl)-8-methoxy-[1,2,4]triazolo[1,5-a]pyridin-2-yl]-cyclopropanecarboxylic acid (2-methanesulfonylamino-ethyl)-amide (Compound 217)

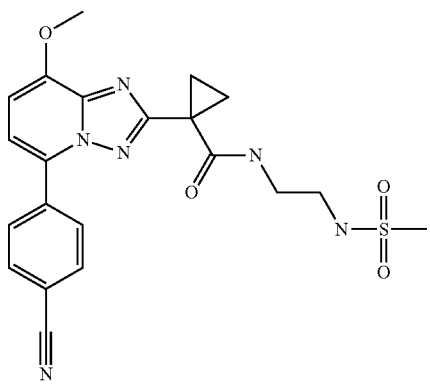 [SMILES: COc1ccc(-c2ccc(C#N)cc2)n2nc(C3(C(=O)NCCNS(C)(=O)=O)CC3)nc12]

1H NMR (300 MHz, DMSO) δ 8.33 (t, J=5.6 Hz, 1H), 8.24-8.16 (m, 2H), 8.08-7.96 (m, 2H), 7.44 (d, J=8.2 Hz, 1H), 7.26 (d, J=8.3 Hz, 1H), 7.09 (s, 1H), 4.05 (s, 3H), 3.28 (dd, J=12.5, 6.3 Hz, 2H), 3.03 (s, 2H), 2.90 (s, 3H), 1.52 (dd, J=7.0, 3.6 Hz, 2H), 1.38 (dd, J=7.0, 3.5 Hz, 2H).

1-[5-(4-Cyano-phenyl)-8-methoxy-[1,2,4]triazolo[1,5-a]pyridin-2-yl]-cyclopropanecarboxylic acid (3-morpholin-4-yl-3-oxo-propyl)-amide (Compound 218)

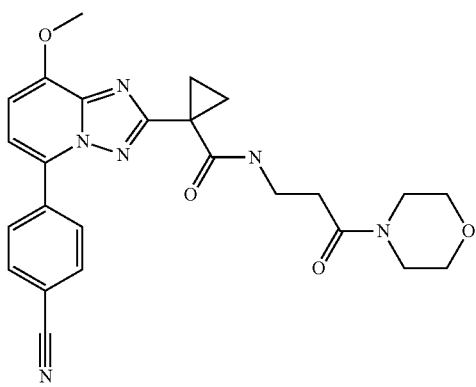 [SMILES: COc1ccc(-c2ccc(C#N)cc2)n2nc(C3(C(=O)NCCC(=O)N4CCOCC4)CC3)nc12]

1H NMR (300 MHz, CDCl3) δ 9.09 (t, J=5.8 Hz, 1H), 8.12-8.06 (m, 2H), 7.90-7.85 (m, 2H), 7.10-7.06 (m, 1H), 6.93 (d, J=8.3 Hz, 1H), 4.10 (d, J=4.3 Hz, 3H), 3.70-3.61 (m, 6H), 3.58 (d, J=4.9 Hz, 2H), 3.50-3.39 (m, 2H), 2.60 (t, J=6.1 Hz, 2H), 1.80 (dd, J=7.3, 3.6 Hz, 2H), 1.63 (dd, J=7.5, 3.5 Hz, 2H).

1-[5-(4-Cyano-phenyl)-8-methoxy-[1,2,4]triazolo[1,5-a]pyridin-2-yl]-cyclopropanecarboxylic acid (2-dimethylsulfamoyl-ethyl)-amide (Compound 219)

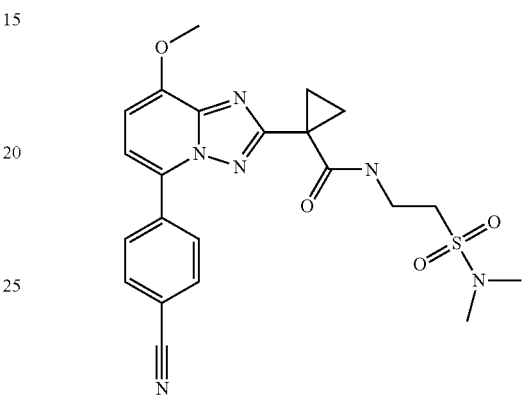

1-[5-(4-Cyano-phenyl)-8-methoxy-[1,2,4]triazolo[1,5-a]pyridin-2-yl]-cyclopropanecarboxylic acid [2-(methanesulfonyl-methyl-amino)-ethyl]-amide (Compound 220)

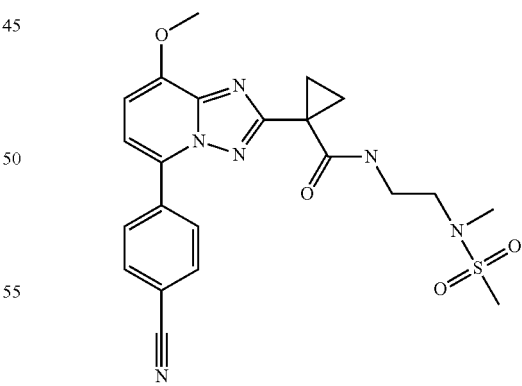

Example 30

Compounds 221-226 were prepared according to General Procedure 4 using compound 193 (1-[5-(3-Acetyl-phenyl)-8- methoxy-[1,2,4]triazolo[1,5-a]pyridin-2-yl]-cyclopropan-ecarboxylic acid) as the starting compound.

1-[5-(3-Acetyl-phenyl)-8-methoxy-[1,2,4]triazolo[1,5-a]pyridin-2-yl]-cyclopropanecarboxylic acid (pyridin-3-ylmethyl)-amide (Compound 221)

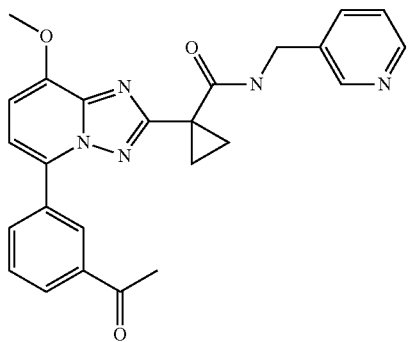

1H NMR (600 MHz, DMSO) δ 8.77 (t, J=6.0 Hz, 1H), 8.50 (t, J=1.7 Hz, 1H), 8.47 (d, J=1.8 Hz, 1H), 8.44 (dd, J=4.8, 1.6 Hz, 1H), 8.21-8.17 (m, 1H), 8.07-8.03 (m, 1H), 7.64 (ddd, J=7.7, 4.8, 2.8 Hz, 2H), 7.38 (d, J=8.1 Hz, 1H), 7.31-7.26 (m, 1H), 7.25-7.21 (m, 1H), 4.39 (d, J=6.0 Hz, 2H), 4.03 (s, 3H), 2.62 (s, 3H), 1.52 (dd, J=7.1, 3.5 Hz, 2H), 1.40 (dd, J=7.2, 3.5 Hz, 2H).

1-(3-{8-Methoxy-2-[1-(4-methyl-piperazine-1-carbonyl)-cyclopropyl]-[1,2,4]triazolo[1,5-a]pyridin-5-yl}-phenyl)-ethanone (Compound 222)

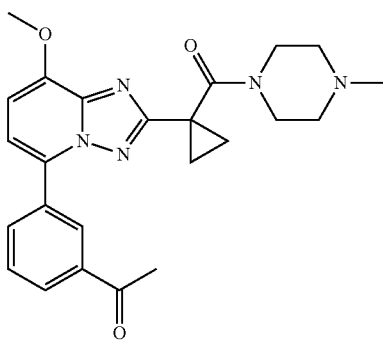 [SMILES: COc1ccc(-c2cccc(C(C)=O)c2)n2nc(C3(C(=O)N4CCN(C)CC4)CC3)nc12]

1H NMR (600 MHz, DMSO) δ 8.51 (t, J=1.7 Hz, 1H), 8.20-8.17 (m, 1H), 8.10-8.06 (m, 1H), 7.69 (dd, J=9.7, 5.9 Hz, 1H), 7.36 (d, J=8.2 Hz, 1H), 7.22-7.19 (m, 1H), 4.02 (s, 3H), 3.49 (s, 2H), 3.41-3.36 (m, 2H), 2.65 (s, 3H), 2.20 (s, 2H), 2.07 (s, 2H), 2.01 (s, 3H), 1.47 (dd, J=7.1, 4.2 Hz, 2H), 1.39 (dd, J=7.1, 4.1 Hz, 2H).

1-(3-{8-Methoxy-2-[1-(morpholine-4-carbonyl)-cyclopropyl]-[1,2,4]-triazolo[1,5-a]pyridin-5-yl}-phenyl)-ethanone (Compound 223)

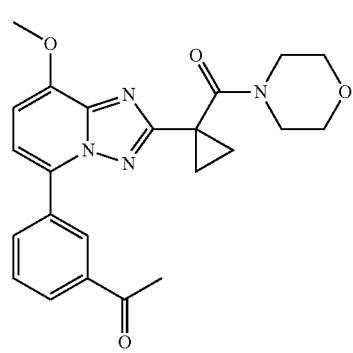 [SMILES: COc1ccc(-c2cccc(C(C)=O)c2)n2nc(C3(C(=O)N4CCOCC4)CC3)nc12]

1H NMR (600 MHz, DMSO) δ 8.52 (t, J=1.7 Hz, 1H), 8.19-8.13 (m, 1H), 8.11-8.05 (m, 1H), 7.70 (dd, J=9.7, 5.9 Hz, 1H), 7.36 (d, J=8.1 Hz, 1H), 07.23-7.17 (m, 1H), 4.02 (s, 3H), 3.51 (s, 4H), 3.42 (d, J=15.2 Hz, 4H), 2.65 (s, 3H), 1.49-1.45 (m, 2H), 1.45-1.40 (m, 2H).

1-[5-(3-Acetyl-phenyl)-8-methoxy-[1,2,4]triazolo[1,5-a]pyridin-2-yl]-cyclopropanecarboxylic acid benzylamide (Compound 224)

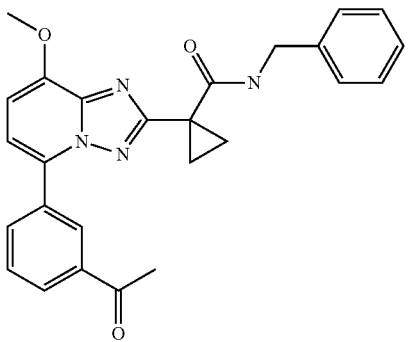 [SMILES: COc1ccc(-c2cccc(C(C)=O)c2)n2nc(C3(C(=O)NCc4ccccc4)CC3)nc12]

1H NMR (600 MHz, DMSO) δ 8.84 (t, J=5.9 Hz, 1H), 8.50 (t, J=1.7 Hz, 1H), 8.26-8.13 (m, 1H), 8.10-7.99 (m, 1H), 7.61 (dd, J=9.7, 5.9 Hz, 1H), 7.37 (d, J=8.1 Hz, 1H), 7.30-7.17 (m,

6H), 4.38 (d, J=6.0 Hz, 2H), 4.03 (s, 3H), 2.61 (s, 3H), 1.54 (dd, J=7.1, 3.4 Hz, 2H), 1.42 (dd, J=7.2, 3.4 Hz, 2H).

1-[5-(3-Acetyl-phenyl)-8-methoxy-[1,2,4]triazolo[1,5-a]pyridin-2-yl]-cyclopropanecarboxylic acid (2-sulfamoyl-ethyl)-amide (Compound 225)

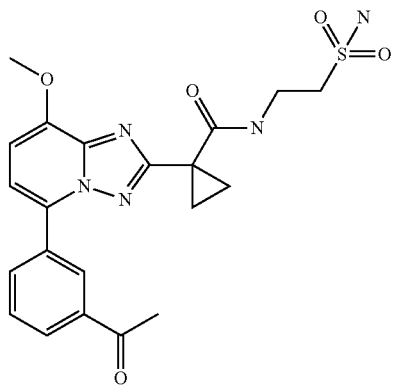 [SMILES: COc1ccc(-c2cccc(C(C)=O)c2)n2nc(C3(C(=O)NCCS(N)(=O)=O)CC3)nc12]

1H NMR (600 MHz, DMSO) δ 8.52 (t, J=1.7 Hz, 1H), 8.36 (t, J=5.8 Hz, 1H), 8.24 (ddd, J=7.7, 1.7, 1.1 Hz, 1H), 8.10-8.05 (m, 1H), 7.71 (dd, J=9.7, 5.9 Hz, 1H), 7.40 (d, J=8.1 Hz, 1H), 7.27-7.21 (m, 1H), 6.90 (s, 2H), 4.04 (s, 3H), 3.58-3.49 (m, 2H), 3.17-3.07 (m, 2H), 2.66 (s, 3H), 1.50 (dd, J=7.1, 3.5 Hz, 2H), 1.37 (dd, J=7.2, 3.5 Hz, 2H).

1-[5-(3-Acetyl-phenyl)-8-methoxy-[1,2,4]triazolo[1,5-a]pyridin-2-yl]-cyclopropanecarboxylic acid (2-methanesulfonyl-ethyl)-amide (Compound 226)

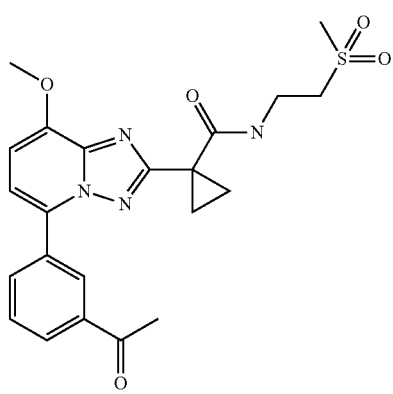 [SMILES: COc1ccc(-c2cccc(C(C)=O)c2)n2nc(C3(C(=O)NCCS(C)(=O)=O)CC3)nc12]

1H NMR (600 MHz, DMSO-SPE) δ 8.53 (t, J=1.7 Hz, 1H), 8.46 (t, J=5.7 Hz, 1H), 8.25-8.18 (m, 1H), 8.11-8.06 (m, 1H), 7.72 (dd, J=9.7, 5.9 Hz, 1H), 7.40 (d, J=8.1 Hz, 1H), 7.27-7.22 (m, 1H), 4.04 (s, 3H), 3.57 (dd, J=12.9, 6.6 Hz, 2H), 3.27 (t, J=6.8 Hz, 2H), 2.97 (s, 3H), 2.66 (s, 3H), 1.51 (dd, J=7.1, 3.5 Hz, 2H), 1.39 (dd, J=7.3, 3.5 Hz, 2H).

Example 31

1-[5-(3-Cyano-phenyl)-8-methoxy-[1,2,4]triazolo[1,5-a]pyridin-2-yl]-cyclopropanecarboxylic acid (2-hydroxy-ethyl)-amide (Compound 228)

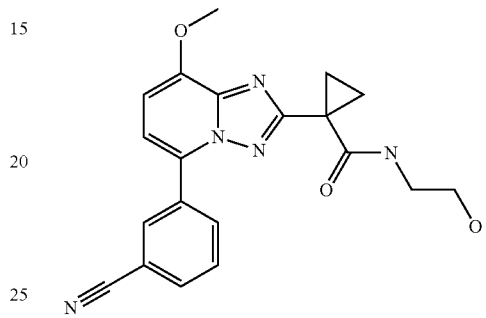

Compound 201

(0.03 g, 0.07 mmol) was dissolved in 1,4-dioxan (3 mL). LiOH (0.09 g, 0.21 mmol) in H$_2$O (0.5 mL) was added. The suspension was stirred at RT overnight. The reaction mixture was concentrated in vacuo and H$_2$O was added. The aqueous phase was acidified with 4N HCl to pH 1. The aqueous phase was extracted with EtOAc (×2) and DCM (×2). The combined organic phases were dried over MgSO$_4$, filtered and concentrated in vacuo. This afforded the title compound.

1H NMR (300 MHz, CDCl3) δ 9.22 (s, 1H), 8.20 (s, 1H), 8.16-8.08 (m, 1H), 7.77 (d, J=7.8 Hz, 1H), 7.66 (t, J=7.8 Hz, 1H), 7.06 (d, J=8.1 Hz, 1H), 6.94 (d, J=8.1 Hz, 1H), 4.11 (s, 3H), 3.81-3.73 (m, 2H), 3.54 (dd, J=10.0, 5.4 Hz, 2H), 1.85 (dd, J=7.5, 3.5 Hz, 2H), 1.68 (dd, J=7.4, 3.6 Hz, 2H).

General Procedure 5

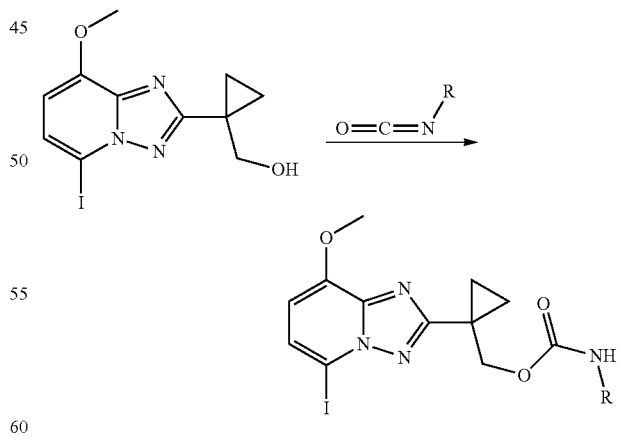

[1-(5-Iodo-8-methoxy-[1,2,4]triazolo[1,5-a]pyridin-2-yl)-cyclopropyl]-methanol (0.1 g, 0.29 mmol) was dissolved in CH$_3$CN (2 mL). Et3N (0.29 g, 2.9 mmol) was added and isocyanate (3.5 mmol) was added. The solution was stirred at 65° C. over night. The crude product was purified by preparative HPLC/MS.

General Procedure 6

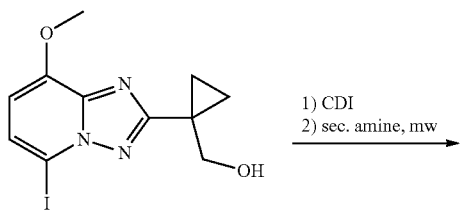

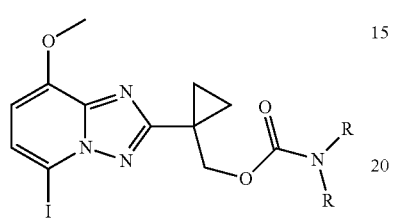

Compound 308 ([1-(5-Iodo-8-methoxy-[1,2,4]triazolo[1,5-a]pyridin-2-yl)-cyclopropyl]-methanol) (0.8 g, 0.23 mmol) was dissolved in CH$_3$CN. 1,1-Carbonyl-diimidazole (0.19 g, 1.2 mmol) was added and mixture was stirred at RT for 15 min. The amine (2.3 mmol) was added and the suspension was heated in the microwave oven at 100° C. for 10 min. The crude product was purified by preparative HPLC/MS.

General Procedure 7 (Suzuki Coupling of Iodo-Derivatives)

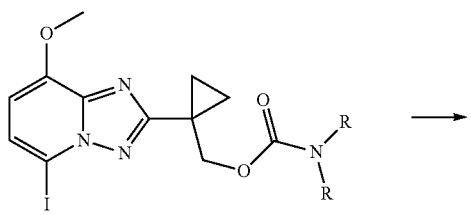

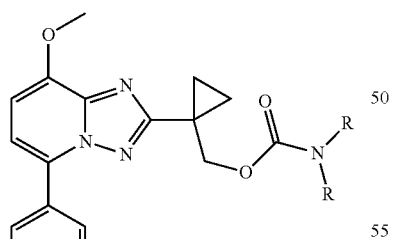

Dioxan and H$_2$O were degassed. Under an argon atmosphere the iodide (0.017 g, 0.04 mmol) and boronic acid or the boronic acid pinacol ester (0.12 mmol) were dissolved in 1,4-dioxan (0.3 mL). Pd$_2$(dba)$_3$ (ca. 0.4 mg, 0.0004 mmol) and PCy$_3$ (ca. 0.2 mg, 0.0008 mmol) were added. K$_3$PO$_4$ (0.03 g, 0.14 mmol) in H$_2$O (0.14 mL) was added. The suspension was heated in the microwave oven at 120° C. for 10 min, after which it was filtered and purified by preparative HPLC/MS.

Example 32

Compounds 229, 230, 232, 233, 235-237, 239-241 were prepared according to General Procedure 5 followed by General Procedure 7.

Example 33

Compounds 231, 234, 238, 242-247 were prepared according to General Procedure 6 followed by General Procedure 7.

Cyclohexyl-carbamic acid 1-[5-(5-cyano-pyridin-3-yl)-8-methoxy-[1,2,4]triazolo[1,5-a]pyridin-2-yl]-cyclopropylmethyl ester (Compound 2291

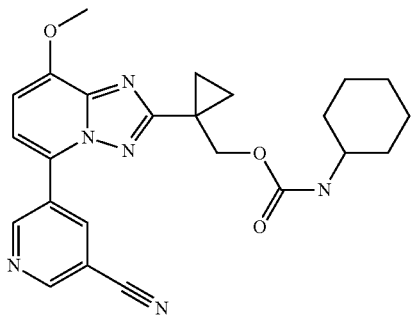 [SMILES: COc1ccc(-c2cncc(C#N)c2)n2nc(C3(COC(=O)NC4CCCCC4)CC3)nc12]

1H NMR (300 MHz, DMSO) δ 9.46 (d, J=1.7 Hz, 1H), 9.10 (d, J=1.8 Hz, 1H), 8.89 (s, 1H), 7.60-7.53 (m, 1H), 7.51 (d, J=8.1 Hz, 1H), 7.22 (d, J=8.3 Hz, 1H), 6.92 (d, J=7.7 Hz, 1H), 4.41 (s, 2H), 4.02 (s, 3H), 3.30-3.10 (bs, 1H), 1.72-1.43 (m, 5H), 1.31-0.89 (m, 9H).

Propyl-carbamic acid 1-[8-methoxy-5-(1-oxo-indan-5-yl)-[1,2,4]triazolo[1,5-a]pyridin-2-yl]-cyclopropyl-methyl ester (Compound 230)

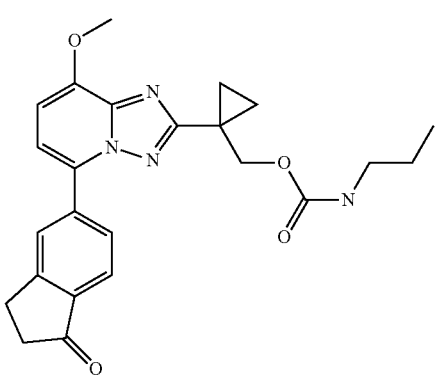 [SMILES: CCCNC(=O)OCC1(c2nc3c(OC)ccc(-c4ccc5c(c4)CCC5=O)n3n2)CC1]

1H NMR (300 MHz, DMSO) δ 8.20 (s, 1H), 8.00 (dd, J=8.1, 1.2 Hz, 1H), 7.73 (d, J=8.1 Hz, 1H), 7.36 (d, J=8.2 Hz, 1H), 7.20-7.14 (m, 1H), 7.05 (t, J=5.5 Hz, 1H), 4.40 (s, 2H), 4.01 (s, 3H), 3.24-3.15 (m, 2H), 2.88 (dd, J=13.2, 6.6 Hz, 2H), 2.77-2.65 (m, 2H), 1.39-1.21 (m, 4H), 1.12 (dd, J=6.6, 4.0 Hz, 2H), 0.76 (t, J=7.4 Hz, 3H).

Dimethyl-carbamic acid 1-[5-(4-cyano-3-methoxy-phenyl)-8-methoxy-[1,2,4]triazolo[1,5-a]pyridin-2-yl]-cyclopropylmethyl ester (Compound 231)

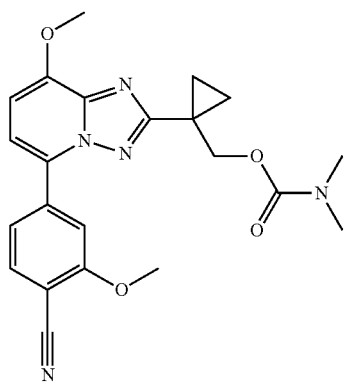 [SMILES: COc1cc(-c2ccc(OC)c3nc(C4(COC(=O)N(C)C)CC4)nn23)ccc1C#N]

1H NMR (300 MHz, DMSO) δ 8.00 (d, J=1.4 Hz, 1H), 7.86 (d, J=8.1 Hz, 1H), 7.68 (dd, J=8.2, 1.5 Hz, 1H), 7.46 (d, J=8.2 Hz, 1H), 7.18 (d, J=8.3 Hz, 1H), 4.44 (s, 2H), 4.02 (s, 3H), 4.00 (s, 3H), 2.73 (bs, 6H), 1.28 (dd, J=6.7, 4.1 Hz, 2H), 1.15 (dd, J=6.6, 4.0 Hz, 2H).

Isopropyl-carbamic acid 1-[5-(5-cyano-pyridin-3-yl)-8-methoxy-[1,2,4]triazolo[1,5-a]pyridin-2-yl]-cyclopropylmethyl ester (Compound 232)

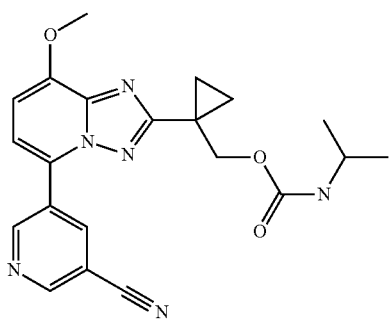 [SMILES: COc1ccc(-c2cncc(C#N)c2)n2nc(C3(COC(=O)NC(C)C)CC3)nc12]

1H NMR (300 MHz, DMSO) δ 9.46 (d, J=2.2 Hz, 1H), 9.10 (d, J=1.9 Hz, 1H), 8.89 (t, J=2.1 Hz, 1H), 7.51 (d, J=8.2 Hz, 1H), 7.22 (d, J=8.3 Hz, 1H), 6.91 (d, J=7.1 Hz, 1H), 4.41

(s, 2H), 4.04 (s, 3H), 3.66-3.46 (m, 1H), 1.26 (dd, J=6.6, 4.1 Hz, 2H), 1.13 (dd, J=6.6, 4.0 Hz, 2H), 0.97 (d, J=6.5 Hz, 6H).

Propyl-carbamic acid 1-[8-methoxy-5-(1-oxo-indan-4-yl)-[1,2,4]triazolo[1,5-a]pyridin-2-yl]-cyclopropyl-methyl ester (Compound 233)

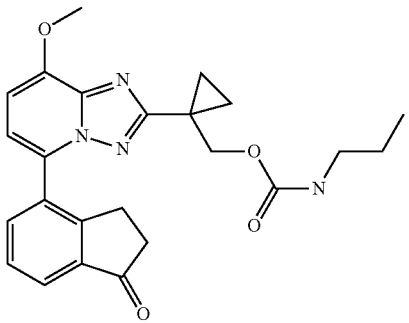 [SMILES: CCCNC(=O)OCC1(c2nc3c(OC)ccc(-c4cccc5c4CCC5=O)n3n2)CC1]

1H NMR (300 MHz, DMSO) δ 7.87 (dd, J=7.5, 1.0 Hz, 1H), 7.83-7.76 (m, 1H), 7.59 (t, J=7.6 Hz, 1H), 7.21-7.12 (m, 2H), 7.04 (t, J=5.7 Hz, 1H), 4.31 (s, 2H), 4.02 (s, 3H), 3.05-2.96 (m, 2H), 2.85 (dd, J=13.3, 6.6 Hz, 2H), 2.63 (dd, J=6.7, 4.8 Hz, 2H), 1.40-1.24 (m, 2H), 1.21 (dd, J=6.5, 4.1 Hz, 2H), 1.08 (dd, J=6.5, 4.0 Hz, 2H), 0.78 (t, J=7.4 Hz, 3H).

Pyrrolidine-1-carboxylic acid 1-[5-(4-cyano-3-methoxy-phenyl)-8-methoxy-[1,2,4]-triazolo[1,5-a]pyridin-2-yl]-cyclopropylmethyl ester (Compound 234)

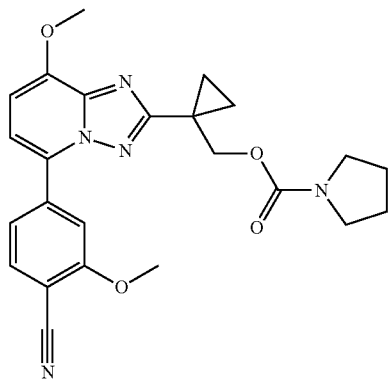 [SMILES: COc1cc(-c2ccc(OC)c3nc(C4(COC(=O)N5CCCC5)CC4)nn23)ccc1C#N]

1H NMR (300 MHz, DMSO) δ 8.01 (d, J=1.2 Hz, 1H), 7.86 (d, J=8.2 Hz, 1H), 7.67 (dd, J=8.2, 1.4 Hz, 1H), 7.46 (d, J=8.3 Hz, 1H), 7.18 (d, J=8.3 Hz, 1H), 4.44 (s, 2H), 4.02 (s,

3H), 4.00 (s, 3H), 3.25-3.15 (m, 2H), 3.15-3.00 (m, 2H), 1.68 (bs, 4H), 1.27 (dd, J=7.1, 4.1 Hz, 2H), 1.15 (dd, J=7.1, 4.1 Hz, 2H).

Isopropyl-carbamic acid 1-[5-(4-cyano-3-methoxy-phenyl)-8-methoxy-[1,2,4]triazolo[1,5-a]pyridin-2-yl]-cyclopropylmethyl ester (Compound 235)

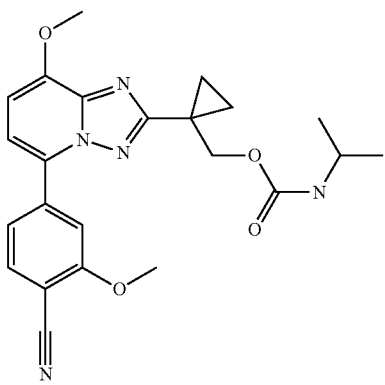 [SMILES: COc1cc(-c2ccc(OC)c3nc(C4(COC(=O)NC(C)C)CC4)nn23)ccc1C#N]

1H NMR (300 MHz, DMSO) δ 8.03 (s, 1H), 7.87-7.81 (m, 1H), 7.68 (dd, J=8.2, 1.3 Hz, 1H), 7.48 (d, J=8.2 Hz, 1H), 7.19 (d, J=8.3 Hz, 1H), 6.94 (d, J=7.5 Hz, 1H), 4.41 (s, 2H), 4.02 (s, 3H), 4.01 (s, 3H), 3.60-3.44 (m, 1H), 1.27 (dd, J=6.5, 4.1 Hz, 2H), 1.14 (dd, J=6.5, 4.0 Hz, 2H), 0.96 (d, J=6.5 Hz, 6H).

Propyl-carbamic acid 1-[5-(5-cyano-pyridin-3-yl)-8-methoxy-[1,2,4]triazolo[1,5-a]pyridin-2-yl]-cyclopropylmethyl ester (Compound 236)

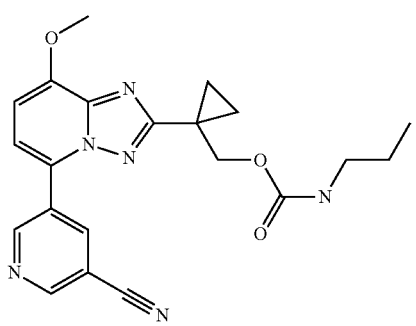 [SMILES: CCCNC(=O)OCC1(c2nc3c(OC)ccc(-c4cncc(C#N)c4)n3n2)CC1]

1H NMR (300 MHz, DMSO) δ 9.46 (d, J=2.1 Hz, 1H), 9.10 (d, J=1.9 Hz, 1H), 8.89 (t, J=2.1 Hz, 1H), 7.51 (d, J=8.3 Hz, 1H), 7.22 (d, J=8.3 Hz, 1H), 7.02 (s, 1H), 4.41 (s, 2H), 4.02 (s, 3H), 2.88 (q, 7.4 Hz, 2H), 1.40-1.20 (m, 4H), 1.13 (dd, J=6.6, 4.0 Hz, 2H), 0.76 (t, J=7.4 Hz, 3H).

Propyl-carbamic acid 1-[5-(4-cyano-3-methoxy-phenyl)-8-methoxy-[1,2,4]triazolo[1,5-a]pyridin-2-yl]-cyclopropylmethyl ester (Compound 237)

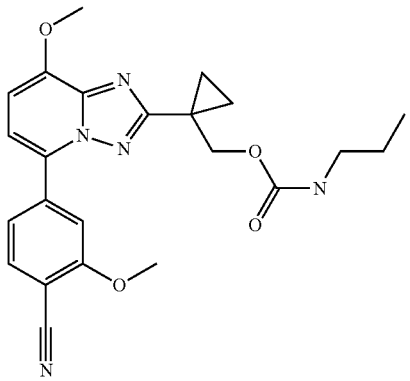 [SMILES: CCCNC(=O)OCC1(c2nc3c(OC)ccc(-c4ccc(C#N)c(OC)c4)n3n2)CC1]

1H NMR (300 MHz, DMSO) δ 8.04 (s, 1H), 7.85 (d, J=8.1 Hz, 1H), 7.68 (d, J=7.7 Hz, 1H), 7.48 (d, J=8.2 Hz, 1H), 7.19 (d, J=8.3 Hz, 1H), 7.03 (bs, 1H), 4.42 (s, 2H), 4.02 (s, 3H), 4.01 (s, 3H), 2.86 (q, J=5.8 Hz, 2H), 1.35-1.25 (m, 4H), 1.15 (d, J=3.4 Hz, 2H), 0.76 (t, J=7.4 Hz, 3H).

Pyrrolidine-1-carboxylic acid 1-[8-methoxy-5-(1-oxo-indan-5-yl)-[1,2,4]triazolo[1,5-a]pyridin-2-yl]-cyclopropylmethyl ester (Compound 238)

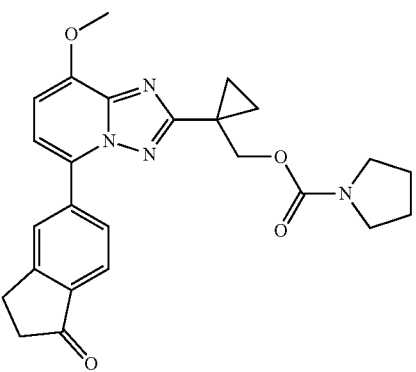 [SMILES: COc1ccc(-c2ccc3c(c2)CCC3=O)n2nc(C3(COC(=O)N4CCCC4)CC3)nc12]

1H NMR (300 MHz, DMSO) δ 8.20 (s, 1H), 7.99 (d, J=8.1 Hz, 1H), 7.73 (d, J=8.1 Hz, 1H), 7.35 (d, J=8.1 Hz, 1H), 7.18

(d, J=8.2 Hz, 1H), 4.42 (s, 2H), 4.02 (s, 3H), 3.25-3.07 (m, 6H), 2.72 (dd, J=6.6, 5.0 Hz, 2H), 1.70 (bs, 4H), 1.30-1.22 (m, 2H), 1.18-1.13 (m, 2H).

Isopropyl-carbamic acid 1-[8-methoxy-5-(1-oxo-indan-5-yl)-[1,2,4]triazolo[1,5-a]pyridin-2-yl]-cyclopropylmethyl ester (Compound 239)

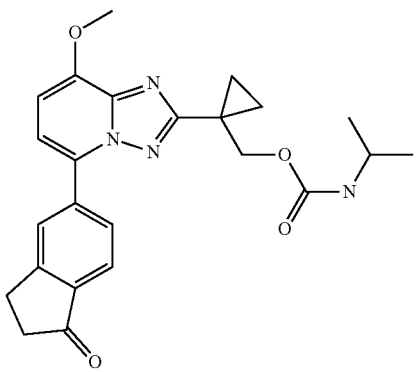 [SMILES: COc1ccc(-c2ccc3c(c2)CCC3=O)n2nc(C3(COC(=O)NC(C)C)CC3)nc12]

1H NMR (300 MHz, DMSO) δ 8.19 (s, 1H), 8.00 (dd, J=8.1, 1.3 Hz, 1H), 7.74 (d, J=8.1 Hz, 1H), 7.35 (d, J=8.1 Hz, 1H), 7.20-7.14 (m, 1H), 6.95 (d, J=7.5 Hz, 1H), 4.40 (s, 2H), 4.01 (s, 3H), 3.64-3.48 (m, 1H), 3.24-3.14 (m, 2H), 2.77-2.64 (m, 2H), 1.26 (dd, J=6.5, 4.0 Hz, 2H), 1.12 (dd, J=6.5, 4.0 Hz, 2H), 0.97 (d, J=6.5 Hz, 6H).

Cyclohexyl-carbamic acid 1-[8-methoxy-5-(1-oxo-indan-4-yl)-[1,2,4]triazolo[1,5-a]pyridin-2-yl]-cyclopropylmethyl ester (Compound 240)

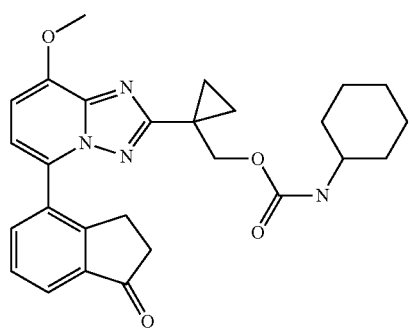 [SMILES: COc1ccc(-c2cccc3c2CCC3=O)n2nc(C3(COC(=O)NC4CCCCC4)CC3)nc12]

1H NMR (300 MHz, DMSO) δ 7.87 (dd, J=7.4, 0.9 Hz, 1H), 7.80 (d, J=7.6 Hz, 1H), 7.59 (t, J=7.6 Hz, 1H), 7.21-7.13 (m, 2H), 6.95 (d, J=8.1 Hz, 1H), 4.30 (s, 2H), 4.02 (d, J=3.6 Hz, 3H), 3.23-3.06 (m, 1H), 3.05-2.92 (m, 2H), 2.69-2.59 (m, 2H), 1.80-1.40 (m, 5H), 1.29-0.93 (m, 9H).

Cyclohexyl-carbamic acid 1-[5-(4-cyano-3-methoxy-phenyl)-8-methoxy-[1,2,4]triazolo[1,5-a]pyridin-2-yl]-cyclopropylmethyl ester (Compound 241)

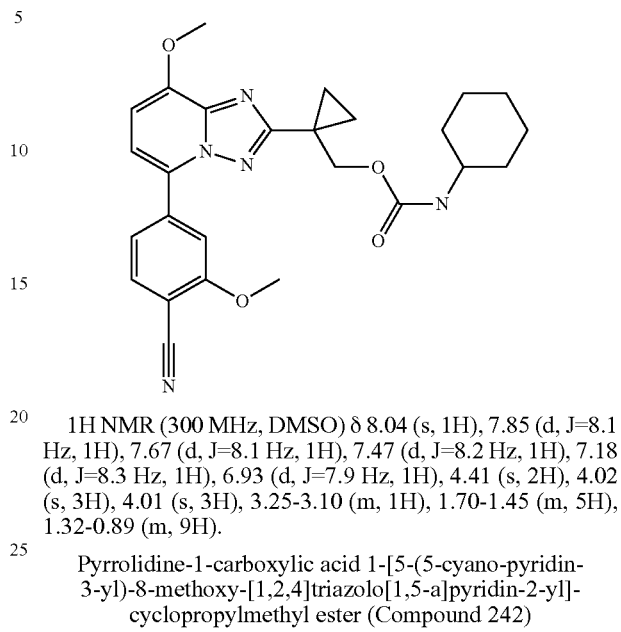

1H NMR (300 MHz, DMSO) δ 8.04 (s, 1H), 7.85 (d, J=8.1 Hz, 1H), 7.67 (d, J=8.1 Hz, 1H), 7.47 (d, J=8.2 Hz, 1H), 7.18 (d, J=8.3 Hz, 1H), 6.93 (d, J=7.9 Hz, 1H), 4.41 (s, 2H), 4.02 (s, 3H), 4.01 (s, 3H), 3.25-3.10 (m, 1H), 1.70-1.45 (m, 5H), 1.32-0.89 (m, 9H).

Pyrrolidine-1-carboxylic acid 1-[5-(5-cyano-pyridin-3-yl)-8-methoxy-[1,2,4]triazolo[1,5-a]pyridin-2-yl]-cyclopropylmethyl ester (Compound 242)

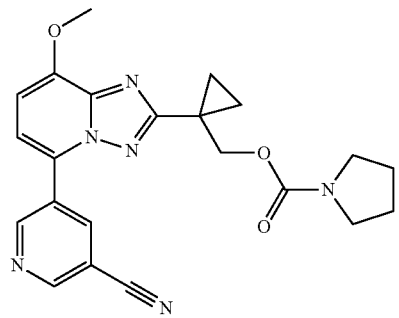 [SMILES: COc1ccc(-c2cncc(C#N)c2)n2nc(C3(COC(=O)N4CCCC4)CC3)nc12]

1H NMR (300 MHz, DMSO) δ 9.45 (d, J=2.1 Hz, 1H), 9.11 (d, J=2.0 Hz, 1H), 8.90 (t, J=2.1 Hz, 1H), 7.50 (d, J=8.2 Hz, 1H), 7.22 (d, J=8.2 Hz, 1H), 4.41 (s, 2H), 4.02 (s, 3H), 3.30-3.10 (m, 4H), 1.72 (bs, 4H), 1.31-1.24 (m, 2H), 1.19-1.14 (m, 2H).

Dimethyl-carbamic acid 1-[8-methoxy-5-(1-oxo-indan-5-yl)-[1,2,4]triazolo[1,5-a]pyridin-2-yl]-cyclopropylmethyl ester (Compound 2431

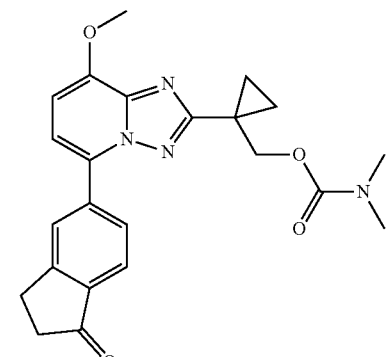

1H NMR (300 MHz, DMSO) δ 8.20 (d, J=0.6 Hz, 1H), 7.98 (dd, J=8.1, 1.4 Hz, 1H), 7.74 (d, J=8.1 Hz, 1H), 7.35 (d, J=8.2 Hz, 1H), 7.18 (d, J=8.3 Hz, 1H), 4.41 (s, 2H), 4.02 (s, 3H), 3.22-3.12 (m, 2H), 2.84-2.65 (m, 8H), 1.27 (dd, J=6.6, 4.1 Hz, 2H), 1.14 (dd, J=6.9, 4.3 Hz, 2H).

Dimethyl-carbamic acid 1-[5-(5-cyano-pyridin-3-yl)-8-methoxy-[1,2,4]triazolo[1,5-a]pyridin-2-yl]-cyclopropylmethyl ester (Compound 244)

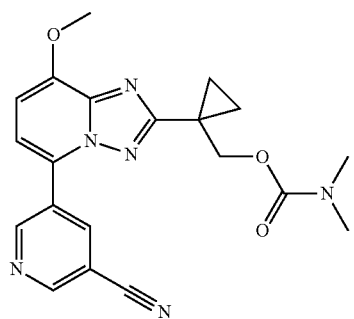 [SMILES: COc1ccc(-c2cncc(C#N)c2)n2nc(C3(COC(=O)N(C)C)CC3)nc12]

1H NMR (300 MHz, DMSO) δ 9.45 (d, J=2.2 Hz, 1H), 9.10 (d, J=1.9 Hz, 1H), 8.90 (t, J=2.1 Hz, 1H), 7.50 (d, J=8.2 Hz, 1H), 7.21 (d, J=8.3 Hz, 1H), 4.41 (s, 2H), 4.03 (s, 3H), 2.78 (s, 6H), 1.28 (dd, J=6.5, 4.1 Hz, 2H), 1.16 (dd, J=6.5, 4.1 Hz, 2H).

Diethyl-carbamic acid 1-[5-(4-cyano-3-methoxyphenyl)-8-methoxy-[1,2,4]triazolo[1,5-a]pyridin-2-yl]-cyclopropylmethyl ester (Compound 245)

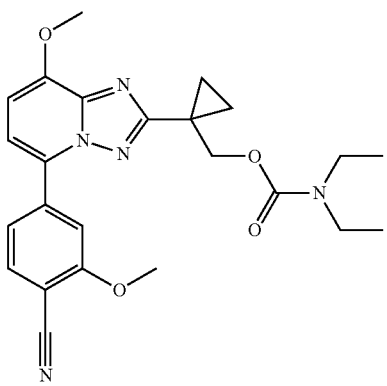 [SMILES: CCN(CC)C(=O)OCC1(c2nc3c(OC)ccc(-c4ccc(C#N)c(OC)c4)n3n2)CC1]

1H NMR (300 MHz, DMSO) δ 8.01 (s, 1H), 7.85 (d, J=8.1 Hz, 1H), 7.67 (dd, J=8.2, 1.4 Hz, 1H), 7.47 (d, J=8.3 Hz, 1H), 7.19 (d, J=8.3 Hz, 1H), 4.43 (s, 2H), 4.02 (s, 3H), 4.00 (s, 3H), 3.10 (s, 4H), 1.29 (d, J=7.1 Hz, 2H), 1.15 (t, J=3.0 Hz, 2H), 0.88 (2s, 6H).

Diethyl-carbamic acid 1-[8-methoxy-5-(1-oxo-indan-4-yl)-[1,2,4]triazolo[1,5-a]pyridin-2-yl]-cyclopropylmethyl ester (Compound 246)

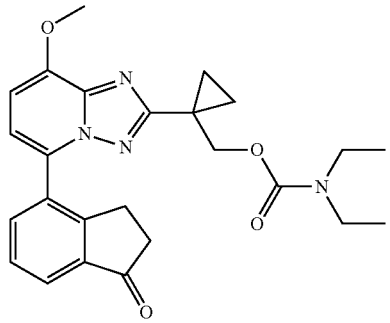 [SMILES: CCN(CC)C(=O)OCC1(c2nc3c(OC)ccc(-c4cccc5c4CCC5=O)n3n2)CC1]

1H NMR (300 MHz, DMSO) δ 7.86 (d, J=7.1 Hz, 1H), 7.80 (d, J=7.6 Hz, 1H), 7.59 (t, J=7.6 Hz, 1H), 7.17 (s, 2H), 4.33 (s, 2H), 4.02 (s, 3H), 3.07 (s, 4H), 3.00 (d, J=5.5 Hz, 2H), 2.63 (d, J=5.7 Hz, 2H), 1.22 (m, 2H), 1.09 (m, 2H), 0.94 (s, 3H), 0.82 (s, 3H).

Diethyl-carbamic acid 1-[5-(5-cyano-pyridin-3-yl)-8-methoxy-[1,2,4]triazolo[1,5-a]pyridin-2-yl]-cyclopropylmethyl ester (Compound 247)

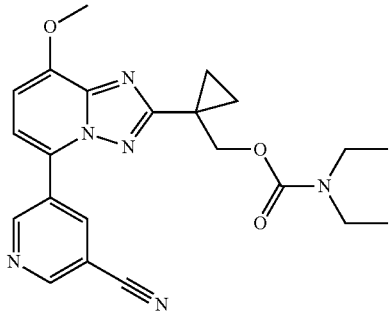 [SMILES: CCN(CC)C(=O)OCC1(c2nc3c(OC)ccc(-c4cncc(C#N)c4)n3n2)CC1]

1H NMR (300 MHz, DMSO) δ 9.45 (d, J=2.2 Hz, 1H), 9.10 (d, J=1.9 Hz, 1H), 8.89 (t, J=2.1 Hz, 1H), 7.53-7.46 (m, 1H), 7.21 (d, J=8.3 Hz, 1H), 4.42 (s, 2H), 4.02 (s, 3H), 3.13 (m, 4H), 1.28 (dd, J=6.6, 4.1 Hz, 2H), 1.20-1.10 (m, 2H), 0.96 (m, 6H).

Example 34

5-[2-(1-Hydroxymethyl-cyclopropyl)-8-methoxy-[1,2,4]triazolo[1,5-a]pyridin-5-yl]-nicotinonitrile (Compound 248)

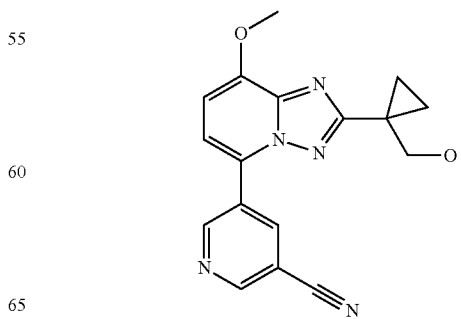

The title compound was prepared according to general procedure 7 starting from compound 308.

1H NMR (300 MHz, DMSO) δ 9.47 (d, J=2.2 Hz, 1H), 9.10 (d, J=1.9 Hz; 1H), 8.92 (t, J=2.1 Hz, 1H), 7.48 (d, J=8.2 Hz, 1H), 7.20 (d, J=8.2 Hz, 1H), 4.65 (t, J=5.8 Hz, 1H), 4.02 (s, 3H), 3.89 (d, J=5.7 Hz, 2H), 1.12 (dd, J=6.3, 3.8 Hz, 2H), 1.04 (dd, J=6.3, 3.9 Hz, 2H).

Preparation 11

8-Bromo-2-cyclopropyl-5-methoxy-[1,2,4]triazolo[1,5-a]pyridine (Compound 311)

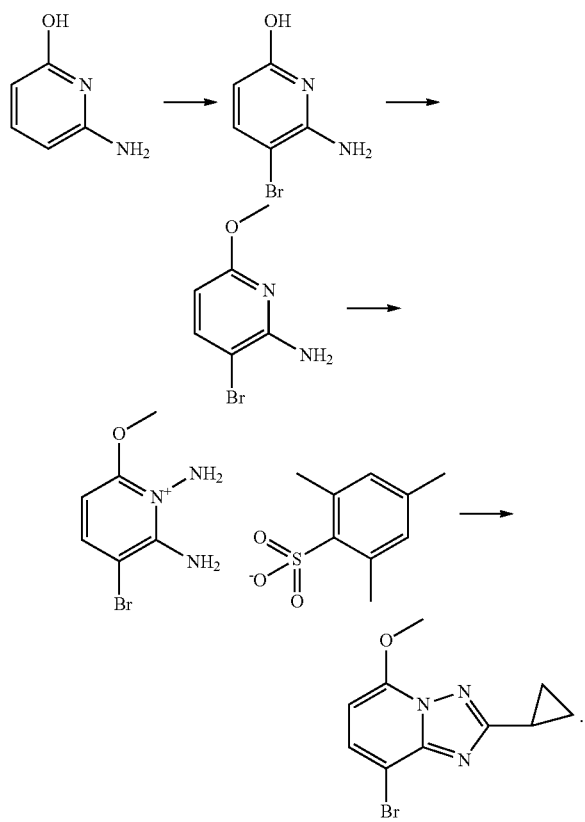

Under an argon atmosphere 2-amino-6-hydroxy-pyridine (19.6 g, 178 mmol) was suspended in acetic acid (100%, 390 mL). Br$_2$ (9.2 mL, 178 mmol) was added at 20° C. over 5 min. The green suspension was stirred at RT for 20 min. The mixture was poured onto H$_2$O (400 mL) and filtered. The filtrate was mixed with brine (200 mL) and extracted with EtOAc (10×400 mL). The combined organic phases were dried (Na$_2$SO$_4$), filtered and concentrated to afford 6-Amino-5-bromo-pyridin-2-ol as a yellow solid (23 g).

Under an argon atmosphere 6-amino-5-bromo-pyridin-2-ol (23 g, 122 mmol) was dissolved in DMF (300 mL). K$_2$CO$_3$ (50.6 g, 366 mmol) was added followed by the addition of methyl iodide (11.4 mL, 183 mmol). The mixture was stirred for 4 h while keeping the temperature at 20-25° C. The suspension was poured onto H$_2$O (1 L) and the aqueous phase was extracted with EtOAc (×2). The combined organic phases washed with H$_2$O (0.5 L) and brine (200 mL), dried over Na$_2$SO$_4$, filtered and concentrated in vacuo. The crude product was purified by flash chromatography, eluent toluene: heptane 2:1->100:0 followed by toluene:EtOAc 95:5 to afford 3-bromo-6-methoxy-pyridin-2-ylamine as a solid (3 g).

Ethyl O-mesitylsulfonylacetohydroxamate (0.88 gg, 3.0 mmol, 97% pure) and dioxane (0.56 mL) were mixed under Argon. The suspension was cooled on ice and treated with 70% HClO$_4$ (0.34 mL). Stirring was maintained for 10 min. after which ice-cooled water (4 mL) was added and stirred thoroughly. The white precipitate was filtered and washed with additional ice-cooled water (2×3 mL). The precipitate was re-dissolved in DCM (5 mL) and dried with Na$_2$SO$_4$. After filtration the DCM solution was used directly to the next step. Under an argon atmosphere the solution was slowly (3 min) added to a cold (0° C.) solution of 3-bromo-6-methoxy-pyridin-2-ylamine (0.51 g, 2.5 mmol) in DCM (3.9 mL). The yellow suspension was stirred at rt for 2 h and then treated with tert-butyl methyl ether (5 mL). The precipitate formed was filtered and washed with DCM:tert-butyl methyl ether (1:1) to provide 0.62 g of a white solid (2,4,6-Trimethyl-benzenesulfonate 1,2-diamino-3-bromo-6-methoxy-pyridinium).

0.82 g (2.0 mmol) of the above product was dissolved in dioxane (7.5 mL), under argon, and treated with cyclopropanecarboxaldehyde (0.29 mL, 4.0 mmol) and heated to 90° C. for 2 hours and 15 min. The red solution was cooled to rt and treated with 1N KOH in MeOH (2.0 mL) and left at rt for 18 hours. The solvent was evaporated in vacuo and a NaCl solution was added to the product. The product was extracted with DCM (×3) and the combined organic phases was dried over Na$_2$SO$_4$, filtered and concentrated in vacuo. The product was purified by flash chromatography on silica using DCM:EtOAc 96:4->90:10 as eluent.

The title compound was obtained as a light yellow solid (0.3 g).

1H NMR (300 MHz, CDCl3) δ 7.63 (d, J=8.2 Hz, 1H), 6.16 (d, J=8.2 Hz, 1H), 4.15 (s, 3H), 2.35-2.25 (m, 1H), 1.25-1.18 (m, 2H), 1.12-1.04 (m, 2H).

Example 35

4-(2-Cyclopropyl-5-methoxy-[1,2,4]triazolo[1,5-a]pyridin-8-yl)-2-methoxy-benzonitrile (Compound 249)

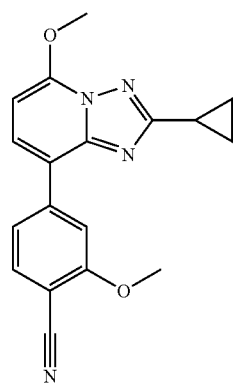 [SMILES: COc1cc(-c2ccc(OC)n3nc(C4CC4)nc23)ccc1C#N]

In a screw cap vial compound 311 (8-Bromo-2-cyclopropyl-5-methoxy-[1,2,4]triazolo[1,5-a]pyridine) (0.025 g, 0.093 mmol) was dissolved in DME (0.6 mL) and 1 M K$_2$CO$_3$ (0.2 mL) under argon. 4-CN-3-methoxyphenyl boronic acid (0.033 g, 0.19 mmol) and Pd(PPh$_3$)$_4$ (0.005 g, 0.005 mmol)

were added. The suspension was shaken at 80° C. for 5 h after which brine was added, and the aqueous phase was extracted with DCM (×3). The combined organic phases were dried, filtered and concentrated. The crude product was purified by flash chromatography, eluent DCM:EtOAc 9:1. This afforded the title compound as a solid.

1H NMR (300 MHz, DMSO) δ 8.14 (d, J=8.3 Hz, 1H), 8.11 (d, J=1.3 Hz, 1H), 7.87 (dd, J=8.1, 1.5 Hz, 1H), 7.80 (d, J=8.2 Hz, 1H), 6.74 (d, J=8.4 Hz, 1H), 4.18 (s, 3H), 4.01 (s, 3H), 2.21 (tt, J=8.0, 5.0 Hz, 1H), 1.13-0.97 (m, 4H).

Example 36

4-(2-Cyclopropyl-5-methoxy-[1,2,4]triazolo[1,5-a]pyridin-8-yl)-2-methyl-benzonitrile (Compound 250)

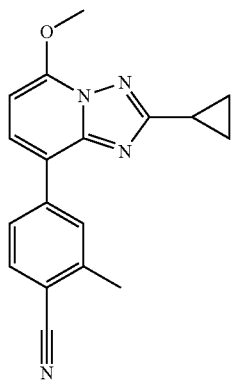 [SMILES: COc1ccc(-c2ccc(C#N)c(C)c2)c2nc(C3CC3)nn12]

The compound was prepared according to the procedure described for the preparation of compound 249.

1H NMR (300 MHz, DMSO) δ 8.22-8.12 (m, 2H), 8.04 (d, J=8.3 Hz, 1H), 7.90-7.80 (m, 1H), 6.73 (d, J=8.4 Hz, 1H), 4.17 (s, 3H), 2.56 (s, 3H), 2.21 (tt, J=8.1, 5.1 Hz, 1H), 1.13-0.94 (m, 4H).

Example 37

3-(2-Cyclopropyl-5-methoxy-[1,2,4]triazolo[1,5-a]pyridin-8-yl)-benzonitrile (Compound 251)

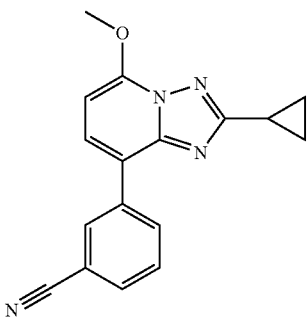 [SMILES: COc1ccc(-c2cccc(C#N)c2)c2nc(C3CC3)nn12]

The compound was prepared according to the procedure described for the preparation of compound 249.

Example 38

5-(2-Cyclopropyl-5-methoxy-[1,2,4]triazolo[1,5-a]pyridin-8-yl)-indan-1-one (Compound 252)

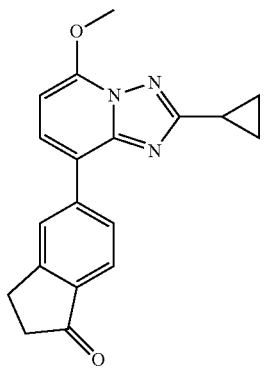 [SMILES: COc1ccc(-c2ccc3c(c2)CCC3=O)c2nc(C3CC3)nn12]

The compound was prepared according to the procedure described for the preparation of compound 249.

1H NMR (300 MHz, DMSO) δ 8.29 (s, 1H), 8.15 (dd, J=8.1, 1.4 Hz, 1H), 8.03 (d, J=8.3 Hz, 1H), 7.72 (d, J=8.1 Hz, 1H), 6.74 (d, J=8.3 Hz, 1H), 4.17 (s, 3H), 3.24-3.10 (m, 2H), 2.74-2.64 (m, 2H), 2.21 (tt, J=8.0, 5.1 Hz, 1H), 1.05-0.98 (m, 3H).

Example 39

4-(2-Cyclopropyl-5-methoxy-[1,2,4]triazolo[1,5-a]pyridin-8-yl)-indan-1-one (Compound 253)

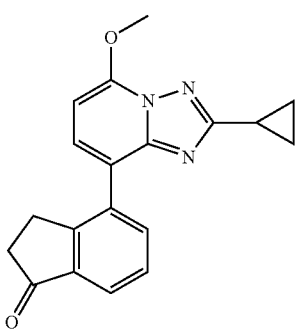 [SMILES: COc1ccc(-c2cccc3c2CCC3=O)c2nc(C3CC3)nn12]

The compound was prepared according to the procedure described for the preparation of compound 249.

1H NMR (300 MHz, DMSO) δ 7.83 (dd, J=7.4, 1.2 Hz, 1H), 7.75-7.65 (m, 2H), 7.56 (t, J=7.5 Hz, 1H), 6.72 (d, J=8.2 Hz, 1H), 4.17 (s, 3H), 3.13-3.01 (m, 2H), 2.69-2.57 (m, 2H), 2.15 (tt, J=8.3, 4.9 Hz, 1H), 1.04-0.88 (m, 4H).

Preparation 12

1-(8-Bromo-5-methoxy-[1,2,4]triazolo[1,5-a]pyridin-2-yl)-cyclopropanecarboxylic acid ethyl ester (Compound 312)

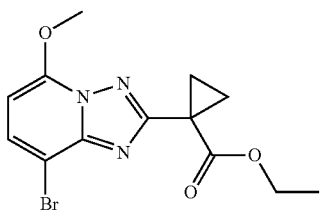 [SMILES: CCOC(=O)C1(c2nc3c(Br)ccc(OC)n3n2)CC1]

1.0 g (2.6 mmol) of crude 2,4,6-Trimethyl-benzenesulfonate 1,2-diamino-3-bromo-6-methoxy-pyridinium (see preparation of compound 311) was dissolved in dioxane (8.5 mL), under argon, and treated with 1-formyl-cyclopropanecarboxylic acid ethyl ester (0.56 g, 3.9 mmol) and heated to 90° C. for 22 hours. The brown solution was cooled to rt and treated with 1N KOH in MeOH (2.6 mL) and left at rt for 6 hours. The solvent was evaporated in vacuo and a NaCl solution was added to the product as well as aq. NaHCO₃. The product was extracted with DCM (×3) and the combined organic phases was dried over Na₂SO₄, filtered and concentrated in vacuo. The product was purified by flash chromatography on silica using DCM:EtOAc 96:4->85:15 as eluent. The title compound was obtained as a colourless solid (0.22 g).

1H NMR (300 MHz, CDCl3) δ 7.69 (d, J=8.2 Hz, 1H), 6.23 (d, J=8.3 Hz, 1H), 4.16 (s, 3H), 4.15 (q, J=7.1 Hz, 2H), 1.74 (dd, J=7.5, 4.3 Hz, 2H), 1.58 (dd, J=7.1, 3.9 Hz, 3H), 1.18 (t, J=7.1 Hz, 3H).

Preparation 13

1-(8-Bromo-5-methoxy-[1,2,4]triazolo[1,5-a]pyridin-2-yl)-cyclopropanecarboxylic acid (Compound 313)

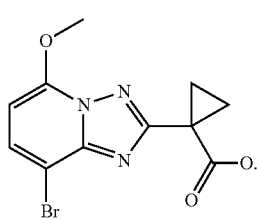

1-(8-Bromo-5-methoxy-[1,2,4]triazolo[1,5-a]pyridin-2-yl)-cyclopropanecarboxylic acid ethyl ester (0.22 g, 0.64 mmol) was dissolved in 1,4-dioxan (15 mL). LiOH (0.085 g, 1.9 mmol) in H₂O (3 mL) was added. The mixture was stirred at RT overnight. The solvent was evaporated. H₂O (50 mL) was added and the aqueous phase was adjusted to pH 1 with 2 N HCl. The aqueous phase was extracted (×3) with EtOH/DCM 1/10. The combined organic phases were washed with brine, dried (Na₂SO₄), filtered and concentrated in vacuo to afford the title compound as a solid.

1H NMR (300 MHz, DMSO) δ 7.96 (d, J=8.3 Hz, 1H), 6.63 (d, J=8.4 Hz, 1H), 4.13 (s, 3H), 1.54 (dd, J=7.2, 4.1 Hz, 2H), 1.42 (dd, J=7.2, 4.1 Hz, 2H).

Preparation 14

4-(4,4,5,5-Tetramethyl-[1,3,2]dioxaborolan-2-yl)-indan-1-one Compound (314)

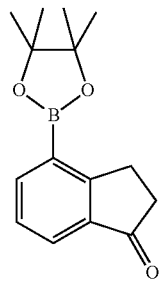

4-Bromo-indan-1-one (1.0 g, 4.9 mmol) was dissolved in 1,4 dioxan (40 mL) and the mixture was bubbled through with argon. Bis-(pinacolato)-diborane (1.3 g, 5.1 mmol) and PdCl₂(dppf)₂*CH₂Cl₂ (0.16 g, 0.19 mmol) were added followed by the addition of KOAc (1.4 g, 14.6 mmol). The mixture was stirred under an argon atmosphere at 80° C. for 3 h. The mixture was diluted with EtOAC and filtered. The filtrate was purified by flash chromatography using heptane:EtOAc as the eluent. This afforded the title compound as a solid.

Preparation 15

5-(4,4,5,5-Tetramethyl-[1,3,2]dioxaborolan-2-yl)-indan-1-one (Compound 315)

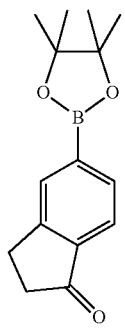 [SMILES: CC1(C)OB(c2ccc3c(c2)CCC3=O)OC1(C)C]

The title compound was prepared as described in Preparation 14 using 5-Bromo-indan-1-one as the starting material.

Preparation 16

5-(4,4,5,5-Tetramethyl-[1,3,2]dioxaborolan-2-yl)-3H-isobenzofuran-1-one (Compound 316)

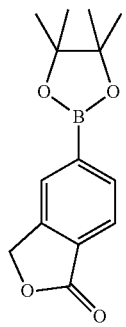

The title compound was prepared as described in Preparation 14 using 5-Bromo-3H-isobenzofuran-1-one as the starting material.

Example 40

Compounds 254-256, 258-259, 261 and 264-267 were prepared according to General Procedure 3 using compound 313 (1-(8-Bromo-5-methoxy-[1,2,4]triazolo[1,5-a]pyridin-2-yl)-cyclopropanecarboxylic acid) as starting compound.

Example 41

Compounds 257 and 268 were prepared according to General Procedure 2 using compound 313 (1-(8-Bromo-5-methoxy-[1,2,4]triazolo[1,5-a]pyridin-2-yl)-cyclopropanecarboxylic acid) as starting compound.

1-[8-(4-Cyano-3-methoxy-phenyl)-5-methoxy-[1,2,4]triazolo[1,5-a]pyridin-2-yl]-cyclopropanecarboxylic acid isopropylamide (Compound 254)

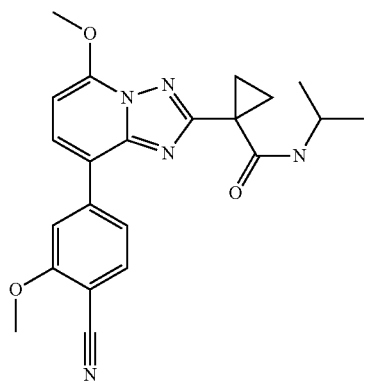 [SMILES: COc1cc(-c2ccc(OC)n3nc(C4(C(=O)NC(C)C)CC4)nc23)ccc1C#N]

1H NMR (300 MHz, DMSO) δ 8.78 (d, J=7.3 Hz, 1H), 8.20 (d, J=8.2 Hz, 1H), 7.95-7.87 (m, 2H), 7.85-7.81 (m, 1H), 6.85 (d, J=8.4 Hz, 1H), 4.21 (s, 3H), 4.03 (s, 3H), 4.00-3.87 (m, 1H), 1.60-1.51 (m, 2H), 1.51-1.41 (m, 2H), 1.13 (s, 3H), 1.10 (s, 3H).

1-[5-Methoxy-8-(1-oxo-1,3-dihydro-isobenzofuran-5-yl)-[1,2,4]triazolo[1,5-a]pyridin-2-yl]-cyclopropanecarboxylic acid isopropylamide (Compound 255)

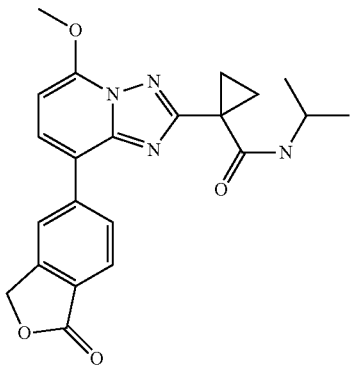 [SMILES: COc1ccc(-c2ccc3c(c2)COC3=O)c2nc(C3(C(=O)NC(C)C)CC3)nn12]

1H NMR (300 MHz, DMSO) δ 8.89 (d, J=7.2 Hz, 1H), 8.37 (s, 1H), 8.33 (d, J=8.2 Hz, 1H), 8.14 (d, J=8.3 Hz, 1H), 7.95 (d, J=8.1 Hz, 1H), 6.88 (d, J=8.4 Hz, 1H), 5.49 (s, 2H), 4.21 (s, 3H), 3.96 (dq, J=13.4, 6.6 Hz, 1H), 1.57 (dd, J=6.8, 3.5 Hz, 2H), 1.51-1.41 (m, 2H), 1.15 (s, 3H), 1.12 (s, 3H).

1-[5-Methoxy-8-(1-oxo-indan-5-yl)-[1,2,4]triazolo[1,5-a]pyridin-2-yl]-cyclopropanecarboxylic acid isopropylamide (Compound 256)

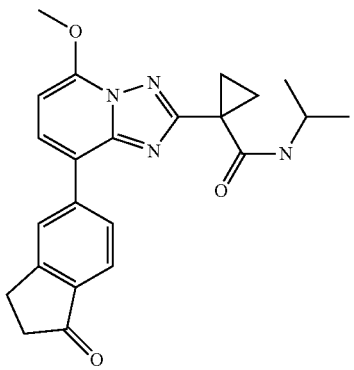 [SMILES: COc1ccc(-c2ccc3c(c2)CCC3=O)c2nc(C3(C(=O)NC(C)C)CC3)nn12]

1H NMR (300 MHz, DMSO) δ 9.00 (d, J=7.2 Hz, 1H), 8.29 (s, 1H), 8.13 (m, 1H), 7.74 (d, J=8.5 Hz, 2H), 6.85 (d, J=8.4 Hz, 1H), 4.20 (s, 3H), 3.98 (dq, J=13.2, 6.6 Hz, 1H), 3.25-3.13 (m, 2H), 2.70 (m, 2H), 1.58 (dd, J=7.0, 3.5 Hz, 2H), 1.46 (dd, J=7.0, 3.5 Hz, 2H), 1.16 (s, 3H), 1.14 (s, 3H).

1-[5-Hydroxy-8-(1-oxo-indan-4-yl)-[1,2,4]triazolo[1,5-a]pyridin-2-yl]-cyclopropanecarboxylic acid isopropylamide (Compound 257)

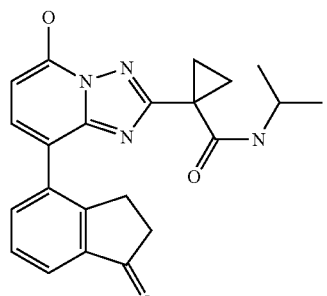

1H NMR (300 MHz, DMSO) δ 9.27-8.94 (m, 1H), 7.87 (d, J=7.3 Hz, 1H), 7.69-7.56 (m, 2H), 7.51 (t, J=7.5 Hz, 1H), 6.18 (d, J=8.4 Hz, 1H), 3.89 (dt, J=13.3, 6.7 Hz, 2H), 3.11 (m, 2H), 2.67-2.59 (m, 2H), 1.56-1.46 (m, 2H), 1.45-1.36 (m, 2H), 1.05 (s, 3H), 1.03 (s, 3H).

1-[5-Methoxy-8-(1-oxo-indan-4-yl)-[1,2,4]triazolo [1,5-a]pyridin-2-yl]-cyclopropanecarboxylic acid (2-methanesulfonyl-ethyl)-amide (Compound 258)

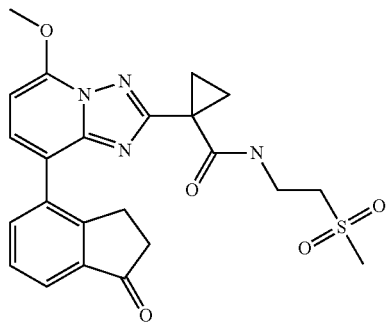 [SMILES: COc1ccc(-c2cccc3c2CCC3=O)c2nc(C3(C(=O)NCCS(C)(=O)=O)CC3)nn12]

1H NMR (300 MHz, DMSO) δ 8.45 (t, J=5.7 Hz, 1H), 7.94 (dd, J=7.5, 1.1 Hz, 1H), 7.84 (d, J=8.1 Hz, 1H), 7.73 (d, J=6.6 Hz, 1H), 7.59 (t, J=7.5 Hz, 1H), 6.82 (d, J=8.1 Hz, 1H), 4.20 (s, 3H), 3.52 (m, 2H), 3.24 (m, 2H), 3.16-3.07 (m, 3H), 2.94 (s, 3H), 2.74-2.61 (m, 2H), 1.50 (dd, J=7.0, 3.6 Hz, 2H), 1.37 (dd, J=7.1, 3.6 Hz, 2H).

1-[8-(5-Cyano-pyridin-3-yl)-5-methoxy-[1,2,4]tria-zolo[1,5-a]pyridin-2-yl]-cyclopropanecarboxylic acid (2-methanesulfonyl-ethyl)-amide (Compound 259)

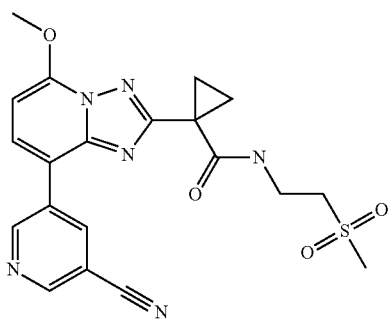 [SMILES: COc1ccc(-c2cncc(C#N)c2)c2nc(C3(C(=O)NCCS(C)(=O)=O)CC3)nn12]

1H NMR (300 MHz, DMSO) δ 9.61 (d, J=2.1 Hz, 1H), 9.03 (d, J=1.9 Hz, 2H), 8.99 (t, J=2.1 Hz, 1H), 8.40 (t, J=5.4 Hz, 1H), 8.24 (d, J=8.3 Hz, 1H), 6.89 (d, J=8.4 Hz, 1H), 4.22 (s, 3H), 3.58 (dd, J=12.5, 6.5 Hz, 2H), 3.27 (dd, J=13.9, 7.3 Hz, 2H), 3.03-2.98 (s, 3H), 1.55 (dd, J=6.9, 3.7 Hz, 2H), 1.42 (dd, J=6.9, 3.7 Hz, 2H).

1-[5-Methoxy-8-(1-oxo-indan-5-yl)-[1,2,4]triazolo [1,5-a]pyridin-2-yl]-cyclopropanecarboxylic acid isobutyl-amide (Compound 261)

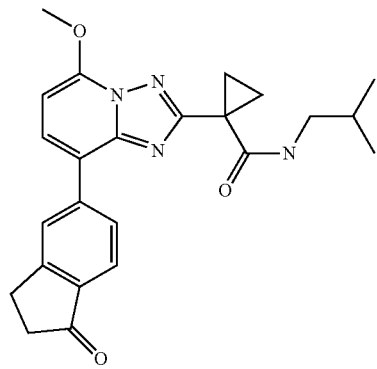 [SMILES: COc1ccc(-c2ccc3c(c2)CCC3=O)c2nc(C3(C(=O)NCC(C)C)CC3)nn12]

1H NMR (300 MHz, DMSO) δ 8.85 (t, J=5.6 Hz, 1H), 8.26 (s, 1H), 8.11 (m, 2H), 7.72 (d, J=8.1 Hz, 1H), 6.84 (d, J=8.4 Hz, 1H), 4.20 (s, 3H), 3.22-3.13 (m, 2H), 3.09-2.95 (m, 2H), 2.72-2.64 (m, 2H), 1.85-1.69 (m, 2H), 1.62-1.51 (m, 2H), 1.50-1.40 (m, 2H), 0.89 (s, 3H), 0.86 (s, 3H).

1-[8-(4-Cyano-3-methoxy-phenyl)-5-methoxyl-[1,2,4]triazolo[1,5-a]pyridin-2-yl]-cyclopropanecarboxy-lic acid (2-methanesulfonyl-ethyl)-amide (Compound 264)

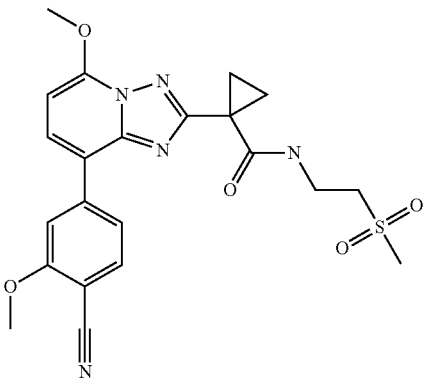 [SMILES: COc1cc(-c2ccc(OC)n3nc(C4(C(=O)NCCS(C)(=O)=O)CC4)nc23)ccc1C#N]

1H NMR (300 MHz, DMSO) δ 8.55-8.48 (m, 1H), 8.21 (d, J=8.4 Hz, 1H), 7.99 (d, J=1.2 Hz, 1H), 7.93 (dd, J=8.1, 1.4 Hz, 1H), 7.84 (d, J=8.1 Hz, 1H), 6.85 (d, J=8.4 Hz, 1H), 4.21 (s,

3H), 4.02 (s, 3H), 3.58 (q, J=6.4 Hz, 2H), 3.30-3.23 (m, 2H), 3.00 (s, 3H), 1.55 (dd, J=6.9, 3.6 Hz, 2H), 1.44 (dd, J=7.0, 3.7 Hz, 2H).

1-[5-Methoxy-8-(1-oxo-indan-5-yl)-[1,2,4]triazolo[1,5-a]pyridin-2-yl]-cyclopropanecarboxylic acid (2-methanesulfonyl-ethyl)-amide (Compound 265)

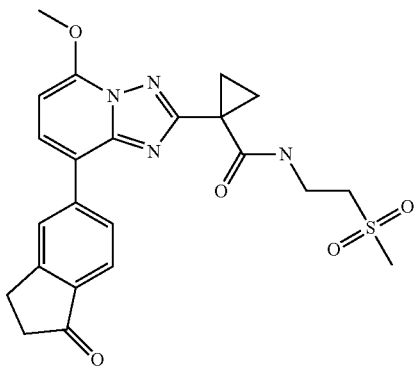 [SMILES: COc1ccc(-c2ccc3c(c2)CCC3=O)c2nc(C3(C(=O)NCCS(C)(=O)=O)CC3)nn12]

1H NMR (300 MHz, DMSO) δ 8.62 (t, J=5.5 Hz, 1H), 8.29 (s, 1H), 8.16 (d, J=8.3 Hz, 1H), 8.11 (d, J=8.3 Hz, 1H), 7.77 (d, J=8.1 Hz, 1H), 6.85 (d, J=8.3 Hz, 1H), 4.20 (s, 3H), 3.59 (q, J=6.4 Hz, 2H), 3.44-3.26 (m, 2H), 3.20 (dd, J=12.0, 6.0 Hz, 2H), 2.98 (s, 3H), 2.75-2.66 (m, 2H), 1.56 (dd, J=7.0, 3.6 Hz, 2H), 1.43 (dd, J=7.0, 3.6 Hz, 2H).

1-[5-Methoxy-8-(1-oxo-1,3-dihydro-isobenzofuran-5-yl)-[1,2,4]triazolo[1,5-a]pyridin-2-yl]-cyclopropanecarboxylic acid (2-methanesulfonyl-ethyl)-amide (Compound 266)

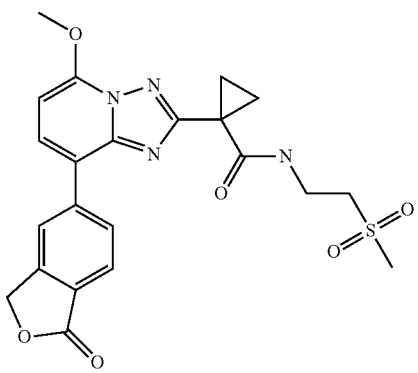 [SMILES: COc1ccc(-c2ccc3c(c2)COC3=O)c2nc(C3(C(=O)NCCS(C)(=O)=O)CC3)nn12]

1H NMR (300 MHz, DMSO) δ 8.64 (t, J=5.7 Hz, 1H), 8.43 (s, 1H), 8.30 (d, J=8.1 Hz, 1H), 8.17-8.11 (m, 1H), 7.98 (d, J=8.1 Hz, 1H), 6.87 (d, J=8.4 Hz, 1H), 5.52 (s, 2H), 4.21 (s, 3H), 3.60 (q, J=6.3 Hz, 2H), 3.3 (m, 2H), 3.00 (s, 3H), 1.56 (dd, J=6.9, 3.6 Hz, 2H), 1.44 (dd, J=7.1, 3.6 Hz, 2H).

1-[5-Methoxy-8-(1-oxo-1,3-dihydro-isobenzofuran-5-yl)-[1,2,4]triazolo[1,5-a]pyridin-2-yl]-cyclopropanecarboxylic acid isobutyl-amide (Compound 267)

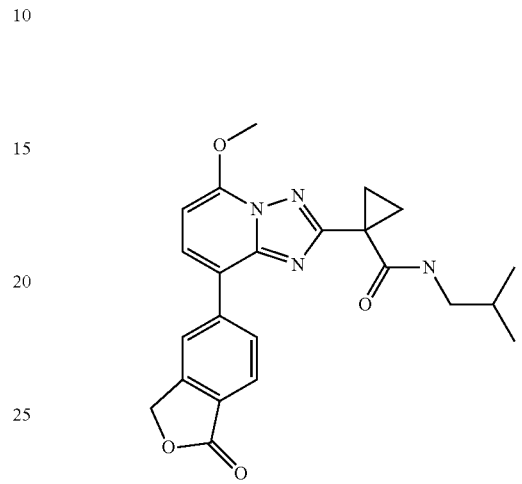

1H NMR (300 MHz, DMSO) δ 8.75 (t, J=5.5 Hz, 1H), 8.35 (s, 1H), 8.30 (dd, J=8.1, 1.3 Hz, 1H), 8.12 (d, J=8.3 Hz, 1H), 7.94 (d, J=8.0 Hz, 1H), 6.87 (d, J=8.4 Hz, 1H), 5.49 (s, 2H), 4.21 (s, 3H), 3.02 (dd, J=6.5, 5.9 Hz, 2H), 1.55 (dd, J=6.9, 3.6 Hz, 2H), 1.46 (dd, J=7.0, 3.5 Hz, 2H), 0.87 (s, 3H), 0.85 (s, 3H).

1-[5-Hydroxy-8-(1-oxo-indan-5-yl)-[1,2,4]triazolo[1,5-a]pyridin-2-yl]-cyclopropanecarboxylic acid isopropylamide (Compound 268)

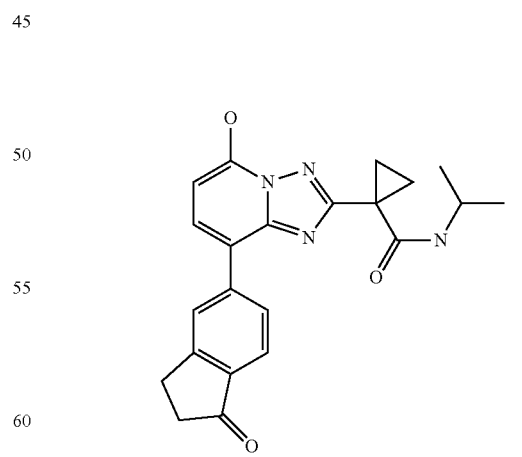

1H NMR (300 MHz, DMSO) δ 9.14-8.85 (m, 1H), 8.19 (s, 1H), 8.05 (s, 1H), 7.96 (d, J=8.4 Hz, 1H), 7.69 (d, J=8.1 Hz, 1H), 6.43 (s, 1H), 4.00 (m, 1H), 3.25-3.08 (m, 2H), 2.73-2.64

(m, 2H), 1.56 (dd, J=6.7, 3.4 Hz, 2H), 1.46 (dd, J=6.8, 3.4 Hz, 2H), 1.16 (s, 3H), 1.14 (s, 3H).

Example 42

Compounds 269-270 were prepared according to General Procedure 3

1-[8-Methoxy-5-(1-oxo-1,3-dihydro-isobenzofuran-5-yl)-[1,2,4]triazolo[1,5-a]pyridin-2-yl]-cyclopropanecarboxylic acid (2-methanesulfonyl-ethyl)-amide (Compound 269)

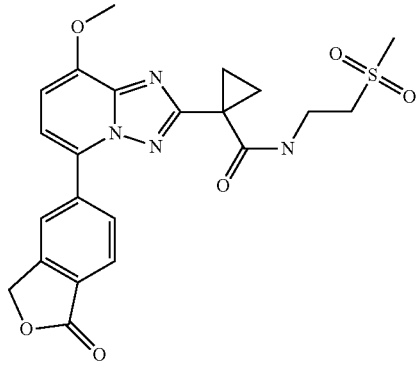 [SMILES: COc1ccc(-c2ccc3c(c2)COC3=O)n2nc(C3(C(=O)NCCS(C)(=O)=O)CC3)nc12]

1H NMR (300 MHz, DMSO) δ 8.39 (t, J=5.7 Hz, 1H), 8.26 (d, J=0.6 Hz, 1H), 8.15 (dd, J=8.1, 1.2 Hz, 1H), 8.02 (d, J=8.0 Hz, 1H), 7.41 (d, J=8.2 Hz, 1H), 7.27 (d, J=8.3 Hz, 1H), 5.52 (s, 2H), 4.05 (s, 3H), 3.63-3.49 (m, 2H), 3.26 (m, 2H), 2.97 (s, 3H), 1.52 (dd, J=7.0, 3.6 Hz, 2H), 1.39 (dd, J=7.1, 3.6 Hz, 2H).

1-[8-Methoxy-5-(1-oxo-1,3-dihydro-isobenzofuran-5-yl)-[1,2,4]triazolo[1,5-a]pyridin-2-yl]-cyclopropanecarboxylic acid cyclohexylmethyl-amide (Compound 270)

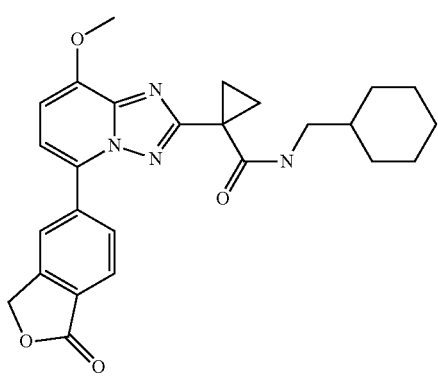 [SMILES: COc1ccc(-c2ccc3c(c2)COC3=O)n2nc(C3(C(=O)NCC4CCCCC4)CC3)nc12]

1H NMR (300 MHz, DMSO) δ 8.55 (s, 1H), 8.19 (s, 1H), 8.15 (d, J=8.0 Hz, 1H), 7.99 (d, J=8.0 Hz, 1H), 7.38 (d, J=8.2 Hz, 1H), 7.27 (d, J=8.2 Hz, 1H), 5.51 (s, 2H), 4.05 (s, 3H), 3.00 (t, J=6.2 Hz, 2H), 1.53-0.81 (m, 15H).

Example 43

Compound 273 was prepared according to General Procedure 6 followed by General Procedure 7.

Dimethyl-carbamic acid 1-[8-methoxy-5-(1-oxo-1,3-dihydro-sobenzofuran-5-yl)-[1,2,4]triazolo[1,5-a]pyridin-2-yl]-cyclopropylmethyl ester (Compound 273)

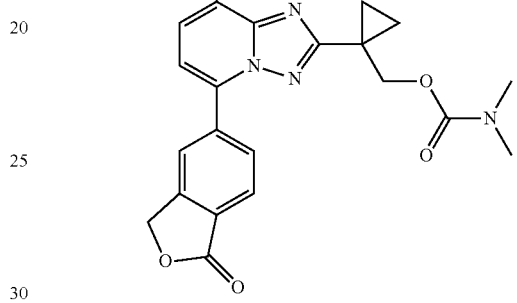

1H NMR (300 MHz, DMSO) δ 8.28 (s, 1H), 8.16 (d, J=8.1 Hz, 1H), 7.96 (d, J=8.1 Hz, 1H), 7.38 (d, J=8.2 Hz, 1H), 7.20 (d, J=8.3 Hz, 1H), 5.50 (s, 2H), 4.42 (s, 2H), 4.04 (d, J=8.7 Hz, 3H), 2.75 (s, 6H), 1.27 (dd, J=6.6, 4.1 Hz, 2H), 1.14 (dd, J=6.6, 4.1 Hz, 2H).

Example 44

Cyclohexyl-carbamic acid 1-[8-methoxy-5-(1-oxo-1,3-dihydro-isobenzofuran-5-yl)-[1,2,4]triazolo[1,5-a]pyridin-2-yl]-cyclopropylmethyl ester (Compound 276)

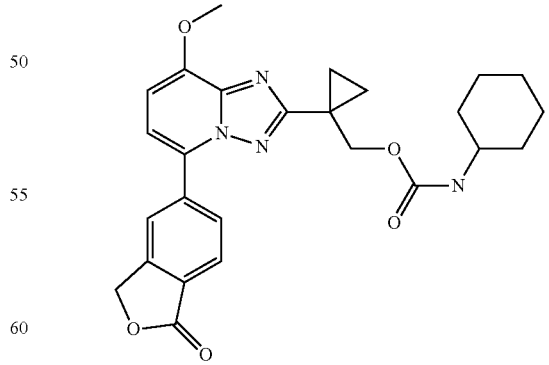

Compound 276 was prepared according to General Procedure 5 followed by General Procedure 7.

1H NMR (300 MHz, DMSO) δ 8.33 (d, J=0.5 Hz, 1H), 8.16 (dd, J=8.1, 1.2 Hz, 1H), 7.96 (d, J=8.1 Hz, 1H), 7.39 (d,

J=8.1 Hz, 1H), 7.20 (d, J=8.3 Hz, 1H), 5.49 (s, 2H), 4.41 (s, 2H), 4.01 (s, 3H), 3.17 (m, 1H), 1.54 (m, 5H), 1.33-0.87 (m, 9H).

Example 45

4-[2-(1-Hydroxymethyl-cyclopropyl)-8-methoxy-[1,2,4]triazolo[1,5-a]pyridin-5-yl]-2-methoxy-benzonitrile (Compound 277)

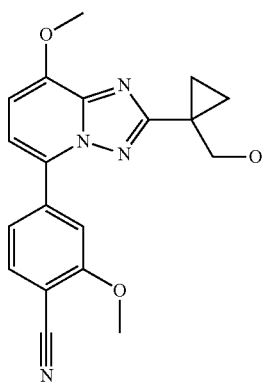 [SMILES: COc1cc(-c2ccc(OC)c3nc(C4(CO)CC4)nn23)ccc1C#N]

The title compound was prepared according to General Procedure 7 starting from compound 308.

1H NMR (300 MHz, DMSO) δ 8.04 (s, 1H), 7.88 (d, J=8.1 Hz, 1H), 7.70 (dd, J=8.1, 1.4 Hz, 1H), 7.45 (d, J=8.3 Hz, 1H), 7.17 (d, J=8.3 Hz, 1H), 4.60 (t, J=5.8 Hz, 1H), 4.02 (m, 6H), 3.95-3.85 (m, 2H), 1.17-1.09 (m, 2H), 1.04 (dd, J=6.2, 3.8 Hz, 2H).

Example 46

4-[2-(1-Isobutoxymethyl-cyclopropyl)-8-methoxyl-[1,2,4]triazolo[1,5-a]pyridin-5-yl]-2-methoxy-benzonitrile (Compound 278)

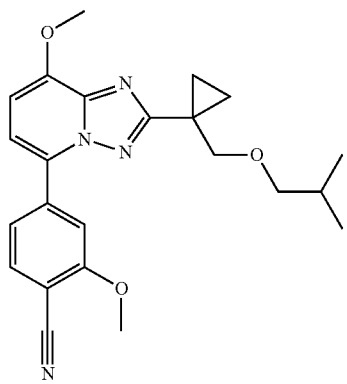 [SMILES: COc1cc(-c2ccc(OC)c3nc(C4(COCC(C)C)CC4)nn23)ccc1C#N]

The title compound was prepared according to the method described in example 48 for the preparation of compound 283 using compound 277 as the starting material.

1H NMR (300 MHz, DMSO) δ 7.96 (s, 1H), 7.87 (d, J=8.2 Hz, 1H), 7.71 (d, J=8.1 Hz, 1H), 7.44 (d, J=8.3 Hz, 1H), 7.17 (d, J=8.2 Hz, 1H), 4.02 (m, 6H), 3.85 (s, 2H), 3.19 (d, J=6.6 Hz, 2H), 1.72 (dd, J=13.4, 6.6 Hz, 1H), 1.19 (t, J=5.0 Hz, 2H), 1.06 (t, J=2.9 Hz, 2H), 0.77 (s, 3H), 0.75 (s, 3H).

Example 47

Compounds 279-282 were prepared according to General Procedure 4 using compound 191 as starting material.

1-[5-(3-Cyano-phenyl)-8-methoxy-[1,2,4]triazolo[1,5-a]pyridin-2-yl]-cyclopropanecarboxylic acid isobutyl-amide (Compound 279)

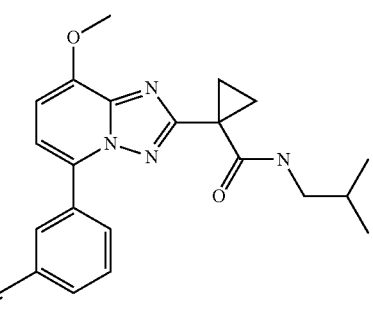

1H NMR (300 MHz, DMSO) δ 8.51 (t, J=5.5 Hz, 1H), 8.4 (m, 1H) 8.31-8.23 (m, 1H), 8.01-7.93 (m, 1H), 7.74 (t, J=7.8 Hz, 1H), 7.38 (d, J=8.1 Hz, 1H), 7.24 (d, J=8.3 Hz, 1H), 4.04 (s, 3H), 3.00 (dd, J=6.7, 5.9 Hz, 2H), 1.80-1.62 (m, 1H), 1.52 (dd, J=6.9, 3.5 Hz, 2H), 1.41 (dd, J=7.0, 3.5 Hz, 2H), 0.82 (s, 3H), 0.80 (s, 3H).

1-[5-(3-Cyano-phenyl)-8-methoxy-[1,2,4]triazolo[1,5-a]pyridin-2-yl]-cyclopropanecarboxylic acid (2-methanesulfonylamino-ethyl)-amide (Compound 280)

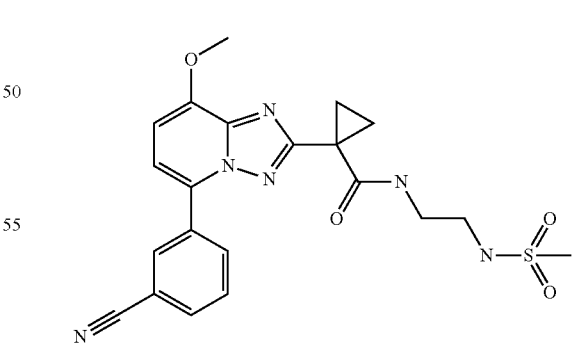

1H NMR (300 MHz, DMSO) δ 8.4 (m, 1H), 8.34 (m, 2H), 8.06-7.87 (m, 1H), 7.77 (t, J=7.9 Hz, 1H), 7.43 (d, J=8.2 Hz, 1H), 7.25 (d, J=8.3 Hz, 1H), 7.07 (t, J=5.9 Hz, 1H), 4.04 (s, 3H), 3.27 (m, 2H), 3.09-2.94 (m, 2H), 2.88 (s, 3H), 1.51 (dd, J=7.0, 3.6 Hz, 2H), 1.37 (dd, J=7.1, 3.5 Hz, 2H).

1-[5-(3-Cyano-phenyl)-8-methoxy-[1,2,4]triazolo[1,5-a]pyridin-2-yl]-cyclopropanecarboxylic acid cyclopropylamide (Compound 281)

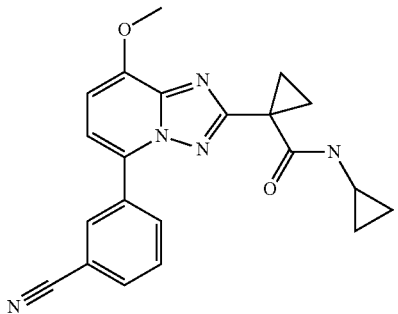 [SMILES: COc1ccc(-c2cccc(C#N)c2)n2nc(C3(C(=O)NC4CC4)CC3)nc12]

1H NMR (300 MHz, DMSO) δ 8.40 (m, 2H), 8.30-8.23 (m, 1H), 7.98 (m, 1H), 7.75 (m, 1H), 7.39 (m, 1H), 7.23 (m, 1H), 4.02 (s, 3H), 2.72 (tq, J=7.8, 4.0 Hz, 4H), 1.57-1.46 (m, 7H), 1.39 (dd, J=7.0, 3.6 Hz, 8H), 1.37 (s, 2H), 0.70-0.58 (m, 7H), 0.42 (dt, J=7.0, 4.6 Hz, 7H).

1-[5-(3-Cyano-phenyl)-8-methoxy-[1,2,4]triazolo[1,5-a]pyridin-2-yl]-cyclopropanecarboxylic acid cyclohexylmethyl-amide (Compound 282)

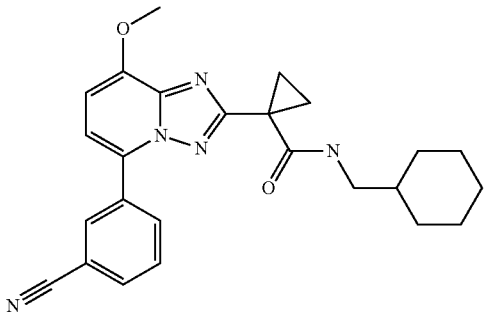 [SMILES: COc1ccc(-c2cccc(C#N)c2)n2nc(C3(C(=O)NCC4CCCCC4)CC3)nc12]

1H NMR (300 MHz, DMSO) δ 8.54 (d, J=5.6 Hz, 1H), 8.41 (t, J=1.4 Hz, 1H), 8.28 (dd, J=8.0, 1.2 Hz, 1H), 7.99 (dd, J=7.9, 1.2 Hz, 1H), 7.75 (t, J=7.9 Hz, 1H), 7.39 (d, J=8.1 Hz, 1H), 7.24 (d, J=8.3 Hz, 1H), 4.04 (s, 3H), 3.01 (t, J=6.2 Hz, 2H), 1.61 (m, 5H), 1.54-1.48 (m, 2H), 1.45-1.38 (m, 3H), 1.10 (m, 3H), 0.84 (m, 2H).

Example 48

5-[2-(1-Isobutoxymethyl-cyclopropyl)-8-methoxy-[1,2,4]triazolo[1,5-a]pyridin-5-yl]-nicotinonitrile (Compound 283)

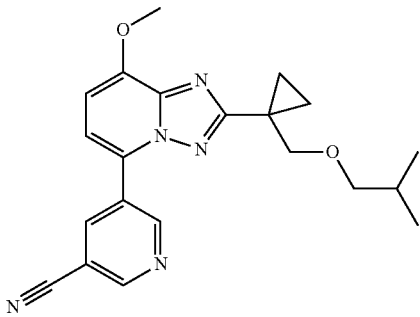 [SMILES: COc1ccc(-c2cncc(C#N)c2)n2nc(C3(COCC(C)C)CC3)nc12]

Compound 248 (0.02 g, 0.06 mmol) was dissolved in DCM (2 mL). TEA (0.035 mL, 0.25 mmol) and methanesulfonyl chloride (0.007 mL, 0.09 mmol) were added and stirred under argon for 30 min. The reaction mixture was washed with $H_2O$ and the organic phase was filtered through a phase separation cartridge (chromabond PTS). The solvent was concentrated and the crude product was suspended in iso-butanol (6 mL) under an argon atmosphere. DIPEA (0.05 mL, 0.31 mmol) was added and the mixture was stirred at 60° C. for 18 h. Iso-butanol was evaporated and the crude product was purified by preparative HPLC/MS to afford the title compound.

1H NMR (300 MHz, CDCl3) δ 9.29 (d, J=2.2 Hz, 1H), 8.92 (d, J=2.0 Hz, 1H), 8.79 (t, J=2.1 Hz, 1H), 7.06 (d, J=8.1 Hz, 1H), 6.86 (d, J=8.2 Hz, 1H), 4.09 (s, 3H), 3.90 (s, 2H), 3.29 (d, J=6.8 Hz, 2H), 1.87 (dp, J=13.4, 6.7 Hz, 1H), 1.43 (q, J=4.2 Hz, 2H), 1.17-1.08 (m, 2H), 0.86 (s, 3H), 0.84 (s, 3H).

Example 49

5-(2-Cyclopropyl-5-methoxy-[1,2,4]triazolo[1,5-a]pyridin-8-yl)-nicotinonitrile (Compound 284)

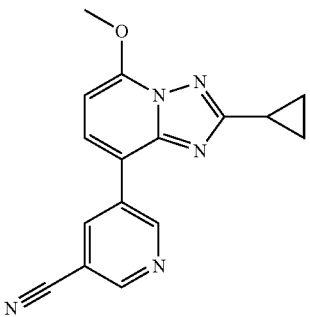 [SMILES: COc1ccc(-c2cncc(C#N)c2)c2nc(C3CC3)nn12]

The compound was prepared according to the procedure described for the preparation of compound 249.

1H NMR (300 MHz, DMSO) δ 9.62 (d, J=2.2 Hz, 1H), 9.04-8.91 (m, 2H), 8.17 (d, J=8.3 Hz, 1H), 6.78 (d, J=8.3 Hz, 1H), 4.19 (s, 3H), 2.22 (tt, J=8.1, 5.0 Hz, 1H), 1.17-0.99 (m, 4H).

Example 50

Compounds 285 and 286 were prepared according to General Procedure 4 using compound 192 as starting material.

1-[5-(4-Cyano-phenyl)-8-methoxy-[1,2,4]triazolo[1,5-a]pyridin-2-yl]-cyclopropanecarboxylic acid (2-dimethylsulfamoyl-ethyl)-amide (Compound 285)

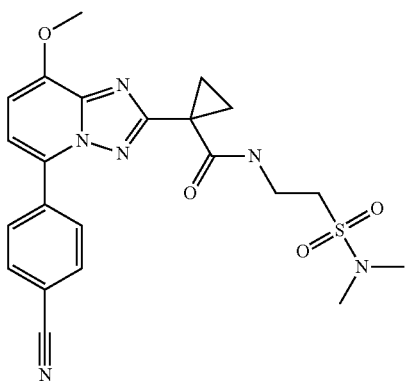 [SMILES: COc1ccc(-c2ccc(C#N)cc2)n2nc(C3(C(=O)NCCS(=O)(=O)N(C)C)CC3)nc12]

1H NMR (300 MHz, CDCl3) δ 9.34 (t, J=5.7 Hz, 1H), 8.08-8.00 (m, 2H), 7.90-7.80 (m, 2H), 7.08 (d, J=8.1 Hz, 1H), 6.97-6.88 (m, 1H), 4.10 (s, 3H), 3.80 (dd, J=12.3, 6.0 Hz, 2H), 3.18 (t, J=6.2 Hz, 2H), 2.87 (s, 6H), 1.82 (dd, J=7.3, 3.6 Hz, 2H), 1.67 (dd, J=7.4, 3.6 Hz, 2H).

1-[5-(4-Cyano-phenyl)-8-methoxy-[1,2,4]triazolo[1,5-a]pyridin-2-yl]-cyclopropanecarboxylic acid [2-(methanesulfonyl-methyl-amino)-ethyl]-amide (Compound 286)

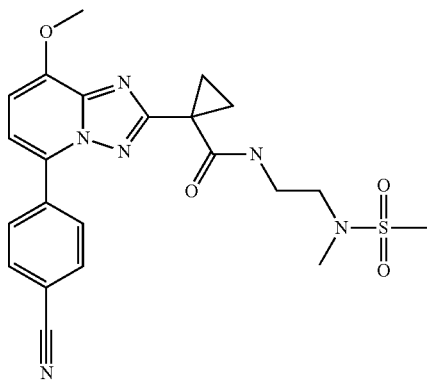 [SMILES: COc1ccc(-c2ccc(C#N)cc2)n2nc(C3(C(=O)NCCN(C)S(C)(=O)=O)CC3)nc12]

1H NMR (300 MHz, CDCl3) δ 9.10 (d, J=5.5 Hz, 1H), 8.07-7.98 (m, 2H), 7.88-7.80 (m, 2H), 7.08 (dd, J=8.1, 2.7 Hz, 1H), 6.98-6.89 (m, 1H), 4.10 (s, 3H), 3.57 (q, J=6.1 Hz, 2H), 3.31 (t, J=6.2 Hz, 2H), 2.92 (s, 3H), 2.80 (s, 3H), 1.81 (dd, J=7.4, 3.6 Hz, 2H), 1.68-1.61 (m, 2H).

Example 51

Compounds 287-289 were prepared according to General Procedure 2.

1-[5-(4-Cyano-3-methoxy-phenyl)-8-methoxy-[1,2,4]triazolo[1,5-a]pyridin-2-yl]-cyclopropanecarboxylic acid (2-dimethylsulfamoyl-ethyl)-amide (Compound 287)

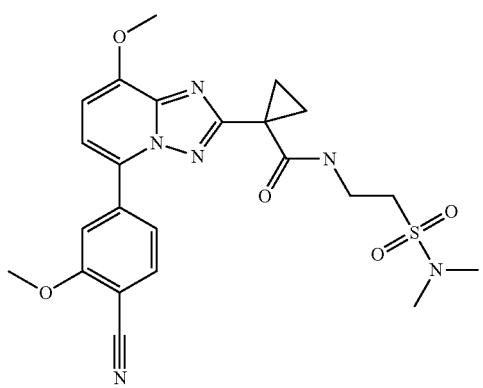

1H NMR (300 MHz, DMSO) δ 8.43 (s, 1H), 7.92-7.82 (m, 2H), 7.73 (d, J=8.1 Hz, 1H), 7.50 (d, J=8.2 Hz, 1H), 7.26 (d, J=8.2 Hz, 1H), 4.05 (s, 3H), 3.99 (s, 3H), 3.49 (dd, J=15.3, 9.4 Hz, 2H), 3.16 (t, J=7.1 Hz, 2H), 2.75 (s, 6H), 1.52 (d, J=3.4 Hz, 2H), 1.39 (d, J=3.4 Hz, 2H).

1-[5-(5-Cyano-pyridin-3-yl)-8-methoxy-[1,2,4]triazolo[1,5-a]pyridin-2-yl]-cyclopropanecarboxylic acid (2-dimethylsulfamoyl-ethyl)-amide (Compound 288)

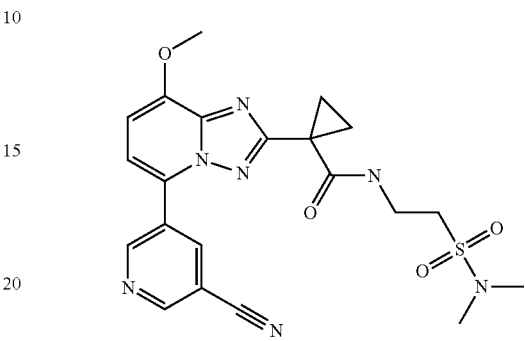

1H NMR (300 MHz, DMSO) δ 9.46 (d, J=2.1 Hz, 1H), 9.12 (d, J=1.8 Hz, 1H), 8.91 (s, 1H), 8.34 (s, 1H), 7.56 (d, J=8.1 Hz, 1H), 7.29 (d, J=8.2 Hz, 1H), 4.05 (s, 3H), 3.52 (d, J=7.9 Hz, 2H), 3.21-3.12 (m, 2H), 2.76 (s, 6H), 1.52 (m, 2H), 1.40 (m, 2H).

1-[8-Methoxy-5-(1-oxo-indan-5-yl)-[1,2,4]triazolo[1,5-a]pyridin-2-yl]-cyclopropanecarboxylic acid (2-dimethylsulfamoyl-ethyl)-amide (Compound 289)

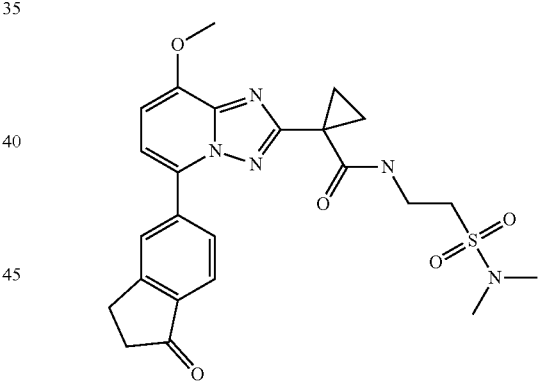

1H NMR (300 MHz, DMSO) δ 8.45 (d, J=5.7 Hz, 1H), 8.15 (s, 1H), 8.01 (d, J=8.1 Hz, 1H), 7.78 (d, J=8.0 Hz, 1H), 7.41 (d, J=8.3 Hz, 1H), 7.26 (d, J=8.3 Hz, 1H), 4.04 (s, 3H), 3.56-3.45 (m, 2H), 3.19 (m, 4H), 2.79-2.67 (m, 8H), 1.57-1.48 (m, 2H), 1.39 (m, 2H).

Example 52

PDE4 Assay

Human recombinant PDE4 (Genbank accession no NM_006203) was incubated for 1 hour with the test compound at concentrations up to 10 μM, with cAMP (1×10-5M), and with a low amount (0.021 MBq) of radioactively labelled cAMP. At the end of the incubation, the cleavage of the substrate was evaluated by the binding of the AMP product to SPA beads, which generate chemoluminescence when bound to the radioactive tracer. The AMP product inhibited the binding of the radioactive tracer to the beads, and the luminescent signal was competed. The results were calculated as the molar concentrations resulting in 50% inhibition of the substrate cleavage compared to controls samples, and are expressed as a range of $IC_{50}$ (M).

PDE4 IC$_{50}$ ranges

| Compound | Name | PDE4 IC50 range |
|---|---|---|
| 101 | 2-Cyclopropyl-8-methoxy-5-(3-acetyl-phenyl)-[1,2,4]triazolo[1,5-a]pyridine | *** |
| 102 | 2-Cyclopropyl-8-methoxy-5-phenyl-[1,2,4]triazolo[1,5-a]pyridine | *** |
| 103 | 2-Cyclopropyl-8-methoxy-5-(4-methoxy-phenyl)-[1,2,4]triazolo[1,5-a]pyridine | *** |
| 104 | 2-Cyclopropyl-8-methoxy-5-(4-trifluoromethyl-phenyl)-[1,2,4]triazolo[1,5-a]pyridine | ** |
| 105 | 2-Cyclopropyl-5-(3,4-dimethoxy-phenyl)-8-methoxy-[1,2,4]triazolo[1,5-a]pyridine | *** |
| 106 | 2-Cyclopropyl-8-methoxy-5-thiophen-2-yl-[1,2,4]triazolo[1,5-a]pyridine | *** |
| 107 | N-[3-(2-Cyclopropyl-8-methoxy-[1,2,4]triazolo[1,5-a]pyridin-5-yl)-phenyl]-acetamide | * |
| 108 | 2-Cyclopropyl-8-methoxy-5-(3-trifluoromethoxy-phenyl)-[1,2,4]triazolo[1,5-a]pyridine | *** |
| 109 | 2-Cyclopropyl-8-methoxy-5-(3-methoxy-phenyl)-[1,2,4]triazolo[1,5-a]pyridine | *** |
| 110 | 1-[5-(2-Cyclopropyl-8-methoxy-[1,2,4]triazolo[1,5-a]pyridin-5-yl)-thiophen-2-yl]-ethanone | *** |
| 111 | 2-Cyclopropyl-8-methoxy-5-pyrimidin-5-yl-[1,2,4]triazolo[1,5-a]pyridine | ** |
| 112 | 2-Cyclopropyl-5-(3-methanesulfonyl-phenyl)-8-methoxy-[1,2,4]triazolo[1,5-a]pyridine | ** |
| 113 | N-[3-(2-Cyclopropyl-8-methoxy-[1,2,4]triazolo[1,5-a]pyridin-5-yl)-phenyl]-methanesulfonamide | ** |
| 114 | 3-(2-Cyclopropyl-8-methoxy-[1,2,4]triazolo[1,5-a]pyridin-5-yl)-N-methyl-benzamide | * |
| 115 | 2-Cyclopropyl-8-methoxy-5-(4-acetyl-phenyl)-[1,2,4]triazolo[1,5-a]pyridine | *** |
| 116 | N-[4-(2-Cyclopropyl-8-methoxy-[1,2,4]triazolo[1,5-a]pyridin-5-yl)-phenyl]-acetamide | * |
| 117 | 3-(2-Cyclopropyl-8-methoxy-[1,2,4]triazolo[1,5-a]pyridin-5-yl)-benzoic acid methyl ester | *** |
| 118 | 2-Cyclopropyl-8-methoxy-5-pyridin-3-yl-[1,2,4]triazolo[1,5-a]pyridine | *** |
| 119 | 4-(2-Cyclopropyl-8-methoxy-[1,2,4]triazolo[1,5-a]pyridin-5-yl)-benzoic acid methyl ester | * |
| 120 | 2-Cyclopropyl-5-(4-methanesulfonyl-phenyl)-8-methoxy-[1,2,4]triazolo[1,5-a]pyridine | * |
| 121 | 2-Cyclopropyl-5-(2-fluoro-phenyl)-8-methoxy-[1,2,4]triazolo[1,5-a]pyridine | ** |
| 122 | 2-Cyclopropyl-8-methoxy-5-[4-(2-methoxy-ethoxy)-phenyl]-[1,2,4]triazolo[1,5-a]pyridine | * |
| 123 | 4-(2-Cyclopropyl-8-methoxy-[1,2,4]triazolo[1,5-a]pyridin-5-yl)-benzamide | *** |
| 124 | 5-(3-Butoxy-phenyl)-2-cyclopropyl-8-methoxy-[1,2,4]triazolo[1,5-a]pyridine | *** |
| 125 | 2-Cyclopropyl-5-(3-fluoro-phenyl)-8-methoxy-[1,2,4]triazolo[1,5-a]pyridine | *** |
| 126 | 2-Cyclopropyl-8-methoxy-5-pyridin-4-yl-[1,2,4]triazolo[1,5-a]pyridine | *** |
| 127 | 2-Cyclopropyl-5-(2,4-dichloro-phenyl)-8-methoxy-[1,2,4]triazolo[1,5-a]pyridine | ** |
| 128 | 2-Cyclopropyl-8-methoxy-5-[4-(morpholine-4-sulfonyl)-phenyl]-[1,2,4]triazolo[1,5-a]pyridine | * |
| 129 | N-[4-(2-Cyclopropyl-8-methoxy-[1,2,4]triazolo[1,5-a]pyridin-5-yl)-benzyl]-acetamide | * |
| 130 | N-[4-(2-Cyclopropyl-8-methoxy-[1,2,4]triazolo[1,5-a]pyridin-5-yl)-benzyl]-methanesulfonamide | * |
| 131 | 2-Cyclopropyl-5-(4-fluoro-phenyl)-8-methoxy-[1,2,4]triazolo[1,5-a]pyridine | *** |
| 132 | 4-(2-Cyclopropyl-8-methoxy-[1,2,4]triazolo[1,5-a]pyridin-5-yl)-benzonitrile | *** |
| 133 | 3-[4-(2-Cyclopropyl-8-methoxy-[1,2,4]triazolo[1,5-a]pyridin-5-yl)-phenyl]-propionic acid methyl ester | ** |
| 134 | 4-(2-Cyclopropyl-8-methoxy-[1,2,4]triazolo[1,5-a]pyridin-5-yl)-N-(2-hydroxy-ethyl)-benzenesulfonamide | * |
| 135 | 3-(2-Cyclopropyl-8-methoxy-[1,2,4]triazolo[1,5-a]pyridin-5-yl)-benzonitrile | *** |
| 136 | 3-(2-Cyclopropyl-8-methoxy-[1,2,4]triazolo[1,5-a]pyridin-5-yl)-benzoic acid | ** |
| 137 | [3-(2-Cyclopropyl-8-methoxy-[1,2,4]triazolo[1,5-a]pyridin-5-yl)-phenyl]-methanol | *** |
| 138 | 3-(2-Cyclopropyl-8-methoxy-[1,2,4]triazolo[1,5-a]pyridin-5-yl)-N,N-dimethyl-benzamide | ** |
| 139 | 3-(2-Cyclopropyl-8-methoxy-[1,2,4]triazolo[1,5-a]pyridin-5-yl)-benzamide | *** |
| 140 | 4-(2-Cyclopropyl-8-methoxy-[1,2,4]triazolo[1,5-a]pyridin-5-yl)-benzoic acid | *** |
| 141 | 4-(2-Cyclopropyl-8-methoxy-[1,2,4]triazolo[1,5-a]pyridin-5-yl)-N,N-dimethyl-benzamide | * |
| 142 | 4-(2-Cyclopropyl-8-methoxy-[1,2,4]triazolo[1,5-a]pyridin-5-yl)-N-methyl-benzamide | * |
| 143 | 2-Cyclopropyl-8-methoxy-5-piperidin-1-yl-[1,2,4]triazolo[1,5-a]pyridine | *** |

* indicates that IC$_{50}$ values are ≥ 1000 nM
** indicates that IC$_{50}$ values are ≥ 500 and < 1000 nM
*** indicates that IC$_{50}$ values are < 500 nM

Example 53

A PDE4 assay as disclosed in example 52 above was conducted. The results were calculated as the molar concentrations resulting in 50% inhibition of the substrate cleavage compared to controls samples, and are expressed as a range of $IC_{50}$ (M).

PDE4 IC$_{50}$ ranges

| PDE4 IC$_{50}$ range | Compounds |
|---|---|
| * | 191-193, 204-205 |
| ** | 145-146, 158, 196, 200, 222 |
| *** | 144, 148-156, 159-162, 164-186, 188, 190, 194-195, 197-199, 201-203, 206-221, 223-228, 230-242, 269-270 |

* indicates that IC$_{50}$ values are ≥ 1000 nM
** indicates that IC$_{50}$ values are ≥ 500 and < 1000 nM
*** indicates that IC$_{50}$ values are < 500 nM

The invention claimed is:
1. A compound of general formula I,

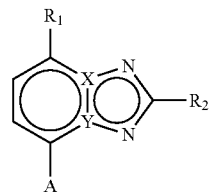

wherein
$R_1$ is $C_{1-6}$ alkoxy, halogen, hydroxyl, monofluoromethoxy, difluoromethoxy, or trifluoromethoxy;

R$_2$ is cycloalkyl, alkylcycloalkyl, or cycloalkyl(C(O)NR$_7$R$_8$), each of which is optionally substituted with one or more substituents selected from R$_4$;

R$_3$ is hydrogen, halogen, aryl, heteroaryl, hydroxy, alkyl, cycloalkyl, heterocycloalkyl, alkoxy, oxo, cyano, amino, aminoalkyl, alkylamino or dialkylamino;

R$_4$ is hydrogen, halogen, hydroxy, oxo, cyano, carboxy, or trihalomethyl, or R$_4$ is NR$_5$R$_6$, —C(O)NR$_7$R$_8$, —C(O)R$_7$, —COOR$_7$, —NR$_5$C(O)NR$_7$R$_8$, —OC(O)NR$_7$R$_8$, —OC(O)R$_3$, NC(O)R$_7$, —OR$_7$, —NC(O)OR$_3$, —NSO$_2$R$_7$, —SO$_2$NR$_7$R$_8$, or —SO$_2$R$_7$R$_8$, alkyl, cycloalkyl, alkenyl, alkynyl, aryl, heteroaryl, cycloalkylalkyl, cycloalkylalkenyl, cycloalkylalkynyl, cycloalkenylalkyl, cycloalkenylalkenyl, cycloalkenylalkynyl, heterocycloalkyl, heterocycloalkylalkyl, heterocycloalkenyl, heterocycloalkenylalkyl, heterocycloalkenylalkenyl, heterocycloalkenylalkynyl, arylalkyl, arylalkenyl, arylalkynyl, heteroarylalkyl, heteroarylalkenyl, heteroarylalkynyl, alkoxy, cycloalkyloxy, alkylthio, cycloalkylthio, sulfamoyl, sulfinamoyl, alkylamino or cycloalkylamino, each of which is optionally substituted with one or more substituents selected from R$_9$;

R$_5$ and R$_6$ each independently represents hydrogen, alkyl, alkenyl, cycloalkyl, heterocycloalkyl, —C(O)alkyl, —C(O)Oalkyl, —C(O)cycloalkyl, —C(O)N-alkyl, carboxyalkyl, —C(O)alkyl-C(O)OH, —C(O)alkyl-C(O)N-alkyl, —C(O)N-aryl, —S(O)$_2$alkyl, —S(O)alkyl, —S(O)$_2$aryl, —S(O)$_2$N-alkyl, —S(O)aryl, aryl, heteroaryl alkylaryl or alkylheteroaryl, each of which is optionally substituted with hydroxy or one or more halogens, or R$_5$ and R$_6$ together with the nitrogen atom to which they are attached form a heterocycloalkyl ring, wherein said ring is optionally substituted with one or more alkyl groups;

R$_7$ and R$_8$ each independently represents hydrogen, alkyl, cycloalkyl, alkenyl, heteroaryl, heterocycloalkyl, carboxyalkyl, carbamoylalkyl, alkyloxyalkyl, alkenyloxyalkyl, aryl, arylalkyl, alkylaryl, heteroaryl, heteroarylalkyl, or alkylheteroaryl, each of which is optionally substituted with one or more substituents selected from the group consisting of hydroxy, halogen, oxo, cyano, alkyl, cycloalkyl, alkenyl, alkoxy, aryl, heteroaryl, heterocycloalkyl, —S(O)$_2$-alkyl, —S(O)$_2$—NR$_{11}$R$_{12}$, —NC(O)-alkyl, —C(O)N-alkyl, —NC(O)O-alkyl, —OC(O)N-alkyl, —NC(O)NR$_{11}$R$_{12}$, —NR$_{11}$SO$_2$-alkyl, —S(O)-alkyl, or R$_7$ and R$_8$ together with the nitrogen atom to which they are attached form a heterocycloalkyl ring, wherein said ring is optionally substituted with one or more alkyl groups;

R$_9$ is hydrogen, halogen, hydroxy, alkoxy, carboxy or trihalomethyl;

X and Y are either C and N or N and C, respectively;

A is aryl, heteroaryl, or piperidinyl, each being optionally substituted with one or more substituents selected from the group consisting of R$_{10}$;

R$_{10}$ is hydrogen, cyano, halogen, hydroxy, or oxo, or R$_{10}$ is alkyl, cycloalkyl, alkenyl, alkynyl, aryl, heteroaryl, cycloalkylalkyl, cycloalkylalkenyl, cycloalkylalkynyl, cycloalkenylalkyl, cycloalkenylalkenyl, cycloalkenylalkynyl, heterocycloalkyl, heterocycloalkenyl, heterocycloalkenylalkyl, heterocycloalkenylalkenyl, heterocycloalkenylalkynyl, arylalkyl, arylalkenyl, arylalkynyl, heteroarylalkyl, heteroarylalkenyl, heteroarylalkynyl, alkoxy, cycloalkyloxy, alkylthio, cycloalkylthio, —S(O)alkyl, —S(O)$_2$-alkyl, sulfamoyl, sulfinamoyl, —C(O)OR$_3$, —C(O)R$_3$, —NR$_5$R$_6$, -alkyl(NR$_5$R$_6$), -cycloalkyl(NR$_5$R$_6$), -cycloalkylalkyl(NR$_5$R$_6$), -alkylcycloalkyl(NR$_5$R$_6$), —C(O)NR$_7$R$_8$, -alkyl(C(O)NR$_7$R$_8$), -cycloalkyl(C(O)NR$_7$R$_8$), -cycloalkylalkyl(C(O)NR$_7$R$_8$) or -alkylcycloalkyl(C(O)NR$_7$R$_8$), each of which is optionally substituted with one or more substituents selected from R$_4$; and R$_{11}$ and R$_{12}$ each independently represents hydrogen or alkyl;

and pharmaceutically acceptable salts, hydrates, N-oxides or solvates thereof.

2. A compound according to claim 1, wherein A is optionally substituted with R$_{10}$, wherein R$_{10}$ is different from hydrogen.

3. A compound according to claim 1, wherein A is optionally substituted aryl.

4. A compound according to claim 1, wherein A is optionally substituted phenyl or optionally substituted indanyl.

5. A compound according to claim 4, wherein R$_{10}$ is cyano, halogen, alkyl, aryl, heteroaryl, sulfamoyl, —C(O)R$_3$, —C(O)OR$_3$, —NR$_5$R$_6$, wherein R$_3$, R$_5$ and R$_6$ are as indicated in claim 1.

6. A compound according to claim 1, wherein A is optionally substituted heteroaryl.

7. A compound according to claim 6, wherein A is optionally substituted pyridyl, optionally substituted benzofuranyl, optionally substituted 3H-isobenzofuran-1-on-yl or optionally substituted 2,3-dihydro-isoindol-1-on-yl.

8. A compound according to claim 1, wherein A is optionally substituted piperidinyl or optionally substituted pyridazinyl.

9. A compound according to claim 3, wherein R$_{10}$ is hydrogen, cyano, halogen, oxo, alkyl, alkoxy, cycloalkyloxy, —S(O)alkyl, —S(O)$_2$-alkyl, —C(O)R$_3$, —C(O)OR$_3$, —C(O)NR$_7$R$_8$.

10. A compound according to claim 9, wherein R$_{10}$ is cyano, halogen, oxo, alkyl, alkoxy, or —C(O)R$_3$.

11. A compound according to claim 1, wherein R$_1$ is methoxy, monofluoromethoxy, difluoromethoxy, trifluoromethoxy, halogen, or hydroxy.

12. A compound according to claim 1, of general formula Ia

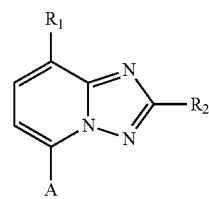

wherein R$_1$, R$_2$ and A are as defined in claim 1.

13. A compound according to claim 1, of general formula Ib

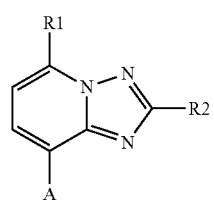

wherein R$_1$, R$_2$ and A are as defined in claim 1.

14. A compound according to claim 1, wherein $R_2$ is optionally substituted $C_{1-6}$ alkyl or optionally substituted $C_{3-6}$ cycloalkyl.

15. A compound according to claim 14, wherein $R_2$ is optionally substituted cyclopropyl.

16. A compound according to claim 1, wherein $R_3$ is halogen, alkyl, cycloalkyl, heterocycloalkyl, or oxo.

17. A compound according to claim 16, wherein $R_3$ is alkyl or heterocycloalkyl.

18. A compound according to claim 1, wherein $R_4$ is halogen, hydroxy, or cyano, or $R_4$ is $NR_5R_6$, —C(O)$NR_7R_8$, —COOR$_7$, —$NR_5$C(O)$NR_7R_8$, —OC(O)$NR_7R_8$, —OC(O)$R_3$, —NC(O)$R_7$, —OR$_7$, —NC(O)OR$_3$, —NSO$_2R_7$, —SO$_2NR_7R_8$, —SO$_2R_7R_8$, alkyl, cycloalkyl, cycloalkylalkyl, heterocycloalkyl, or heterocycloalkylalkyl, each of which is optionally substituted with one or more substituents selected from $R_9$.

19. A compound according to claim 1, wherein $R_4$ is hydroxy or cyano, or $R_4$ is —C(O)$NR_7R_8$, —COOR$_7$, —$NR_5$C(O)$NR_7R_8$, —OC(O)$NR_7R_8$, —NC(O)$R_7$, —OR$_7$, —NC(O)OR$_3$, alkyl, which is optionally substituted with one or more substituents selected from $R_9$; wherein $R_9$ is hydrogen, halogen, or hydroxyl.

20. A compound according to claim 1, wherein $R_5$ and $R_6$ each independently represents hydrogen, alkyl, alkenyl, cycloalkyl, or heterocycloalkyl, or $R_5$ and $R_6$ together with the nitrogen atom to which they are attached form a heterocycloalkyl ring, wherein said ring is optionally substituted with one or more alkyl groups.

21. A compound according to claim 1, wherein $R_7$ and $R_8$ each independently represents hydrogen, alkyl, cycloalkyl, heterocycloalkyl, or alkenyloxyalkyl, each of which is optionally substituted with one or more substituents selected from the group consisting of hydroxy, halogen, oxo, cyano, alkyl, cycloalkyl, alkoxy, aryl, heteroaryl, heterocycloalkyl, —S(O)$_2$-alkyl, —S(O)$_2$—$NR_{11}R_{12}$, —NC(O)-alkyl, —C(O)N-alkyl, —NC(O)O-alkyl, —OC(O)N-alkyl, —$NR_{11}SO_2$-alkyl, —S(O)-alkyl, or $R_7$ and $R_8$ together with the nitrogen atom to which they are attached form a heterocycloalkyl ring, wherein said ring is optionally substituted with one or more alkyl groups; wherein $R_{11}$ and $R_{12}$ are hydrogen or $C_{1-4}$ alkyl.

22. A compound according to claim 1, wherein $R_7$ and $R_8$ each independently represents hydrogen, alkyl, cycloalkyl, alkenyloxyalkyl, each of which is optionally substituted with one or more substituents selected from the group consisting of hydroxy, oxo, cyano, alkyl, cycloalkyl, alkoxy, aryl, heteroaryl, —S(O)$_2$-alkyl, —S(O)$_2$—$NR_{11}R_{12}$, —NC(O)-alkyl, —$NR_{11}SO_2$-alkyl, or $R_7$ and $R_8$ together with the nitrogen atom to which they are attached form a heterocycloalkyl ring, wherein said ring is optionally substituted with one or more alkyl groups; wherein $R_{11}$ and $R_{12}$ are hydrogen or $C_{1-4}$ alkyl.

23. A compound according to claim 1 selected from the group consisting of:

2-Cyclopropyl-8-methoxy-5-(3-acetyl-phenyl)-[1,2,4]triazolo[1,5-a]pyridine,

2-Cyclopropyl-8-methoxy-5-phenyl-[1,2,4]triazolo[1,5-a]pyridine,

2-Cyclopropyl-8-methoxy-5-(4-methoxy-phenyl)-[1,2,4]triazolo[1,5-a]pyridine,

2-Cyclopropyl-8-methoxy-5-(4-trifluoromethyl-phenyl)-[1,2,4]triazolo[1,5-a]pyridine, 2-Cyclopropyl-5-(3,4-dimethoxy-phenyl)-8-methoxy-[1,2,4]triazolo[1,5-a]pyridine, 2-Cyclopropyl-8-methoxy-5-thiophen-2-yl-[1,2,4]triazolo[1,5-a]pyridine, N-[3-(2-Cyclopropyl-8-methoxy-[1,2,4]triazolo[1,5-a]pyridin-5-yl)-phenyl]-acetamide, 2-Cyclopropyl-8-methoxy-5-(3-trifluoromethoxy-phenyl)-[1,2,4]triazolo[1,5-a]pyridine, 2-Cyclopropyl-8-methoxy-5-(3-methoxy-phenyl)-[1,2,4]triazolo[1,5-a]pyridine, 1-[5-(2-Cyclopropyl-8-methoxy-[1,2,4]triazolo[1,5-a]pyridin-5-yl)-thiophen-2-yl]-ethanone, 2-Cyclopropyl-8-methoxy-5-pyrimidin-5-yl-[1,2,4]triazolo[1,5-a]pyridine, 2-Cyclopropyl-5-(3-methanesulfonyl-phenyl)-8-methoxy-[1,2,4]triazolo[1,5-a]pyridine, N-[3-(2-Cyclopropyl-8-methoxy-[1,2,4]triazolo[1,5-a]pyridin-5-yl)-phenyl]-methanesulfonamide, 3-(2-Cyclopropyl-8-methoxy-[1,2,4]triazolo[1,5-a]pyridin-5-yl)-N-methyl-benzamide, 2-Cyclopropyl-8-methoxy-5-(4-acetyl-phenyl)-[1,2,4]triazolo[1,5-a]pyridine, N-[4-(2-Cyclopropyl-8-methoxy-[1,2,4]triazolo[1,5-a]pyridin-5-yl)-phenyl]-acetamide, 3-(2-Cyclopropyl-8-methoxy-[1,2,4]triazolo[1,5-a]pyridin-5-yl)-benzoic acid methyl ester, 2-Cyclopropyl-8-methoxy-5-pyridin-3-yl-[1,2,4]triazolo[1,5-a]pyridine, 4-(2-Cyclopropyl-8-methoxy-[1,2,4]triazolo[1,5-a]pyridin-5-yl)-benzoic acid methyl ester, 2-Cyclopropyl-5-(4-methanesulfonyl-phenyl)-8-methoxy-[1,2,4]triazolo[1,5-a]pyridine, 2-Cyclopropyl-5-(2-fluoro-phenyl)-8-methoxy-[1,2,4]triazolo[1,5-a]pyridine, 2-Cyclopropyl-8-methoxy-5-[4-(2-methoxy-ethoxy)-phenyl]-[1,2,4]triazolo[1,5-a]pyridine, 4-(2-Cyclopropyl-8-methoxy-[1,2,4]triazolo[1,5-a]pyridin-5-yl)-benzamide 5-(3-Butoxy-phenyl)-2-cyclopropyl-8-methoxy-[1,2,4]triazolo[1,5-a]pyridine, 2-Cyclopropyl-5-(3-fluoro-phenyl)-8-methoxy-[1,2,4]triazolo[1,5-a]pyridine, 2-Cyclopropyl-8-methoxy-5-pyridin-4-yl-[1,2,4]triazolo[1,5-a]pyridine, 2-Cyclopropyl-5-(2,4-dichloro-phenyl)-8-methoxy-[1,2,4]triazolo[1,5-a]pyridine, 2-Cyclopropyl-8-methoxy-5-[4-(morpholine-4-sulfonyl)-phenyl]-[1,2,4]triazolo[1,5-a]pyridine, N-[4-(2-Cyclopropyl-8-methoxy-[1,2,4]triazolo[1,5-a]pyridin-5-yl)-benzyl]-acetamide, N-[4-(2-Cyclopropyl-8-methoxy-[1,2,4]triazolo[1,5-a]pyridin-5-yl)-benzyl]-methanesulfonamide, 2-Cyclopropyl-5-(4-fluoro-phenyl)-8-methoxy-[1,2,4]triazolo[1,5-a]pyridine, 4-(2-Cyclopropyl-8-methoxy-[1,2,4]triazolo[1,5-a]pyridin-5-yl)-benzonitrile, 3-[4-(2-Cyclopropyl-8-methoxy-[1,2,4]triazolo[1,5-a]pyridin-5-yl)-phenyl]-propionic acid methyl ester, 4-(2-Cyclopropyl-8-methoxy-[1,2,4]triazolo[1,5-a]pyridin-5-yl)-N-(2-hydroxy-ethyl)-benzenesulfonamide, 3-(2-Cyclopropyl-8-methoxy-[1,2,4]triazolo[1,5-a]pyridin-5-yl)-benzonitrile, 3-(2-Cyclopropyl-8-methoxy-[1,2,4]triazolo[1,5-a]pyridin-5-yl)-benzoic acid,

[3-(2-Cyclopropyl-8-methoxy-[1,2,4]triazolo[1,5-a]pyridin-5-yl)-phenyl]-methanol, 3-(2-Cyclopropyl-8-methoxy-[1,2,4]triazolo[1,5-a]pyridin-5-yl)-N,N-dimethyl-benzamide, 3-(2-Cyclopropyl-8-methoxy-[1,2,4]triazolo[1,5-a]pyridin-5-yl)-benzamide, 4-(2-Cyclopropyl-8-methoxy-[1,2,4]triazolo[1,5-a]pyridin-5-yl)-benzoic acid, 4-(2-Cyclopropyl-8-methoxy-[1,2,4]triazolo[1,5-a]pyridin-5-yl)-N,N-dimethyl-benzamide,
4-(2-Cyclopropyl-8-methoxy-[1,2,4]triazolo[1,5-a]pyridin-5-yl)-N-methyl-benzamide,
2-Cyclopropyl-8-methoxy-5-piperidin-1-yl-[1,2,4]triazolo[1,5-a]pyridine,
1-[3-(2-Cyclopropyl-8-hydroxy-[1,2,4]triazolo[1,5-a]pyridin-5-yl)-phenyl]-ethanone,
2-(2-Cyclopropyl-8-methoxy-[1,2,4]triazolo[1,5-a]pyridin-5-yl)-isonicotinonitrile,
1-[5-(4-Cyano-phenyl)-8-methoxy-[1,2,4]triazolo[1,5-a]pyridin-2-yl]-cyclopropanecarboxylic acid ethyl ester,
1-[5-(4-Cyano-phenyl)-8-methoxy-[1,2,4]triazolo[1,5-a]pyridin-2-yl]-cyclopropanecarboxylic acid,
1-[5-(4-Cyano-phenyl)-8-methoxy-[1,2,4]triazolo[1,5-a]pyridin-2-yl]-cyclopropanecarboxylic acid amide,
1-[5-(5-Cyano-pyridin-3-yl)-8-methoxy-[1,2,4]triazolo[1,5-a]pyridin-2-yl]-cyclopropanecarboxylic acid isopropylamide,
3-[2-(1-Hydroxymethyl-cyclopropyl)-8-methoxy-[1,2,4]triazolo[1,5-a]pyridin-5-yl]-benzonitrile,
Pyrrolidine-1-carboxylic acid 1-[5-(3-cyano-phenyl)-8-methoxy-[1,2,4]triazolo[1,5-a]pyridin-2-yl]-cyclopropylmethyl ester,
Isopropyl-carbamic acid 1-[5-(3-cyano-phenyl)-8-methoxy-[1,2,4]triazolo[1,5-a]pyridin-2-yl]-cyclopropylmethyl ester,
3-[2-(1-Benzyloxymethyl-cyclopropyl)-8-methoxy-[1,2,4]triazolo[1,5-a]pyridin-5-yl]-benzonitrile,
N-{1-[5-(3-Cyano-phenyl)-8-methoxy-[1,2,4]triazolo[1,5-a]pyridin-2-yl]-cyclopropylmethyl}-isobutyramide,
{1-[5-(3-Cyano-phenyl)-8-methoxy-[1,2,4]triazolo[1,5-a]pyridin-2-yl]-cyclopropylmethyl}-carbamic acid cyclopentyl ester,
Pyrrolidine-1-carboxylic acid {1-[5-(3-cyano-phenyl)-8-methoxy-[1,2,4]triazolo[1,5-a]pyridin-2-yl]-cyclopropylmethyl}-amide,
5-(2-Cyclopropyl-8-methoxy-[1,2,4]triazolo[1,5-a]pyridin-5-yl)-nicotinonitrile,
5-(2-Cyclopropyl-8-methoxy-[1,2,4]triazolo[1,5-a]pyridin-5-yl)-indan-1-one,
4-(2-Cyclopropyl-8-methoxy-[1,2,4]triazolo[1,5-a]pyridin-5-yl)-2-methyl-benzonitrile,
4-(2-Cyclopropyl-8-methoxy-[1,2,4]triazolo[1,5-a]pyridin-5-yl)-indan-1-one,
3-(2-Cyclopropyl-8-methoxy-[1,2,4]triazolo[1,5-a]pyridin-5-yl)-5-fluoro-benzonitrile,
4-(2-Cyclopropyl-8-methoxy-[1,2,4]triazolo[1,5-a]pyridin-5-yl)-2-fluoro-benzonitrile,
4-(2-Cyclopropyl-8-methoxy-[1,2,4]triazolo[1,5-a]pyridin-5-yl)-2-methoxy-benzonitrile,
5-(2-Cyclopropyl-8-methoxy-[1,2,4]triazolo[1,5-a]pyridin-5-yl)-3H-isobenzofuran-1-one,
3-(2-Cyclopropyl-8-methoxy-[1,2,4]triazolo[1,5-a]pyridin-5-yl)-5-hydroxymethyl-benzonitrile,
3-(2-Cyclopropyl-8-methoxy-[1,2,4]triazolo[1,5-a]pyridin-5-yl)-5-methoxy-benzonitrile,
4-(2-Cyclopropyl-8-methoxy-[1,2,4]triazolo[1,5-a]pyridin-5-yl)-3H-isobenzofuran-1-one,
5-(2-Cyclopropyl-8-methoxy-[1,2,4]triazolo[1,5-a]pyridin-5-yl)-2,3-dihydro-isoindol-1-one,
1-[8-Methoxy-5-(1-oxo-indan-4-yl)-[1,2,4]triazolo[1,5-a]pyridin-2-yl]-cyclopropanecarboxylic acid benzylamide,
1[5-(5-Cyano-pyridin-3-yl)-8-methoxy-[1,2,4]triazolo[1,5-a]pyridin-2-yl]-cyclopropanecarboxylic acid benzylamide,
1-[5-(4-Cyano-3-methoxy-phenyl)-8-methoxy-[1,2,4]triazolo[1,5-a]pyridin-2-yl]-cyclopropanecarboxylic acid cyclohexylmethyl-amide,
1-[5-(4-Cyano-3-methoxy-phenyl)-8-methoxy-[1,2,4]triazolo[1,5-a]pyridin-2-yl]-cyclopropanecarboxylic acid isopropylamide,
1-[8-Methoxy-5-(1-oxo-indan-4-yl)-[1,2,4]triazolo[1,5-a]pyridin-2-yl]-cyclopropanecarboxylic acid cyclohexylmethyl-amide,
1-[5-(4-Cyano-3-methoxy-phenyl)-8-methoxy-[1,2,4]triazolo[1,5-a]pyridin-2-yl]-cyclopropanecarboxylic acid (2-methanesulfonyl-ethyl)-amide,
1[5-(4-Cyano-3-methoxy-phenyl)-8-methoxy-[1,2,4]triazolo[1,5-a]pyridin-2-yl]-cyclopropanecarboxylic acid benzylamide,
1-[8-Methoxy-5-(1-oxo-1,3-dihydro-isobenzofuran-5-yl)-[1,2,4]triazolo[1,5-a]pyridin-2-yl]-cyclopropanecarboxylic acid benzylamide,
1-[8-Methoxy-5-(1-oxo-indan-4-yl)-[1,2,4]triazolo[1,5-a]pyridin-2-yl]-cyclopropanecarboxylic acid isopropylamide,
1-[8-Methoxy-5-(1-oxo-indan-5-yl)-[1,2,4]triazolo[1,5-a]pyridin-2-yl]-cyclopropanecarboxylic acid isopropylamide,
1-[8-Methoxy-5-(1-oxo-indan-5-yl)-[1,2,4]triazolo[1,5-a]pyridin-2-yl]-cyclopropanecarboxylic acid benzylamide,
1-[8-Methoxy-5-(1-oxo-indan-4-yl)-[1,2,4]triazolo[1,5-a]pyridin-2-yl]-cyclopropanecarboxylic acid (2-methanesulfonyl-ethyl)-amide,
1-[8-Methoxy-5-(1-oxo-indan-5-yl)-[1,2,4]triazolo[1,5-a]pyridin-2-yl]-cyclopropanecarboxylic acid (2-methanesulfonyl-ethyl)-amide,
1-[5-(5-Cyano-pyridin-3-yl)-8-methoxy-[1,2,4]triazolo[1,5-a]pyridin-2-yl]-cyclopropanecarboxylic acid cyclohexylmethyl-amide,
1-[5-(5-Cyano-pyridin-3-yl)-8-methoxy-[1,2,4]triazolo[1,5-a]pyridin-2-yl]-cyclopropanecarboxylic acid (2-methanesulfonyl-ethyl)-amide,
1-[8-Methoxy-5-(1-oxo-1,3-dihydro-isobenzofuran-5-yl)-[1,2,4]triazolo[1,5-a]pyridin-2-yl]-cyclopropanecarboxylic acid (2-dimethylsulfamoyl-ethyl)-amide,
1-[5-(3-Cyano-phenyl)-8-methoxy-[1,2,4]triazolo[1,5-a]pyridin-2-yl]-cyclopropanecarboxylic acid ethyl ester,
1-[5-(4-Cyano-phenyl)-8-methoxy-[1,2,4]triazolo[1,5-a]pyridin-2-yl]-cyclopropanecarboxylic acid ethyl ester,
1-[5-(3-Acetyl-phenyl)-8-methoxy-[1,2,4]triazolo[1,5-a]pyridin-2-yl]-cyclopropanecarboxylic acid ethyl ester,
1-[5-(3-Cyano-phenyl)-8-methoxy-[1,2,4]triazolo[1,5-a]pyridin-2-yl]-cyclopropanecarboxylic acid,
1-[5-(4-Cyano-phenyl)-8-methoxy-[1,2,4]triazolo[1,5-a]pyridin-2-yl]-cyclopropanecarboxylic acid,
1-[5-(3-Acetyl-phenyl)-8-methoxy-[1,2,4]triazolo[1,5-a]pyridin-2-yl]-cyclopropanecarboxylic acid,
1-[5-(3-Cyano-phenyl)-8-methoxy-[1,2,4]triazolo[1,5-a]pyridin-2-yl]-cyclopropanecarboxylic acid isopropylamide,
1-[5-(3-Cyano-phenyl)-8-methoxy-[1,2,4]triazolo[1,5-a]pyridin-2-yl]-cyclopropanecarboxylic acid (pyridin-3-ylmethyl)-amide,
3-{8-Methoxy-2-[1-(morpholine-4-carbonyl)-cyclopropyl]-[1,2,4]triazolo-[1,5-a]pyridin-5-yl}-benzonitrile,
1-[5-(3-Cyano-phenyl)-8-methoxy-[1,2,4]triazolo[1,5-a]pyridin-2-yl]-cyclopropanecarboxylic acid benzylamide, 1-[5-(3-Cyano-phenyl)-8-methoxy-[1,2,4]triazolo[1,5-a]pyridin-2-yl]-cyclopropanecarboxylic acid (2-sulfamoyl-ethyl)-amide,
1-[5-(3-Cyano-phenyl)-8-methoxy-[1,2,4]triazolo[1,5-a]pyridin-2-yl]-cyclopropanecarboxylic acid (2-methanesulfonyl-ethyl)-amide,
3-{8-Methoxy-2-[1-(pyrrolidine-1-carbonyl)-cyclopyl]-[1,2,4]triazolo[1,5-a]pyridin-5-yl}-benzonitrile,
2-Methyl-acrylic acid 2-({1-[5-(3-cyano-phenyl)-8-methoxy-[1,2,4]triazolo[1,5-a]pyridin-2-yl-cyclopropanecarbonyl}-amino)-ethyl ester,
1-[5-(3-Cyano-phenyl)-8-methoxy-[1,2,4]triazolo[1,5-a]pyridin-2-yl]-cyclopropanecarboxylic acid (2-methoxy-ethyl)-amide,
1-[5-(4-Cyano-phenyl)-8-methoxy-[1,2,4]triazolo[1,5-a]pyridin-2-yl]-cyclopropanecarboxylic acid (pyridin-3-ylmethyl)-amide,
4-{8-Methoxy-2-[1-(4-methyl-piperazine-1-carbonyl)-cyclopropyl]-[1,2,4]triazolo[1,5-a]pyridin-5-yl}-benzonitrile,
4-{8-Methoxy-2-[1-(morpholine-4-carbonyl)-cyclopyl]-[1,2,4]triazolo[1,5-a]pyridin-5-yl}-benzonitrile,
1-[5-(4-Cyano-phenyl)-8-methoxy-[1,2,4]triazolo[1,5-a]pyridin-2-yl]-cyclopropanecarboxylic acid benzylamide,
1-[5-(4-Cyano-phenyl)-8-methoxy-[1,2,4]triazolo[1,5-a]pyridin-2-yl]-cyclopropanecarboxylic acid (2-sulfamoyl-ethyl)-amide,
1-[5-(4-Cyano-phenyl)-8-methoxy-[1,2,4]triazolo[1,5-a]pyridin-2-yl]-cyclopropanecarboxylic acid (2-methanesulfonyl-ethyl)-amide,
1-[5-(4-Cyano-phenyl)-8-methoxy-[1,2,4]triazolo[1,5-a]pyridin-2-yl]-cyclopropanecarboxylic acid isopropylamide,
1-[5-(4-Cyano-phenyl)-8-methoxy-[1,2,4]triazolo[1,5-a]pyridin-2-yl]-cyclopropanecarboxylic acid methylamide,
1-[5-(4-Cyano-phenyl)-8-methoxy-[1,2,4]triazolo[1,5-a]pyridin-2-yl]-cyclopropanecarboxylic acid ethylamide,
1-[5-(4-Cyano-phenyl)-8-methoxy-[1,2,4]triazolo[1,5-a]pyridin-2-yl]-cyclopropanecarboxylic acid propylamide,
1-[5-(4-Cyano-phenyl)-8-methoxy-[1,2,4]triazolo[1,5-a]pyridin-2-yl]-cyclopropanecarboxylic acid cyclopropylamide,
1-[5-(4-Cyano-phenyl)-8-methoxy-[1,2,4]triazolo[1,5-a]pyridin-2-yl]-cyclopropanecarboxylic acid isobutylamide,
1-[5-(4-Cyano-phenyl)-8-methoxy-[1,2,4]triazolo[1,5-a]pyridin-2-yl]-cyclopropanecarboxylic acid cyanomethyl-amide,
1-[5-(4-Cyano-phenyl)-8-methoxy-[1,2,4]triazolo[1,5-a]pyridin-2-yl]-cyclopropanecarboxylic acid (2-acetylamino-ethyl)-amide,
1-[5-(4-Cyano-phenyl)-8-methoxy-[1,2,4]triazolo[1,5-a]pyridin-2-yl]-cyclopropanecarboxylic acid (2-methanesulfonylamino-ethyl)-amide,
1-[5-(4-Cyano-phenyl)-8-methoxy-[1,2,4]triazolo[1,5-a]pyridin-2-yl]-cyclopropanecarboxylic acid (3-morpholin-4-yl-3-oxo-propyl)-amide,
1-[5-(4-Cyano-phenyl)-8-methoxy-[1,2,4]triazolo[1,5-a]pyridin-2-yl]-cyclopropanecarboxylic acid (2-dimethylsulfamoyl-ethyl)-amide,
1-[5-(4-Cyano-phenyl)-8-methoxy-[1,2,4]triazolo[1,5-a]pyridin-2-yl]-cyclopropanecarboxylic acid[2-(methanesulfonyl-methyl-amino)-ethyl]-amide,
1-[5-(3-Acetyl-phenyl)-8-methoxy-[1,2,4]triazolo[1,5-a]pyridin-2-yl]-cyclopropanecarboxylic acid (pyridin-3-ylmethyl)-amide,
1-(3-{8-Methoxy-2-[1-(4-methyl-piperazine-1-carbonyl)-cyclopropyl]-[1,2,4]triazolo[1,5 -a]pyridin-5-yl}-phenyl)-ethanone,
1-(3-{8-Methoxy-2-[1-(morpholine-4-carbonyl)-cyclopropyl]-[1,2,4]triazolo[1,5-a]pyridin-5-yl}-phenyl)-ethanone,
1-[5-(3-Acetyl-phenyl)-8-methoxy-[1,2,4]triazolo[1,5-a]pyridin-2-yl]-cyclopropanecarboxylic acid benzylamide,
1-[5-(3-Acetyl-phenyl)-8-methoxy-[1,2,4]triazolo[1,5-a]pyridin-2-yl]-cyclopropanecarboxylic acid (2-sulfamoyl-ethyl)-amide,
1-[5-(3-Acetyl-phenyl)-8-methoxy-[1,2,4]triazolo[1,5-a]pyridin-2-yl]-cyclopropanecarboxylic acid (2-methanesulfonyl-ethyl)-amide,
2-Methyl-acrylic acid 2-({1-[5-(3-cyano-phenyl)-8-methoxy-[1,2,4]triazolo[1,5-a]pyridin-2-yl-cyclopropanecarbonyl}-amino)-ethyl ester,
1-[5-(3-Cyano-phenyl)-8-methoxy-[1,2,4]triazolo[1,5-a]pyridin-2-yl]-cyclopropanecarboxylic acid (2-hydroxy-ethyl)-amide,
Cyclohexyl-carbamic acid 1-[5-(5-cyano-pyridin-3-yl)-8-methoxy-[1,2,4]triazolo[1,5-a]pyridin-2-yl]-cyclopropylmethyl ester,
Propyl-carbamic acid 1-[8-methoxy-5-(1-oxo-indan-5-yl)-[1,2,4]triazolo [1,5-a]pyridin-2-yl]-cyclopropylmetyl ester,
Dimethyl-carbamic acid 1-[5-(4-cyano-3-methoxy-phenyl)-8-methoxy-[1,2,4]triazolo[1,5-a]pyridin-2-yl]-cyclopropylmethyl ester,
Isopropyl-carbamic acid 1-[5-(5-cyano-pyridin-3-yl)-8-methoxy-[1,2,4]triazolo[1,5-a]pyridin-2-yl]-cyclopropylmethyl ester,
Propyl-carbamic acid 1-[8-methoxy-5-(1-oxo-indan-4-yl)-[1,2,4]triazolo[1,5-a]pyridin-2-yl]-cyclopropylmethyl ester,
Pyrrolidine-1-carboxylic acid 1-[5-(4-cyano-3-methoxyphenyl)-8-methoxy-[1,2,4]triazolo[1,5-a]pyridin-2-yl]-cyclopropylmethyl ester,
Isopropyl-carbamic acid 1-[5-(4-cyano-3-methoxy-phenyl)-8-methoxy-1,2,4]triazolo[1,5-a]pyridin-2-yl]-cyclopropylmethyl ester,
Propyl-carbamic acid 1-[5-(5-cyano-pyridin-3-yl)-8-methoxy-[1,2,4]triazolo[1,5-a]pyridin-2-yl]-cyclopropylmethyl ester,
Propyl-carbamic acid 1-[5-(4-cyano-3-methoxy-phenyl)-8-methoxy-[1,2,4]triazolo[1,5-a]pyridin-2-yl]-cyclopropylmethyl ester,
Pyrrolidine-1-carboxylic acid 1-[8-methoxy-5-(1-oxo-indan-5-yl)-[1,2,4]triazolo[1,5-a]pyridin-2-yl]-cyclopropylmethyl ester,
Isopropyl-carbamic acid 1-[8-methoxy-5-(1-oxo-indan-5-yl)-[1,2,4]triazolo[1,5-a]pyridin-2-yl]-cyclopropylmethyl ester,
Cyclohexyl-carbamic acid 1-[8-methoxy-5-(1-oxo-indan-4-yl)-[1,2,4]triazolo[1,5-a]pyridin-2-yl]-cyclopropylmethyl ester,
Cyclohexyl-carbamic acid 1-[5-(4-cyano-3-methoxy-phenyl)-8-methoxy-1,2,4]triazolo[1,5-a]pyridin-2-yl]-cyclopropylmethyl ester,
Pyrrolidine-1-carboxylic acid 1-[5-(5-cyano-pyridin-3-yl)-8-methoxy-[1,2,4]triazolo[1,5-a]pyridin-2-yl]-cyclopropylmethyl ester, Dimethyl-carbamic acid 1-[8-methoxy-5-(1-oxo-indan-5-yl)-[1,2,4]triazolo[1,5-a]pyridin-2-yl]-cyclopropylmethyl ester,
Dimethyl-carbamic acid 1-[5-(5-cyano-pyridin-3-yl)-8-methoxy-[1,2,4]triazolo[1,5-a]pyridin-2-yl]-cyclopropylmethyl ester,
Diethyl-carbamic acid 1-[5-(4-cyano-3-methoxy-phenyl)-8-methoxy-1,2,4]triazolo[1,5-a]pyridin-2-yl]-cyclopropylmethyl ester,
Diethyl-carbamic acid 1-[8-methoxy-5-(1-oxo-indan-4-yl)-[1,2,4]triazolo[1,5-a]pyridin-2-yl]-cyclopropylmethyl ester,
Diethyl-carbamic acid 1-[5-(5-cyano-pyridin-3-yl)-8-methoxy-[1,2,4]triazolo[1,5-a]pyridin-2-yl]-cyclopropylmethyl ester,
5-[2-(1-Hydroxymethyl-cyclopropyl)-8-methoxy-[1,2,4]triazolo[1,5-a]pyridin-5-yl]-nicotinonitrile,
4-(2-Cyclopropyl-5-methoxy-[1,2,4]triazolo[1,5-a]pyridin-8-yl)-2-methoxy-benzonitrile,
4-(2-Cyclopropyl-5-methoxy-[1,2,4]triazolo[1,5-a]pyridin-8-yl)-2-methyl-benzonitrile,
3-(2-Cyclopropyl-5-methoxy-[1,2,4]triazolo[1,5-a]pyridin-8-yl)-benzonitrile,
5-(2-Cyclopropyl-5-methoxy-[1,2,4]triazolo[1,5-a]pyridin-8-yl)-indan-1-one,
4-(2-Cyclopropyl-5-methoxy-[1,2,4]triazolo[1,5-a]pyridin-8-yl)-indan-1-one,
1-[8-(4-Cyano-3-methoxy-phenyl)-5-methoxy-[1,2,4]triazolo[1,5-a]pyridin-2-yl]-cyclopropanecarboxylic acid isopropylamide,
1-[5-Methoxy-8-(1-oxo-1,3-dihydro-isobenzofuran-5-yl)-[1,2,4]triazolo[1,5-a]pyridin-2-yl]-cyclopropanecarboxylic acid isopropylamide,
1-[5-Methoxy-8-(1-oxo-indan-5-yl)-[1,2,4]triazolo[1,5-a]pyridin-2-yl]-cyclopropanecarboxylic acid isopropylamide,
1-[5-Hydroxy-8-(1-oxo-indan-4-yl)-[1,2,4]triazolo[1,5-a]pyridin-2-yl]-cyclopropanecarboxylic acid isopropylamide,
1-[5-Methoxy-8-(1-oxo-indan-4-yl)-[1,2,4]triazolo[1,5-a]pyridin-2-yl]-cyclopropanecarboxylic acid (2-methanesulfonyl-ethyl)-amide,
1-[8-(5-Cyano-pyridin-3-yl)-5-methoxy-[1,2,4]triazolo[1,5-a]pyridin-2-yl]-cyclopropanecarboxylic acid (2-methanesulfonyl-ethyl)-amide,
1-[5-Methoxy-8-(1-oxo-indan-5-yl)-[1,2,4]triazolo[1,5-a]pyridin-2-yl]-cyclopropanecarboxylic acid isopropylamide,
1-[5-Methoxy-8-(1-oxo-indan-5-yl)-[1,2,4]triazolo[1,5-a]pyridin-2-yl]-cyclopropanecarboxylic acid isobutyl-amide,
1-[5-Methoxy-8-(1-oxo-1,3-dihydro-isobenzofuran-5-yl)-[1,2,4]triazolo[1,5-a]pyridin-2-yl]-cyclopropanecarboxylic acid isopropylamide,
1-[8-(4-Cyano-3-methoxy-phenyl)-5-methoxy-[1,2,4]triazolo[1,5-a]pyridin-2-yl]-cyclopropanecarboxylic acid isopropylamide,
1-[8-(4-Cyano-3-methoxy-phenyl)-5-methoxy-[1,2,4]triazolo[1,5-a]pyridin-2-yl]-cyclopropanecarboxylic acid (2-methanesulfonyl-ethyl)-amide,
1-[5-Methoxy-8-(1-oxo-indan-5-yl)-[1,2,4]triazolo[1,5-a]pyridin-2-yl]-cyclopropanecarboxylic acid (2-methanesulfonyl-ethyl)-amide,
1-[5-Methoxy-8-(1-oxo-1,3-dihydro-isobenzofuran-5-yl)-[1,2,4]triazolo[1,5-a]pyridin-2-yl]-cyclopropanecarboxylic acid (2-methanesulfonyl-ethyl)-amide,
1-[8-(4-Cyano-3-methoxy-phenyl)-5-methoxy-[1,2,4]triazolo[1,5-a]pyridin-2-yl]-cyclopropanecarboxylic acid isobutyl-amide,
1-[5-Hydroxy-8-(1-oxo-indan-5-yl)-[1,2,4]triazolo[1,5-a]pyridin-2-yl]-cyclopropanecarboxylic acid isopropylamide,
1-[8-Methoxy-5-(1-oxo-1,3-dihydro-isobenzofuran-5-yl)-[1,2,4]triazolo[1,5-a]pyridin-2-yl]-cyclopropanecarboxylic acid (2-methanesulfonyl-ethyl)-amide,
1-[8-Methoxy-5-(1-oxo-1,3-dihydro-isobenzofuran-5-yl)-[1,2,4]triazolo[1,5-a]pyridin-2-yl]-cyclopropanecarboxylic acid cyclohexylmethyl-amide,
1-[8-Methoxy-5-(1-oxo-1,3-dihydro-isobenzofuran-5-yl)-[1,2,4]triazolo[1,5-a]pyridin-2-yl]-cyclopropanecarboxylic acid (2-dimethylsulfamoyl-ethyl)-amide,
Diethyl-carbamic acid 1-[8-methoxy-5-(1-oxo-indan-4-yl)-[1,2,4]triazolo[1,5-a]pyridin-2-yl]-cyclopropylmethyl ester,
Dimethyl-carbamic acid 1-[8-methoxy-5-(1-oxo-1,3-dihydro-isobenzofuran-5-yl)-[1,2,4]triazolo[1,5-a]pyridin-2-yl]-cyclopropylmethyl ester,
Diethyl-carbamic acid 1-[5-(5-cyano-pyridin-3-yl)-8-methoxy-[1,2,4]triazolo[1,5-a]pyridin-2-yl]-cyclopropylmethyl ester,
Diethyl-carbamic acid 1-[5-(4-cyano-3-methoxy-phenyl)-8-methoxy-[1,2,4]triazolo[1,5-a]pyridin-2-yl]-cyclopropylmethyl ester,
Cyclohexyl-carbamic acid 1-[8-methoxy-5-(1-oxo-1,3-dihydro-isobenzofuran-5-yl)-[1,2,4]triazolo[1,5-a]pyridin-2-yl]-cyclopropylmethyl ester,
4-[2-(1-Hydroxymethyl-cyclopropyl)-8-methoxy-[1,2,4]triazolo[1,5-a]pyridin-5-yl]-2-methoxy-benzonitrile,
4-[2-(1-Isobutoxymethyl-cyclopropyl)-8-methoxy-[1,2,4]triazolo[1,5-a]pyridin-5-yl]-2-methoxy-benzonitrile,
1-[5-(3-Cyano-phenyl)-8-methoxy-[1,2,4]triazolo[1,5-a]pyridin-2-yl]-cyclopropanecarboxylic acid isobutyl-amide,
1-[5-(3-Cyano-phenyl)-8-methoxy-[1,2,4]triazolo[1,5-a]pyridin-2-yl]-cyclopropanecarboxylic acid (2-methanesulfonylamino-ethyl)-amide,
1-[5-(3-Cyano-phenyl)-8-methoxy-[1,2,4]triazolo[1,5-a]pyridin-2-yl]-cyclopropanecarboxylic acid cyclopropylamide,
1-[5-(3-Cyano-phenyl)-8-methoxy-[1,2,4]triazolo[1,5-a]pyridin-2-yl]-cyclopropanecarboxylic acid cyclohexylmethyl-amide,
5-[2-(1-Isobutoxymethyl-cyclopropyl)-8-methoxy-[1,2,4]triazolo[1,5-a]pyridin-5-yl]-nicotinonitrile,
5-(2-Cyclopropyl-5-methoxy-[1,2,4]triazolo[1,5-a]pyridin-8-yl)-nicotinonitrile,
1-[5-(4-Cyano-phenyl)-8-methoxy-[1,2,4]triazolo[1,5-a]pyridin-2-yl]-cyclopropanecarboxylic acid (2-dimethylsulfamoyl-ethyl)-amide,
1-[5-(4-Cyano-phenyl)-8-methoxy-[1,2,4]triazolo[1,5-a]pyridin-2-yl]-cyclopropanecarboxylic acid[2-(methanesulfonyl-methyl-amino)-ethyl]-amide,
1-[5-(4-Cyano-3-methoxy-phenyl)-8-methoxy-[1,2,4]triazolo[1,5-a]pyridin-2-yl]-cyclopropanecarboxylic acid (2-dimethylsulfamoyl-ethyl)-amide,
1-[5-(5-Cyano-pyridin-3-yl)-8-methoxy-[1,2,4]triazolo[1,5-a]pyridin-2-yl]-cyclopropanecarboxylic acid (2-dimethylsulfamoyl-ethyl)-amide,
1-[8-Methoxy-5-(1-oxo-indan-5-yl)-[1,2,4]triazolo[1,5-a]pyridin-2-yl]-cyclopropanecarboxylic acid (2-dimethylsulfamoyl-ethyl)-amide,
and pharmaceutically acceptable salts, hydrates, N-oxides or solvates thereof.

24. A method of treating or ameliorating psoriasis, psoriatic arthritis, dermatitis, atopic dermatitis, seborrheic dermatitis, contact dermatitis, urticaria, pruritis, and eczema which comprises administering to a person suffering from at least one of said diseases an effective amount of one or more compounds according to according to claim 1.

* * * * *